(12) United States Patent
Devarakonda et al.

(10) Patent No.: US 9,433,582 B2
(45) Date of Patent: *Sep. 6, 2016

(54) GASTRIC RETENTIVE EXTENDED RELEASE PHARMACEUTICAL COMPOSITIONS

(71) Applicant: MALLINCKRODT LLC, Hazelwood, MO (US)

(72) Inventors: Krishna R. Devarakonda, St. Louis, MO (US); Michael J. Giuliani, Creve Coeur, MO (US); Vishal K. Gupta, Hillsborough, NJ (US); Ralph A. Heasley, Webster Groves, MO (US); Susan Shelby, Town and Country, MO (US)

(73) Assignee: MALLINCKRODT LLC, Hazelwood, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/301,658

(22) Filed: Jun. 11, 2014

(65) Prior Publication Data

US 2014/0294956 A1 Oct. 2, 2014

Related U.S. Application Data

(63) Continuation of application No. 14/132,500, filed on Dec. 18, 2013, now Pat. No. 8,790,694, which is a continuation of application No. 13/473,571, filed on May 16, 2012, now Pat. No. 8,741,885.

(60) Provisional application No. 61/537,533, filed on Sep. 21, 2011, provisional application No. 61/606,896, filed on Mar. 5, 2012, provisional application No. 61/487,047, filed on May 17, 2011.

(51) Int. Cl.
| | |
|---|---|
| *A61K 9/20* | (2006.01) |
| *A61K 31/485* | (2006.01) |
| *A61K 31/167* | (2006.01) |
| *A61K 9/24* | (2006.01) |
| *A61K 47/34* | (2006.01) |
| *A61K 9/00* | (2006.01) |

(52) U.S. Cl.
CPC ........... *A61K 9/2031* (2013.01); *A61K 9/0065* (2013.01); *A61K 9/209* (2013.01); *A61K 31/167* (2013.01); *A61K 31/485* (2013.01); *A61K 47/34* (2013.01)

(58) Field of Classification Search
CPC ..... A61K 9/20; A61K 31/167; A61K 31/485
See application file for complete search history.

(56) References Cited

U.S. PATENT DOCUMENTS

| | | | |
|---|---|---|---|
| 4,713,243 A | 12/1987 | Schiraldi et al. | |
| 4,851,226 A | 7/1989 | Julian et al. | |
| 4,894,236 A | 1/1990 | Jang | |
| 4,996,058 A | 2/1991 | Sinnreich | |
| 5,075,114 A | 12/1991 | Roche | |
| 5,266,331 A | 11/1993 | Oshlack et al. | |
| 5,336,691 A | 8/1994 | Raffa et al. | |
| 5,478,577 A | 12/1995 | Sackler et al. | |
| 5,508,042 A | 4/1996 | Oshlack et al. | |
| 5,549,912 A | 8/1996 | Oshlack et al. | |
| 5,582,837 A | 12/1996 | Shell | |
| 5,626,874 A | 5/1997 | Conte et al. | |
| 5,656,295 A | 8/1997 | Oshlack et al. | |
| 5,672,360 A | 9/1997 | Sackler et al. | |
| 5,783,212 A | 7/1998 | Fassihi et al. | |
| 5,866,161 A | 2/1999 | Childers et al. | |
| 5,876,759 A | 3/1999 | Gowan, Jr. | |
| 5,891,471 A | 4/1999 | Miller et al. | |
| 5,945,123 A | 8/1999 | Hermelin | |
| 5,945,125 A | 8/1999 | Kim | |
| 5,958,459 A | 9/1999 | Chasin et al. | |
| 5,965,161 A | 10/1999 | Oshlack et al. | |
| 5,965,163 A | 10/1999 | Miller et al. | |
| 5,965,167 A | 10/1999 | Sanghvi et al. | |
| 5,968,551 A | 10/1999 | Oshlack et al. | |
| 5,972,389 A | 10/1999 | Shell et al. | |
| 5,980,882 A | 11/1999 | Eichman | |
| 6,024,982 A | 2/2000 | Oshlack et al. | |

(Continued)

FOREIGN PATENT DOCUMENTS

| | | |
|---|---|---|
| EP | 0159852 A2 | 10/1985 |
| EP | 1140026 B1 | 10/2001 |

(Continued)

OTHER PUBLICATIONS

Banfai et al.; "Content Uniformity and Assay Requirements in Current Regulations;" J. Chromatogr. A.; (2007); 1156; pp. 206-212.

Zhu et al.; "Solid-State Plasticization of an Acrylic Polymer with Chlorpheniramine Maleate and Triethyl Citrate;" International Journal of Pharmaceutics; (2002); 241; pp. 301-310.

Nimmo, et al.; "Inhibition of Gastric Emptying and Drug Absorption by Narcotic Analgesics;" Br. J. Clin. Pharmac.; (1975); 2; pp. 509-513.

Altaf et al.; "Bead Compacts II. Evaluation of Rapidly Disintegrating Nonsegregating Compressed Bead Formulations;" Drug Development and Industrial Pharmacy; (1999); 25(5); pp. 635-642.

International Search Report from Application No. PCT/US2010/061400 with a mailing date of Nov. 25, 2011 (4 pages).

Endo Pharmaceuticals Package Insert for Percocet(Oxycodone and Acetaminophen Tablets, USP); pp. 1-17.

(Continued)

*Primary Examiner* — Jessica Worsham
(74) *Attorney, Agent, or Firm* — Mayer Brown LLP

(57) ABSTRACT

The present disclosure provides extended release pharmaceutical compositions comprising an opioid and an additional active pharmaceutical ingredient, wherein the composition exhibits gastric retentive properties which are achieved by a combination of a physical property of the composition and release of the opioid, wherein upon administration to a subject, the composition has at least one pharmacokinetic parameter that differs by less than about 30% when the subject is in a fasted state as compared to a fed state.

Figure 1:
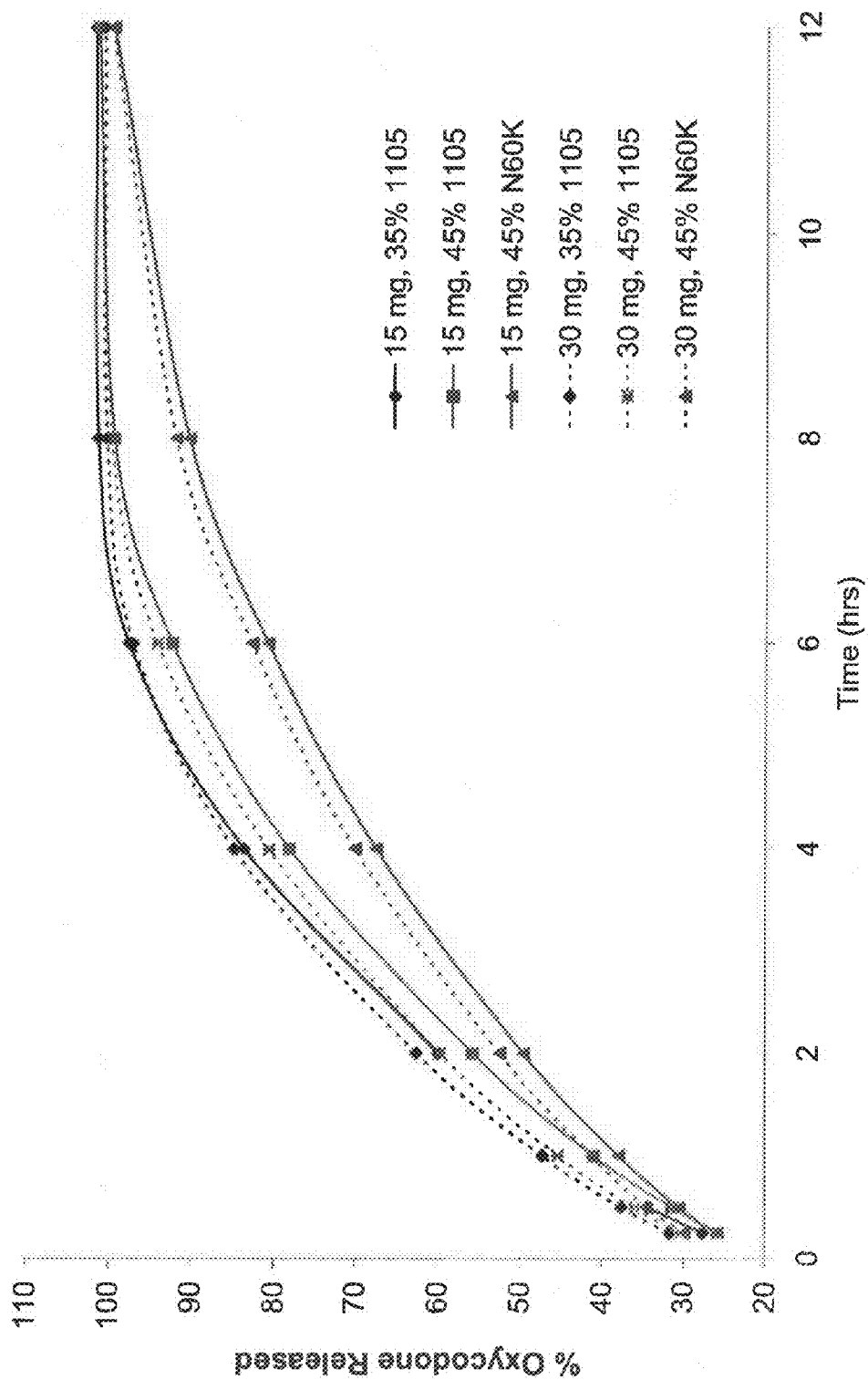

30 Claims, 66 Drawing Sheets (48 of 66 Drawing Sheet(s) Filed in Color)

(56) References Cited

U.S. PATENT DOCUMENTS

| | | | |
|---|---|---|---|
| 6,068,855 A | 5/2000 | Leslie et al. |
| 6,071,208 A | 6/2000 | Koivunen |
| 6,103,219 A | 8/2000 | Sherwood et al. |
| 6,103,261 A | 8/2000 | Chasin et al. |
| 6,126,969 A | 10/2000 | Shah et al. |
| 6,143,322 A | 11/2000 | Sackler et al. |
| 6,210,714 B1 | 4/2001 | Oshlack et al. |
| 6,245,357 B1 | 6/2001 | Edgren et al. |
| 6,251,430 B1 | 6/2001 | Zhang et al. |
| 6,254,887 B1 | 7/2001 | Miller et al. |
| 6,340,475 B2 | 1/2002 | Shell et al. |
| 6,372,254 B1 | 4/2002 | Ting et al. |
| 6,375,957 B1 | 4/2002 | Kaiko et al. |
| 6,387,404 B2 | 5/2002 | Oshlack et al. |
| 6,488,962 B1 | 12/2002 | Berner et al. |
| 6,488,963 B1 | 12/2002 | McGinity et al. |
| 6,500,459 B1 | 12/2002 | Chhabra et al. |
| 6,599,529 B1 | 7/2003 | Skinhoj et al. |
| 6,635,280 B2 | 10/2003 | Shell et al. |
| 6,667,060 B1 | 12/2003 | Vandecruys et al. |
| 6,682,759 B2 | 1/2004 | Lim et al. |
| 6,696,066 B2 | 2/2004 | Kaiko et al. |
| 6,706,281 B2 | 3/2004 | Oshlack et al. |
| 6,723,340 B2 | 4/2004 | Gusler et al. |
| 6,730,321 B2 | 5/2004 | Ting et al. |
| 6,733,783 B2 | 5/2004 | Oshlack et al. |
| 6,797,283 B1 | 9/2004 | Edgren et al. |
| 6,852,336 B2 | 2/2005 | Hunter et al. |
| 6,902,742 B2 | 6/2005 | Devane et al. |
| 7,074,430 B2 | 7/2006 | Miller et al. |
| 7,201,920 B2 | 4/2007 | Kumar et al. |
| 7,374,781 B2 | 5/2008 | Zhang et al. |
| 7,405,238 B2 | 7/2008 | Markey et al. |
| 7,413,751 B2 | 8/2008 | Devane et al. |
| 7,438,927 B2 | 10/2008 | Berner et al. |
| 7,514,100 B2 | 4/2009 | Oshlack et al. |
| 7,674,799 B2 | 3/2010 | Chapman et al. |
| 7,674,800 B2 | 3/2010 | Chapman et al. |
| 7,683,072 B2 | 3/2010 | Chapman et al. |
| 7,691,873 B2 | 4/2010 | Duncalf et al. |
| 7,776,314 B2 | 8/2010 | Bartholomaus et al. |
| 7,846,476 B2 | 12/2010 | Oshlack et al. |
| 7,897,172 B2 | 3/2011 | Qasem et al. |
| 7,939,543 B2 | 5/2011 | Kupper |
| 7,943,170 B2 | 5/2011 | Chan et al. |
| 7,976,870 B2 | 7/2011 | Berner et al. |
| 8,075,872 B2 | 12/2011 | Arkenau-Maric et al. |
| 8,309,060 B2 | 11/2012 | Bartholomaus et al. |
| 8,337,888 B2 | 12/2012 | Wright et al. |
| 8,394,408 B2 | 3/2013 | Han et al. |
| 8,597,681 B2 | 12/2013 | Park et al. |
| 8,658,631 B1 | 2/2014 | Devarakonda et al. |
| 8,741,885 B1 | 6/2014 | Devarakonda et al. |
| 8,790,694 B2 | 7/2014 | Devarakonda et al. |
| 8,858,963 B1 | 10/2014 | Devarakonda et al. |
| 8,980,319 B2 | 3/2015 | Park et al. |
| 8,992,975 B2 | 3/2015 | Devarakonda et al. |
| 9,050,335 B1 | 6/2015 | Devarakonda et al. |
| 2001/0008639 A1 | 7/2001 | Oshlack et al. |
| 2002/0018810 A1 | 2/2002 | Oshlack et al. |
| 2002/0058050 A1 | 5/2002 | Sackler et al. |
| 2002/0192277 A1 | 12/2002 | Oshlack et al. |
| 2003/0035837 A1 | 2/2003 | Sackler et al. |
| 2003/0044466 A1 | 3/2003 | Markey et al. |
| 2003/0091635 A1 | 5/2003 | Baichwal et al. |
| 2003/0092724 A1 | 5/2003 | Kao et al. |
| 2003/0099704 A1 | 5/2003 | Oshlack et al. |
| 2003/0104062 A1 | 6/2003 | Berner et al. |
| 2004/0096500 A1 | 5/2004 | Oshlack et al. |
| 2004/0105887 A1 | 6/2004 | Oshlack et al. |
| 2004/0131671 A1 | 7/2004 | Zhang et al. |
| 2004/0156899 A1 | 8/2004 | Louie-Helm et al. |
| 2005/0013863 A1 | 1/2005 | Lim et al. |
| 2005/0020613 A1 | 1/2005 | Boehm et al. |
| 2005/0031546 A1 | 2/2005 | Bartholomaus et al. |
| 2005/0089570 A1 | 4/2005 | Cruz et al. |
| 2005/0106249 A1 | 5/2005 | Hwang et al. |
| 2005/0112195 A1 | 5/2005 | Cruz et al. |
| 2005/0158382 A1 | 7/2005 | Cruz et al. |
| 2005/0165038 A1 | 7/2005 | Gordon |
| 2005/0232987 A1 | 10/2005 | Srinivasan et al. |
| 2005/0266032 A1 | 12/2005 | Srinivasan et al. |
| 2005/0267189 A1 | 12/2005 | Gao et al. |
| 2006/0002860 A1 | 1/2006 | Bartholomaus et al. |
| 2006/0057210 A1 | 3/2006 | Oshlack et al. |
| 2006/0099255 A1 | 5/2006 | Oshlack et al. |
| 2006/0165791 A1 | 7/2006 | Oshlack et al. |
| 2006/0193782 A1 | 8/2006 | Bartholomaus et al. |
| 2006/0205752 A1 | 9/2006 | Whitehead |
| 2006/0240105 A1 | 10/2006 | Devane et al. |
| 2006/0251721 A1 | 11/2006 | Cruz et al. |
| 2006/0263436 A1 | 11/2006 | Baert et al. |
| 2006/0269604 A1 | 11/2006 | Sackler et al. |
| 2006/0292214 A1 | 12/2006 | Jenkins et al. |
| 2007/0020335 A1 | 1/2007 | Chen et al. |
| 2007/0048228 A1 | 3/2007 | Arkenau-Maric et al. |
| 2007/0059359 A1 | 3/2007 | Backensfeld et al. |
| 2007/0128279 A1 | 6/2007 | Edgren et al. |
| 2007/0183980 A1 | 8/2007 | Arkenau-Maric et al. |
| 2007/0184112 A1 | 8/2007 | Wong et al. |
| 2007/0190142 A1 | 8/2007 | Breitenbach et al. |
| 2007/0207200 A1 | 9/2007 | Plachetka et al. |
| 2007/0237833 A1 | 10/2007 | Sackler et al. |
| 2007/0259033 A1 | 11/2007 | Cruz |
| 2007/0259045 A1 | 11/2007 | Mannion et al. |
| 2007/0275065 A1 | 11/2007 | Oshlack et al. |
| 2007/0281018 A1 | 12/2007 | Qiu et al. |
| 2008/0020039 A1 | 1/2008 | Parikh et al. |
| 2008/0031901 A1 | 2/2008 | Qiu et al. |
| 2008/0031963 A1 | 2/2008 | Sackler et al. |
| 2008/0044482 A1 | 2/2008 | Oshlack et al. |
| 2008/0057122 A1 | 3/2008 | Toney-Parker et al. |
| 2008/0113025 A1 | 5/2008 | Devane et al. |
| 2008/0132532 A1 | 6/2008 | Wright et al. |
| 2008/0138422 A1 | 6/2008 | Staniforth |
| 2008/0220062 A1 | 9/2008 | Ashton |
| 2009/0022798 A1 | 1/2009 | Rosenberg et al. |
| 2009/0028941 A1 | 1/2009 | Cowles et al. |
| 2009/0068269 A1 | 3/2009 | Oshlack et al. |
| 2009/0081290 A1 | 3/2009 | McKenna et al. |
| 2009/0149479 A1 | 6/2009 | Jenkins et al. |
| 2009/0155357 A1 | 6/2009 | Muhuri |
| 2009/0175937 A1 | 7/2009 | Rahmouni et al. |
| 2009/0202629 A1 | 8/2009 | Oshlack et al. |
| 2009/0304793 A1 | 12/2009 | Boehm |
| 2009/0306119 A1 | 12/2009 | Keane |
| 2009/0311320 A1 | 12/2009 | Oury et al. |
| 2009/0317355 A1 | 12/2009 | Roth et al. |
| 2009/0324714 A1 | 12/2009 | Liu et al. |
| 2010/0010030 A1 | 1/2010 | Jain et al. |
| 2010/0015222 A1 | 1/2010 | Han et al. |
| 2010/0034876 A1 | 2/2010 | Oshlack et al. |
| 2010/0040681 A1 | 2/2010 | Park et al. |
| 2010/0092570 A1 | 4/2010 | Oshlack et al. |
| 2010/0168148 A1 | 7/2010 | Wright et al. |
| 2010/0172974 A1 | 7/2010 | Oshlack et al. |
| 2010/0172989 A1 | 7/2010 | Roth et al. |
| 2010/0196425 A1 | 8/2010 | Cruz et al. |
| 2010/0196471 A1 | 8/2010 | Jain et al. |
| 2010/0196474 A1 | 8/2010 | Han et al. |
| 2010/0216829 A2 | 8/2010 | Kumar et al. |
| 2010/0221293 A1 | 9/2010 | Cruz et al. |
| 2010/0239662 A1 | 9/2010 | Rahmouni et al. |
| 2010/0260833 A1 | 10/2010 | Bartholomaus et al. |
| 2011/0020451 A1 | 1/2011 | Bartholomaus et al. |
| 2011/0038927 A1 | 2/2011 | Oshlack et al. |
| 2011/0038930 A1 | 2/2011 | Barnscheid et al. |
| 2011/0052685 A1 | 3/2011 | Hou et al. |
| 2011/0077238 A1 | 3/2011 | Leech et al. |
| 2011/0117196 A1 | 5/2011 | Gordon |
| 2011/0118189 A1 | 5/2011 | Farr et al. |
| 2011/0129507 A1 | 6/2011 | Cruz |
| 2011/0150969 A1 | 6/2011 | Shah et al. |
| 2011/0150970 A1 | 6/2011 | Shah et al. |

(56) References Cited

U.S. PATENT DOCUMENTS

| | | |
|---|---|---|
| 2011/0150971 A1 | 6/2011 | Shah et al. |
| 2011/0150989 A1 | 6/2011 | Park et al. |
| 2011/0150990 A1 | 6/2011 | Shah et al. |
| 2011/0150991 A1 | 6/2011 | Shah et al. |
| 2011/0159046 A1 | 6/2011 | Cruz |
| 2011/0166171 A1 | 7/2011 | Qiu et al. |
| 2011/0177168 A1 | 7/2011 | Chan et al. |
| 2011/0195116 A1 | 8/2011 | Hobbs et al. |
| 2011/0195989 A1 | 8/2011 | Rudnic et al. |
| 2011/0207762 A1 | 8/2011 | Chapman et al. |
| 2011/0212173 A1 | 9/2011 | Young et al. |
| 2011/0229526 A1 | 9/2011 | Rosenberg et al. |
| 2011/0229533 A1 | 9/2011 | Edgren et al. |
| 2011/0262532 A1 | 10/2011 | Oshlack et al. |
| 2011/0287095 A1 | 11/2011 | Park et al. |
| 2011/0301129 A1 | 12/2011 | Berner et al. |
| 2011/0318392 A1 | 12/2011 | Cruz et al. |
| 2012/0321713 A1 | 12/2012 | Han et al. |
| 2013/0273153 A1 | 10/2013 | Park et al. |
| 2014/0170217 A1 | 6/2014 | Devarakonda et al. |
| 2014/0275143 A1 | 9/2014 | Devarakonda et al. |
| 2014/0288113 A1 | 9/2014 | Devarakonda et al. |
| 2014/0378498 A1 | 12/2014 | Devarakonda et al. |

FOREIGN PATENT DOCUMENTS

| | | |
|---|---|---|
| WO | 97/18814 A1 | 5/1997 |
| WO | 98/55107 A1 | 12/1998 |
| WO | 03/024426 A1 | 3/2003 |
| WO | 2005013863 A2 | 2/2005 |
| WO | 2005030182 A1 | 4/2005 |
| WO | 2006022759 A1 | 3/2006 |
| WO | 2006071208 A1 | 7/2006 |
| WO | 2008015221 A2 | 2/2008 |
| WO | 2009049405 A1 | 4/2009 |
| WO | 2009076764 A1 | 6/2009 |
| WO | 2009114648 A1 | 9/2009 |
| WO | 2009135846 A1 | 11/2009 |
| WO | 2010032128 A1 | 3/2010 |
| WO | 2010069050 A1 | 6/2010 |
| WO | 2010078486 A2 | 7/2010 |
| WO | 2010141505 A1 | 12/2010 |
| WO | 2011009603 A1 | 1/2011 |
| WO | 2011009604 A1 | 1/2011 |
| WO | 2011068723 A1 | 6/2011 |
| WO | 2011077451 A2 | 6/2011 |
| WO | 2011/087765 A2 | 7/2011 |
| WO | 2011106416 A2 | 9/2011 |
| WO | 2012007159 A2 | 1/2012 |
| WO | 2012/087377 A1 | 6/2012 |
| WO | 2014/149397 A1 | 9/2014 |

OTHER PUBLICATIONS

U.S. Department of Health & Human Services; "FDA Drugs Safety Communication: Prescription Acetaminophen Products to be Limited to 325mg per Dosage Unit; Boxed Warning Will Highlight Potential for Severe Liver Failure;" (5 pages); Downloaded on Feb. 9, 2012 from: http://www.fda.gov/Drugs/DrugSafety/ucm239821.htm.

"Tylenol Professional Product Information;" (2010); McNeil Consumer Healthcare (62 pages).

Oxycontin; Description and Patient Information; (2010); Purdue Pharma L.P. (32 pages).

Cooperman et al; "A Novel Extended-Release Formulation of Oxycodone/Acetaminophen with Abuse Deterrent Properties"; Abstract and Poster (2 pages).

Khosla et al.; "The Effect of Tablet Size on the Gastric Emptying of Non-Disintegrating Tablets;" International Journal of Pharmaceutics; (1990); 62; R9-R11.

Khosla et al.; "Gastrointestinal Transit of Non-Disintegrating Tablets in Fed Subjects;" International Journal of Pharmaceutics; (1989); 53; pp. 107-117.

Davis et al.; "The Gastrointestinal Transit of a Controlled Release Formulation of Indomethacin;" International Journal of Pharmaceutics; (1990); 60; pp. 191-196.

Brzeznicka et al.; "Dynamics of Glutathione Levels in Liver and Indicatory Enzymes in Serum in Acetaminophen Intoxication in Mice;" Polish Journal of Occupational Medicine; (1989); vol. 2; No. 1; pp. 15-22.

Gammaitoni et al.; "Randomized, Double-Blind, Placebo-Controlled Comparison of the Analgesic Efficacy of Oxycodone 10 mg/Acetaminophen 325 mg versus Controlled-Release Oxycodone 20 mg in Postsurgical Pain;" J. Clin. Pharmacol; (2003); 43; pp. 296-304.

Moller et al.; "Time to Onset of Analgesia and Analgesic Efficacy of Effervescent Acetaminophen 1000 mg Compared to Tablet Acetaminophen 1000 mg in Postperative Dental Pain: A Single-Dose, Double-Blind, Randomized, Placebo-Controlled Study;" J. Clin. Pharmacol.; (2000); 40; pp. 370-378.

Nielsen et al; "Analgesic Efficacy of Immediate and Sustained Release Paracetamol and Plasma Concentration of Paracetamol. Double Blind Placebo-Controlled Evaluation Using Painful Laser Stimulation;" Eur. J. Clin Pharmacol; (1992); 42; pp. 261-264.

James et al; "Acetaminophen-Induced Hepatotoxicity;" Drug Metabolism and Disposition; (2003); vol. 31; No. 12; pp. 1499-1506.

Mirochnitchenko et al.; "Acetaminophen Toxicity: Opposite Effects of Two Forms of Glutathione Peroxidase;" The Journal of Biological Chemistry; (1999); vol. 274; No. 15; pp. 10349-10355.

Dart et al.; "Acetaminophen Poisoning: An Evidence-Based Consensus Guideline for Out-of-Hospital Management;" Clinical Toxicology; (2006); 44; pp. 1-18.

Bolesta et al.; "Hepatotoxicity Associated with Chronic Acetaminophen Administration in Patients without Risk Factors"; The Annals of Pharmacotherapy; (2002); vol. 36; pp. 331-333.

Rinaldi et al.; "Minireview: Reactive Intermediates and the Dynamics of Glutathione Transferases;" Drug Metabolism and Deposition; (2002); vol. 30; No. 10; pp. 1053-1058.

Barry H. Rumack; "Acetaminophen Hepatotoxicity: The First 35 Years;" Clinical Toxicology; (2002); 40(1); pp. 3-20.

Bartels et al.; "Are Recommended Doses of Acetaminophen Hepatotoxic for Recently Abstinent Alcoholics? A Randomized Trial"; (2008); Clinical Toxicology; 46; pp. 243-249.

Corcoran et al.; "Role of Glutathione in Prevention of Acetaminophen-Induced Hepatotoxicity by N-Acetyl-L-Cysteine in Vivo: Studies with N-Acetyl-D-Cysteine in Mice;" The Journal of Pharmacology and Experimental Therapeutics; (1986); vol. 238; No. 1; pp. 54-61.

Davis et al.; "Species Differences in Hepatic Glutathione Depletion, Covalent Binding and Hepatic Necrosis After Acetaminophen;" Life Sciences; vol. 14; pp. 2099-2109.

Mitchell et al.; "Acetaminophen-Induced Hepatic Necrosis. IV. Protective Role of Glutathione;" The Journal of Pharmacology and Experimental Therapeutics; (1973); vol. 187; No. 1; pp. 211-217.

Kaplowitz et al.; "Drug-Induced Liver Disease;" (2003); Marcel Dekker, Inc.; Chapters 13 and 15; pp. 287-325 and pp. 345-375.

Skoglund et al.; "Efficacy of Paracetamol-Esterified Methionine Versus Cysteine or Methionine on Paracetamol-Induced Hepatic GSH Depletion and Plasma ALAT Level in Mice;" Biochemical Pharmacology; (1986); vol. 35; No. 18; pp. 3071-3075.

Talukder et al; "Gastroretentive Delivery Systems: A Mini Review;" Drug Development and Industrial Pharmacy; (2004); vol. 30; No. 10; pp. 1019-1028.

Hou et al; "Gastric Retentive Dosage Forms: A Review"; Critical Reviews in Therapeutic Drug Carrier Systems; (2003); 20(6); pp. 461-497.

Streubel et al.; "Drug Delivery to the Upper Small Intestine Window Using Gastroretentive Technologies;" Current Opinion in Pharmacology; (2006); vol. 6; pp. 501-508.

Streubel et al. "Gastroretentive Drug Delivery Systems"; Expert Opin. Drug Deliv.; (2006); 3(2); pp. 217-233.

Moes, A. J.; "Gastroretentive Dosage Forms;" Critical Reviews in Therapeutic Drug Carrier Systems; (1993); 10(2); pp. 143-195.

Davis S. S.; "Formulation Strategies for Absorption Windows;" DDT; (2005); vol. 10, No. 4; pp. 249-257.

(56) References Cited

OTHER PUBLICATIONS

Bardonnet et al.; "Gastroretentive Dosage Forms: Overview and Special Case of Helicobacter Pylori;" Journal of Controlled Release; (2006); vol. 111; pp. 1-18.
U.S. Appl. No. 13/473,584, filed May 16, 2012; not yet published.
U.S. Appl. No. 13/473,586, filed May 16, 2012; not yet published.
"Foremost NF Fast Flo Lactose: Modified, Spray Dried, Product Code 316; A Spray-Dried Mixture of Crystalline and Amorphose Lactose;" Foremost Farms; USA; (1 page). Online Article downloaded from the site: http://www.foremostfarms.com/Commercial/pdfs/Specifications/TDS_NF_Lactose_316.pdf Document created on Jan. 28, 2010.
Freed et al.; "pH Control on Nucleophilic/Electrophilic Oxidation;" Int. J. Pharm.; (2008); vol. 357; pp. 180-188.
International Search Report for PCT Patent application No. PCT/US2009/036864 mailed on Aug. 31, 2009.
Lab Basics Technical Library; Particle Size Conversion Table; Sigma-Aldrich; 3 pages; online article downloaded from the site: http://www.sigmaaldrich.com/chemistry/stockroom-reagents/learning-center/technical-libraiy/particle-size-conversion.printerview.html on Apr. 17, 2012.
Polyox Water-Soluble Resins, Technical Data, "Degradation of Water-Soluble Resins"; Form 326-00027-1002AMS (2002).
Polyox Water-Soluble Resins, Technical Data, "Water-Soluble Resin Storage Stability;" Form 326-00044-0704MAB (2004).
Waterman et al.; "Stabilization of Pharmaceuticals to Oxidative Degradation;" Pharmaceutical Development and Technology; (2002); vol. 7; No. 1; pp. 1-32.
Zhang et al.; "Effect of Processing Methods and Heat Treatment on the Formation of Wax Matrix Tablets for Sustained Drug Release;" Pharmaceutical Development and Technology; (2001); vol. 6; No. 2; pp. 131-144.
Meert et al.; A Preclinical Comparison Between Different Opioids: Antinociceptive Versus Adverse Effects; Pharmacology, Biochemistry and Behavior; (2005); 80; pp. 309-326.
Doteuchi et al.; "Pharmacological Studies of Oxycodone Hydrochloride: 1. Antinociceptive Effect and General Pharmacology"; Oyo Yakuri/Pharmacometrics; (1995); 49(3); pp. 257-273.
Miller et al.; "Physical and Chemical Characteristics of Some High Purity Magnesium Stearate and Palmitate Powders;" International Journal of Pharmaceutics; (1985); 23; pp. 55-67.
Kim, C.-J.; "Effects of Drug Solubility, Drug Loading, and Polymer Molecular Weight on Drug Release from Polyox Tablets;" Drug Development and Industrial Pharmacy; (1998); 24(7); pp. 645-651.
Waterman K. C.; "A Critical Review of Gastric Retentive Controlled Drug Delivery;" Pharmaceutical Development and Technology; (2007); 12; pp. 1-10.
Arora et al.; "Floating Drug Delivery Systems: A Review;" AAPS PharmSciTech; (2005); 6(3); Article 47 E372-390.
Klausner et al.; "Novel Gastroretentive Dosage Forms: Evaluation of Gastroretentivity and Its Effect on Levodopa Absorption in Humans;" Pharmaceutical Research; ( 2003); vol. 20; No. 9; pp. 1466-1473.
Klausner et al.; "Novel Levodopa Gastroretentive Dosage Form: in-Vivo Evaluation in Dogs;" Journal of Controlled Release; (2003); 88; pp. 117-126.
Aulton M. E.; "Aulton's Pharmaceutics: The Design and Manufacture of Medicines;" Elsevier Limited; Oxford; Third Edition; (2007); pp. 270-278.
Prinderre et al.; "Advances in Gastro Retentive Drug-Delivery Systems;" Expert Opin. Drug. Deliv.; (2011); 8(9); pp. 1189-1203.
Berner et al.; "Case Studies in Swelling Polymeric Gastric Retentive Tablets;" Expert Opin. Drug. Deliv.; (2006); 3(4), pp. 541-548.
Gralise Prescribing Information (24 pages).
Glumetza Prescribing Information (10 pages).
Tylenol® Professional Product Information (62 pages).
Ward et al.; "Modeling the Economic and Health Consequences of Managing Chronic Osteoarthritis Pain with Opioids in Germany: Comparison of Extended Release Oxycodone and OROS Hydromorphone;" Current Medical Research and Opinion; (2007); vol. 23; No. 10; pp. 2333-2345.
Koizumi et al.; "Efficacy and Tolerability of Cancer Pain Management with Controlled-Release Oxycodone Tablets in Opioid-Naïve Cancer Pain Patients, Starting with 5 mg Tablets;" Jpn J Clin Oncol; (2004); 34(10); pp. 608-614.
Gammaitoni et al.; "Effectiveness and Safety of New Oxycodone/Acetaminophen Formulations With Reduced Acetaminophen for the Treatment of Low Back Pain;" Pain Medicine; (2003); vol. 4; No. 1; pp. 21-30.
U.S. Appl. No. 14/627,879, filed Feb. 20, 2015; not yet published.
XARTEMIS™ XR Prescribing Information, revised Mar. 2014 (28 pages).
Requirement for Restriction/Election received in U.S. Appl. No. 13/166,770 and dated Jun. 22, 2012 (6 pages).
Non-Final Office Action received in U.S. Appl. No. 13/166,770 and dated Nov. 26, 2012 (14 pages).
Non-Final Office Action received in U.S. Appl. No. 14/092,375 and dated Feb. 24, 2014 (11 pages).
Requirement for Restriction/Election received in U.S. Appl. No. 13/473,563 and dated Sep. 11, 2012 (5 pages).
Non-Final Office Action received in U.S. Appl. No. 13/473,563 and dated May 6, 2013 (20 pages).
Non-Final Office Action received in U.S. Appl. No. 14/109,052 and dated Apr. 25, 2014 (6 pages).
Final Office Action received in U.S. Appl. No. 14/109,052 and dated Aug. 11, 2014 (7 pages).
Requirement for Restriction/Election received in U.S. Appl. No. 13/473,586 and dated Mar. 28, 2013 (6 pages).
Non-Final Office Action received in U.S. Appl. No. 13/473,586 and dated Aug. 2, 2013 (9 pages).
Non-Final Office Action received in U.S. Appl. No. 13/473,586 and dated Jun. 19, 2014 (7 pages).
Non-Final Office Action received in U.S. Appl. No. 13/473,571 and dated Aug. 31, 2012 (11 pages).
Final Office Action received in U.S. Appl. No. 13/473,571 and dated May 15, 2013 (16 pages).
Requirement for Restriction/Election received in U.S. Appl. No. 13/473,584 and dated Jun. 18, 2013 (15 pages).
Non-Final Office Action received in U.S. Appl. No. 13/473,584 and dated Oct. 24, 2013 (14 pages).
Final Office Action received in U.S. Appl. No. 13/473,584 and dated Aug. 20, 2014 (14 pages).
Non-Final Office Action received in U.S. Appl. No. 13/473,578 and dated Mar. 26, 2013 (11 pages).
Final Office Action received in U.S. Appl. No. 13/473,578 and dated Dec. 17, 2013 (7 pages).
Non-Final Office Action received in U.S. Appl. No. 14/479,129 and dated Apr. 14, 2015 (10 pages).
Requirement for Restriction/Election received in U.S. Appl. No. 14/187,939 and dated Jan. 23, 2015 (7 pages).
Requirement for Restriction/Election received in U.S. Appl. No. 14/188,582 and dated Jan. 29, 2015 (7 pages).
Non-Final Office Action received in U.S. Appl. No. 12/973,962 and dated Feb. 24, 2012 (13 pages).
Final Office Action received in U.S. Appl. No. 12/973,962 and dated Sep. 21, 2012 (15 pages).
Advisory Action received in U.S. Appl. No. 12/973,962 and dated Dec. 5, 2012 (3 pages).
Non-Final Office Action received in U.S. Appl. No. 12/973,962 and dated Jun. 19, 2014 (17 pages).
Requirement for Restriction/Election received in U.S. Appl. No. 13/995,810 and dated Dec. 22, 2014 (10 pages).
Final Office Action received in U.S. Appl. No. 12/973,962 and dated Apr. 20, 2015 (20 pages).
Non-Final Office Action received in U.S. Appl. No. 14/187,939 and dated Jun. 12, 2015 (35 pages).
Non-Final Office Action received in U.S. Appl. No. 14/188,582 and dated Jun. 12, 2015 (62 pages).
Non-Final Office Action received in U.S. Appl. No. 14/627,879 and dated Jul. 20, 2015 (6 pages).

GASTRIC RETENTIVE EXTENDED RELEASE PHARMACEUTICAL COMPOSITIONS

RELATED CASES

This application claims priority to U.S. application Ser. No. 14/132,500 filed on Dec. 18, 2013 which claims priority to U.S. application Ser. No. 13/473,571 filed on May 16, 2012 which claims priority to U.S. Provisional Application No. 61/487,047 filed on May 17, 2011, U.S. Provisional Application No. 61/537,533 filed on Sep. 21, 2011, and U.S. Provisional Application No. 61/606,896 filed on Mar. 5, 2012, which are incorporated herein by reference in their entirety to the full extent permitted by law.

FIELD OF THE INVENTION

The present disclosure relates to gastric retentive extended release pharmaceutical compositions comprising an opioid and an additional active pharmaceutical ingredient wherein the compositions may be administered under fed or fasted conditions.

BACKGROUND OF THE INVENTION

Oral drug administration remains the route of choice for the majority of clinical applications. Extended release (ER) dosage forms that are administered once or twice daily offer advantages over their immediate release (IR) counterparts because they reduce the magnitude of peaks and troughs of drug plasma concentration, provide longer dosing intervals, sustained analgesic effect, and increased patient compliance. For certain types of patients, such as those suffering from pain, these ER products can allow the patient to sleep through the night without having to wake up during the night to take the next dose. Thus, ER dosage forms can significantly increase the quality of life for such patients. Both IR and ER products for pain are widely available on the market. There are, however, no opioid/acetaminophen combination ER products available on the market.

Gastroretentive (GR) dosage formulations have demonstrated successful delivery of drugs for extended durations of action. One way to improve drug absorption is to hold a drug delivery system above the preferred absorption site or window (proximal small intestine), and maintain the drug release at an appropriate rate. For example, one strategy is to retain the formulation in the stomach (gastroretention). Over the last few decades, several gastroretentive drug delivery approaches have been designed and developed, including: high density (sinking) systems, which are retained in the bottom of the stomach, low density systems that float in gastric fluid due to buoyancy, mucoadhesive systems that release drugs following bio-adhesion to the gastric mucosa, superporous hydrogel systems, magnetic systems, and extendible or swellable systems that expand in the presence of water (gastric fluid) and fail to pass through the pyloric sphincter of stomach.

Parameters controlling the gastric retention of oral dosage forms include: density, size and shape of the dosage form, food intake and its nature (particularly fat content), total caloric content and frequency of intake, posture, gender, age, sex, sleep, body mass index, physical activity, disease states of the individual (e.g., diabetes), and administration of drugs with impact on gastrointestinal transit time, for example, drugs acting as anticholinergic agents (e.g., atropine, propantheline), opiates (e.g., codeine) and prokinetic agents (e.g., metoclopramide, cisapride).

Food intake (i.e., viscosity of food, food volume, caloric value, and frequency of feeding) may have a profound effect on the gastric retention of dosage forms. The presence or absence of food in the gastrointestinal tract (GIT) influences the gastric retention time (GRT) of the dosage form. Usually the presence of food in the gastrointestinal tract (GIT) improves the GRT of the dosage form and, thus, absorption increases because the drug stays at the preferred absorption site for a longer period of time. Indeed, GR formulations of the prior art should be administered with food in order to achieve the desired bioavailability.

There is a need, therefore, for extended release GR compositions comprising an opioid and a second active agent, wherein the release of the opioid is optimized to take advantage of the gastrointestinal effects of the opioid. The bioavailability of such composition is independent of food intake, thereby increasing the flexibility and ease of the administration of the composition.

SUMMARY OF THE INVENTION

Among the various aspects of the present disclosure is an extended release pharmaceutical composition comprising at least one extended release portion comprising an opioid, an additional active pharmaceutical ingredient, or a combination thereof, and at least one extended release component. At least one extended release portion comprises from about 60% to about 80% of the total amount of the opioid in the composition, and the composition has gastric retentive properties that are achieved by a combination of a physical property of the composition and release of the opioid. Moreover, when the composition is orally administered to a subject, the opioid or the additional active pharmaceutical ingredient produces a plasma profile characterized by at least one pharmacokinetic parameter that differs by less than about 30% when the subject is in a fasted state as compared to a fed state.

A further aspect of the disclosure encompasses an extended release pharmaceutical composition comprising (a) at least one immediate release portion comprising an opioid, an additional active pharmaceutical ingredient, or a combination thereof, and (b) at least one extended release portion comprising an extended release component and an opioid, an additional active pharmaceutical ingredient, or a combination thereof. At least one immediate release portion comprises from about 20% to about 40% of the total amount of the opioid in the composition, and the composition has gastric retentive properties that are achieved by a combination of a physical property of the composition and release of the opioid. Additionally, when the composition is orally administered to a subject, the opioid or the additional active pharmaceutical ingredient in the composition produce a plasma profile characterized by at least one pharmacokinetic parameter that differs by less than about 30% when the subject is in a fasted state as compared to a fed state.

Still another aspect of the disclosure provides a method for administering a gastric retentive pharmaceutical composition comprising an opioid to a subject in need thereof. The method comprises orally administering an effective amount of the gastric retentive composition to the subject, the subject being in a fasted state, wherein the opioid in the composition produces a plasma profile characterized by at least one pharmacokinetic parameter that differs by less than about 30% when the subject is in a fasted state as compared to a fed state.

Yet another aspect of the disclosure encompasses a method for treating pain in a subject in need thereof. The method comprises orally administering an effective amount of a gastric retentive pharmaceutical composition comprising an opioid to the subject in a fasted state, wherein the opioid in the composition produces a plasma profile characterized by at least one pharmacokinetic parameter that differs by less than about 30% when the subject is in a fasted state as compared to a fed state.

Another aspect of the present disclosure is an extended release pharmaceutical composition comprising at least one extended release portion comprising oxycodone, acetaminophen, or a combination thereof, and at least one extended release component. At least one extended release portion comprises from about 60% to about 80% of the total amount of the oxycodone in the composition, and the composition has gastric retentive properties that are achieved by a combination of a physical property of the composition and release of the oxycodone. Moreover, when the composition is orally administered to a subject, the oxycodone or the acetaminophen produces a plasma profile characterized by at least one pharmacokinetic parameter that differs by less than about 30% when the subject is in a fasted state as compared to a fed state.

A further aspect of the disclosure encompasses an extended release pharmaceutical composition comprising (a) at least one immediate release portion comprising oxycodone, acetaminophen, or a combination thereof, and (b) at least one extended release portion comprising an extended release component and oxycodone, acetaminophen, or a combination thereof. At least one immediate release portion comprises from about 20% to about 40% of the total amount of the oxycodone in the composition, and the composition has gastric retentive properties that are achieved by a combination of a physical property of the composition and release of the oxycodone. Additionally, when the composition is orally administered to a subject, the oxycodone or the acetaminophen in the composition produce a plasma profile characterized by at least one pharmacokinetic parameter that differs by less than about 30% when the subject is in a fasted state as compared to a fed state.

Still another aspect of the disclosure provides a method for administering a gastric retentive pharmaceutical composition comprising oxycodone to a subject in need thereof. The method comprises orally administering an effective amount of the gastric retentive composition to the subject, the subject being in a fasted state, wherein the oxycodone in the composition produces a plasma profile characterized by at least one pharmacokinetic parameter that differs by less than about 30% when the subject is in a fasted state as compared to a fed state.

Yet another aspect of the disclosure encompasses a method for treating pain in a subject in need thereof. The method comprises orally administering an effective amount of a gastric retentive pharmaceutical composition comprising oxycodone to the subject in a fasted state, wherein the oxycodone in the composition produces a plasma profile characterized by at least one pharmacokinetic parameter that differs by less than about 30% when the subject is in a fasted state as compared to a fed state.

Other features and aspects of the disclosure are described in detail below.

BRIEF DESCRIPTION OF THE DRAWINGS & REFERENCE TO COLOR FIGURES

This application file contains at least one drawing executed in color. Copies of this patent application publication with color drawings will be provided by the Office upon request and payment of the necessary fee.

FIG. 1 presents the in vitro release profile of oxycodone from oxycodone-acetaminophen bilayer tablets comprising either 15 or 30 mg of oxycodone, 500 mg of acetaminophen (APAP), and either 35% (w/w) POLYOX® 1105, 45% (w/w) POLYOX® 1105, or 45% (w/w) POLYOX® N60K, as indicated.

Figure 2:
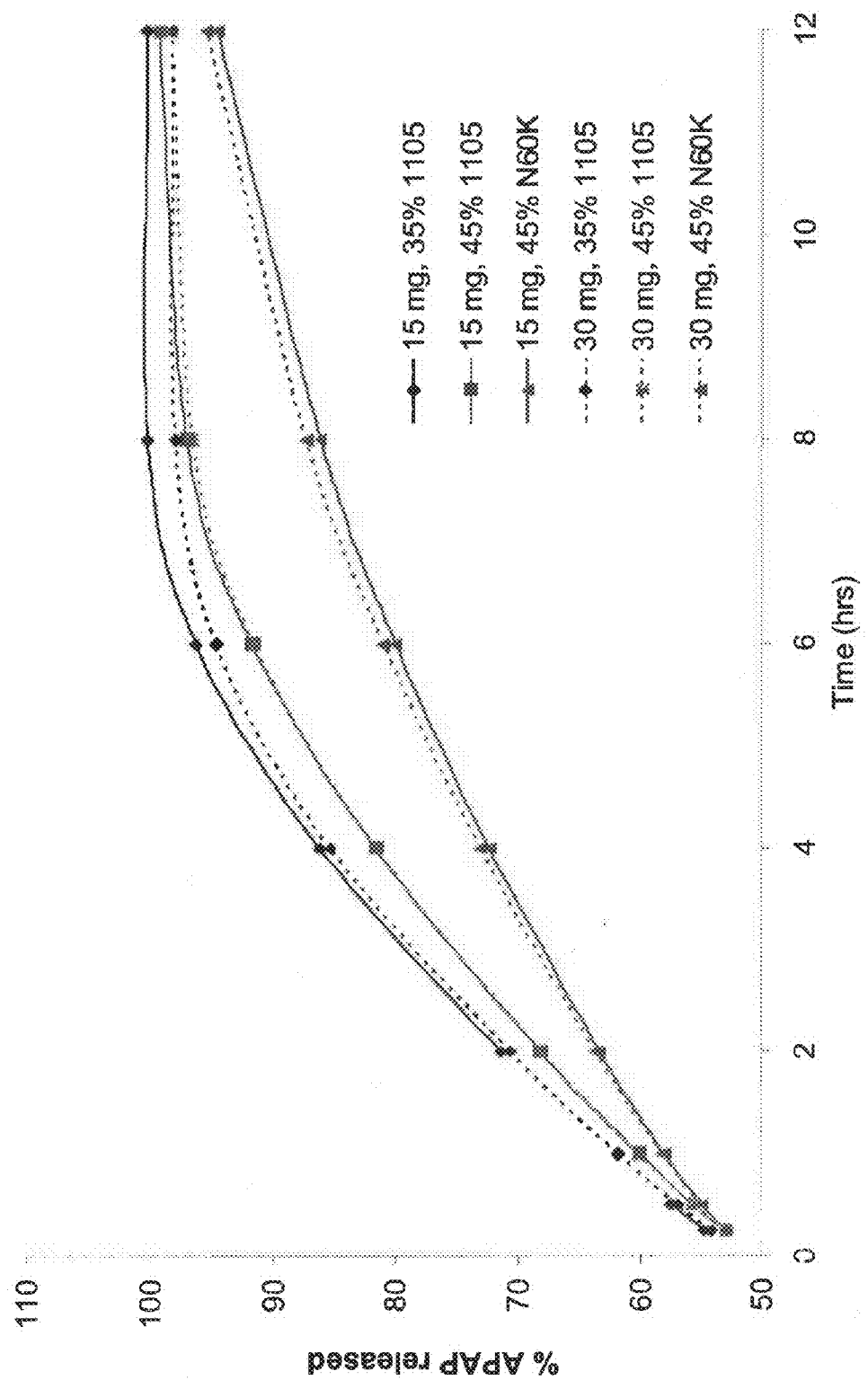

FIG. 2 shows the in vitro release profile of acetaminophen from oxycodone-acetaminophen bilayer tablets comprising either 15 or 30 mg of oxycodone, 500 mg of acetaminophen (APAP), and either 35% (w/w) POLYOX® 1105, 45% (w/w) POLYOX® 1105, or 45% (w/w) POLYOX® N60K, as indicated.

Figure 3:
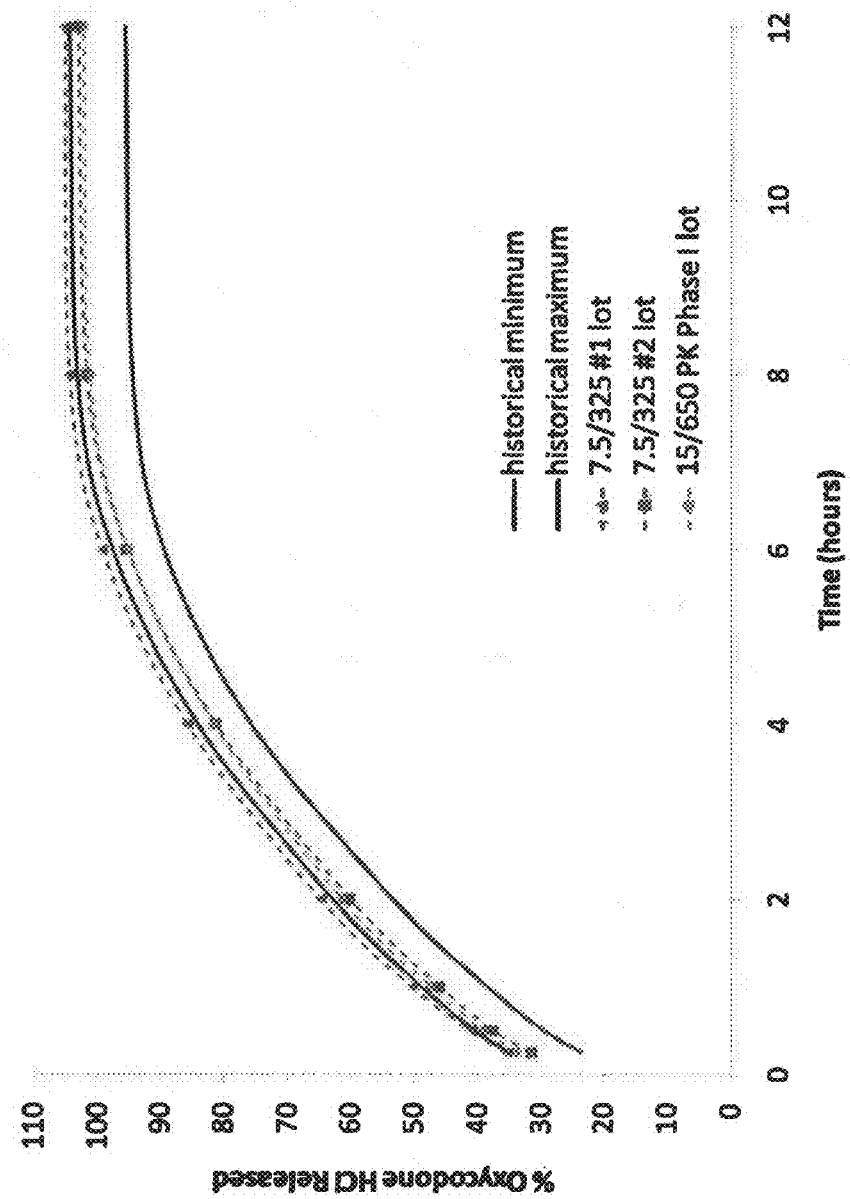

FIG. 3 presents the in vitro release profile of oxycodone from bilayer tablets comprising 7.5 mg of oxycodone and 325 mg of acetaminophen, and bilayer tablets comprising 15 mg of oxycodone and 650 mg of acetaminophen, as indicated.

Figure 4:
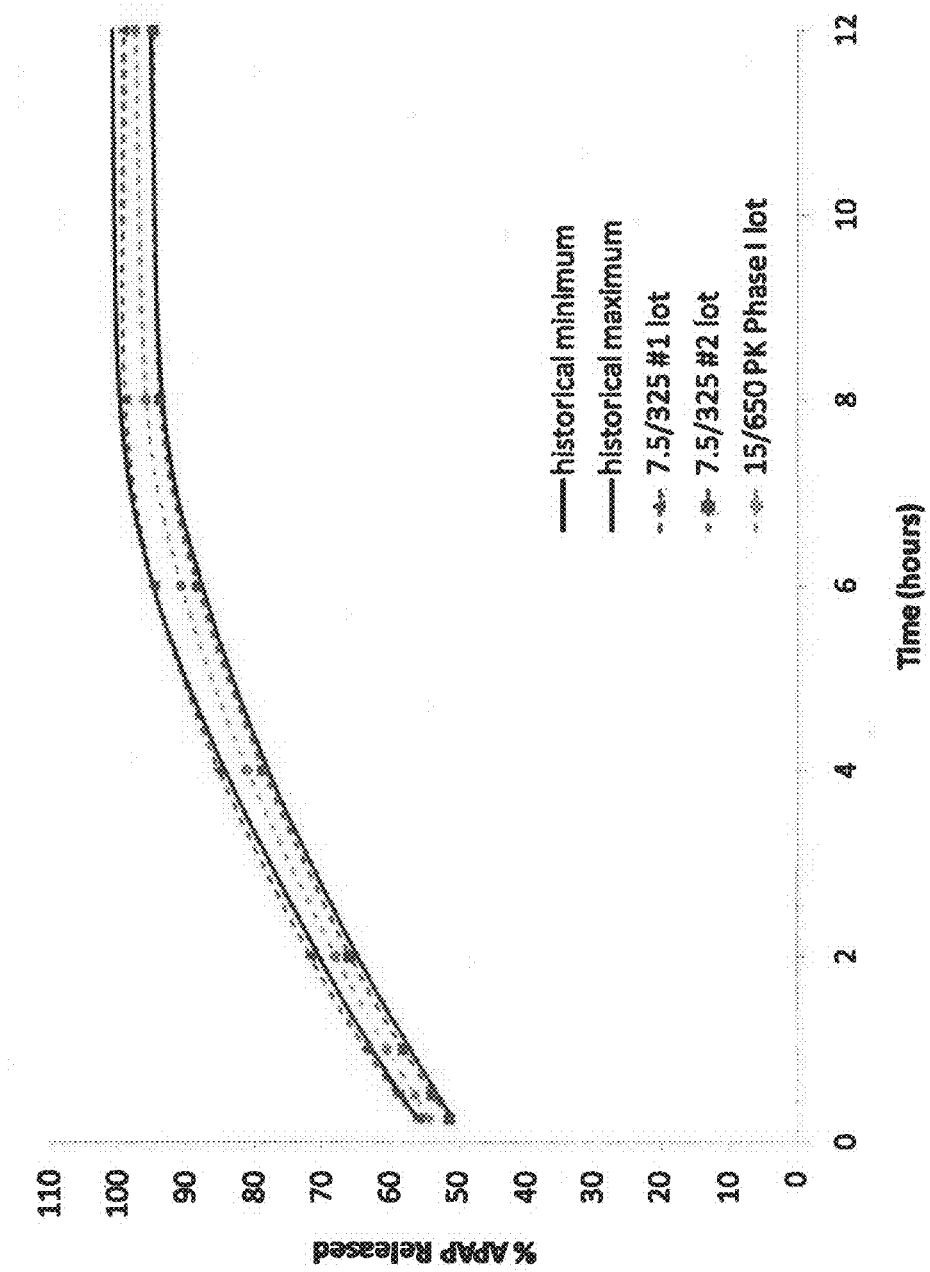

FIG. 4 presents the in vitro release profile of acetaminophen from bilayer tablets comprising 7.5 mg of oxycodone and 325 mg of acetaminophen, and bilayer tablets comprising 15 mg of oxycodone and 650 mg of acetaminophen, as indicated.

Figure 5:
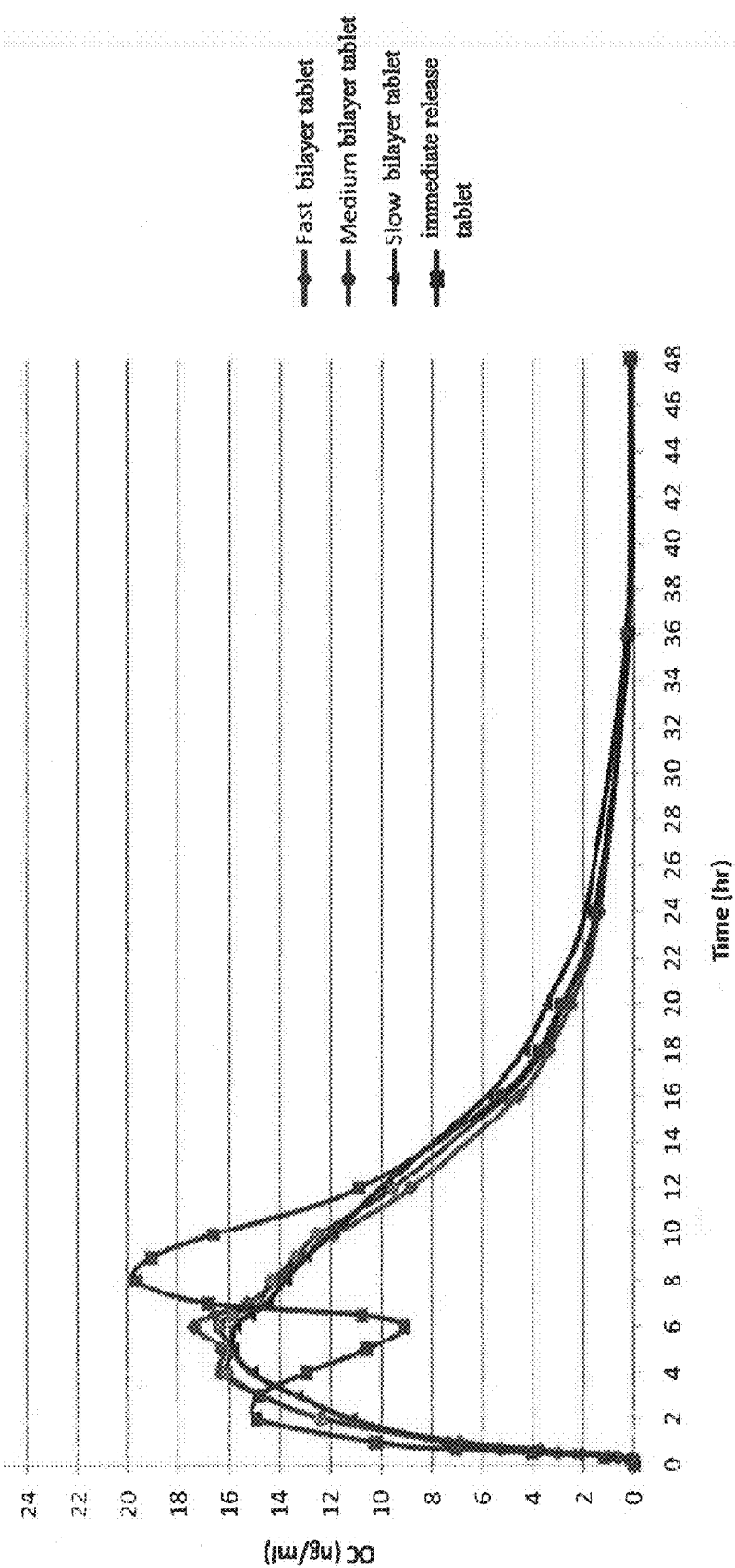

FIG. 5 is a graphical representation of the mean plasma oxycodone concentrations as a function of time after administration of a single dose of bilayer tablet comprising 15 mg oxycodone/500 mg acetaminophen and having fast, medium, or slow release properties as compared to an immediate release 7.5 oxycodone/325 acetaminophen tablet administered twice at a 6 hr interval.

Figure 6:
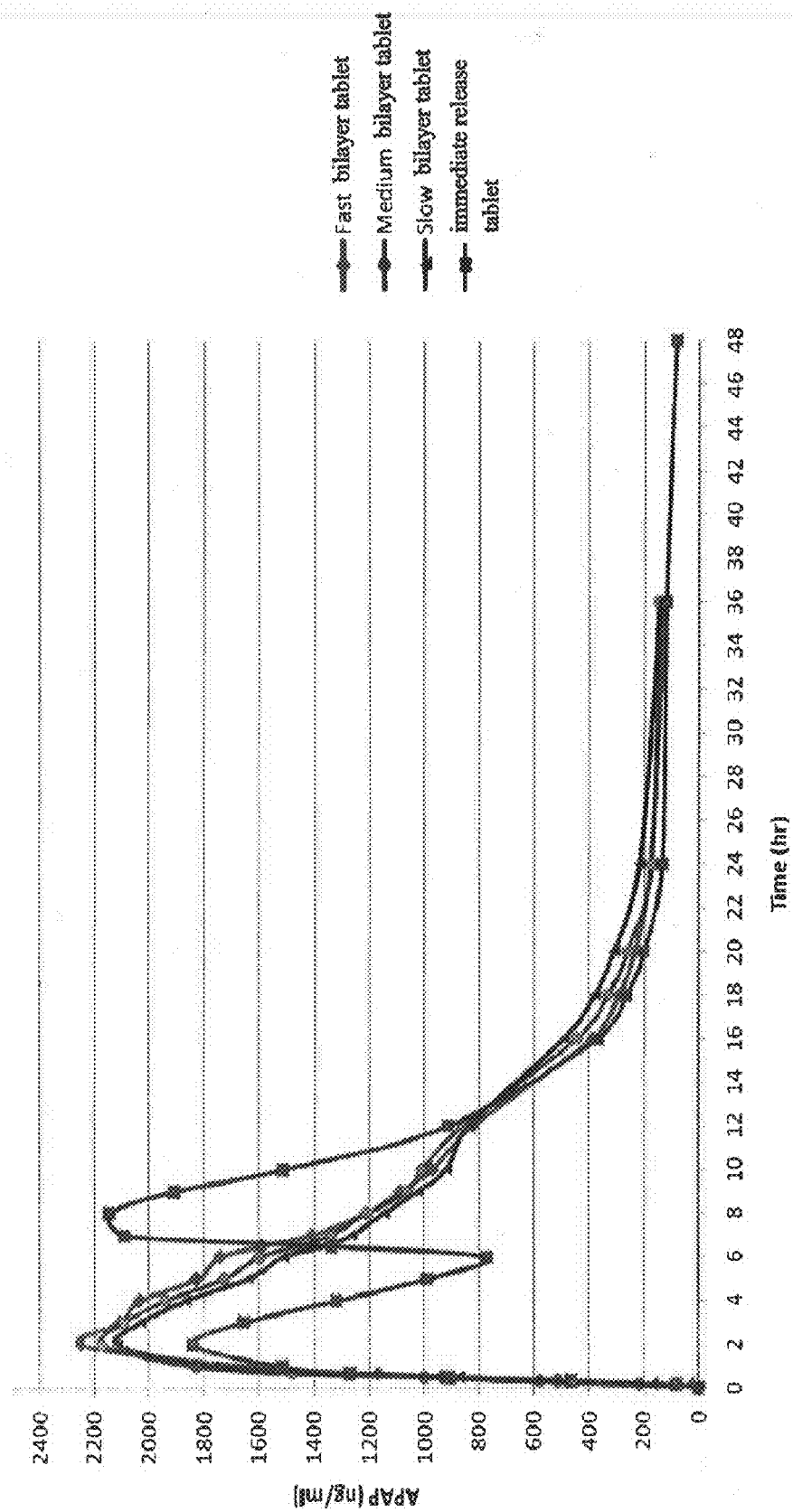

FIG. 6 is a graphical representation of the mean plasma acetaminophen concentrations as a function of time after administration of a single dose of bilayer tablet comprising 15 mg oxycodone/500 mg acetaminophen and having fast, medium, or slow release properties as compared to an immediate release 7.5 oxycodone/325 acetaminophen tablet administered twice at a 6 hr interval. The immediate release 7.5 oxycodone/325 acetaminophen tablet dose was normalized.

Figure 7:
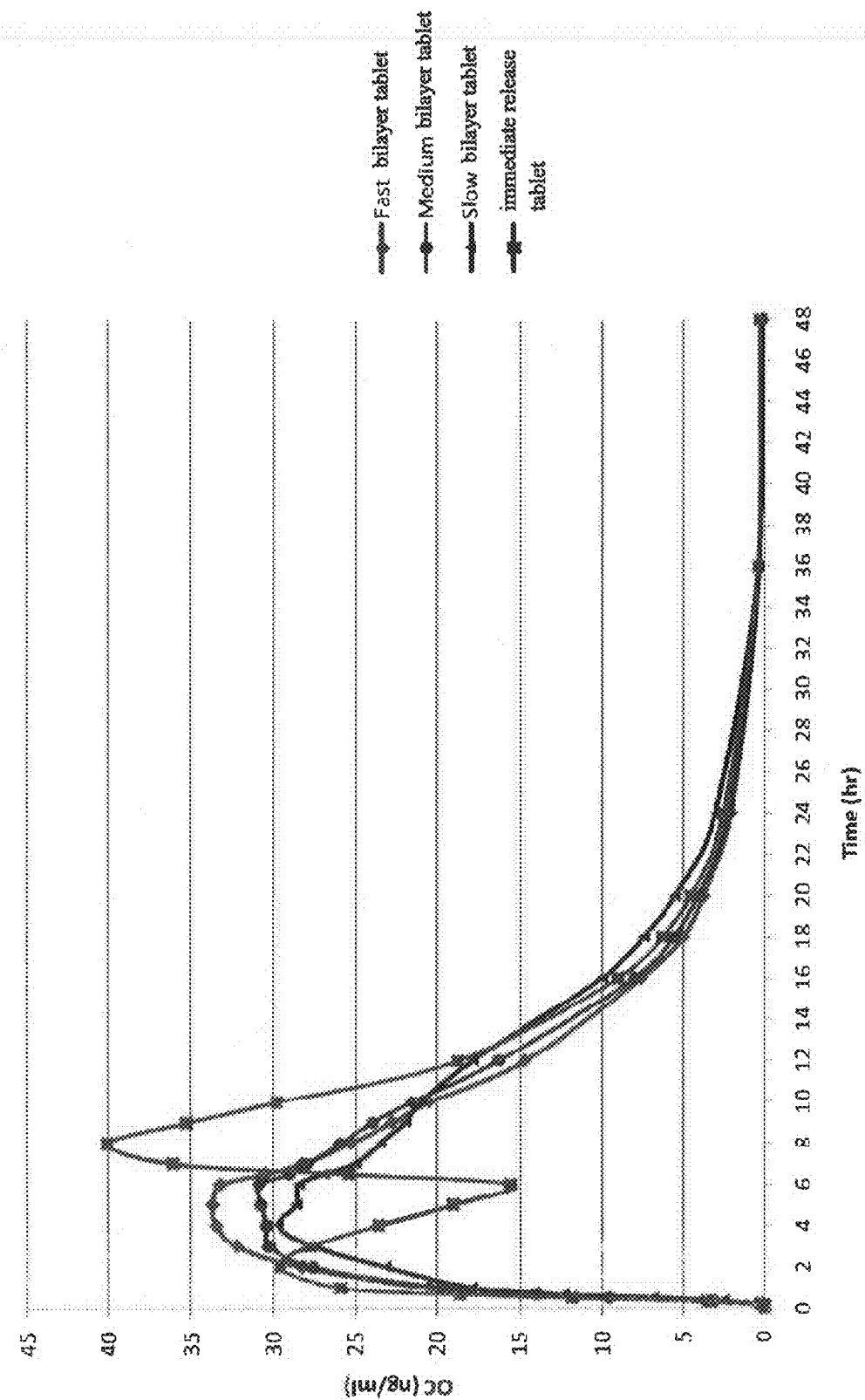

FIG. 7 is a graphical representation of the mean plasma oxycodone concentrations as a function of time after administration of a single dose of bilayer tablet comprising 30 mg oxycodone/500 mg acetaminophen and having fast, medium, or slow release properties as compared to an immediate release 7.5 oxycodone/325 acetaminophen tablet administered twice at a 6 hr interval. The immediate release 7.5 oxycodone/325 acetaminophen tablet dose was normalized.

Figure 8:
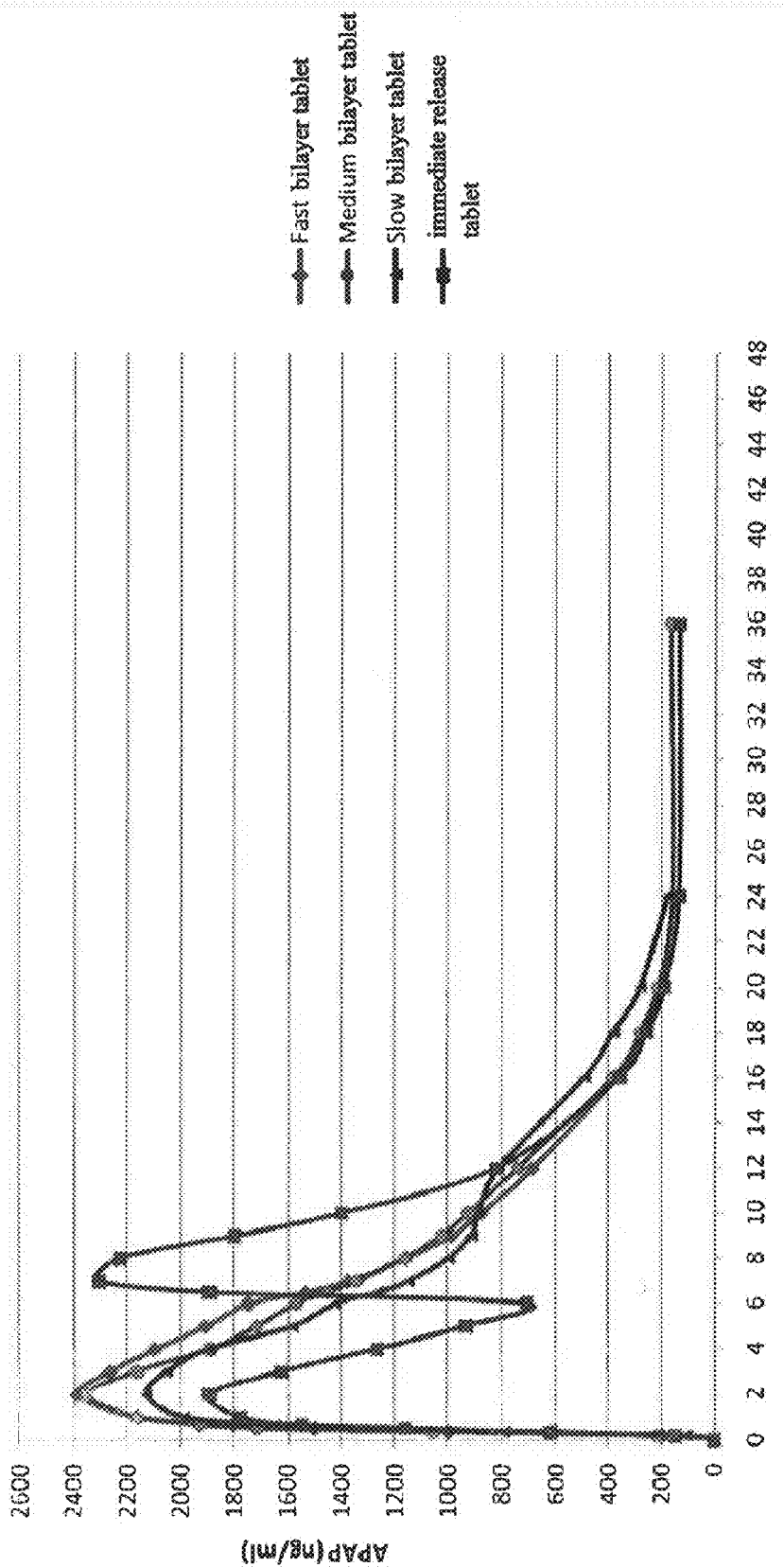

FIG. 8 is a graphical representation of the mean plasma acetaminophen concentrations as a function of time after administration of a single dose of bilayer tablet comprising 30 mg oxycodone/500 mg acetaminophen and having fast, medium, or slow release properties as compared to an immediate release 7.5 oxycodone/325 acetaminophen tablet administered twice at a 6 hr interval. The immediate release 7.5 oxycodone/325 acetaminophen tablet dose was normalized.

Figure 9:
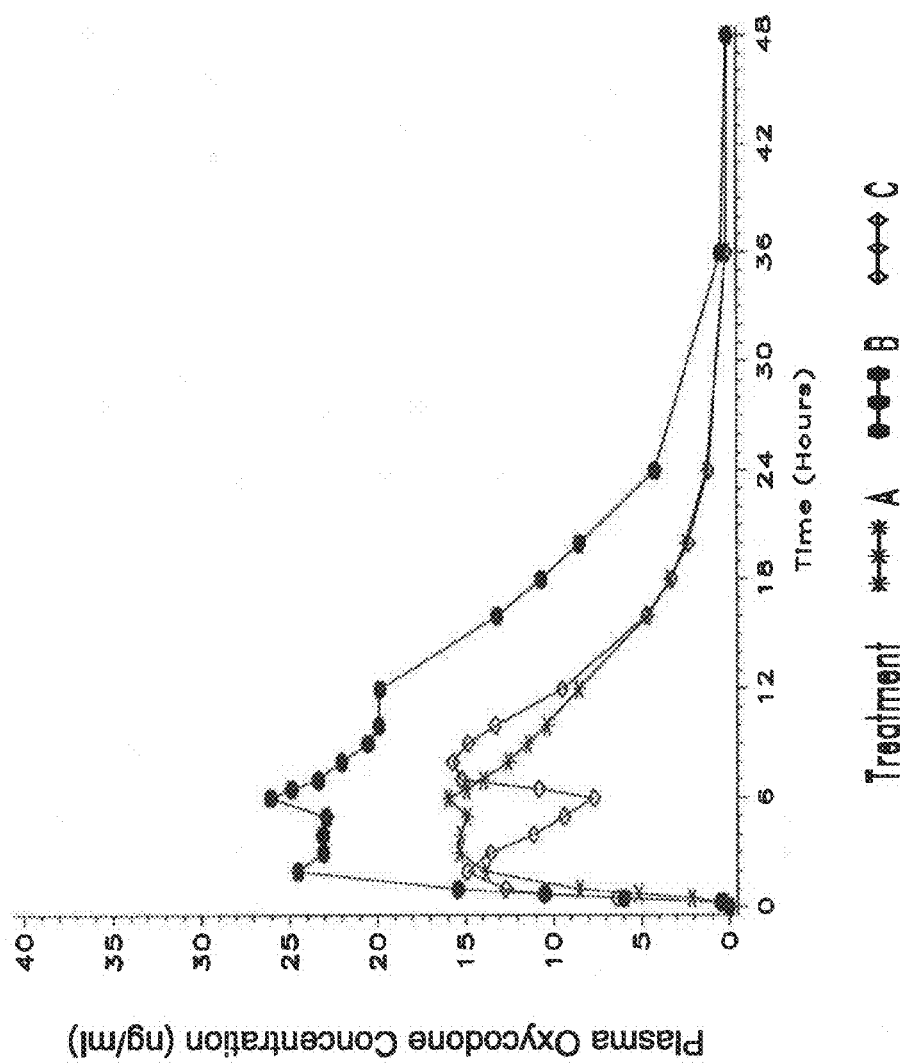

FIG. 9 shows the mean plasma concentrations of oxycodone versus time by treatment. Treatment A was one tablet of 15 mg oxycodone/650 mg acetaminophen administered orally under fed conditions. Treatment B was two tablets of 15 mg oxycodone/650 mg acetaminophen administered orally one at a time under fed conditions. Treatment C was one tablet of an immediate release 7.5 oxycodone/325 acetaminophen tablet administered orally every 6 hours for 2 doses under fed conditions.

Figure 10:
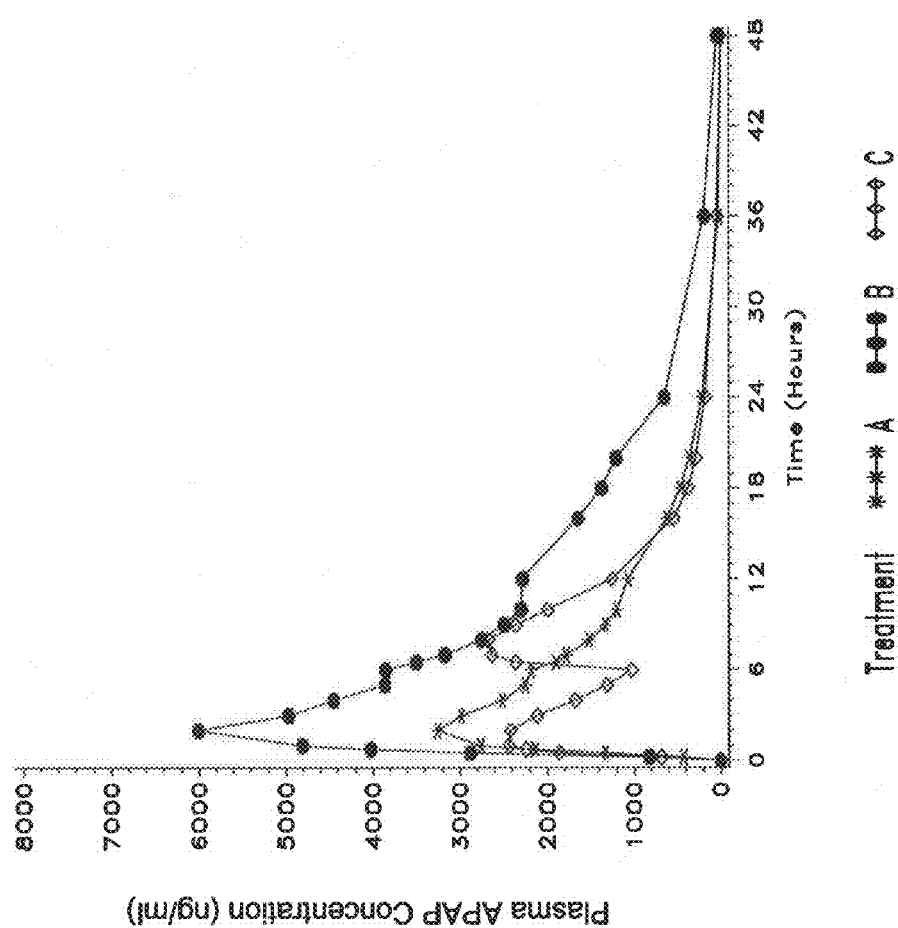

FIG. 10 presents the mean plasma concentrations of acetaminophen versus time by treatment. Treatment A was one tablet of 15 mg oxycodone/650 mg acetaminophen administered orally under fed conditions. Treatment B was two tablets of 15 mg oxycodone/650 mg acetaminophen administered orally one at a time under fed conditions. Treatment C was one tablet of an immediate release 7.5 oxycodone/325 acetaminophen tablet administered orally every 6 hours for 2 doses under fed conditions.

Figure 11:
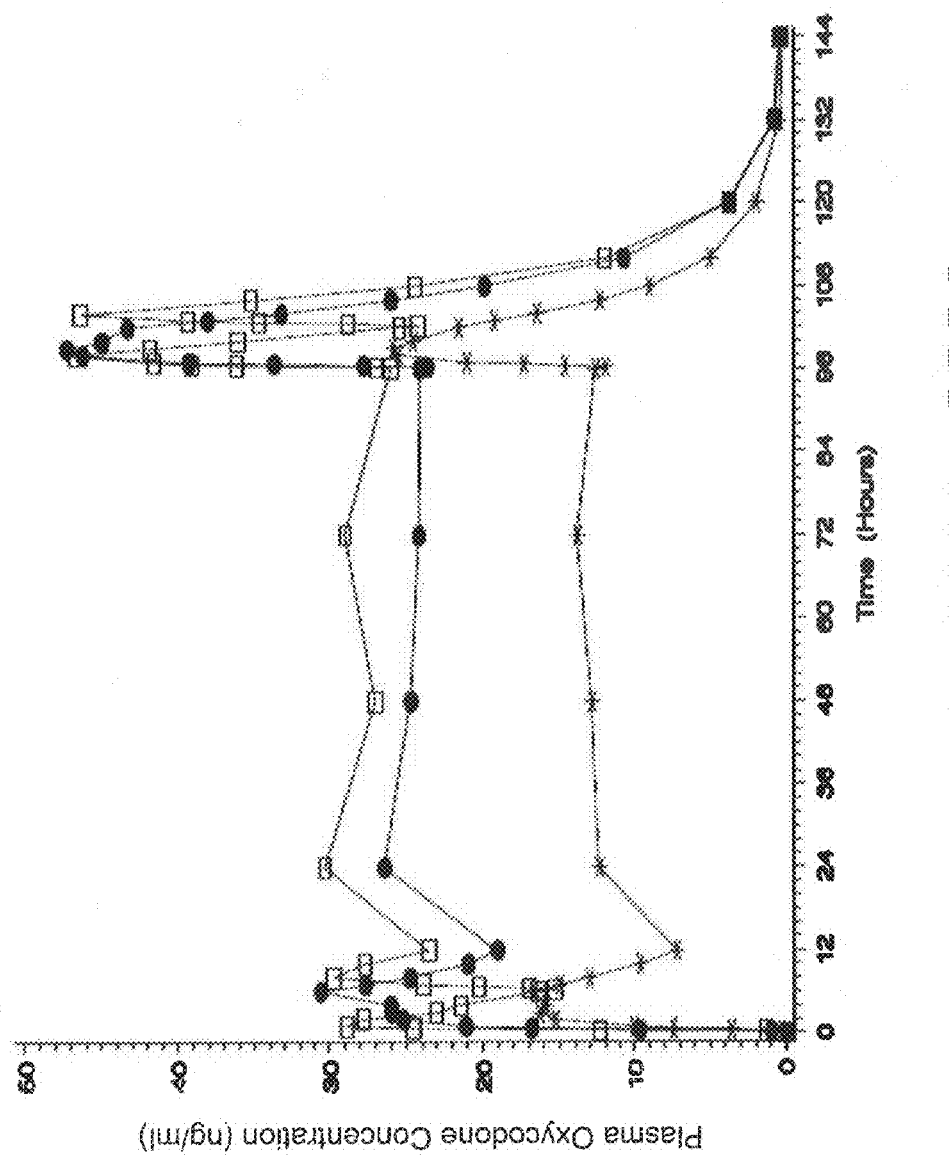

FIG. 11 shows the mean plasma concentrations of oxycodone versus time by treatment. Treatment A was one tablet of 15 mg oxycodone/650 mg acetaminophen administered orally every 12 hours for 4.5 days (9 doses) under fed conditions. Treatment B was two tablets of 15 mg oxycodone/650 mg acetaminophen administered orally one at a time every 12 hours for 4.5 days (9 doses) under fed conditions. Treatment C was two tablets of an immediate release 7.5 oxycodone/325 acetaminophen tablet administered orally every 6 hours for 4.5 days (18 doses) under fed conditions.

Figure 12:
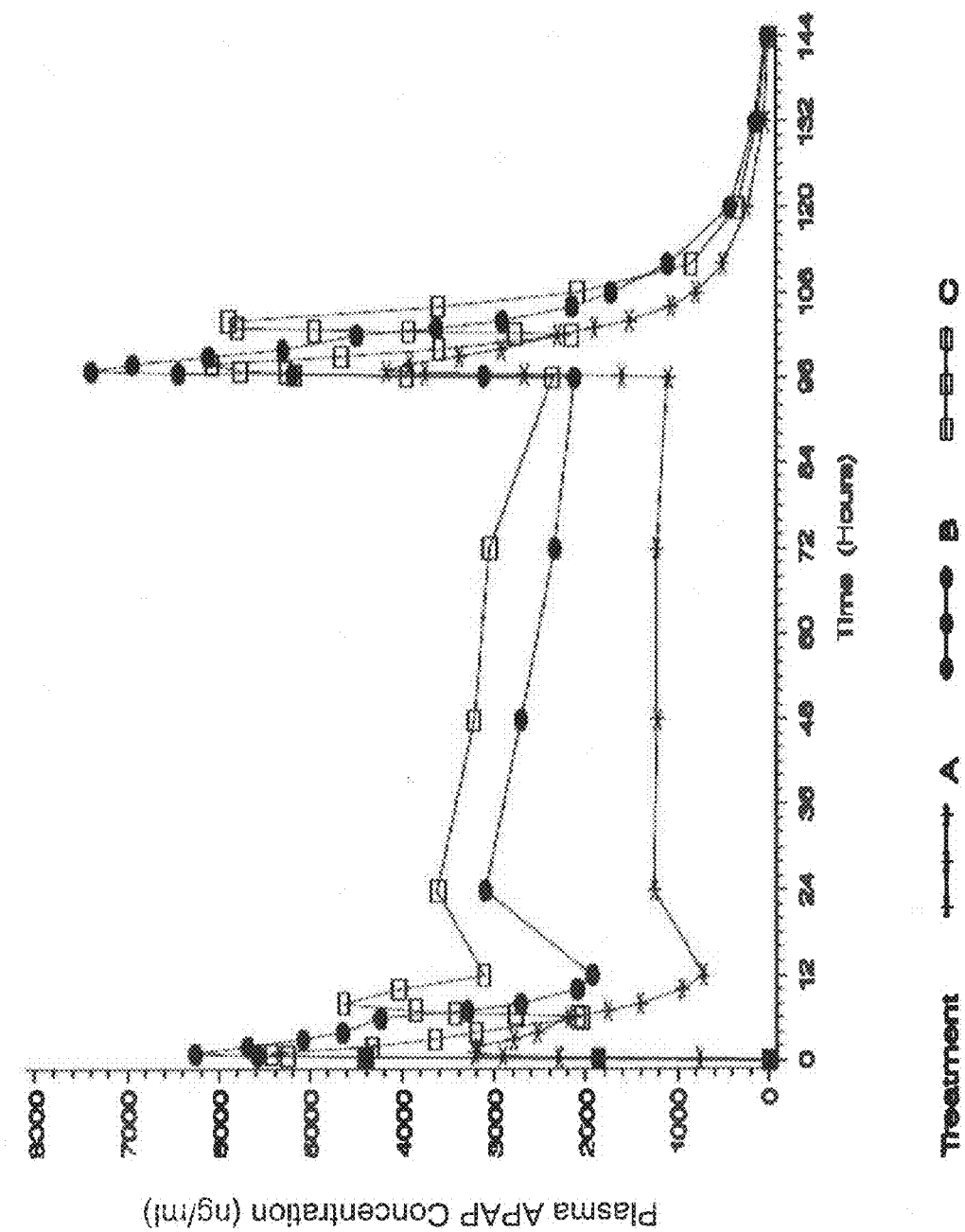

FIG. 12 shows the mean plasma concentrations of acetaminophen versus time by treatment. Treatment A was one tablet of 15 mg oxycodone/650 mg acetaminophen administered orally every 12 hours for 4.5 days (9 doses) under fed conditions. Treatment B was two tablets of 15 mg oxycodone/650 mg acetaminophen administered orally one at a time every 12 hours for 4.5 days (9 doses) under fed conditions. Treatment C was two tablets of an immediate release 7.5 oxycodone/325 acetaminophen tablet administered orally every 6 hours for 4.5 days (18 doses) under fed conditions.

Figure 13:
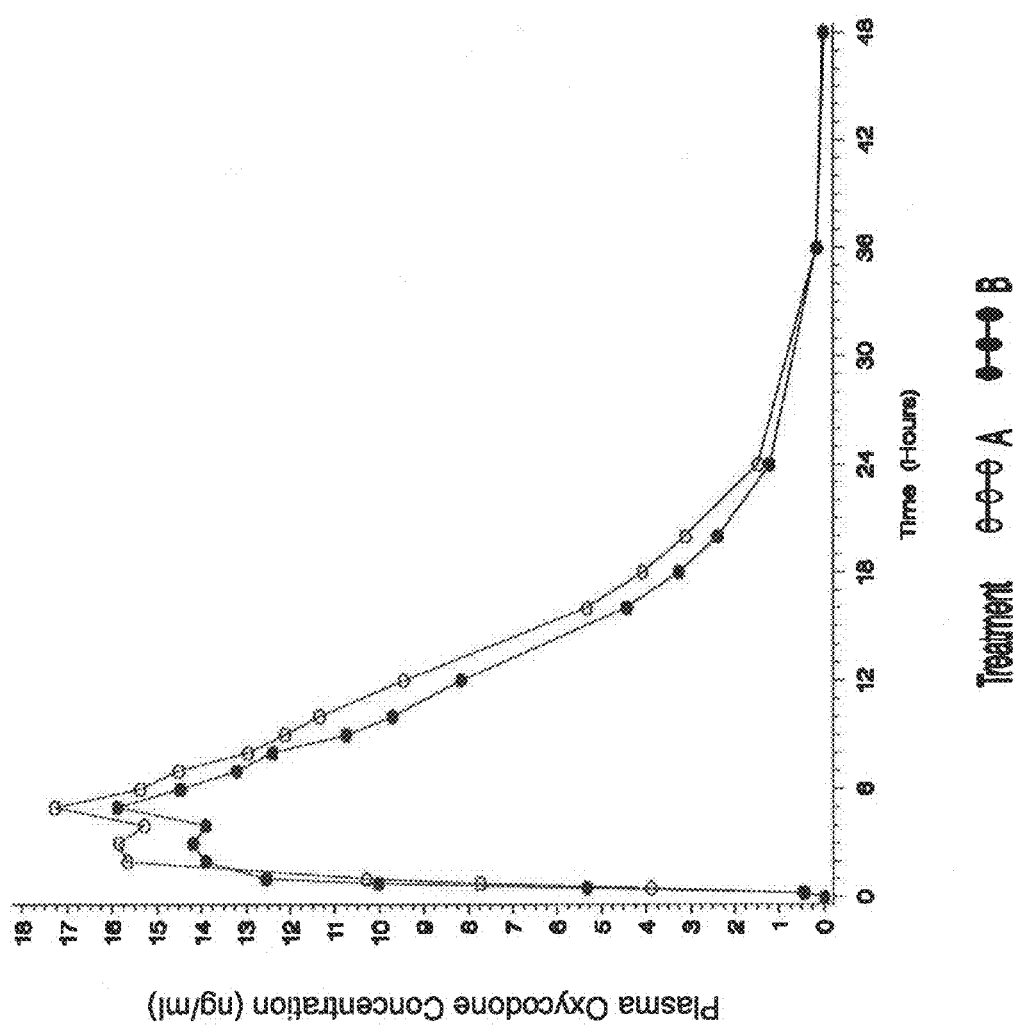

FIG. 13 presents the mean plasma concentrations of oxycodone versus time by treatment following oral administration of one tablet of 15 mg oxycodone/650 mg acetaminophen. Treatment A was under fed conditions. Treatment B was under fasted conditions.

Figure 14:
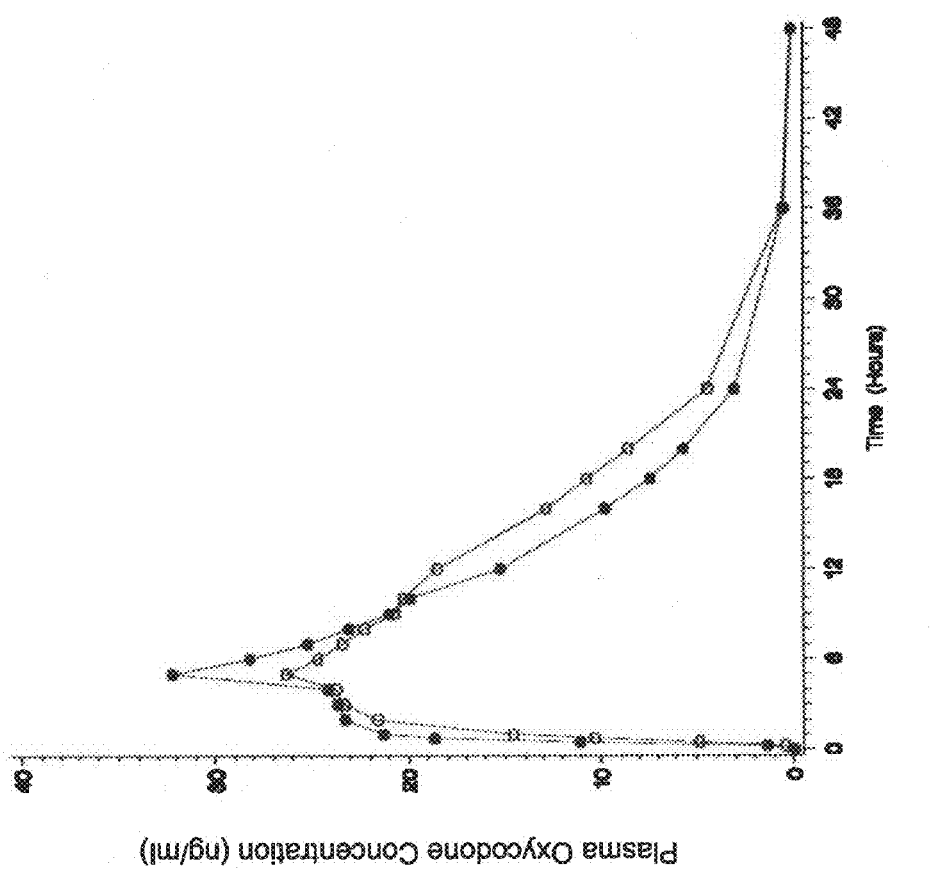

FIG. 14 shows the mean plasma concentrations of oxycodone versus time by treatment following oral administration of two tablets of 15 mg oxycodone/650 mg acetaminophen. Treatment A was under fed conditions. Treatment B was under fasted conditions.

Figure 15:
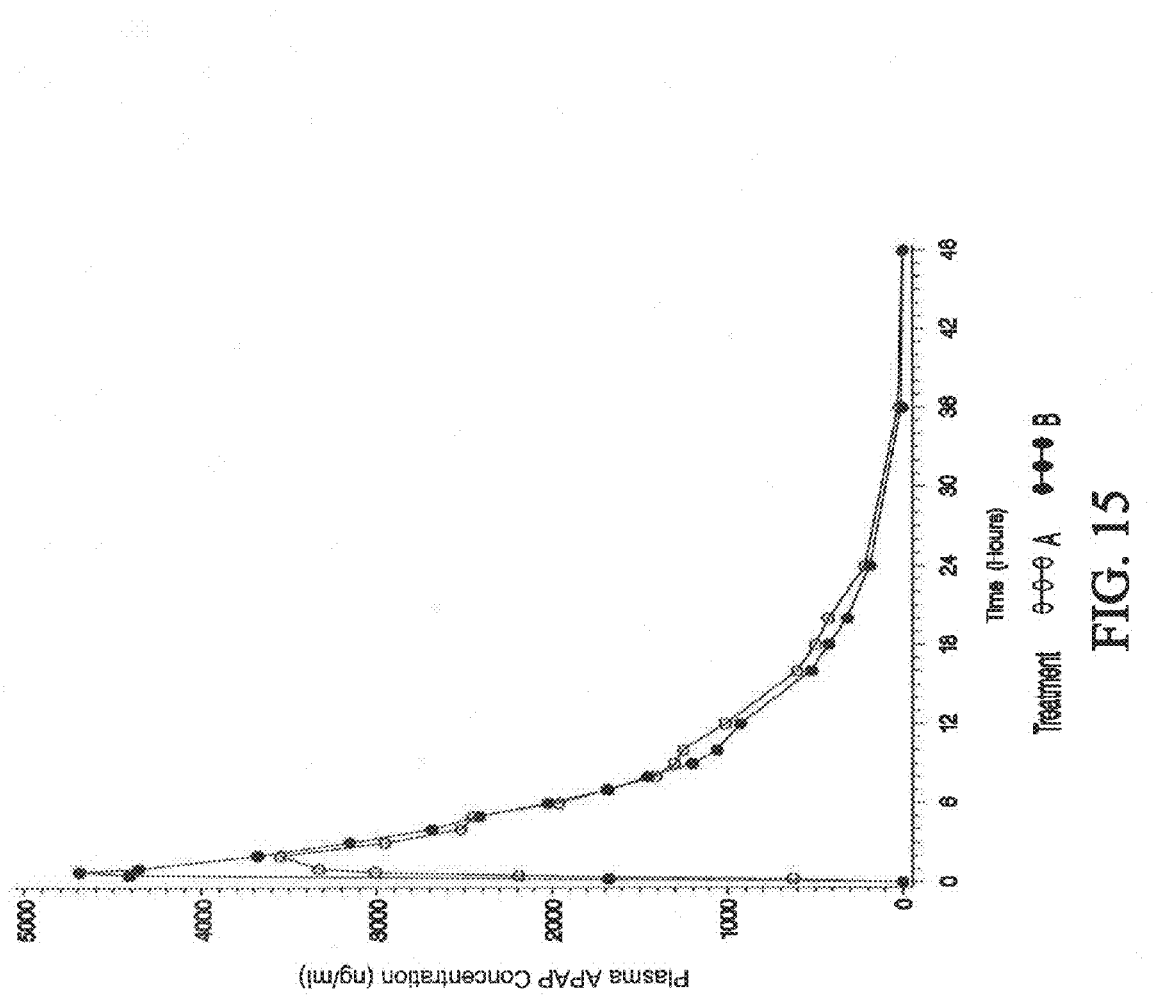

FIG. 15 presents the mean plasma concentrations of acetaminophen versus time by treatment following oral administration of one tablet of 15 mg oxycodone/650 mg acetaminophen. Treatment A was under fed conditions. Treatment B was under fasted conditions.

Figure 16:
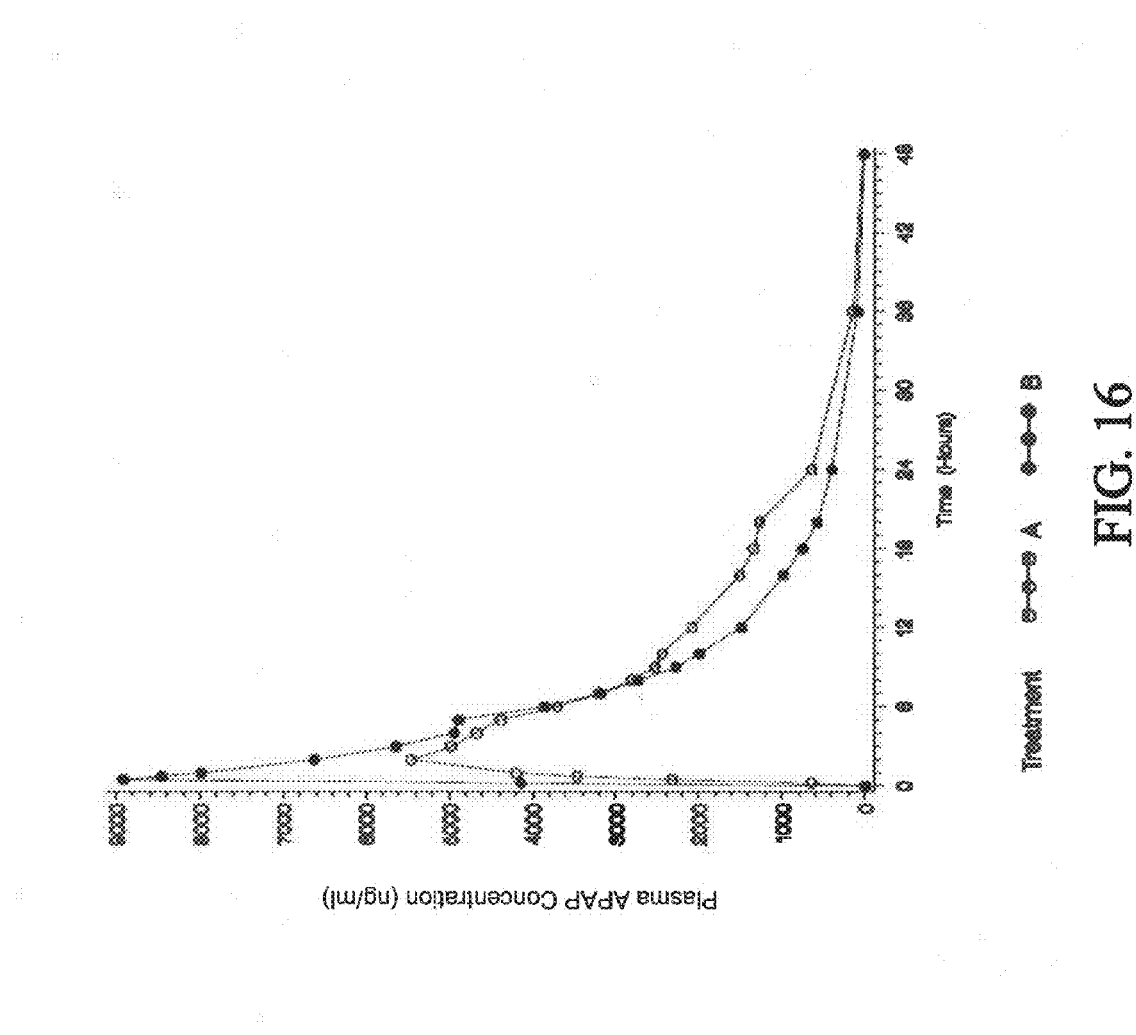

FIG. 16 shows mean plasma concentrations of acetaminophen versus time by treatment following oral administration of two tablets of 15 mg oxycodone/650 mg acetaminophen. Treatment A was under fed conditions. Treatment B was under fasted conditions.

Figure 17:
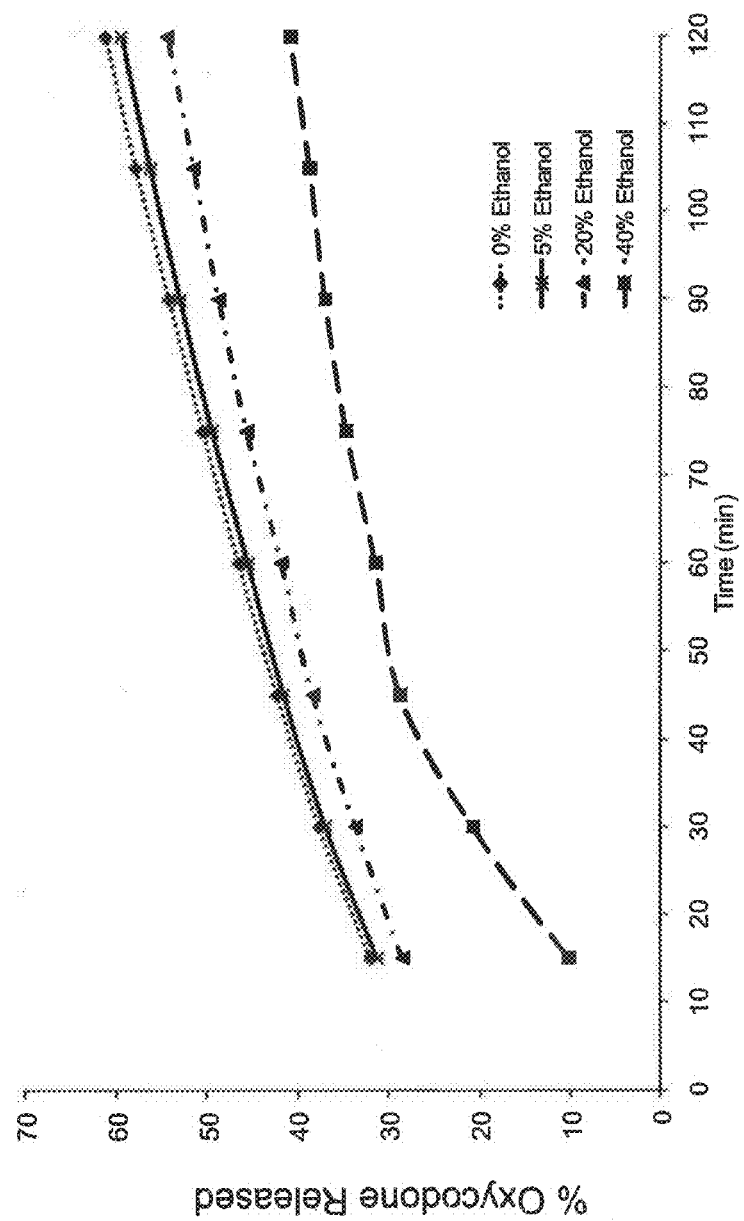

FIG. 17 illustrates the in vitro release of oxycodone from a bilayer tablet comprising 7.5 mg of oxycodone/325 mg of acetaminophen tested in 0.1 N HCl containing 0%, 5%, 20%, or 40% ethanol. Plotted is the percent of oxycodone released over a period of 2 hours.

Figure 18:
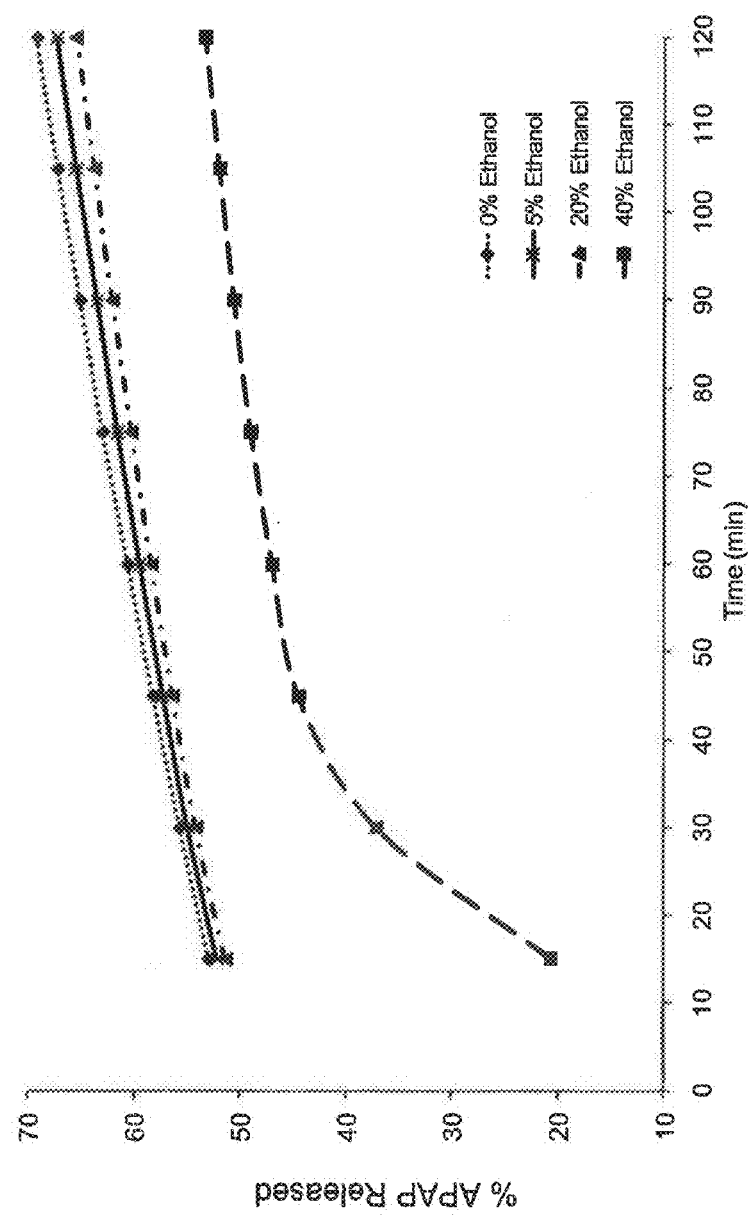

FIG. 18 presents the in vitro release of acetaminophen from a bilayer tablet comprising 7.5 mg of oxycodone/325 mg of acetaminophen tested in 0.1 N HCl containing 0%, 5%, 20%, or 40% ethanol. Plotted is the percent of acetaminophen released over a 2 hour period.

Figure 19:
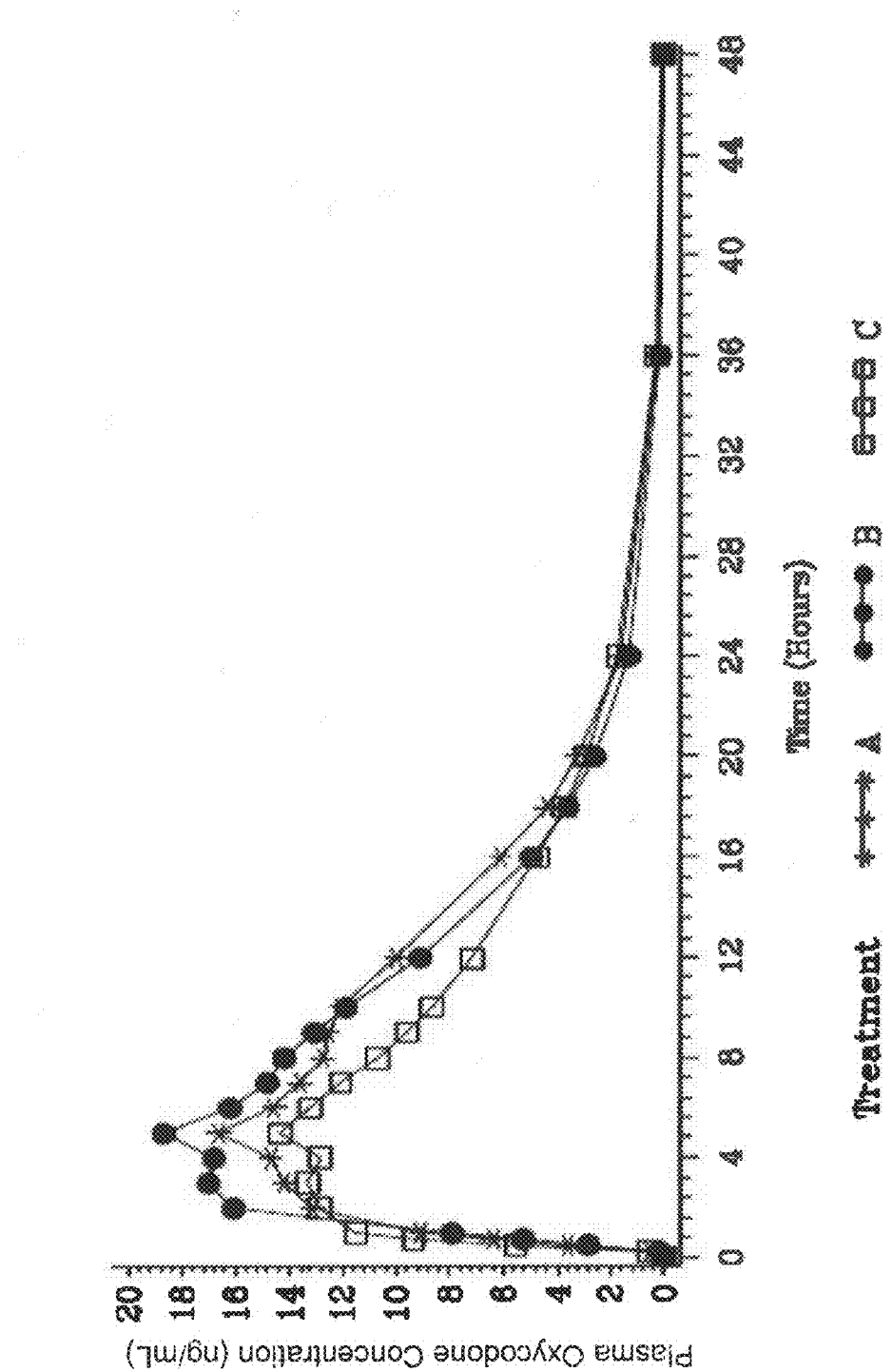

FIG. 19 shows the mean plasma concentrations of oxycodone as a function of time by treatment following oral administration of two tablets of 7.5 mg of oxycodone/325 mg of acetaminophen. Treatment A was under fed (high fat) conditions. Treatment B was under fed (low fat) conditions. Treatment C was under fasted conditions.

Figure 20:
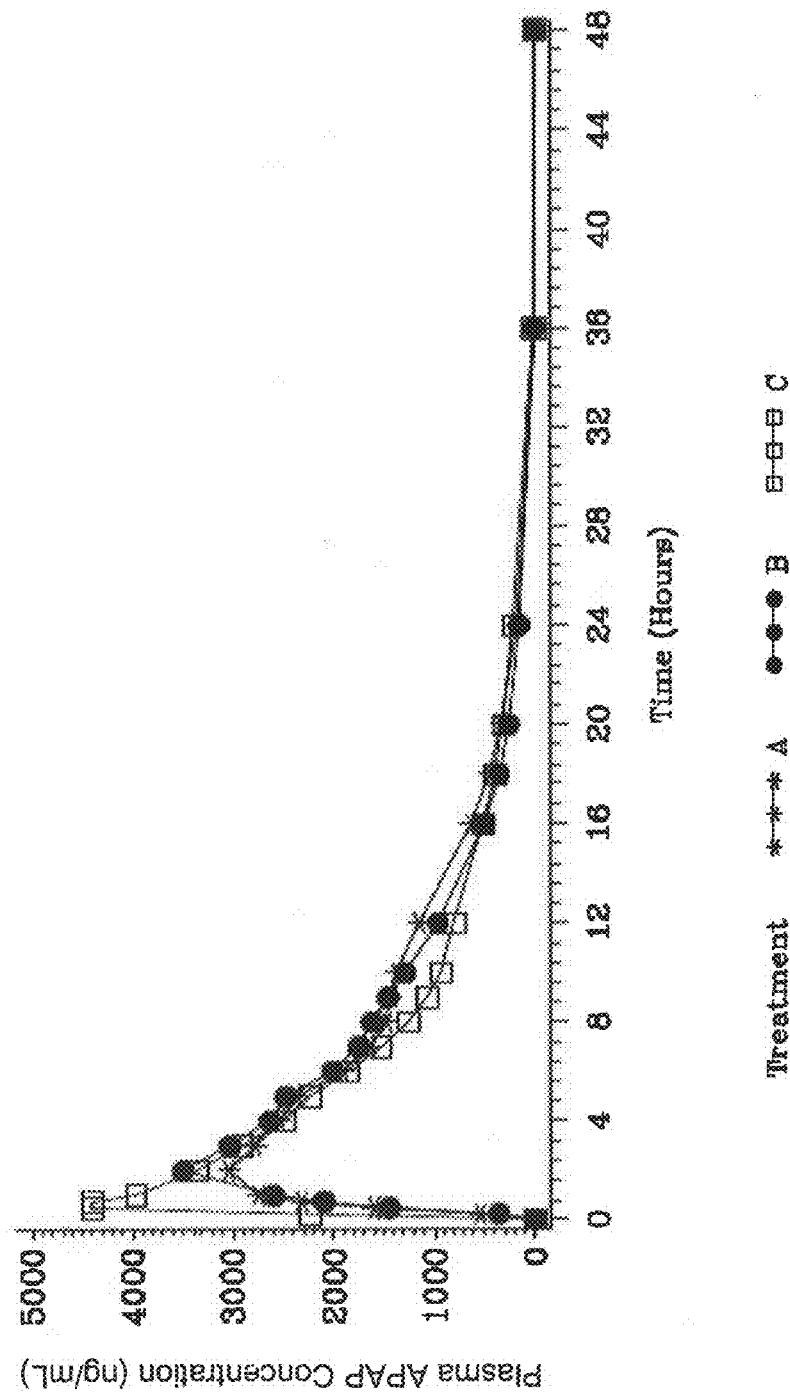

FIG. 20 presents the mean plasma concentrations of acetaminophen as a function of time by treatment following oral administration of two tablets of 7.5 mg of oxycodone/325 mg of acetaminophen. Treatment A was under fed (high fat) conditions. Treatment B was under fed (low fat) conditions. Treatment C was under fasted conditions.

Figure 21:
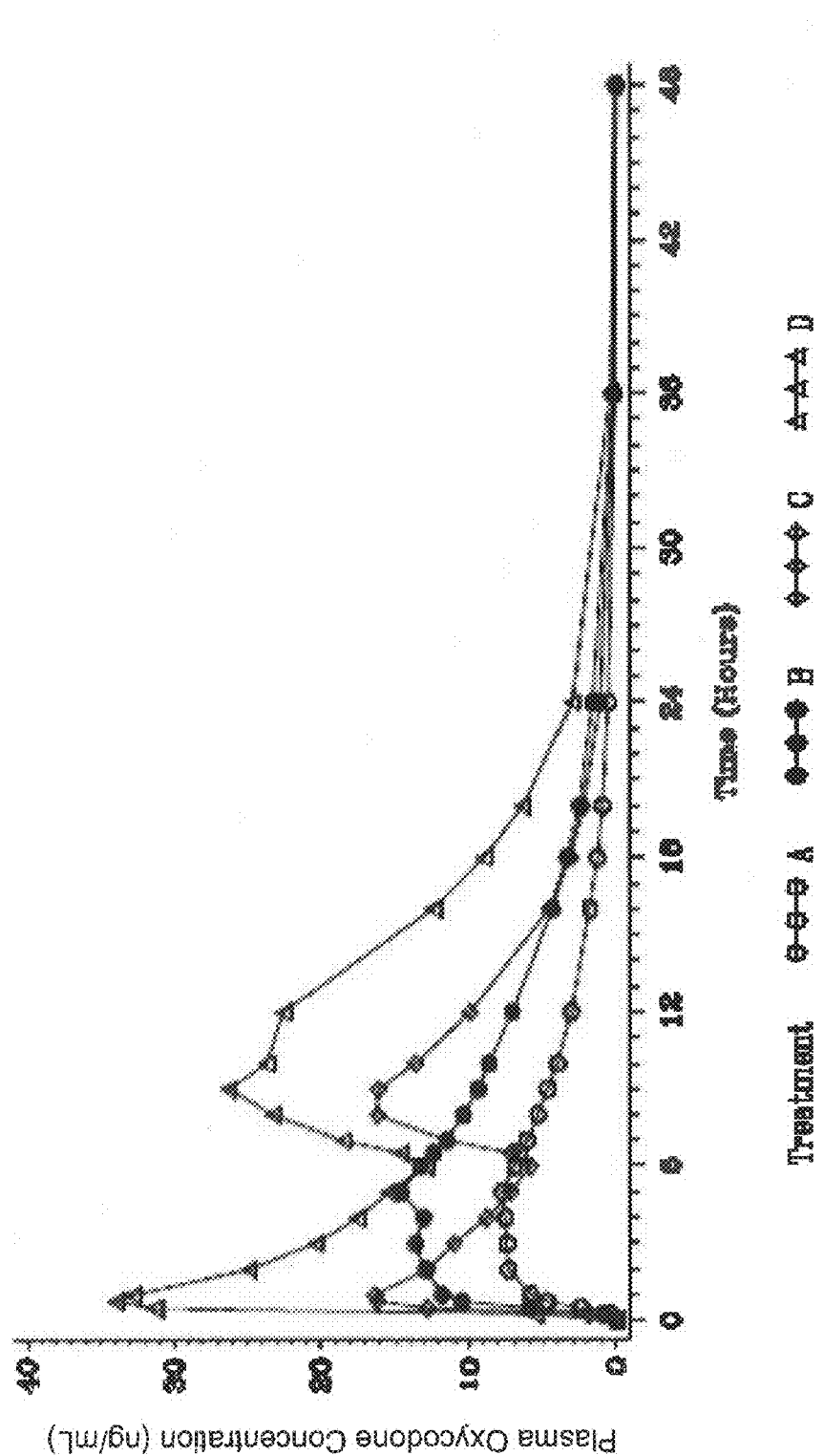

FIG. 21 shows the mean plasma concentrations of oxycodone versus time by treatment. Treatment A was one tablet of 7.5 mg oxycodone/325 mg acetaminophen administered orally under fasted conditions. Treatment B was two tablets of 7.5 mg oxycodone/325 mg acetaminophen administered orally under fasted conditions. Treatment C was one tablet of an immediate release 7.5 oxycodone/325 acetaminophen tablet administered orally every 6 hours for 2 doses under fasted conditions. Treatment D was two tablets of an immediate release 7.5 oxycodone/325 acetaminophen tablet administered orally every 6 hours for 2 doses under fasted conditions.

Figure 22:
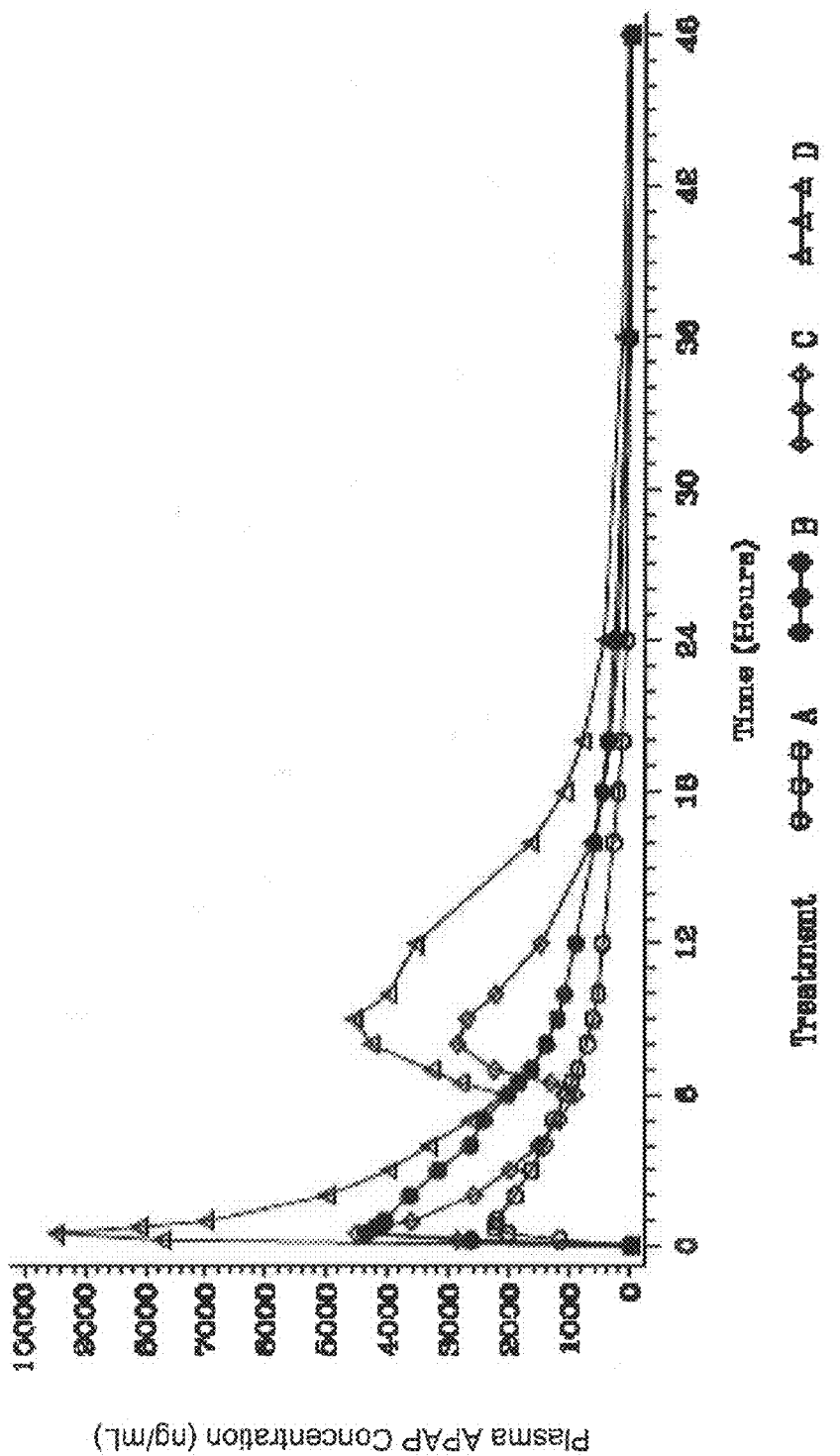

FIG. 22 presents the mean plasma concentrations of acetaminophen versus time by treatment. Treatment A was one tablet of 7.5 mg oxycodone/325 mg acetaminophen administered orally under fasted conditions. Treatment B was two tablets of 7.5 mg oxycodone/325 mg acetaminophen administered orally under fasted conditions. Treatment C was one tablet of an immediate release 7.5 oxycodone/325 acetaminophen tablet administered orally every 6 hours for 2 doses under fasted conditions. Treatment D was two tablets an immediate release 7.5 oxycodone/325 acetaminophen tablet administered orally every 6 hours for 2 doses under fasted conditions.

Figure 23:
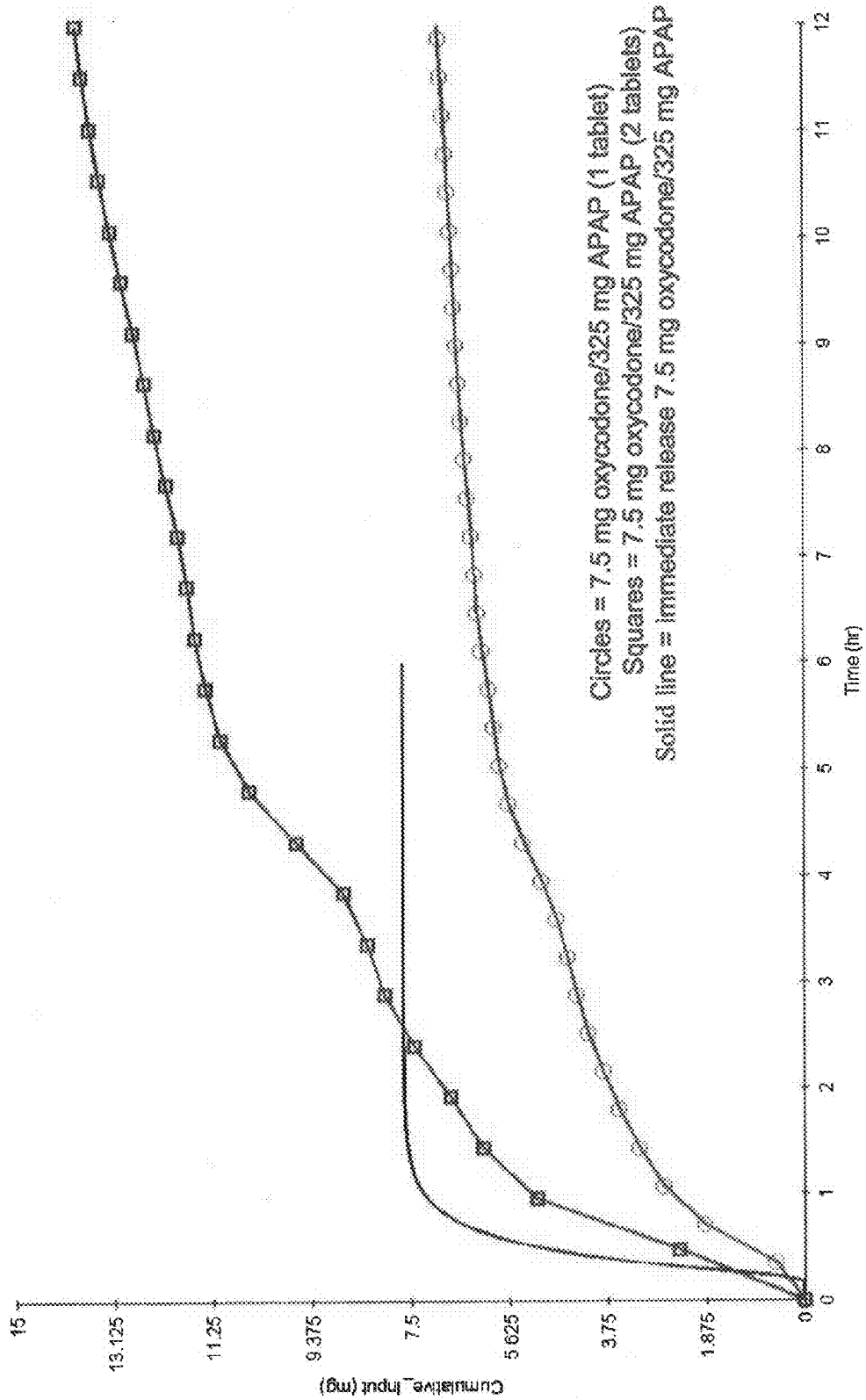

FIG. 23 shows a deconvolution plot of the biphasic absorption of oxycodone from tablets of the 7.5 mg oxycodone/325 mg acetaminophen formulation. The cumulative amount of oxycodone is plotted versus time. Circles represent one tablet of 7.5 mg oxycodone/325 mg acetaminophen; squares represent two tablets of 7.5 mg oxycodone/325 mg acetaminophen; and the immediate release 7.5 oxycodone/325 acetaminophen tablet is shown in a solid line with no symbols.

Figure 24:
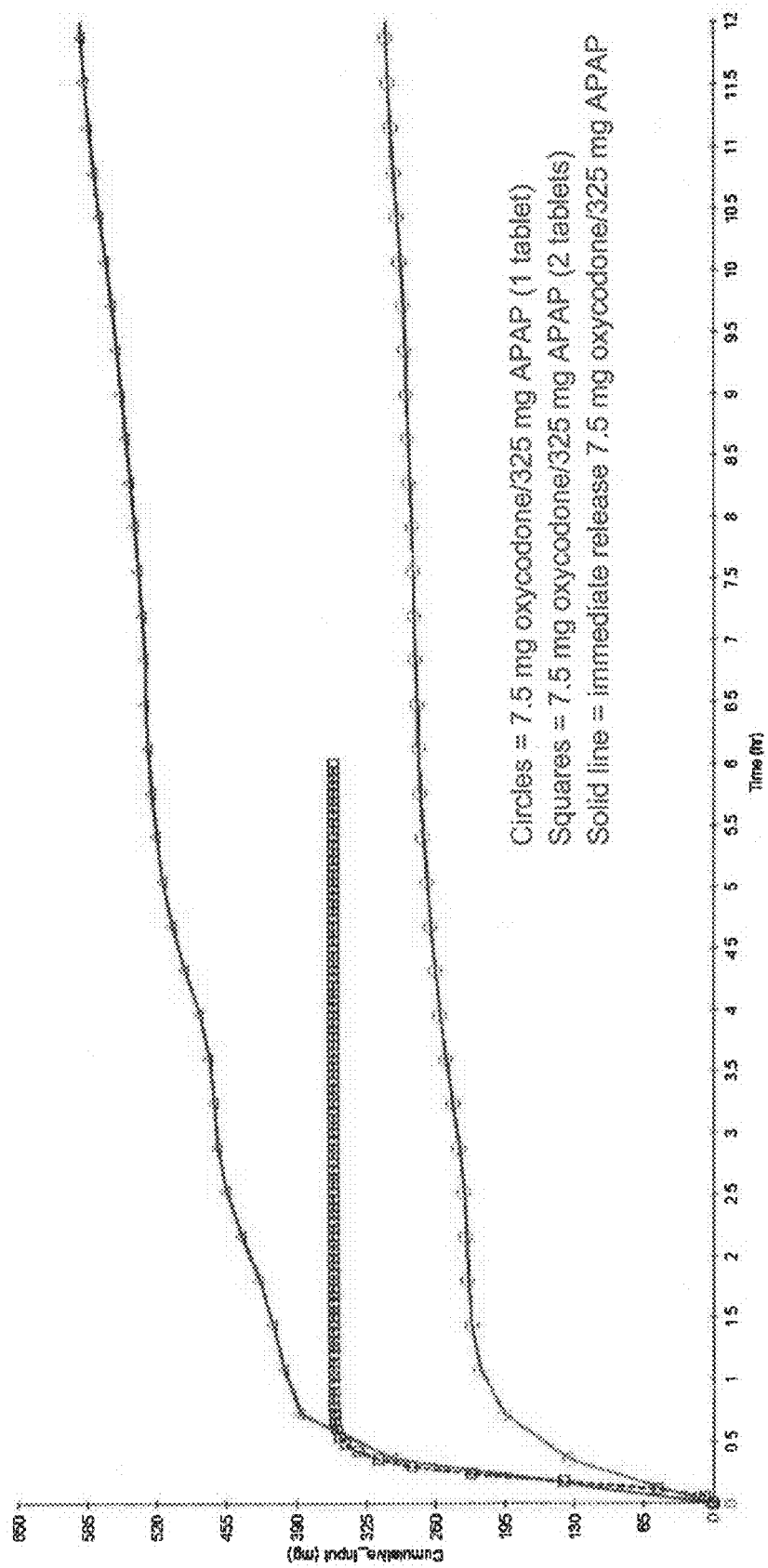

FIG. 24 presents a deconvolution plot of the biphasic absorption of acetaminophen from tablets of the 7.5 mg oxycodone/325 mg acetaminophen formulation. The cumulative amount of acetaminophen is plotted versus time. Circles represent one tablet of 7.5 mg oxycodone/325 mg acetaminophen; triangles represent two tablets of 7.5 mg oxycodone/325 mg acetaminophen; and squares represent the immediate release 7.5 oxycodone/325 acetaminophen product.

Figure 25:
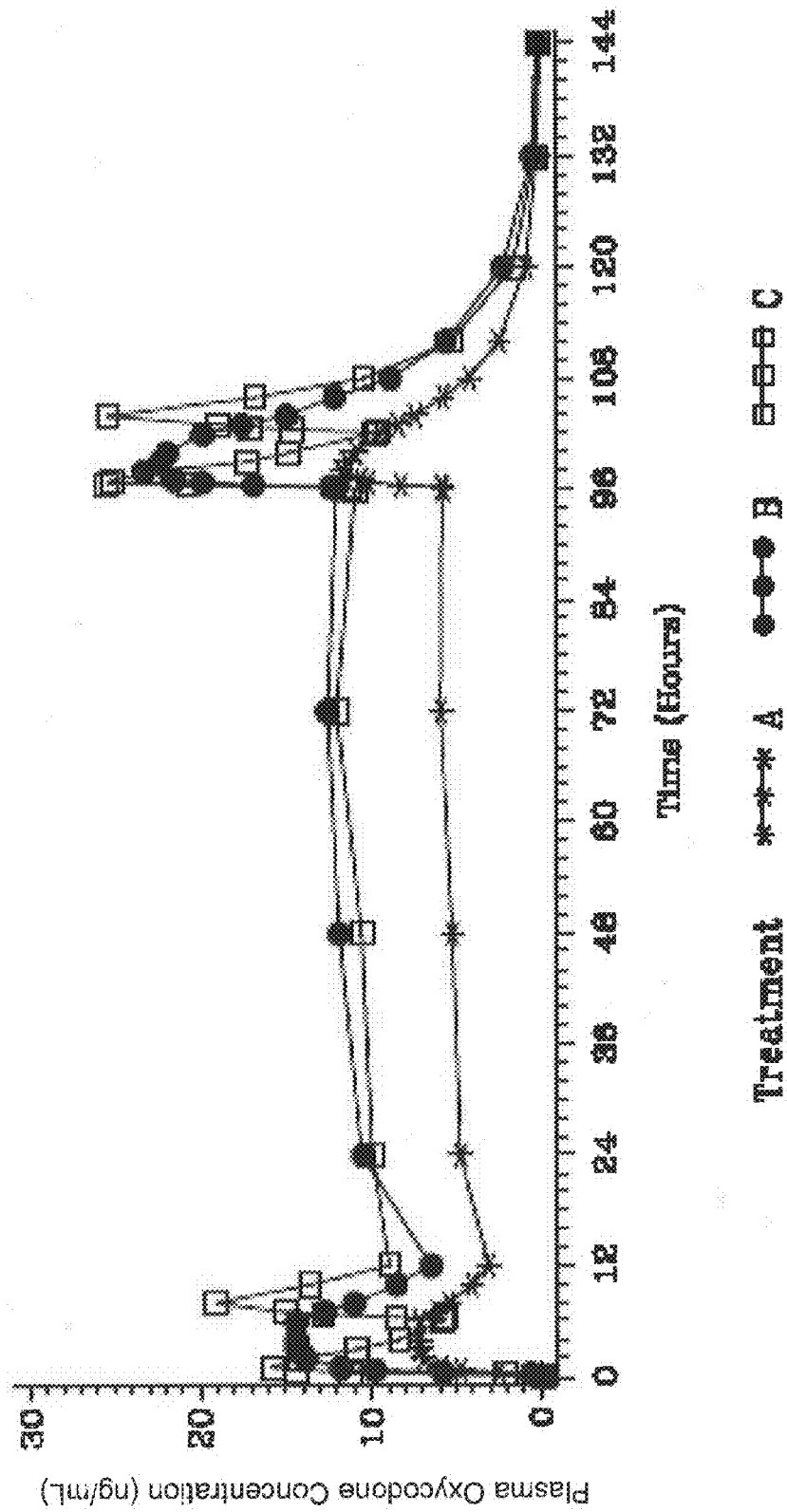

FIG. 25 shows the mean plasma concentrations of oxycodone versus time by treatment. Treatment A was one tablet of 7.5 mg oxycodone/325 mg acetaminophen administered orally every 12 hours for 4.5 days (9 doses) under fasted conditions. Treatment B was two tablets of 7.5 mg oxycodone/325 mg acetaminophen administered orally every 12 hours for 4.5 days (9 doses) under fasted conditions. Treatment C was one tablet of an immediate release 7.5 oxycodone/325 acetaminophen tablet administered orally every 6 hours for 4.5 days (18 doses) under fasted conditions.

Figure 26:
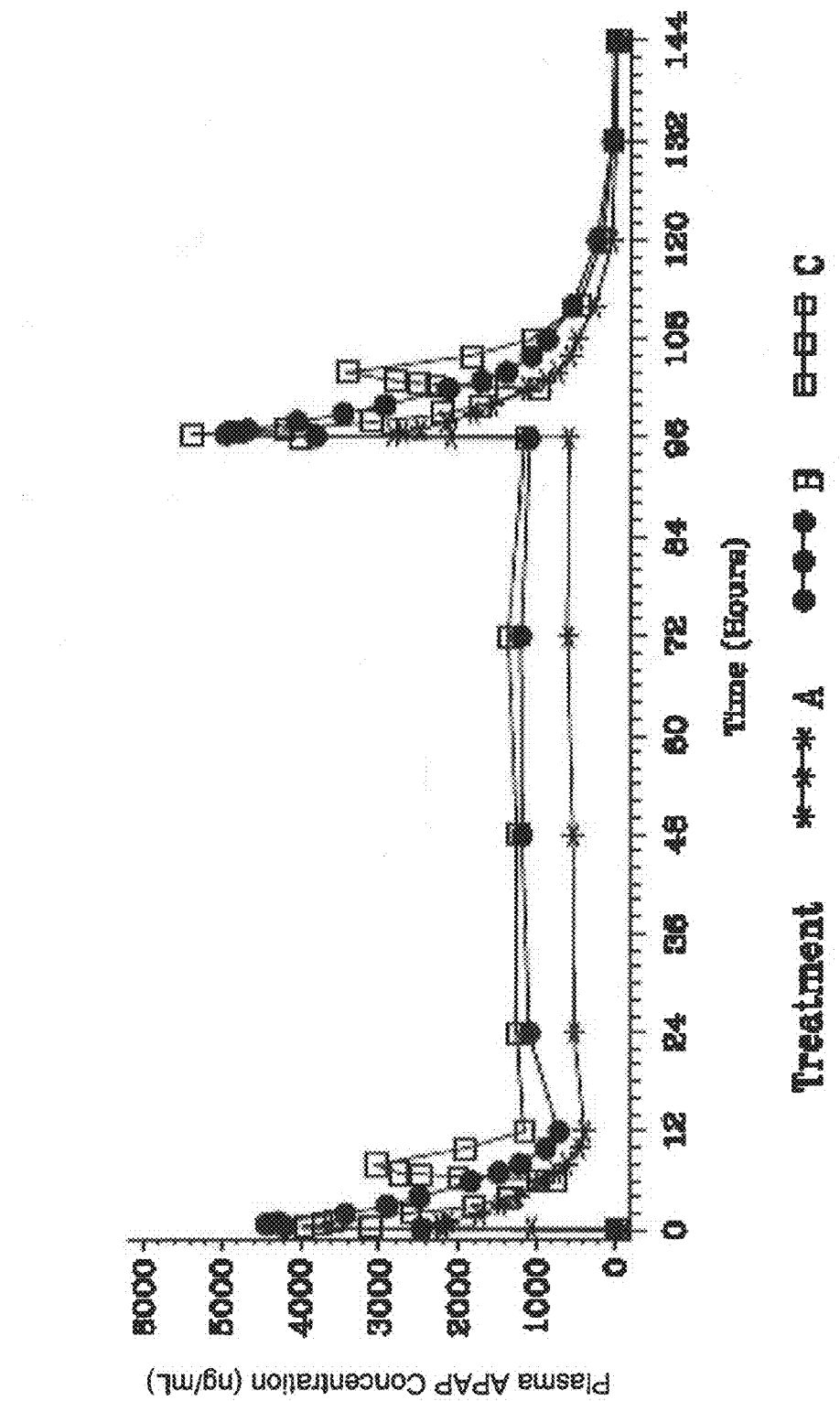

FIG. 26 presents the mean plasma concentrations of acetaminophen versus time by treatment. Treatment A was one tablet of 7.5 mg oxycodone/325 mg acetaminophen administered orally every 12 hours for 4.5 days (9 doses) under fasted conditions. Treatment B was two tablets of 7.5 mg oxycodone/325 mg acetaminophen administered orally every 12 hours for 4.5 days (9 doses) under fasted conditions. Treatment C was one tablet of an immediate release 7.5 oxycodone/325 acetaminophen tablet administered orally every 6 hours for 4.5 days (18 doses) under fasted conditions.

Figure 27A:
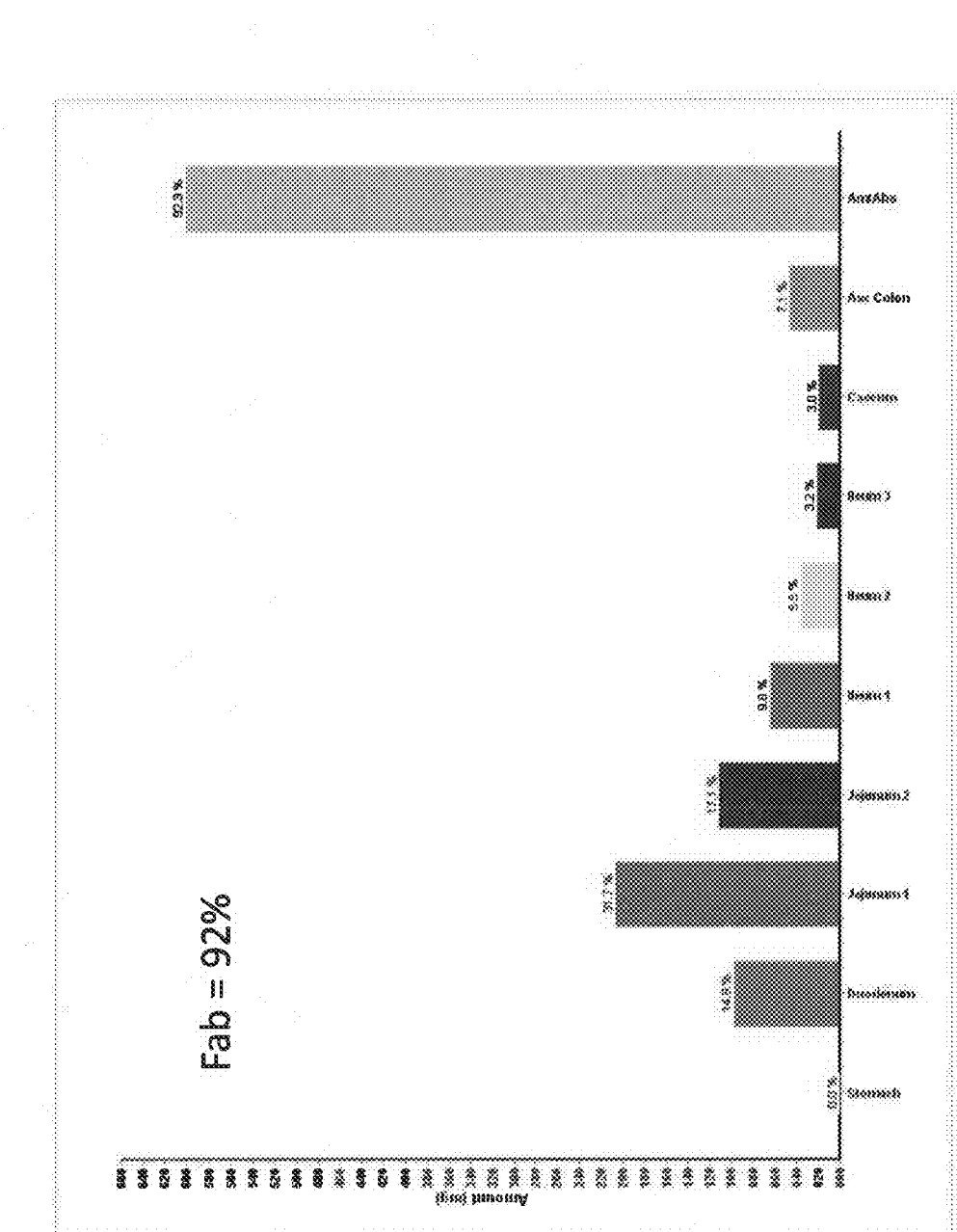
Figure 27B:
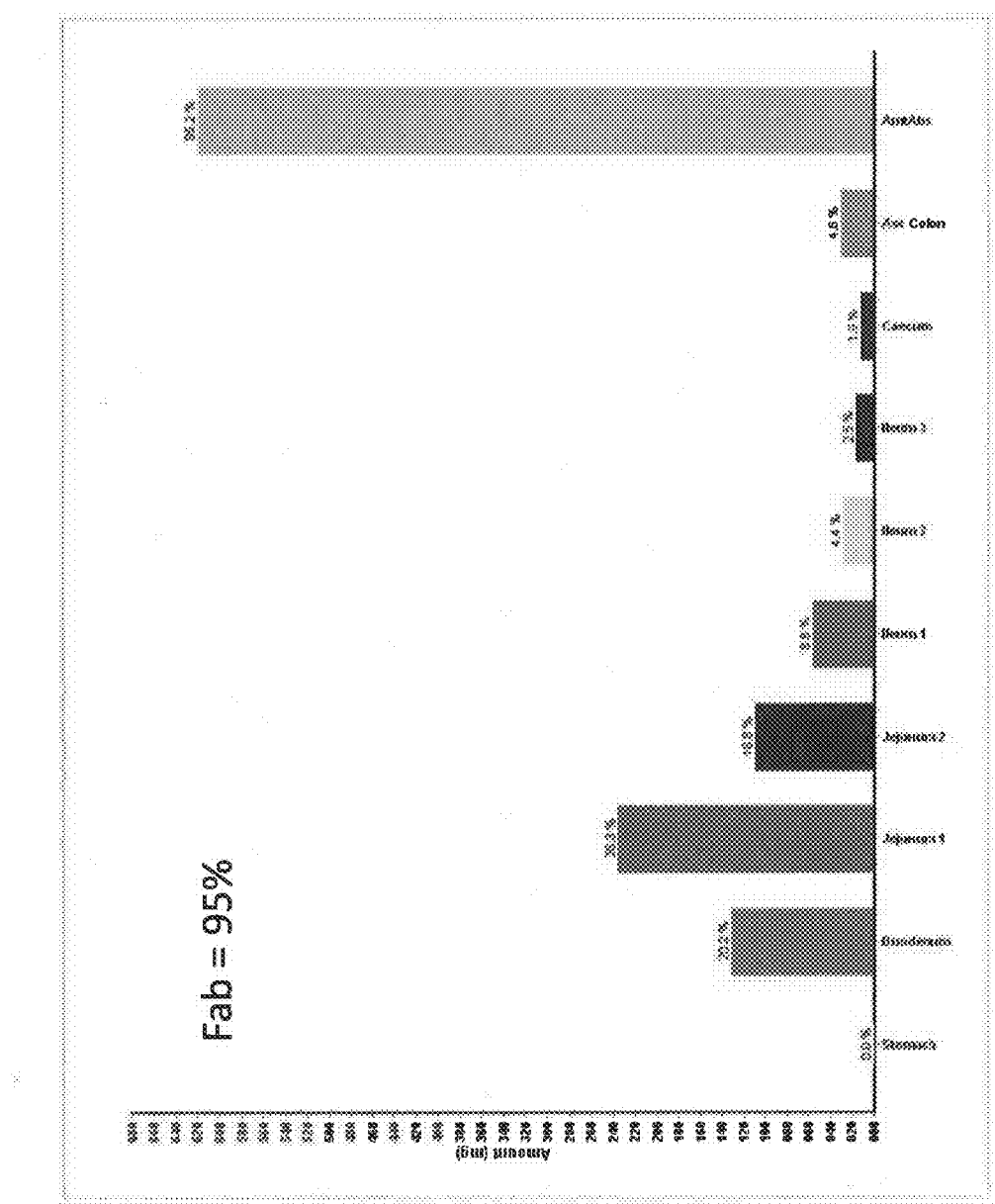
Figure 27C:
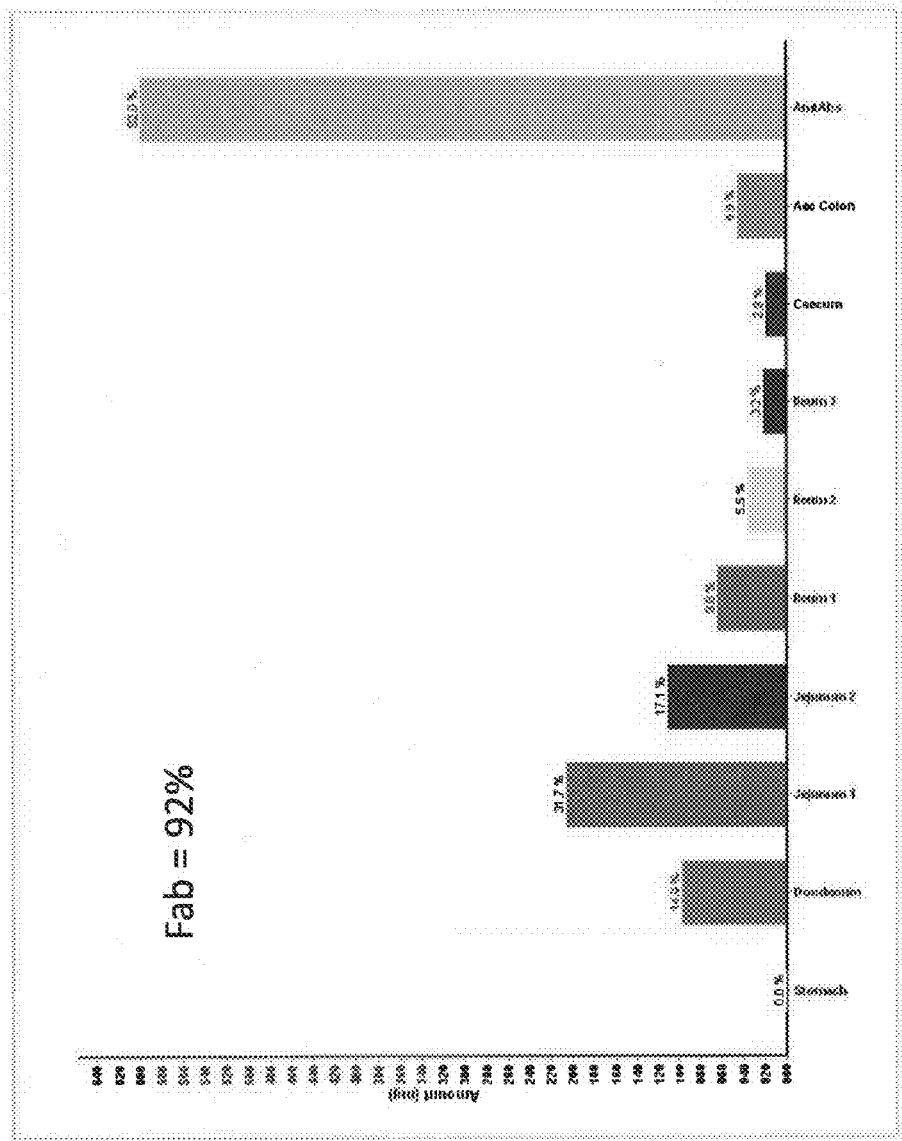

FIG. 27A is a bar graph depicting the simulated fractional absorption of acetaminophen in the upper GIT of a human subject after treatment of a 7.5 mg oxycodone/325 mg acetaminophen immediate release formulation. FIG. 27B is a bar graph depicting the simulated fractional absorption of acetaminophen in the upper GIT of a human subject after treatment of a 7.5 mg oxycodone/325 mg acetaminophen immediate release formulation, wherein the formulation's transit time from the stomach through ileum 3 has been doubled. FIG. 27C is a bar graph depicting the simulated fractional absorption of acetaminophen in the upper GIT of a human subject after treatment of a 7.5 mg oxycodone/325 mg acetaminophen immediate release formulation, wherein the formulation's transit time in the stomach has been increased by two hours.

Figure 28A:
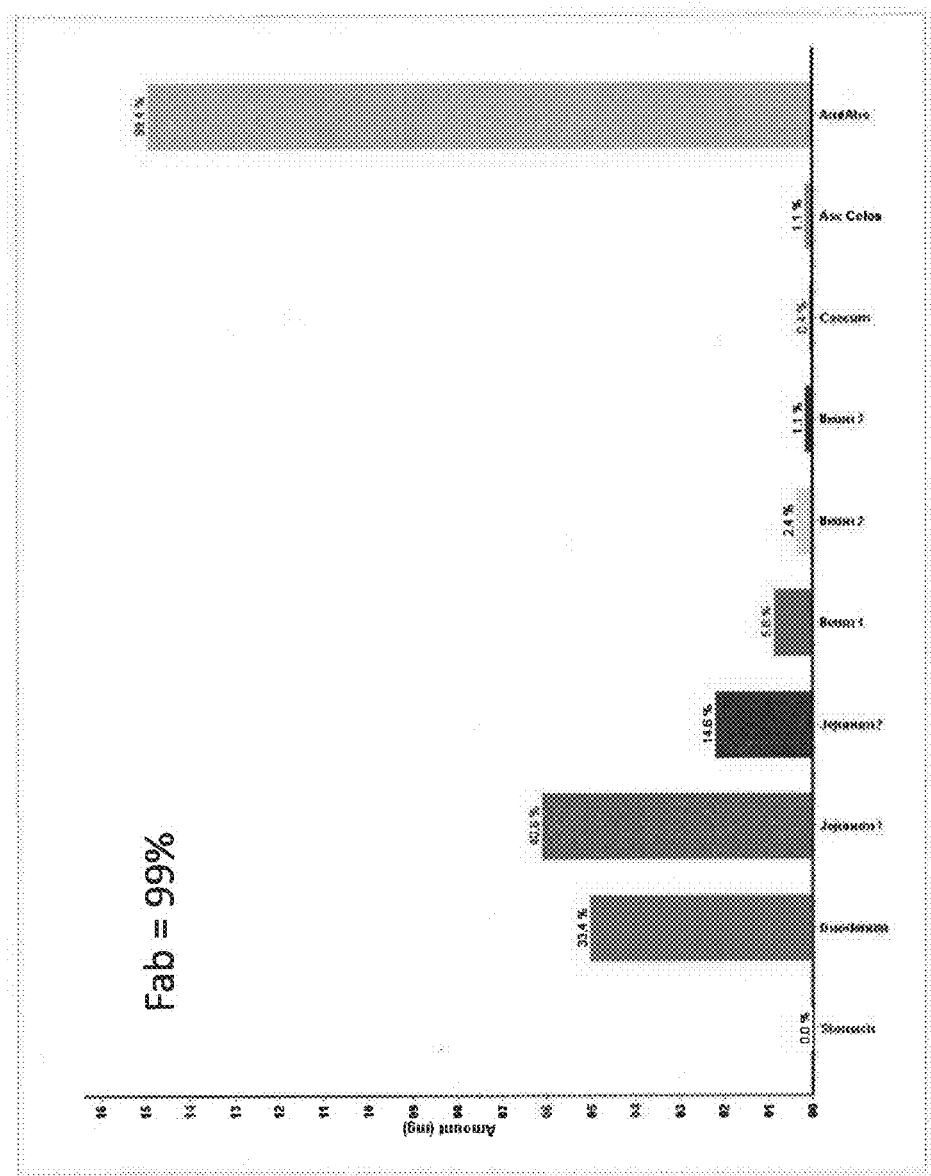
Figure 28B:
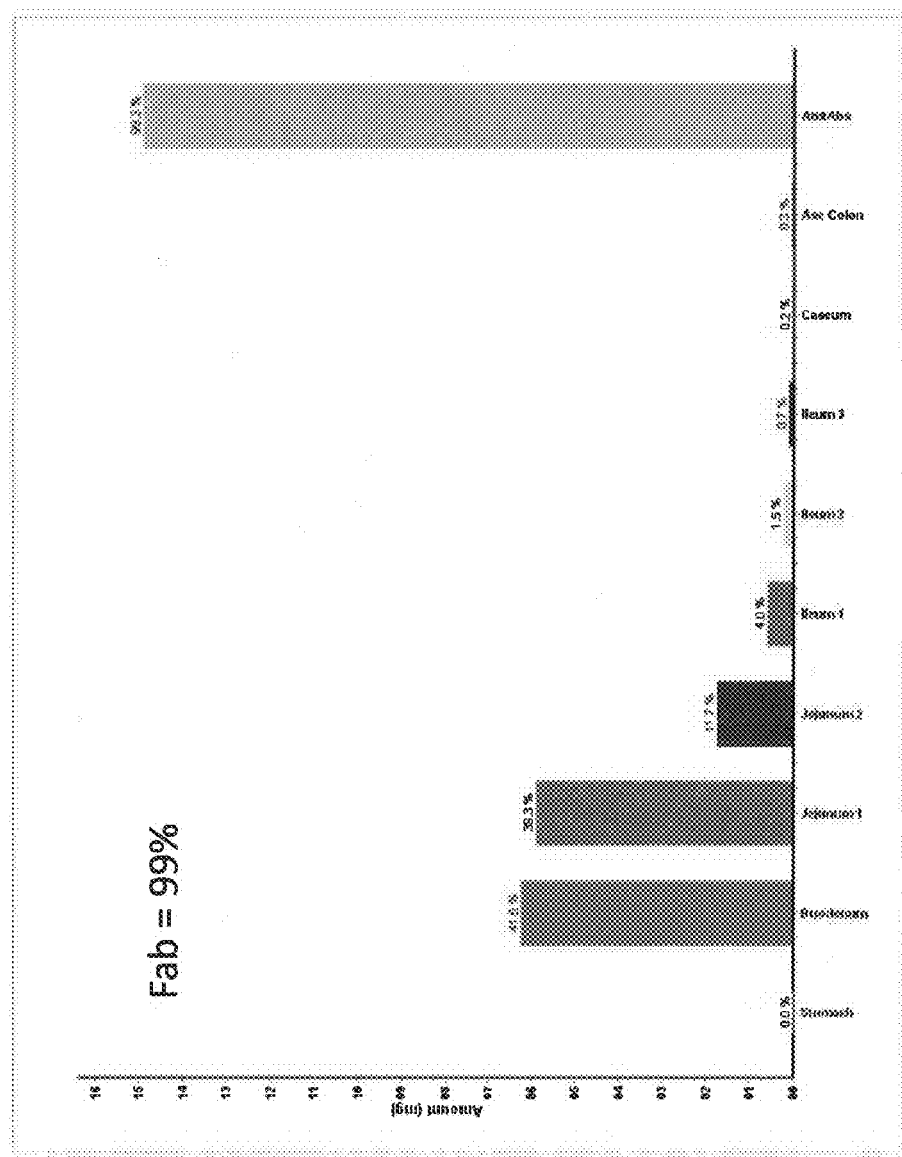
Figure 28C:
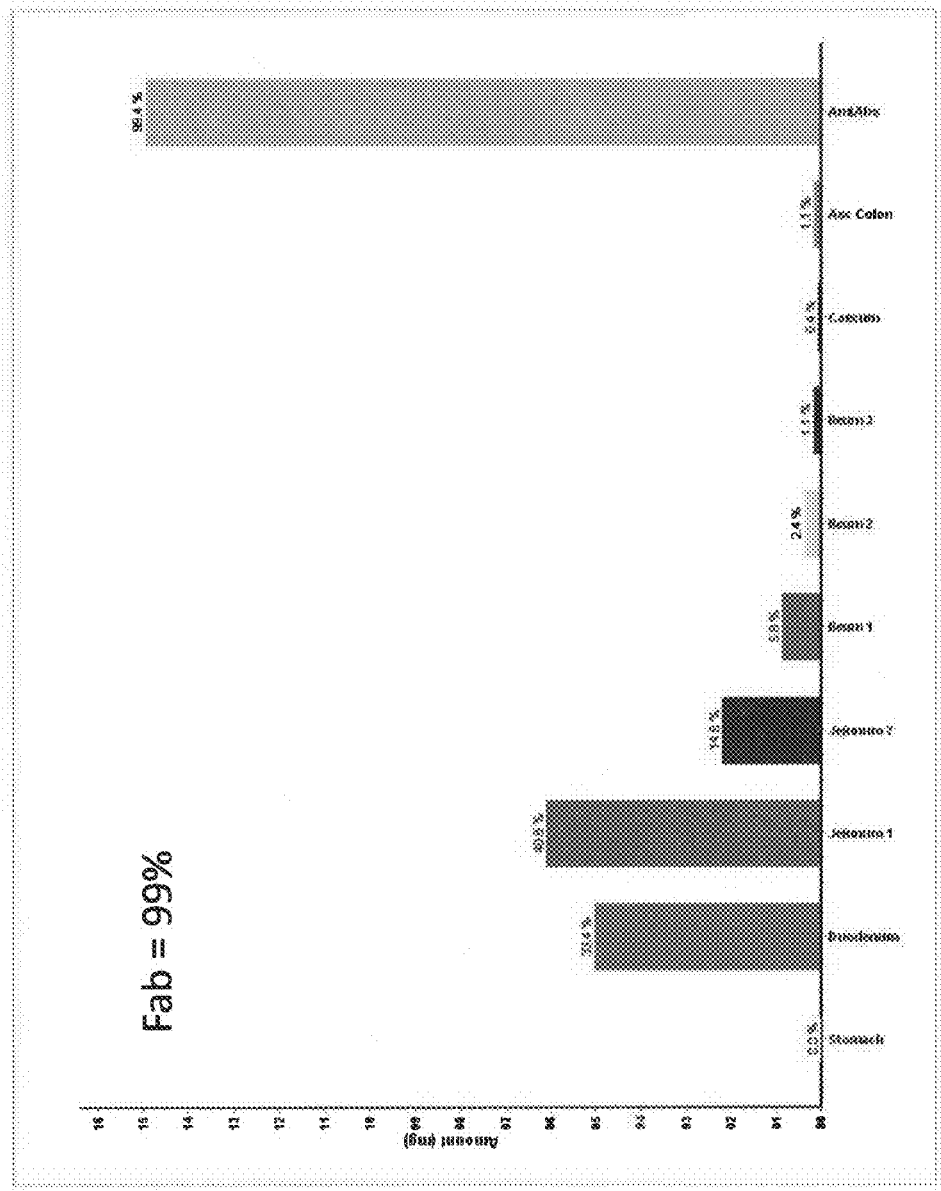

FIG. 28A is a bar graph depicting the simulated fractional absorption of oxycodone in the upper GIT of a human subject after treatment of a 7.5 mg oxycodone/325 mg acetaminophen immediate release formulation. FIG. 28B is a bar graph depicting the simulated fractional absorption of oxycodone in the upper GIT of a human subject after treatment of a 7.5 mg oxycodone/325 mg acetaminophen immediate release formulation, wherein the formulation's transit time from the stomach through ileum 3 has been doubled. FIG. 28C is a bar graph depicting the simulated fractional absorption of oxycodone in the upper GIT of a human subject after treatment of a 7.5 mg oxycodone/325 mg acetaminophen immediate release formulation, wherein the formulation's transit time in the stomach has been increased by two hours.

Figure 29A:
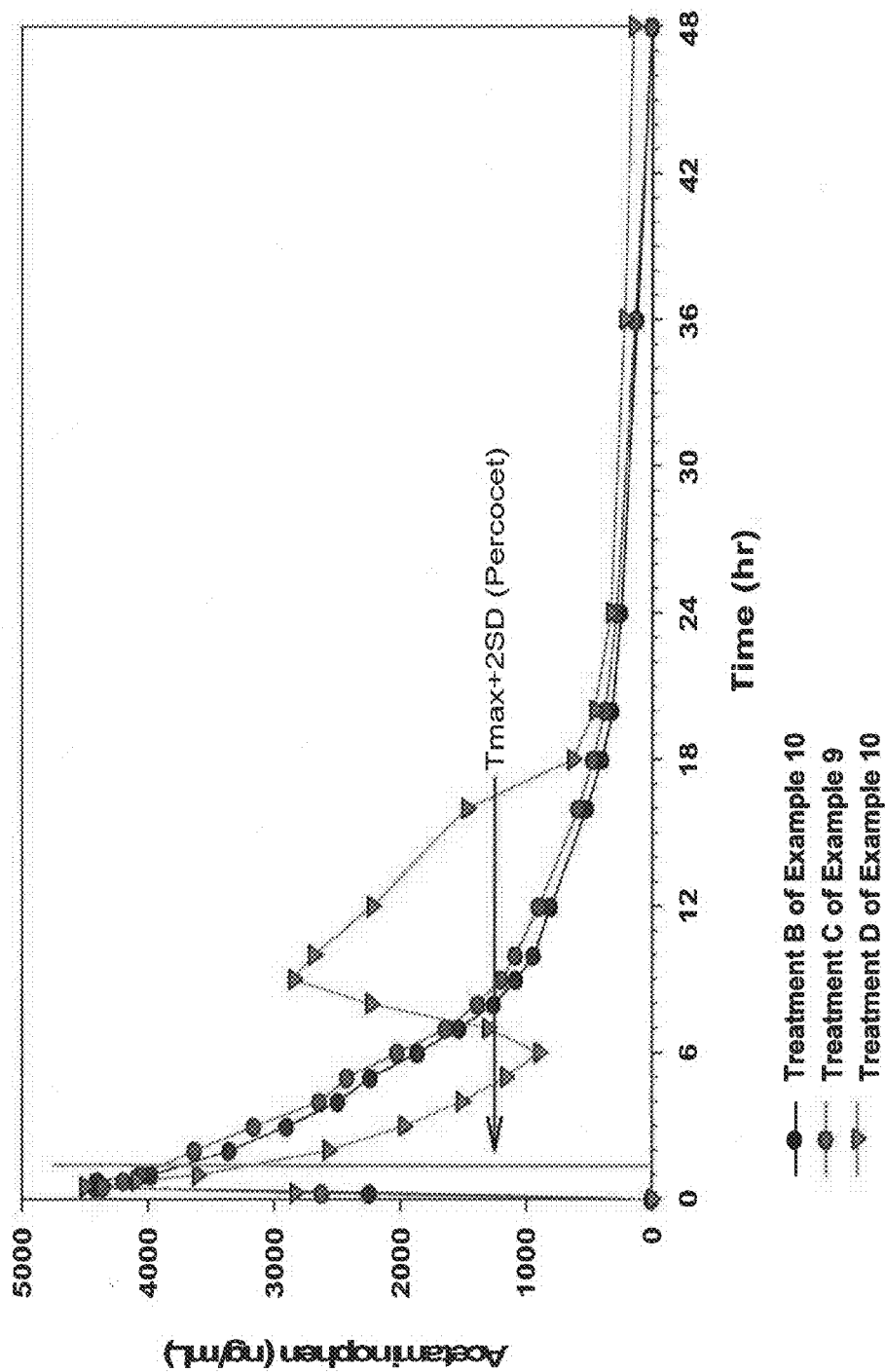

FIG. 29A presents the mean plasma concentrations and Partial AUCs of acetaminophen (e.g., $AUC_{0-1.7h}$ and $AUC_{1.7-48h}$) versus time by the following treatments: (1) Treatment B of Example 10, (2) Treatment C of Example 9, and (3) Treatment D of Example 10.

Figure 29B:
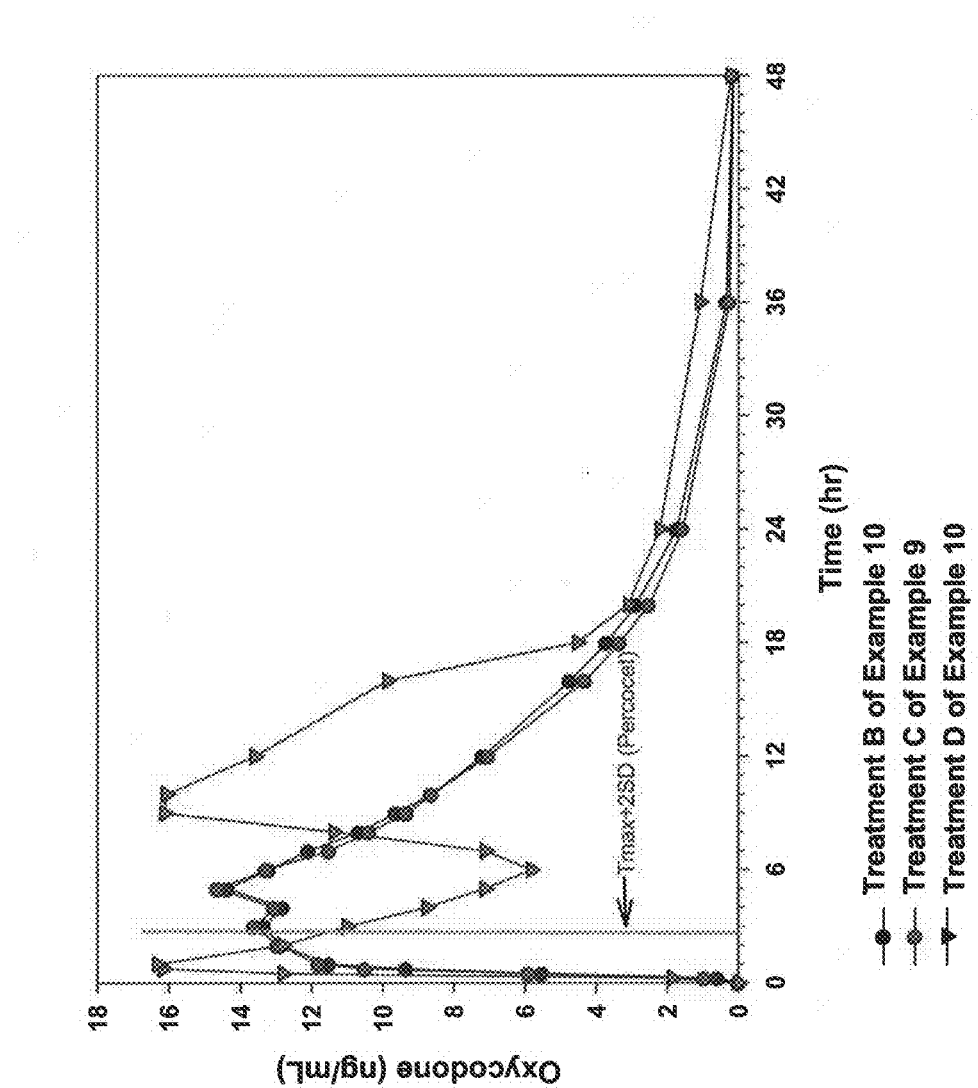

FIG. 29B presents the mean plasma concentrations and Partial AUCs of oxycodone (e.g., $AUC_{0-2.8h}$ and $AUC_{2.8-48h}$) versus time by the following treatments: (1) Treatment B of Example 10, (2) Treatment C of Example 9, and (3) Treatment D of Example 10.

Figure 30A:
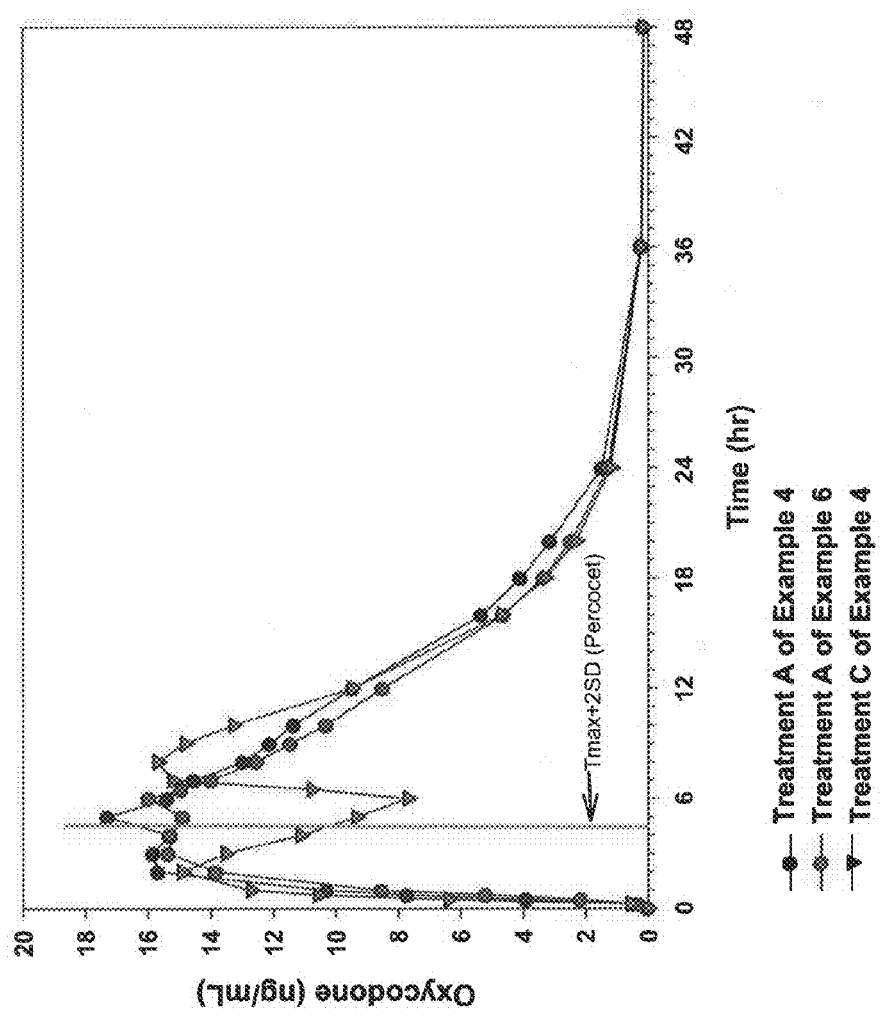

FIG. 30A presents the mean plasma concentrations and Partial AUCs of oxycodone versus time for Treatment A of Example 4, Treatment A of Example 6, and Treatment C of Example 4.

Figure 30B:
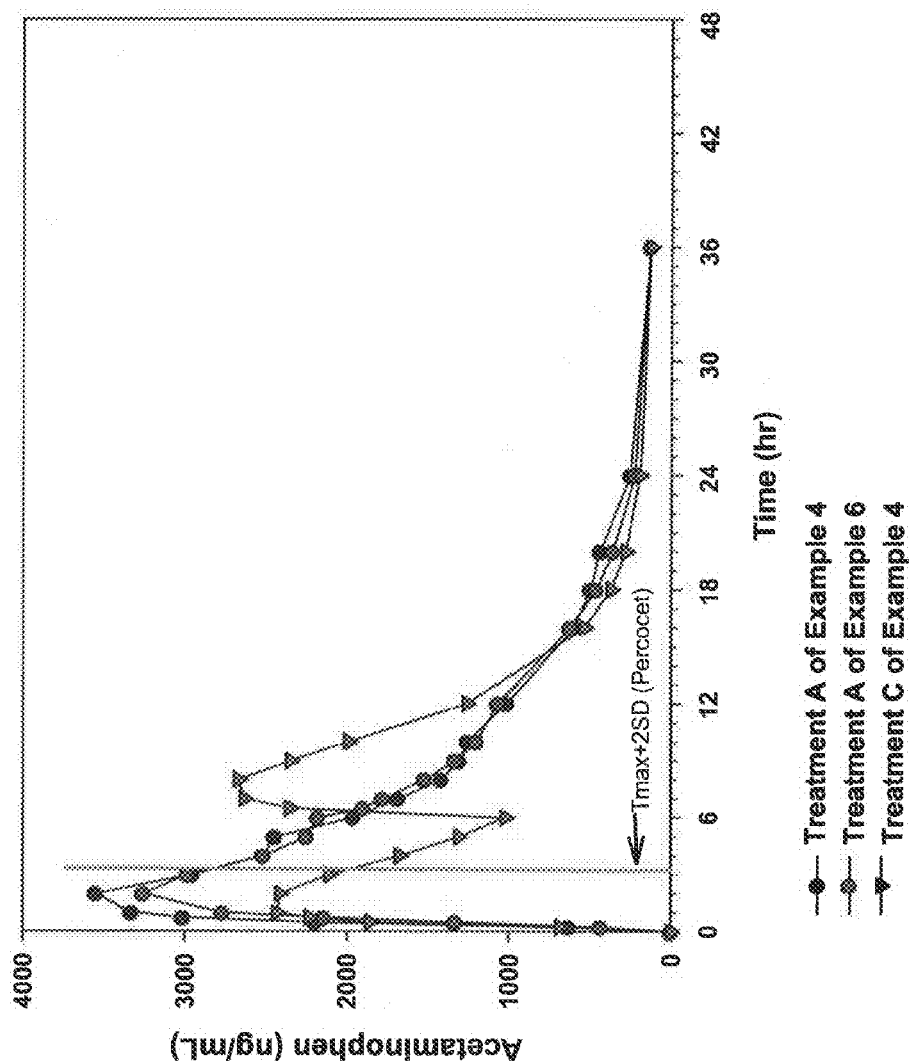

FIG. 30B presents the mean plasma concentrations and Partial AUCs of acetaminophen versus time for Treatment A of Example 4, Treatment A of Example 6, and Treatment C of Example 4.

Figure 31:
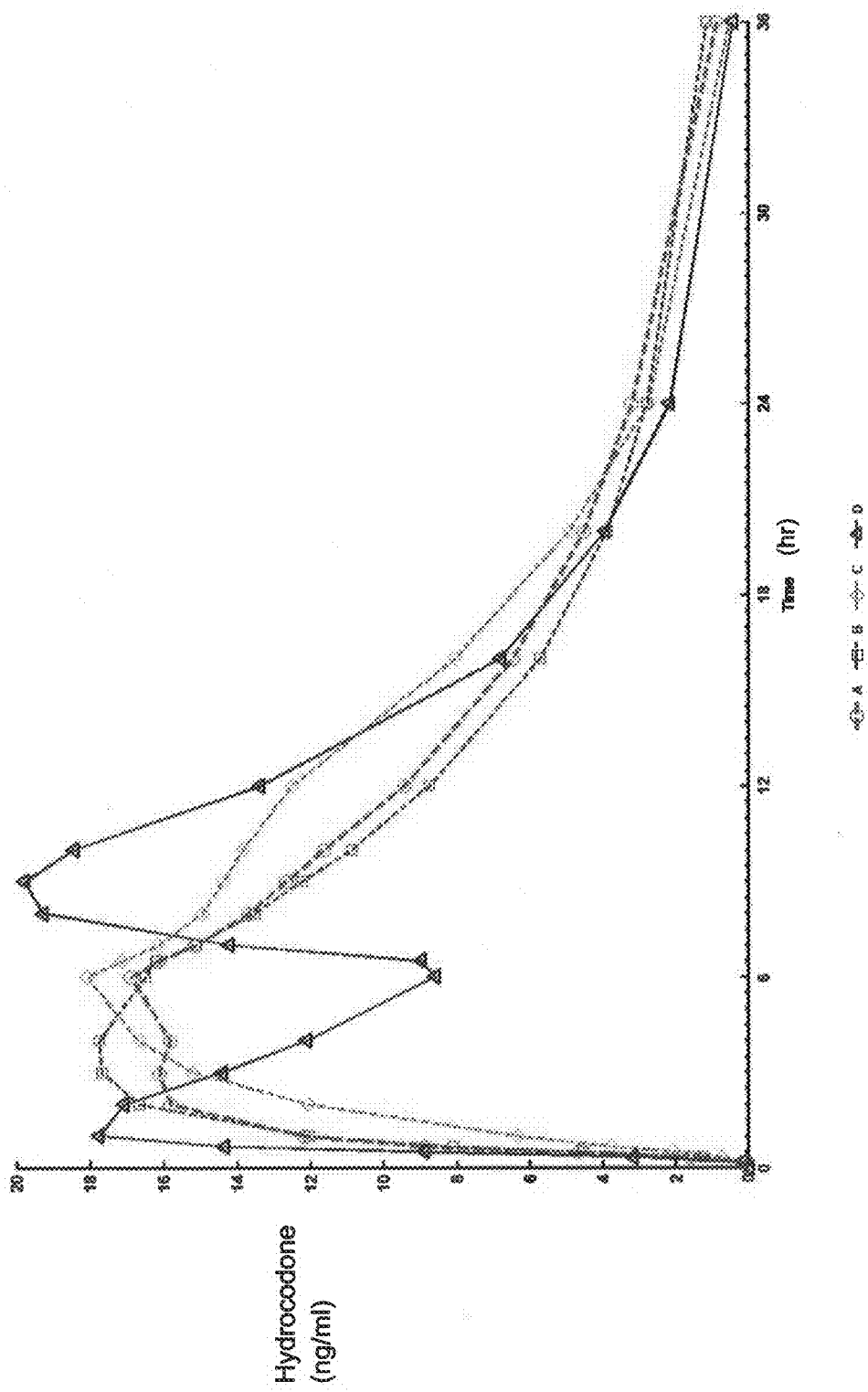

FIG. 31 presents the mean plasma concentrations of hydrocodone versus time by treatment for 0 to 36 hours. Treatment A (formulation A) was a single, two-tablet dose containing a total of 15 mg hydrocodone and 650 mg acetaminophen having slow release properties as compared to formulation B, administered orally under fasted conditions. Treatment B (formulation B) was a single, two-tablet dose containing a total of 15 mg hydrocodone and 650 mg acetaminophen having faster release properties as compared to formulation A, administered orally under fasted conditions. Treatment C (formulation B) was a single, two-tablet dose containing a total of 15 mg hydrocodone and 650 mg acetaminophen administered orally under fed conditions. Treatment D was one tablet of an immediate release 7.5 hydrocodone/325 acetaminophen tablet administered orally every 6 hours for 2 doses under fasted conditions.

Figure 32:
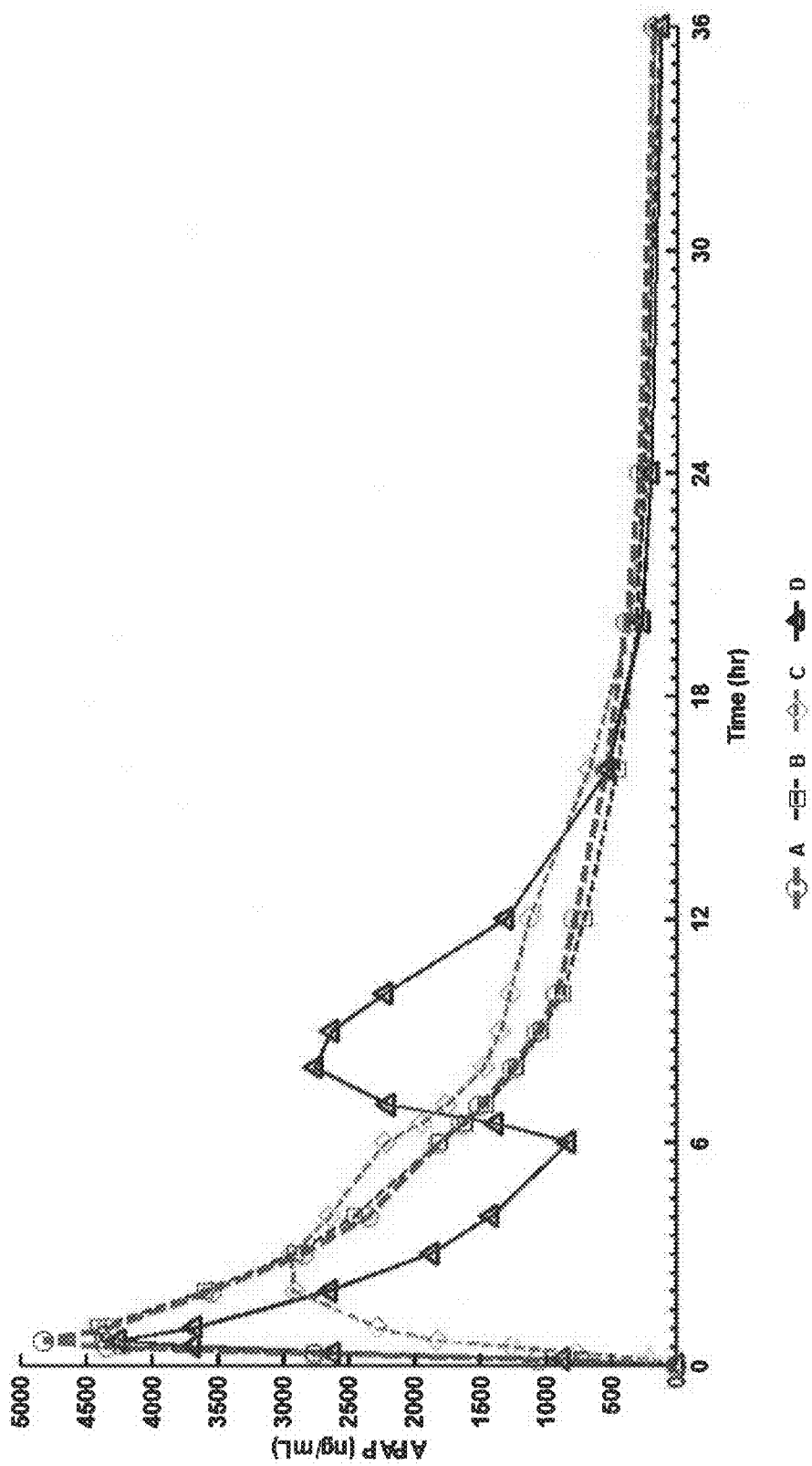

FIG. 32 presents the mean plasma concentrations of acetaminophen versus time by treatment for 0 to 36 hours. Treatment A (formulation A) was a single, two-tablet dose containing a total of 15 mg hydrocodone and 650 mg acetaminophen having slow release properties as compared to formulation B, administered orally under fasted conditions. Treatment B (formulation B) was a single, two-tablet dose containing a total of 15 mg hydrocodone and 650 mg acetaminophen having faster release properties as compared to formulation A, administered orally under fasted conditions. Treatment C (formulation B) was a single, two-tablet dose containing a total of 15 mg hydrocodone and 650 mg acetaminophen administered orally under fed conditions. Treatment D was one tablet of an immediate release 7.5 hydrocodone/325 acetaminophen tablet administered orally every 6 hours for 2 doses under fasted conditions.

Figure 33:
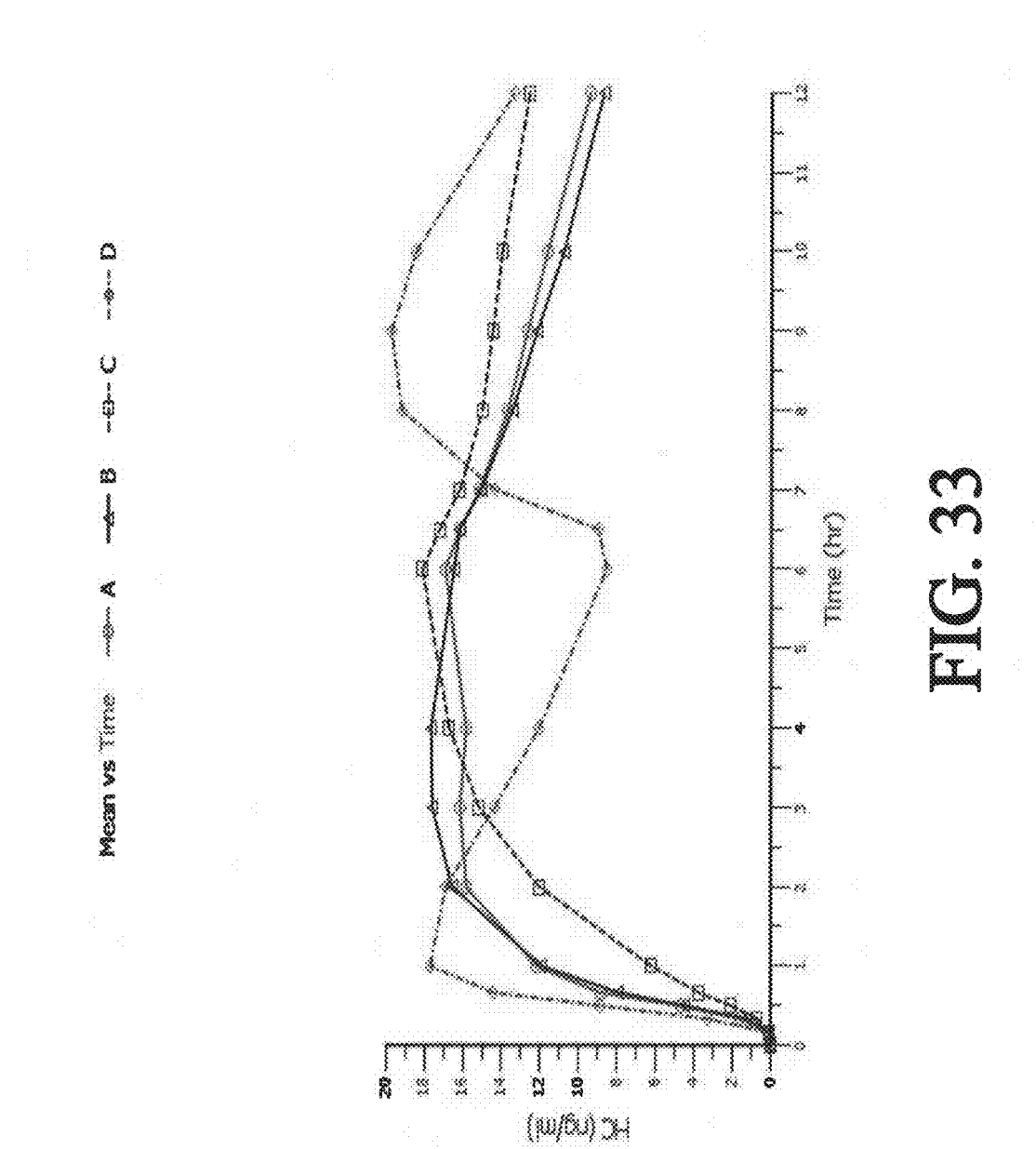

FIG. 33 presents the mean plasma concentrations of hydrocodone versus time by treatment as indicated in FIG. 31, but represented for 0 to 12 hours.

Figure 34:
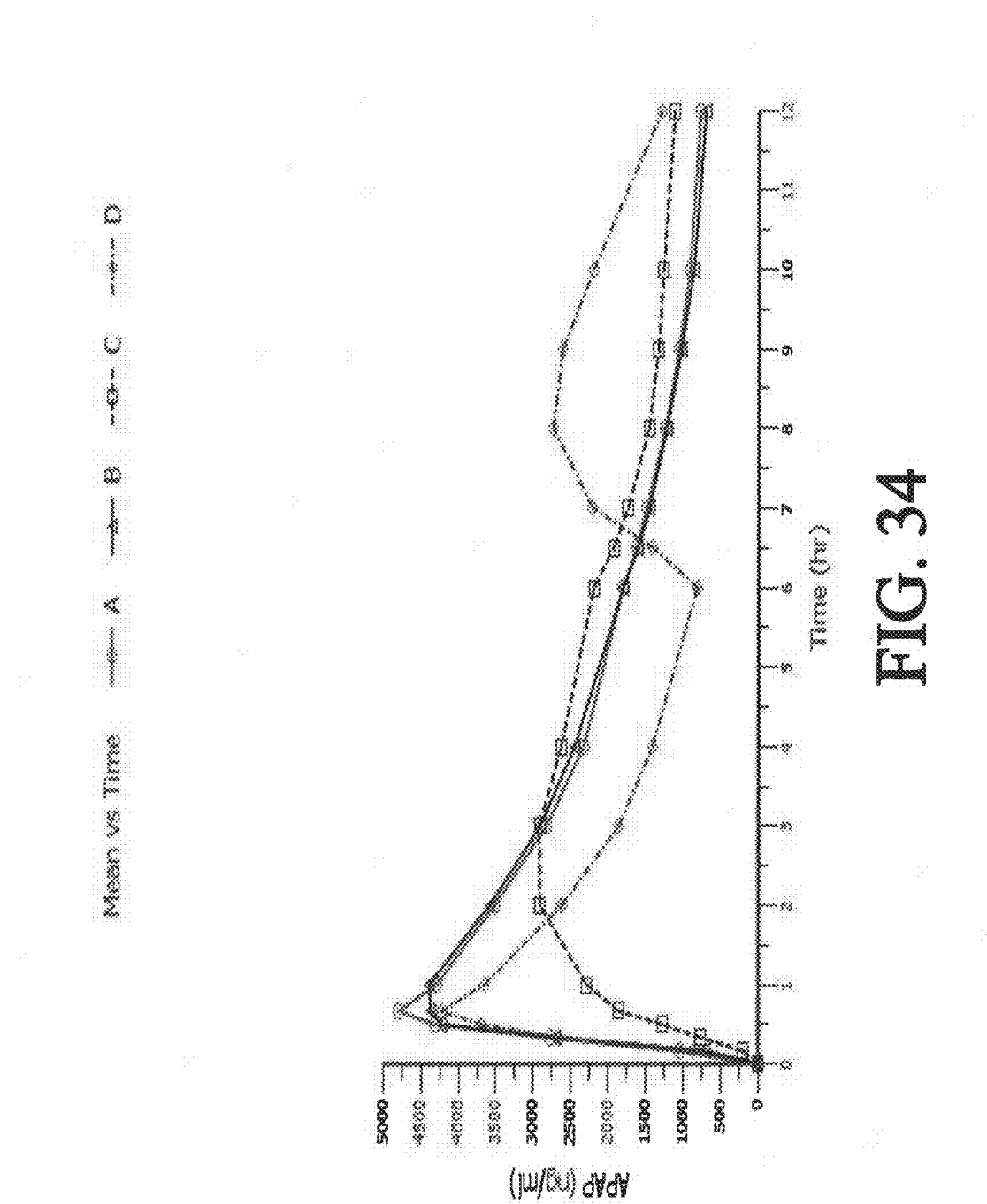

FIG. 34 presents the mean plasma concentrations of acetaminophen versus time by treatment as indicated in FIG. 32, but represented for 0 to 12 hours.

Figure 35:
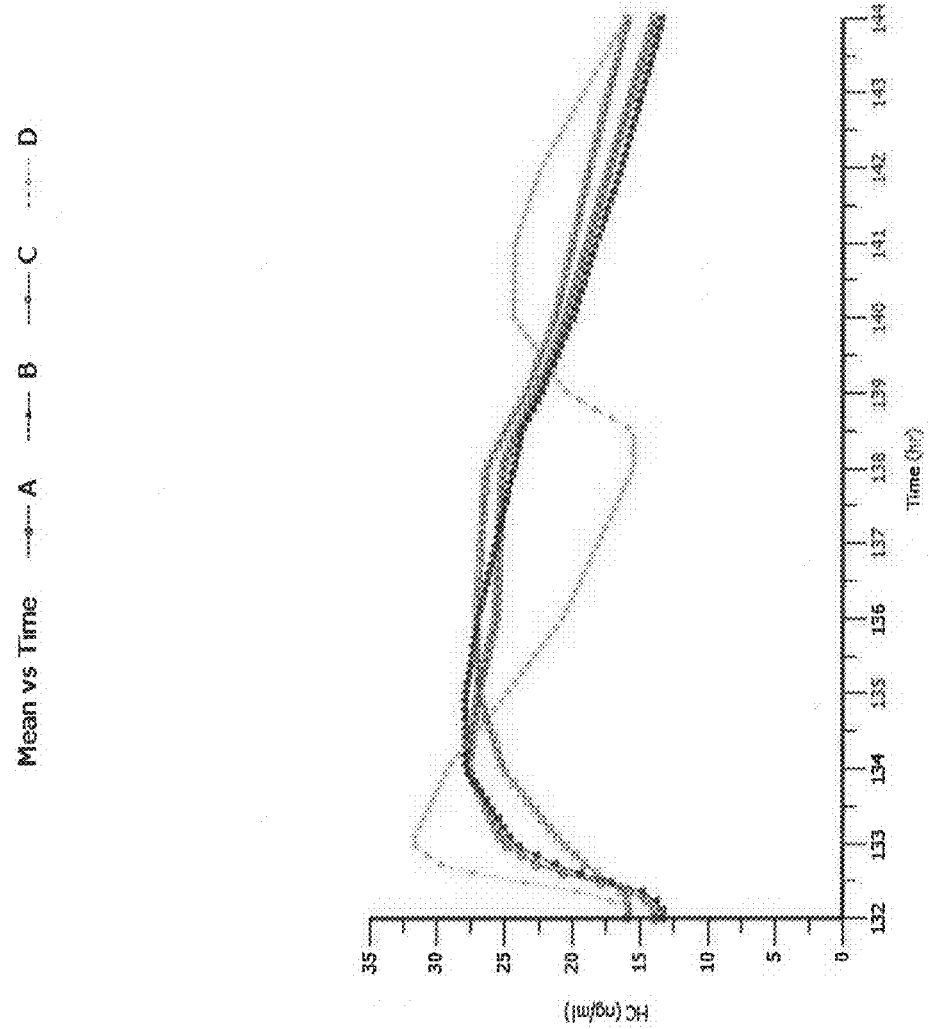

FIG. 35 presents simulated hydrocodone pharmacokinetic profiles at steady state versus time by treatment for 0 to 144 hours for Treatments A, B, C, and D of Example 16.

Figure 36:
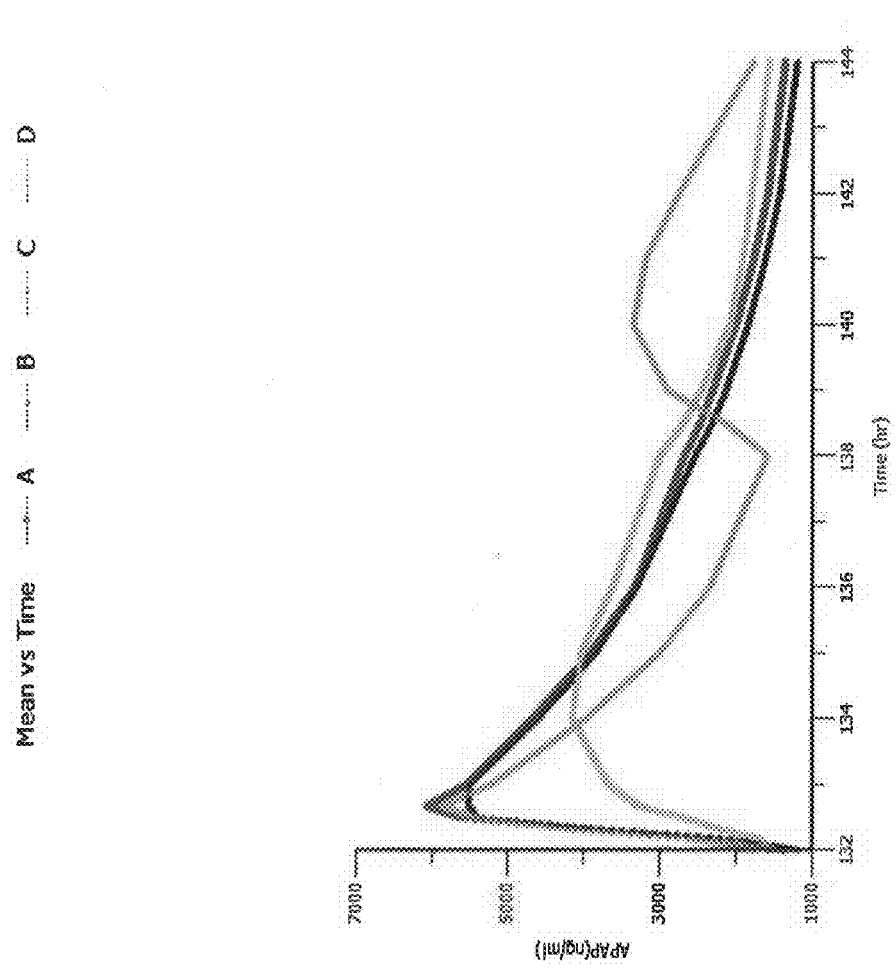

FIG. 36 presents simulated acetaminophen pharmacokinetic profiles at steady state versus time by treatment for 0 to 144 hours for Treatments A, B, C, and D of Example 16.

Figure 37:
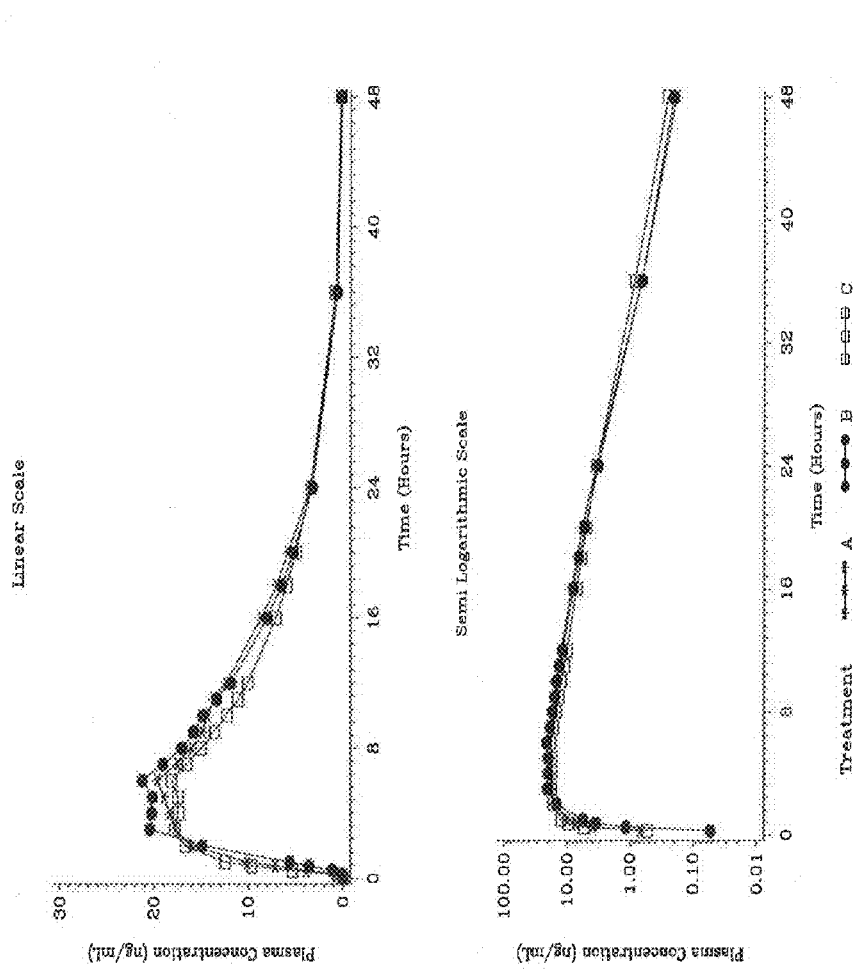

FIG. 37 presents mean plasma concentrations of hydrocodone as a function of time by treatment following oral administration of two tablets of 7.5 mg of hydrocodone and 325 mg of acetaminophen. Treatment A was under fed (high fat) conditions. Treatment B was under fed (low fat) conditions. Treatment C was under fasted conditions.

Figure 38:
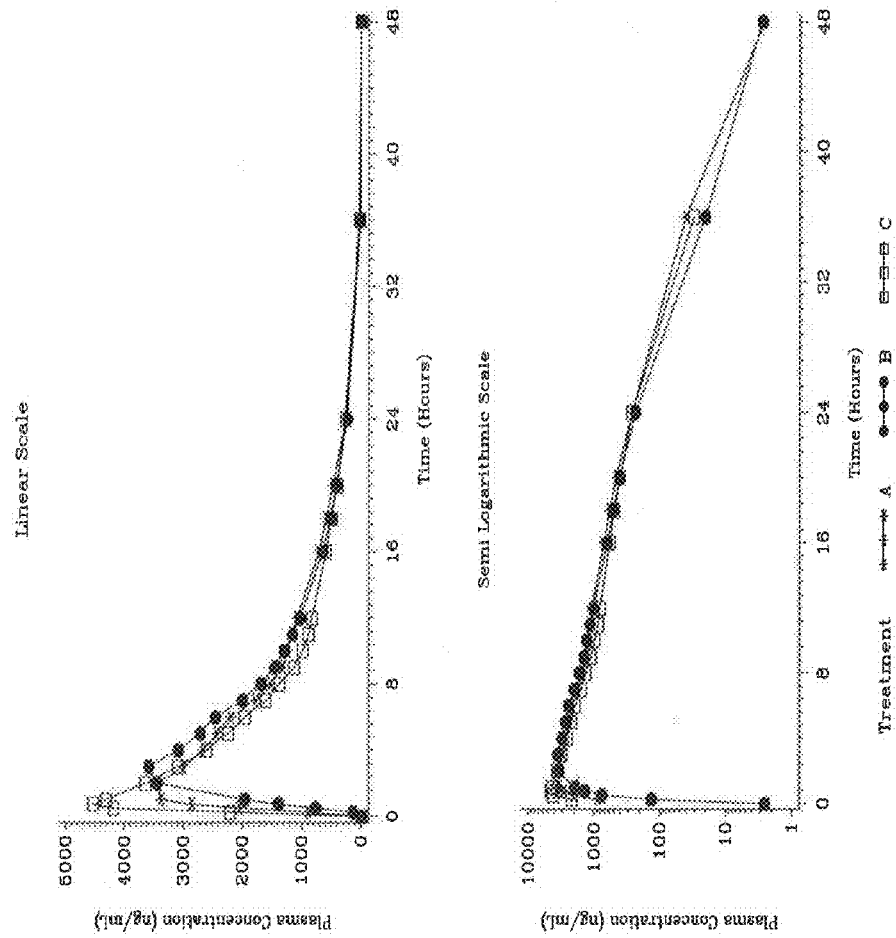

FIG. 38 presents mean plasma concentrations of acetaminophen as a function of time by treatment following oral administration of two tablets of 7.5 mg of hydrocodone and 325 mg of acetaminophen. Treatment A was under fed (high fat) conditions. Treatment B was under fed (low fat) conditions. Treatment C was under fasted conditions.

Figure 39:
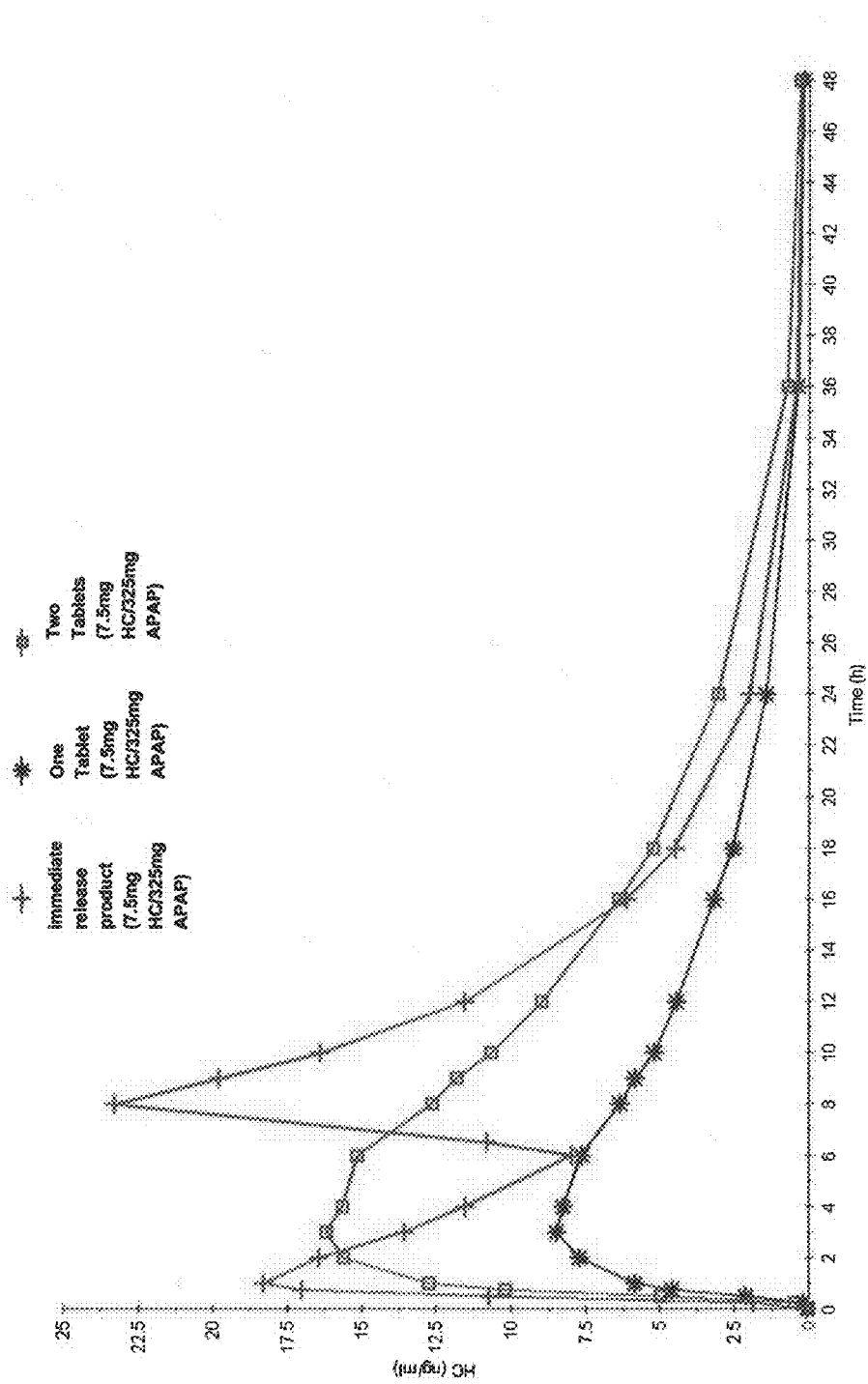

FIG. 39 presents mean plasma concentrations of hydrocodone as a function of time by treatment following oral administration of a single dose of Treatments A, B, and C of Example 18.

Figure 40:
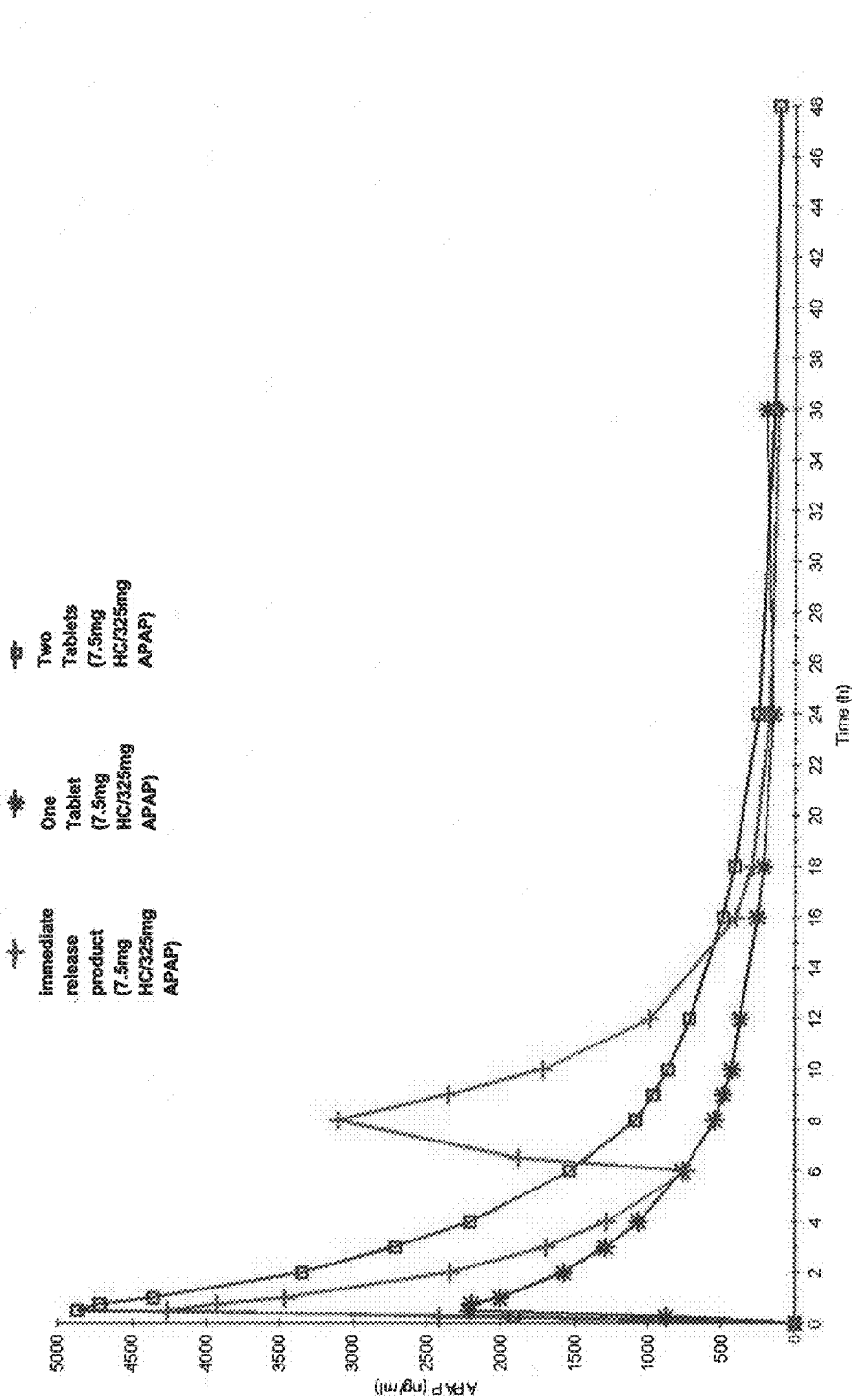

FIG. 40 presents mean plasma concentrations of acetaminophen as a function of time by treatment following oral administration of a single dose of Treatments A, B, and C of Example 18.

Figure 41:
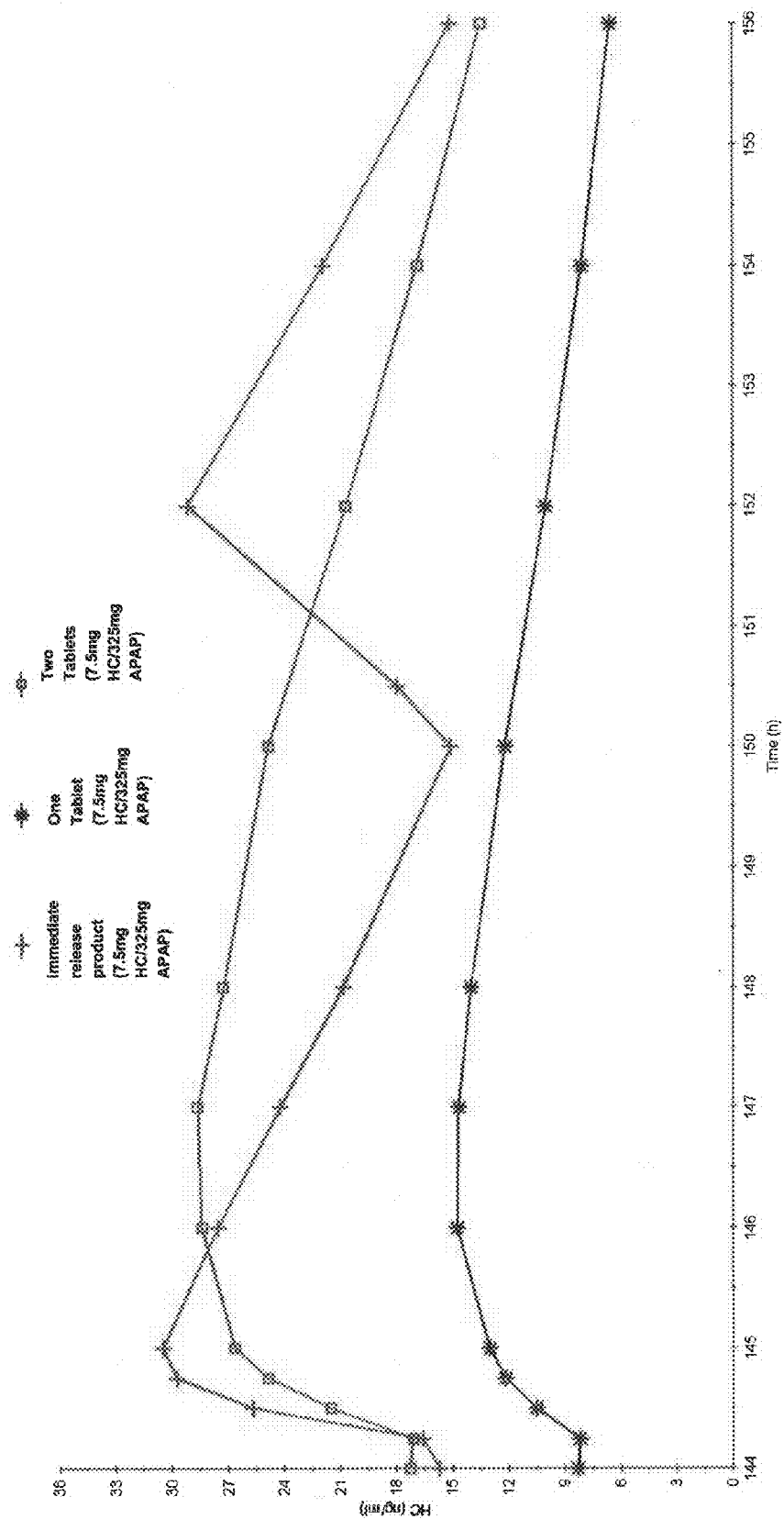

FIG. 41 presents mean plasma concentrations of hydrocodone as a function of time by treatment following oral administration of multiple doses of Treatments A, B, and C of Example 18.

Figure 42:
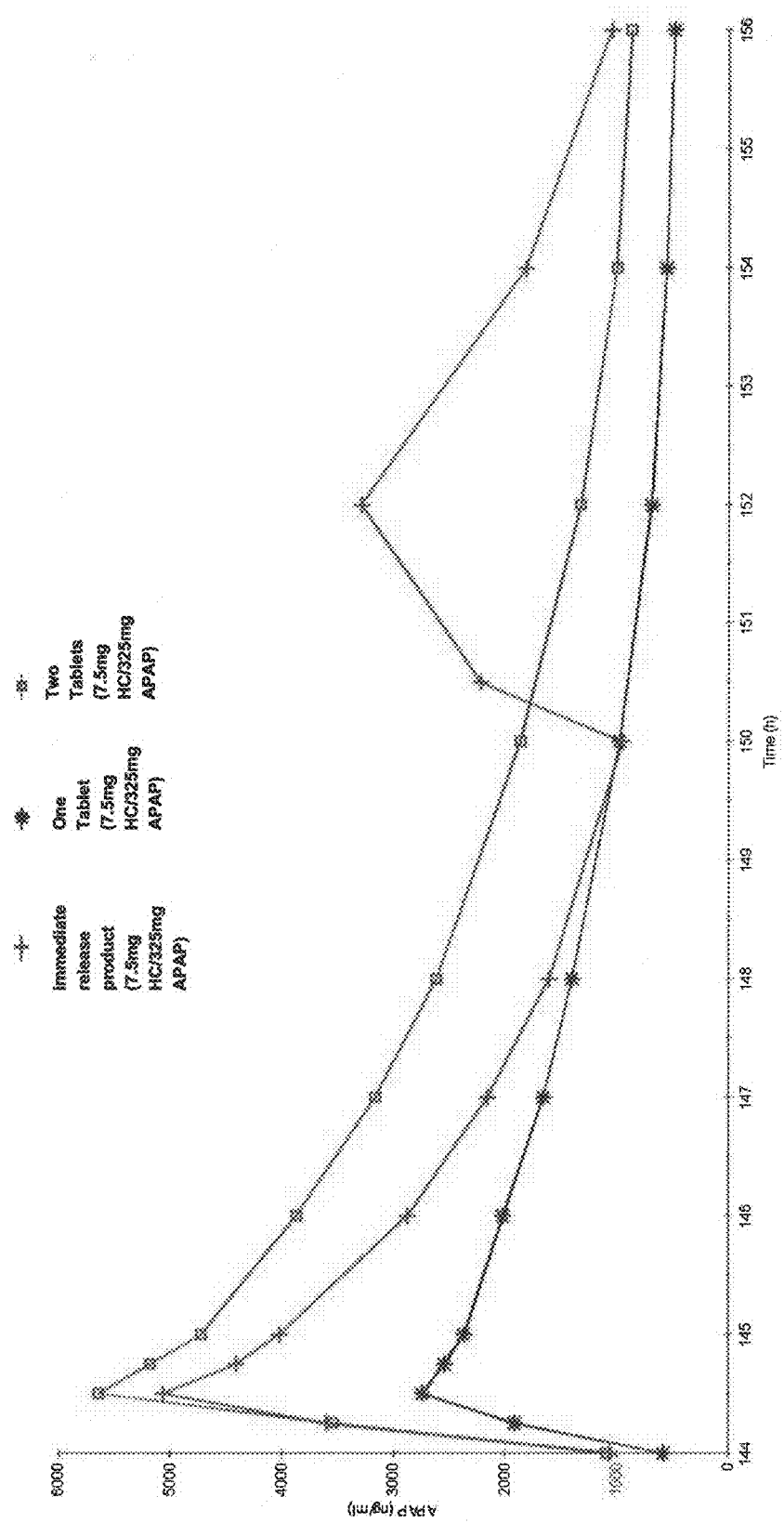

FIG. 42 presents mean plasma concentrations of acetaminophen as a function of time by treatment following oral administration of multiple doses of Treatments A, B, and C of Example 18.

Figure 43:
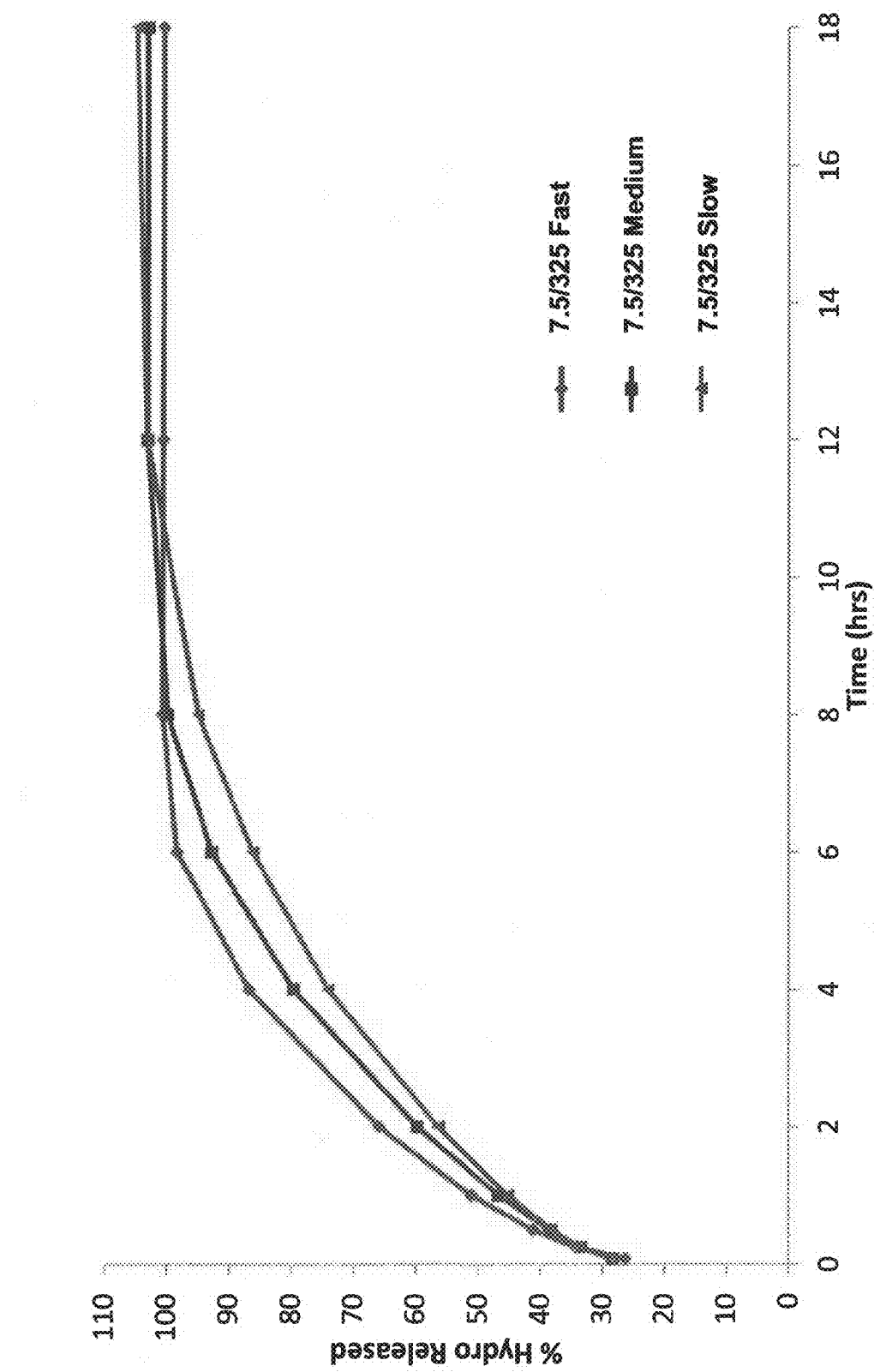

FIG. 43 presents dissolution data for the release of hydrocodone from fast-release, medium-release, and slow-release pharmaceutical compositions containing 7.5 mg hydrocodone and 325 acetaminophen.

Figure 44:
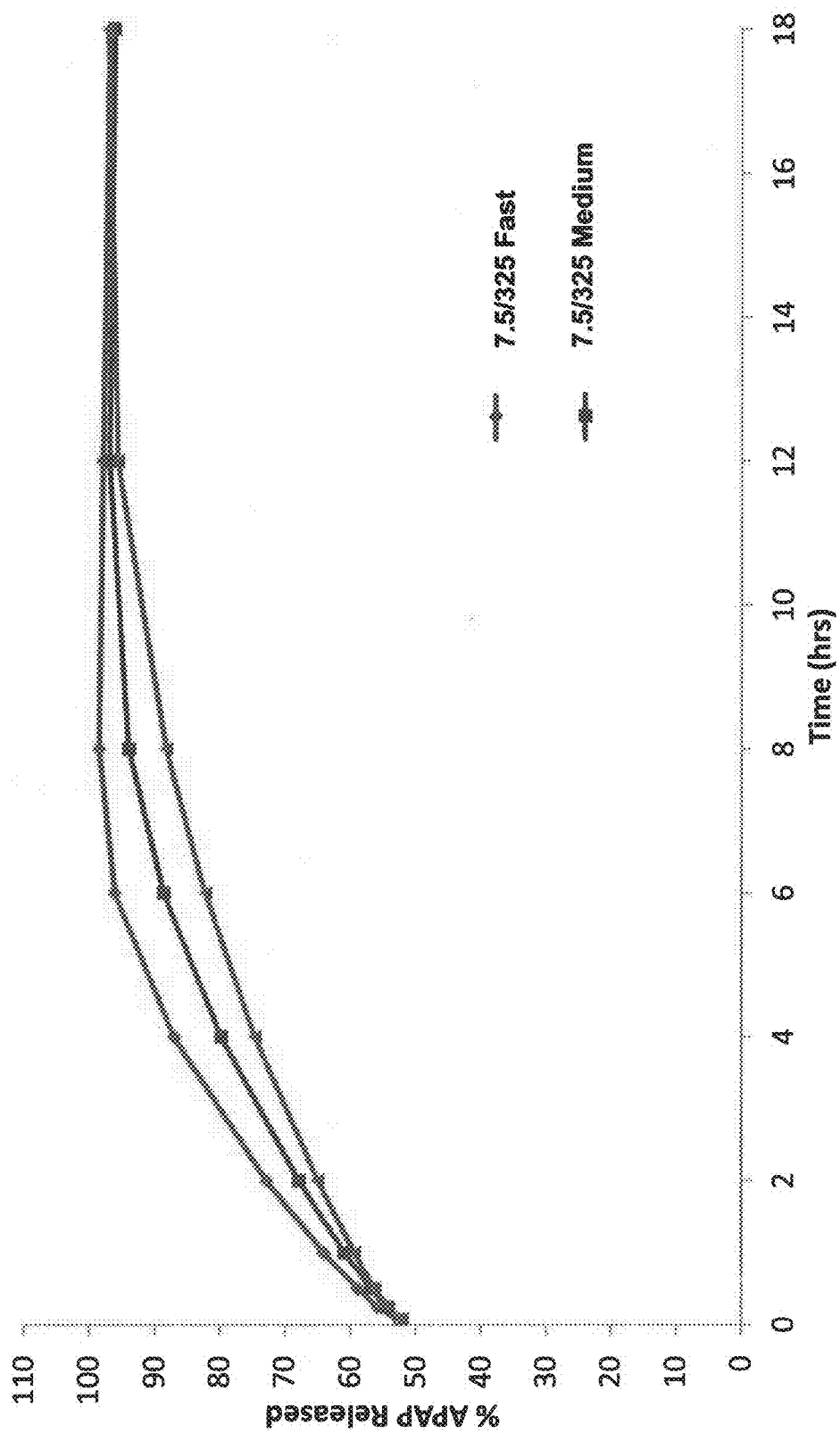

FIG. 44 presents dissolution data for the release of acetaminophen from fast-release, medium-release, and slow-release pharmaceutical compositions containing 7.5 mg hydrocodone and 325 acetaminophen.

Figure 45:
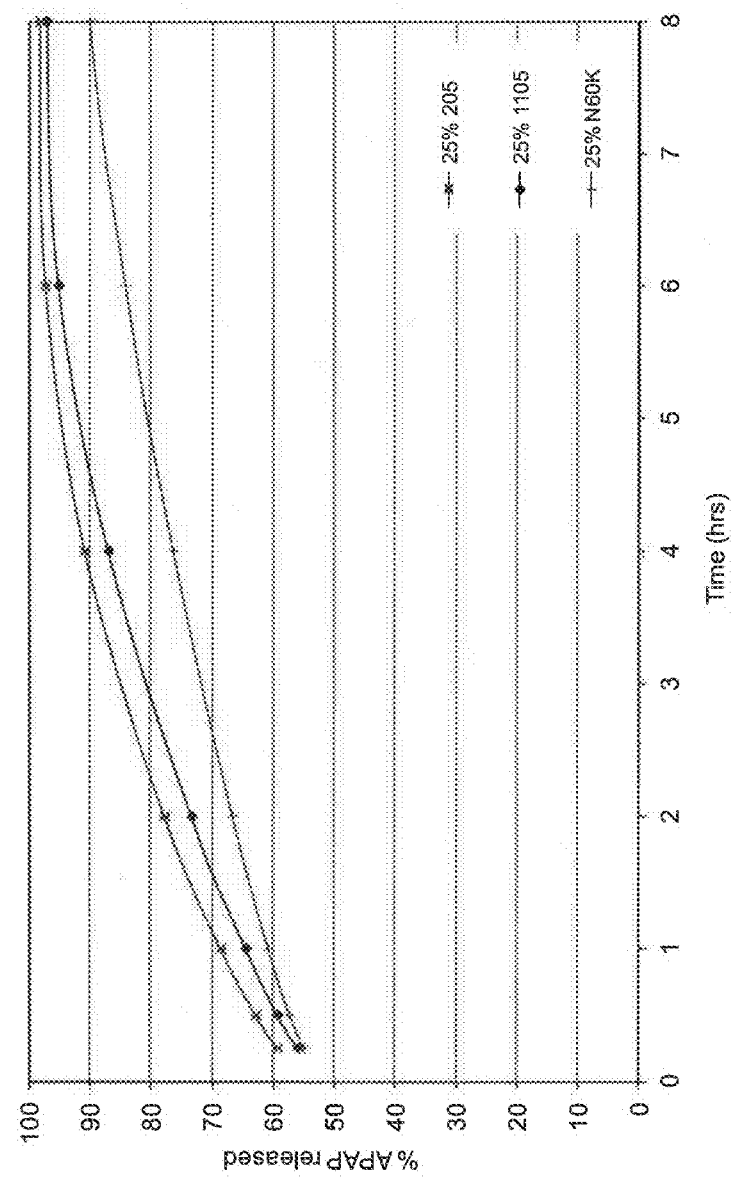

FIG. 45 presents acetaminophen dissolution data for three pharmaceutical formulations described herein. Each formulation tablet contained a total of 9 mg oxycodone HCl and a total of 250 mg acetaminophen. The ER portions of the three pharmaceutical formulations contained 25% by weight POLYOX® 205, 1105, and N-60K, respectively.

Figure 46:
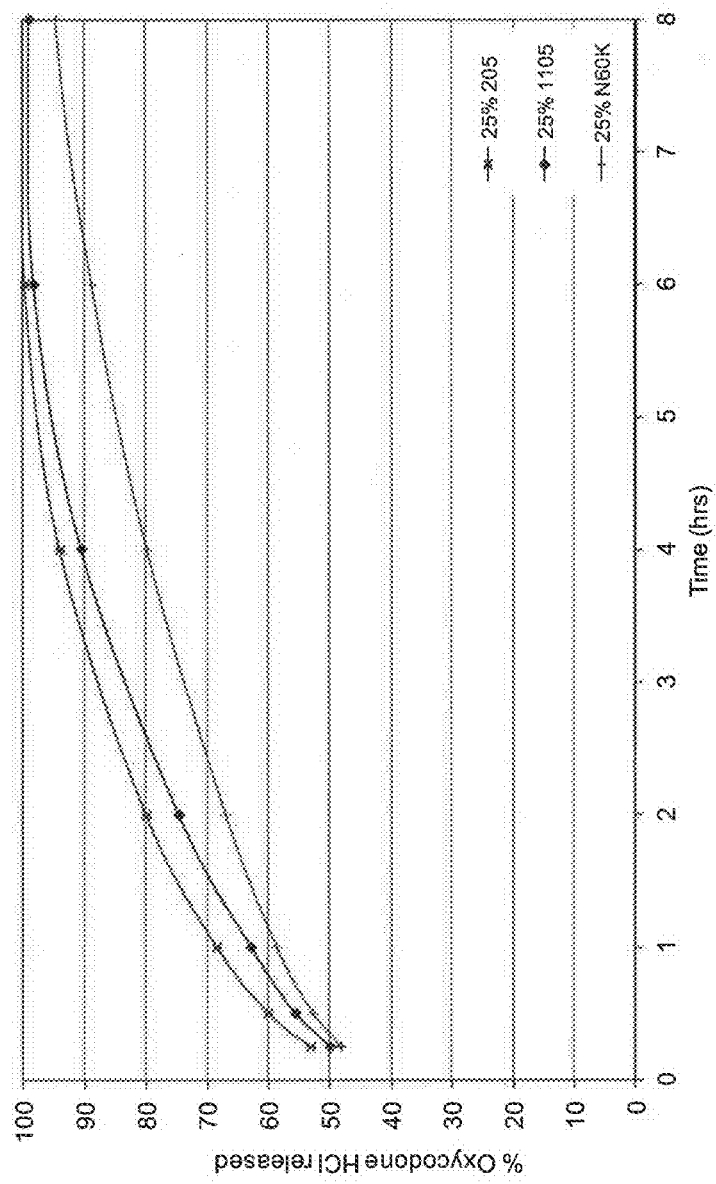

FIG. 46 presents oxycodone HCl dissolution data for the three pharmaceutical formulations described in FIG. 45.

Figure 47:
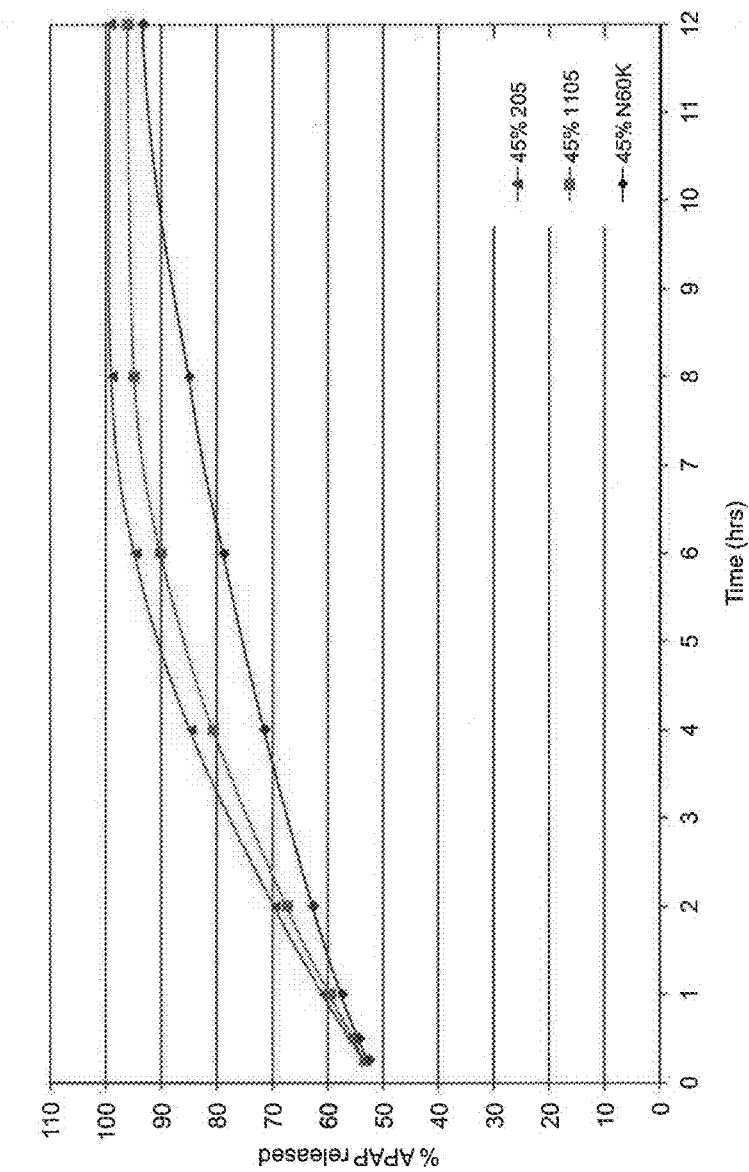

FIG. 47 presents acetaminophen dissolution data for three pharmaceutical formulations described herein. Each formulation tablet contained a total of 9 mg oxycodone HCl and a total of 250 mg acetaminophen. The ER portions of the three pharmaceutical formulations contained 45% by weight POLYOX® 205, 1105, and N-60K, respectively.

Figure 48:
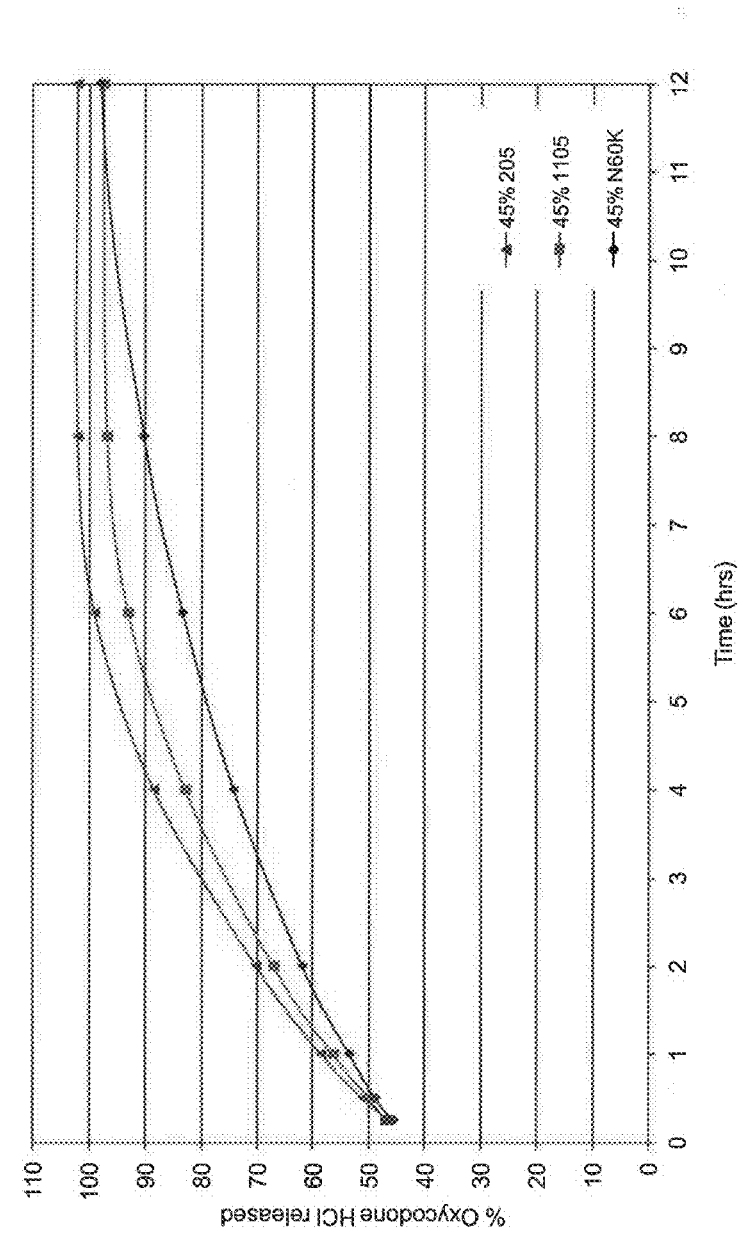

FIG. 48 presents oxycodone HCl dissolution data for the three pharmaceutical formulations described in FIG. 47.

Figure 49:
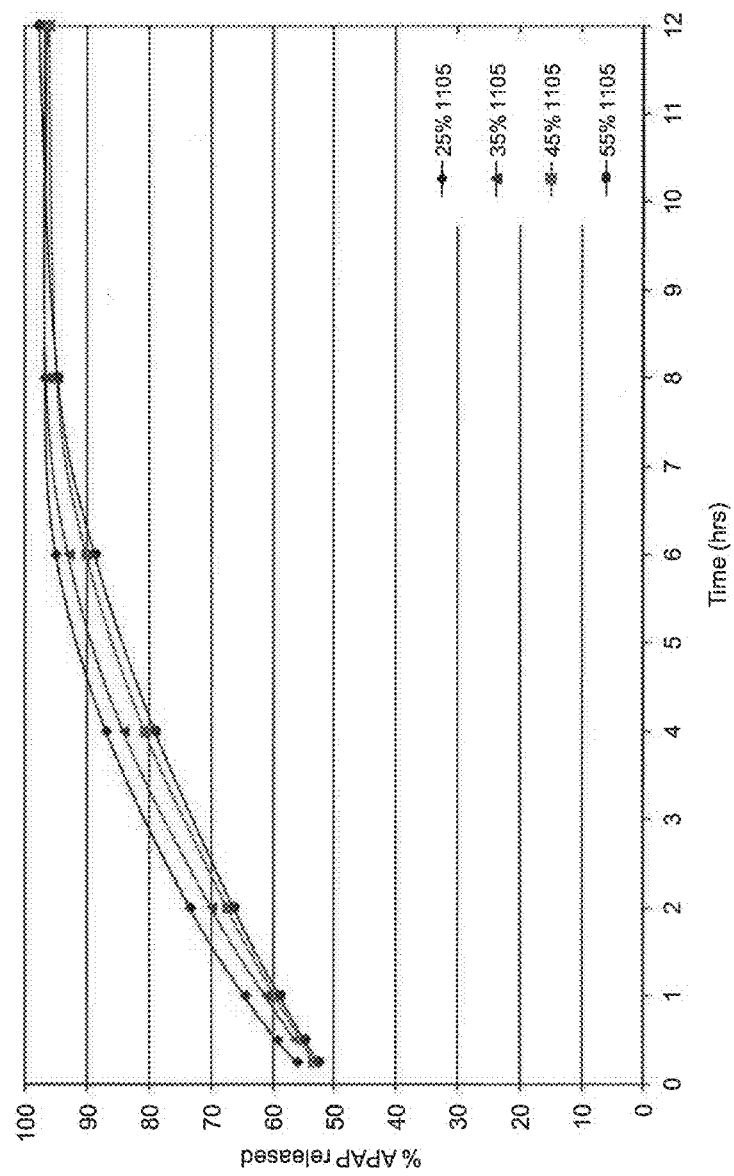

FIG. 49 presents acetaminophen dissolution data for four pharmaceutical formulations described herein. Each formulation tablet contained a total of 9 mg oxycodone HCl and a total of 250 mg acetaminophen. The ER portions of the four pharmaceutical compositions contained 25% by weight, 35% by weight, 45% by weight, and 55% by weight POLYOX® 1105, respectively.

Figure 50:
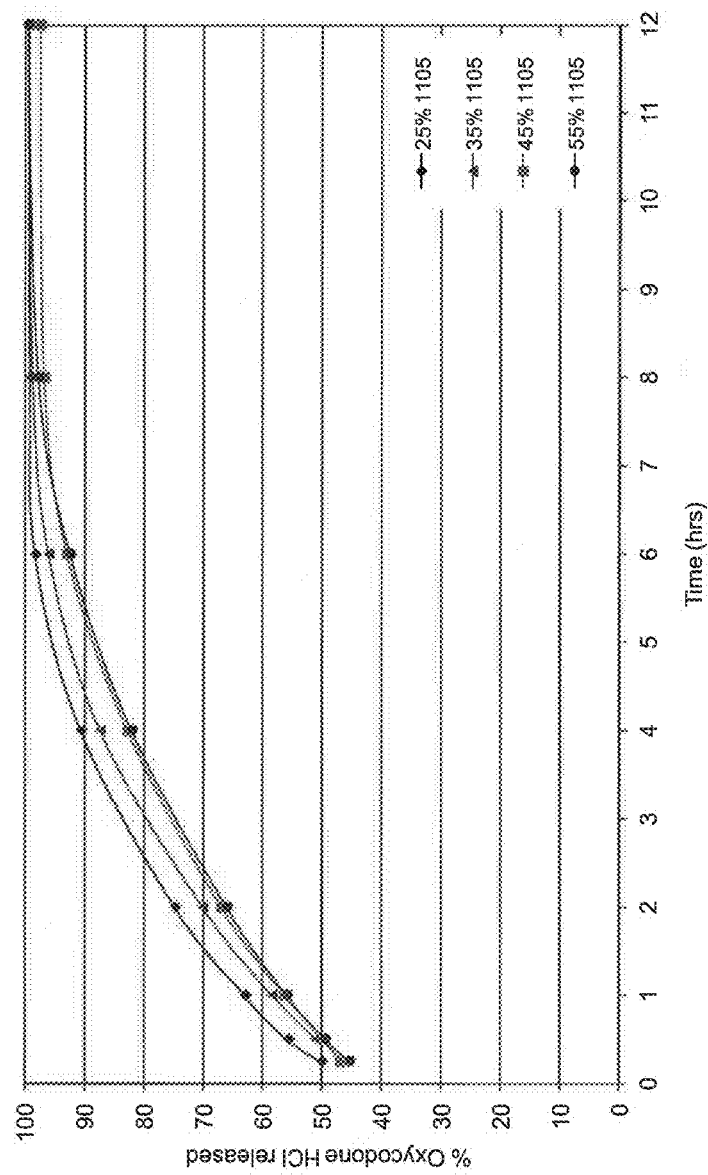

FIG. 50 presents oxycodone HCl dissolution data for the four pharmaceutical formulations described in FIG. 49.

Figure 51:
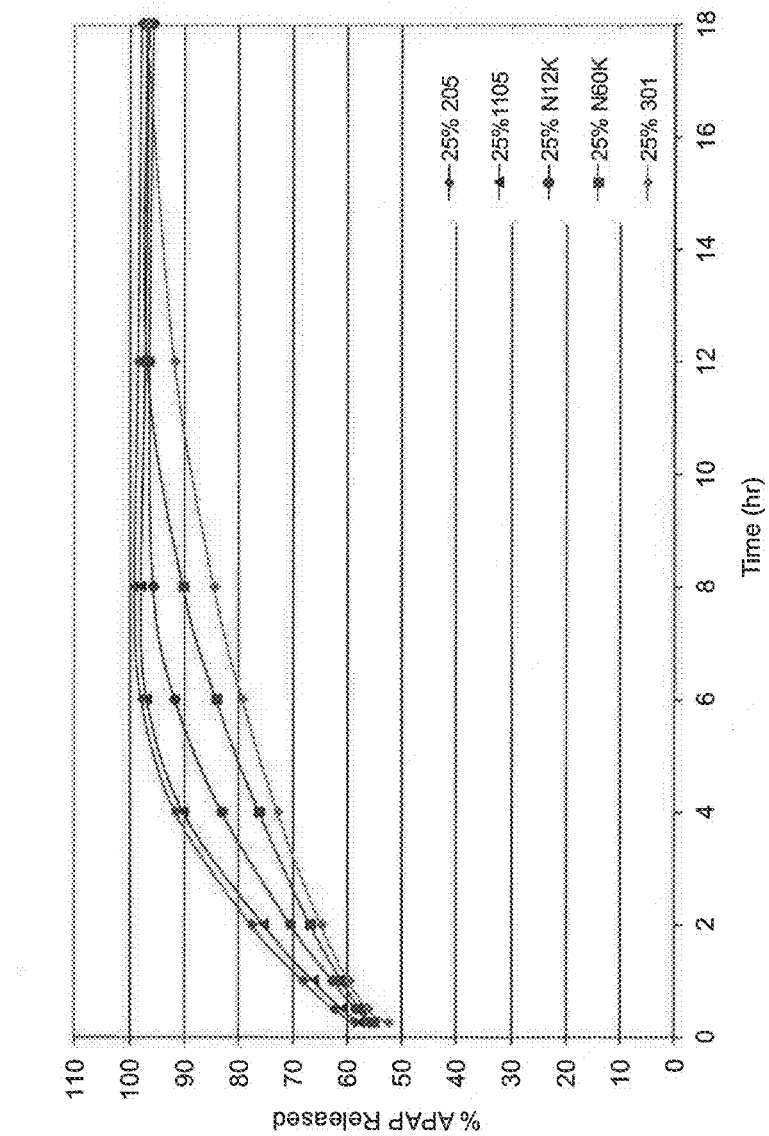

FIG. 51 presents acetaminophen dissolution data for five pharmaceutical formulations described herein. Each formulation tablet contained a total of 15 mg hydrocodone bitartrate HCl and a total of 500 mg acetaminophen. The ER portions of the five pharmaceutical formulations contained 25% by weight POLYOX® 205, 1105, N-12K, N-60K, and 301 respectively.

Figure 52:
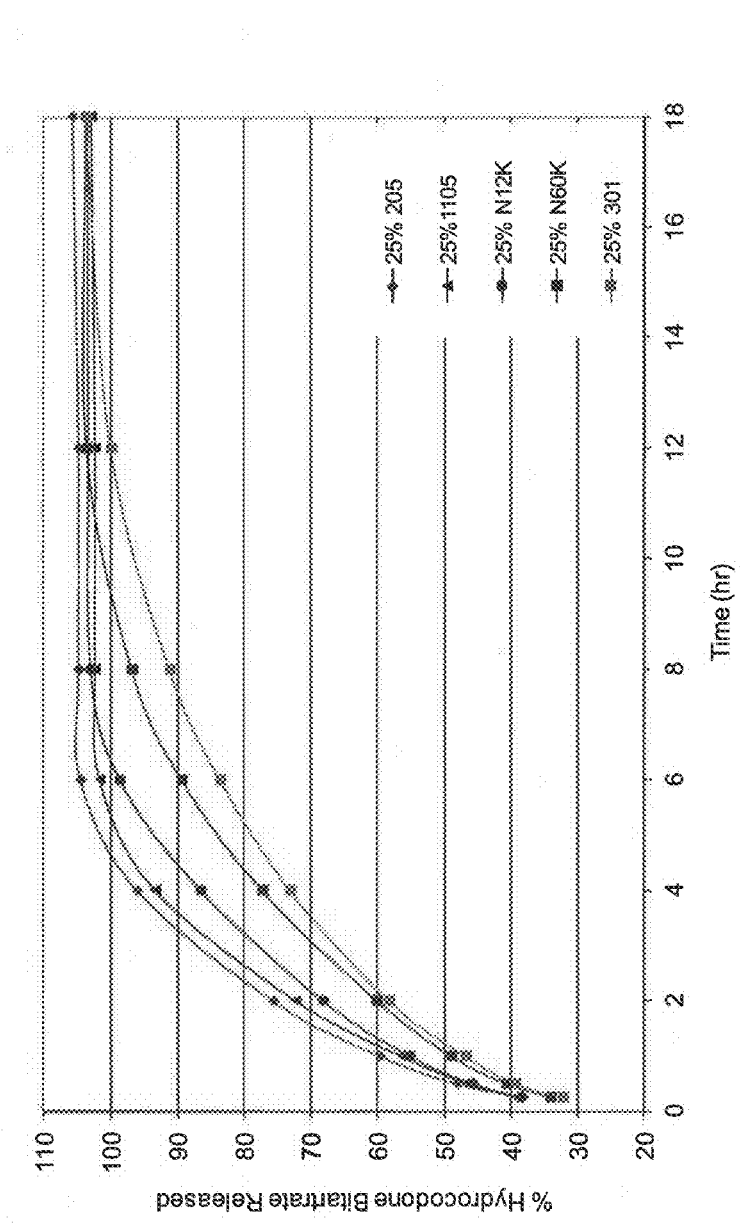

FIG. 52 presents hydrocodone bitartrate dissolution data for the five pharmaceutical formulations described in FIG. 51.

Figure 53:
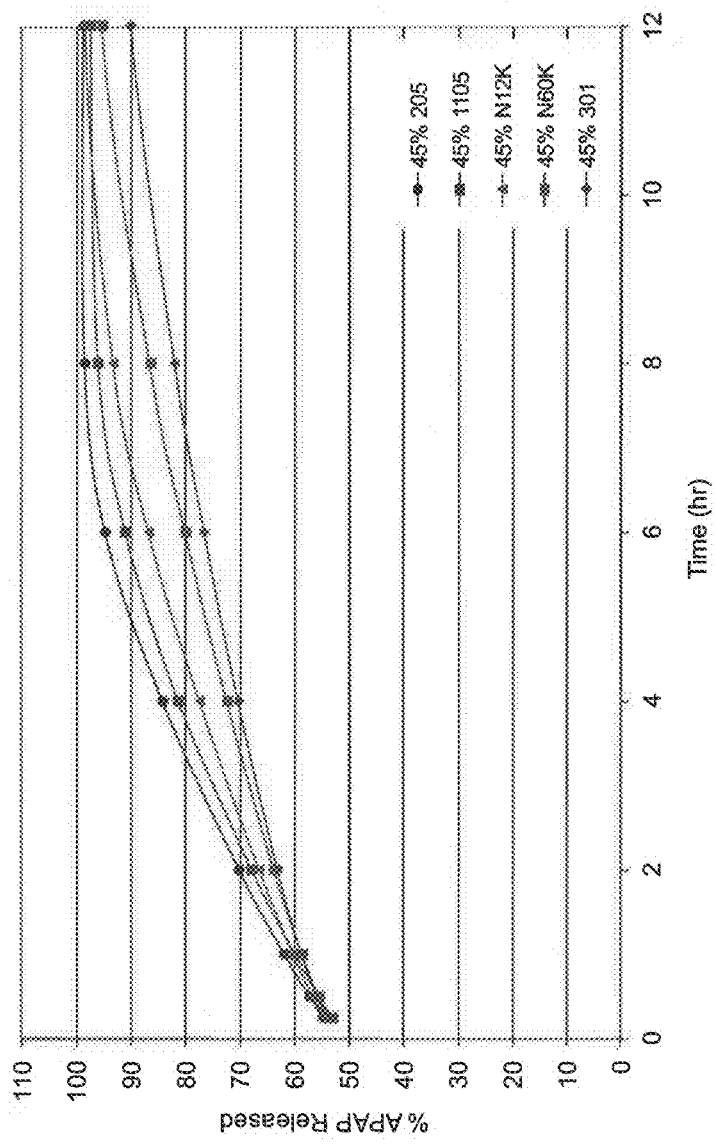

FIG. 53 presents acetaminophen dissolution data for five pharmaceutical formulations described herein. Each formulation tablet contained a total of 15 mg hydrocodone bitartrate and a total of 500 mg acetaminophen. The ER portions of the five pharmaceutical formulations contained 45% by weight POLYOX® 205, 1105, N-12K, N-60K, and 301 respectively.

Figure 54:
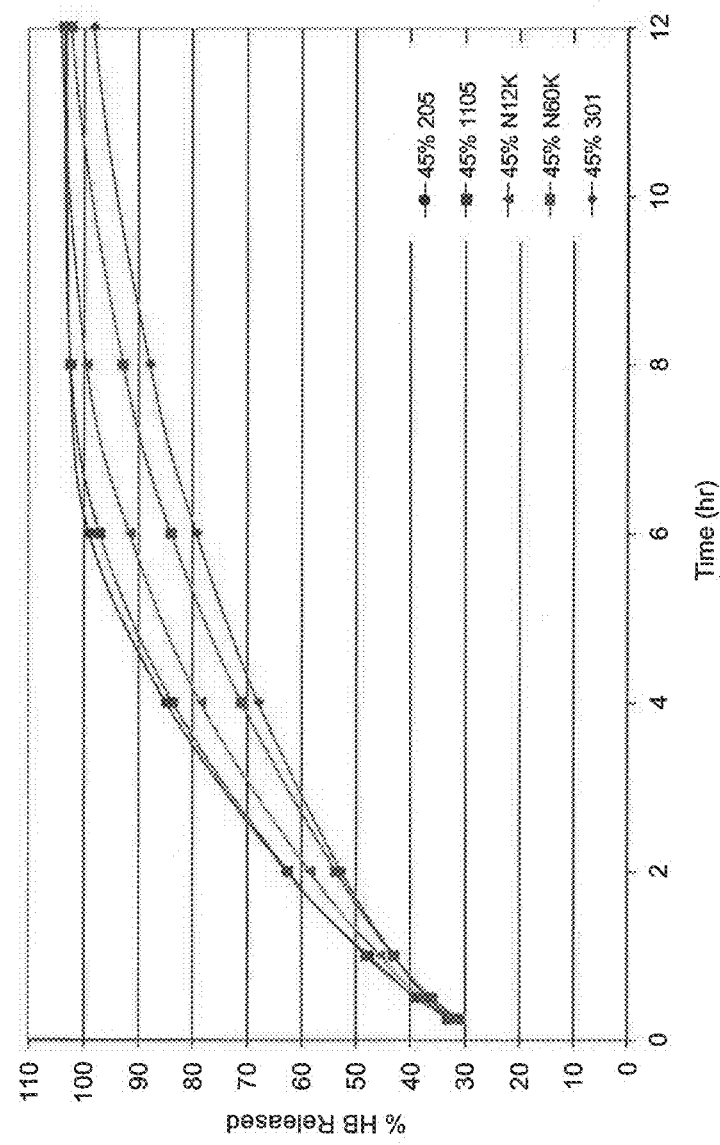

FIG. 54 presents hydrocodone bitartrate dissolution data for the five pharmaceutical formulations described in FIG. 53.

Figure 55:
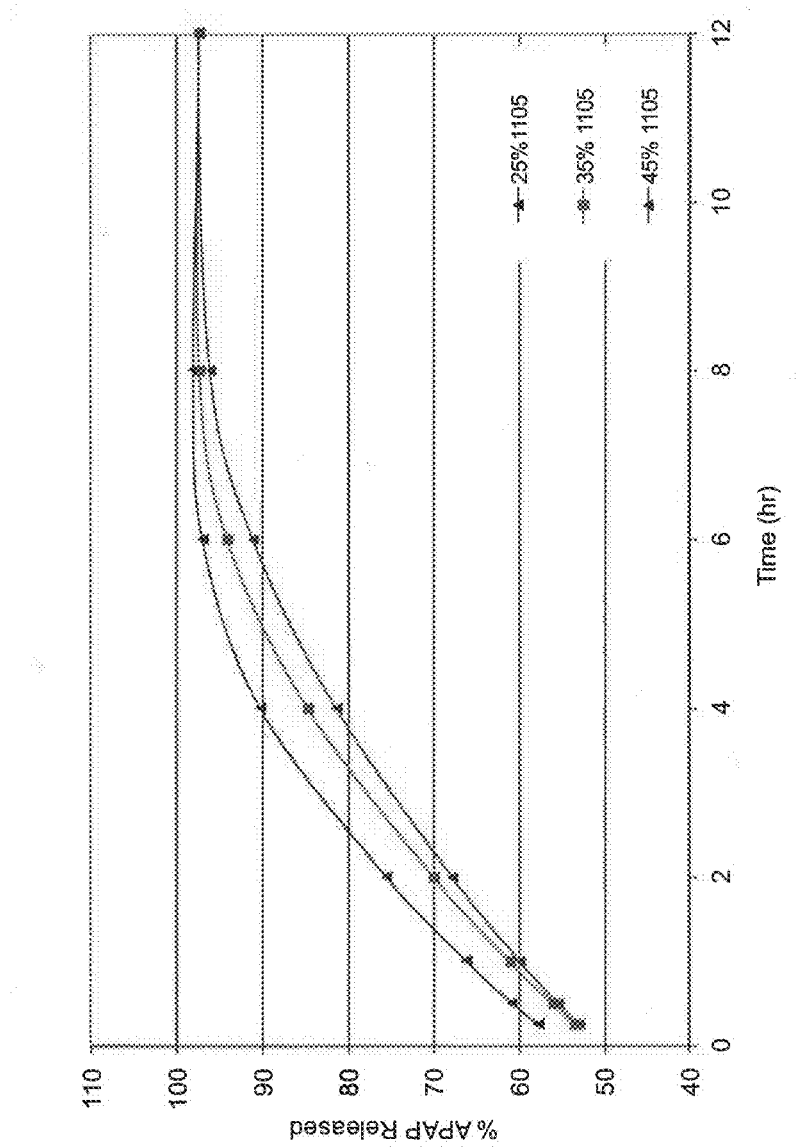

FIG. 55 presents acetaminophen dissolution data for three pharmaceutical formulations described herein. Each formulation tablet contained a total of 15 mg hydrocodone bitartrate and a total of 500 mg acetaminophen. The ER portions of the three pharmaceutical formulations contained 25% by weight, 35% by weight, and 45% by weight POLYOX® 1105, respectively.

Figure 56:
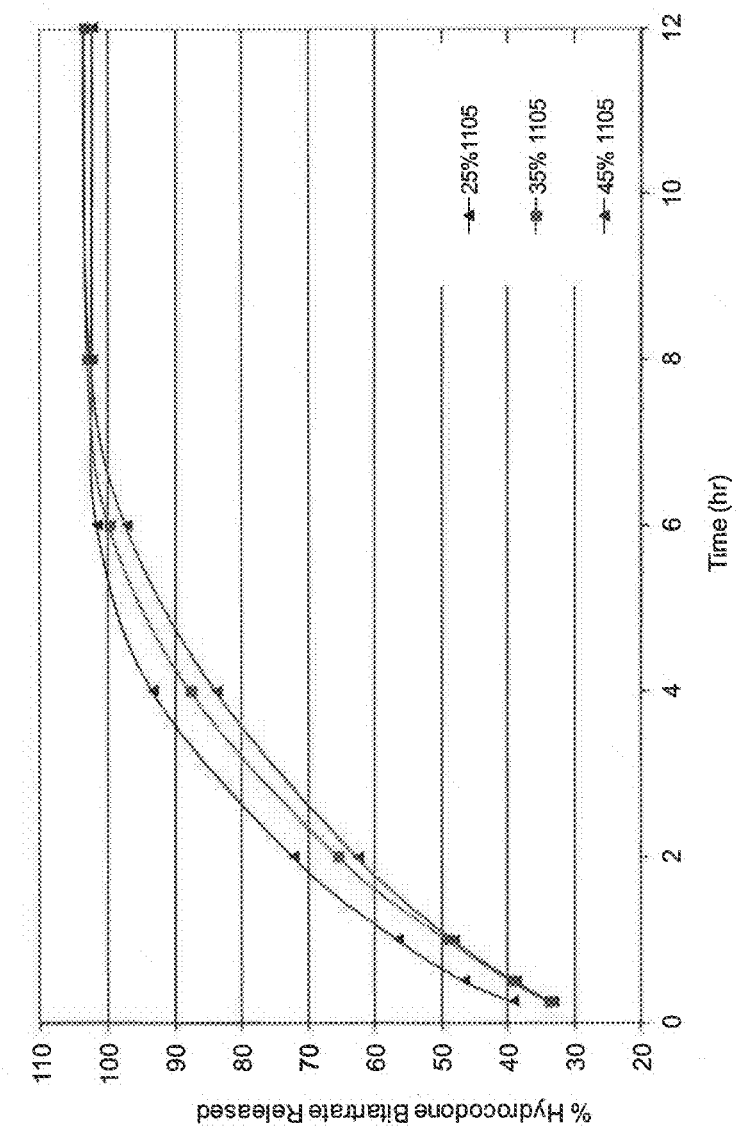

FIG. 56 presents hydrocodone bitartrate dissolution data for the three pharmaceutical formulations described in FIG. 55.

Figure 57:
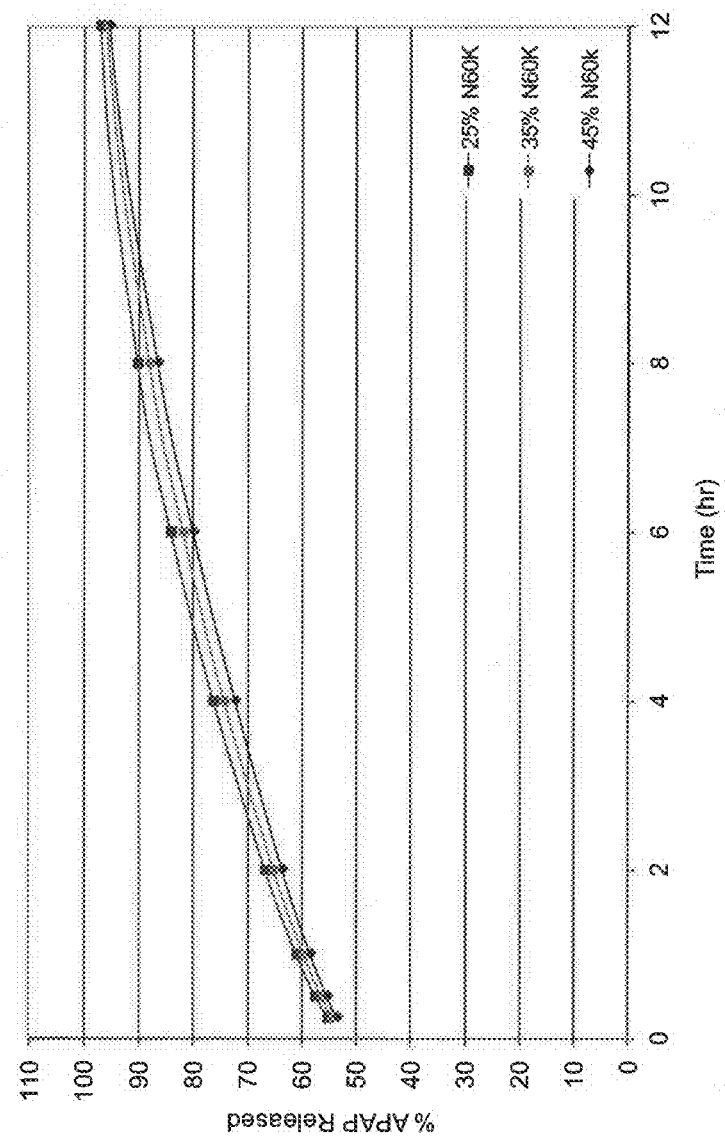

FIG. 57 presents acetaminophen dissolution data for three pharmaceutical formulations described herein. Each formulation tablet contained a total of 15 mg hydrocodone bitartrate and a total of 500 mg acetaminophen. The ER portions of the three pharmaceutical formulations contained 25% by weight, 35% by weight, and 45% by weight POLYOX® N-60K, respectively.

Figure 58:
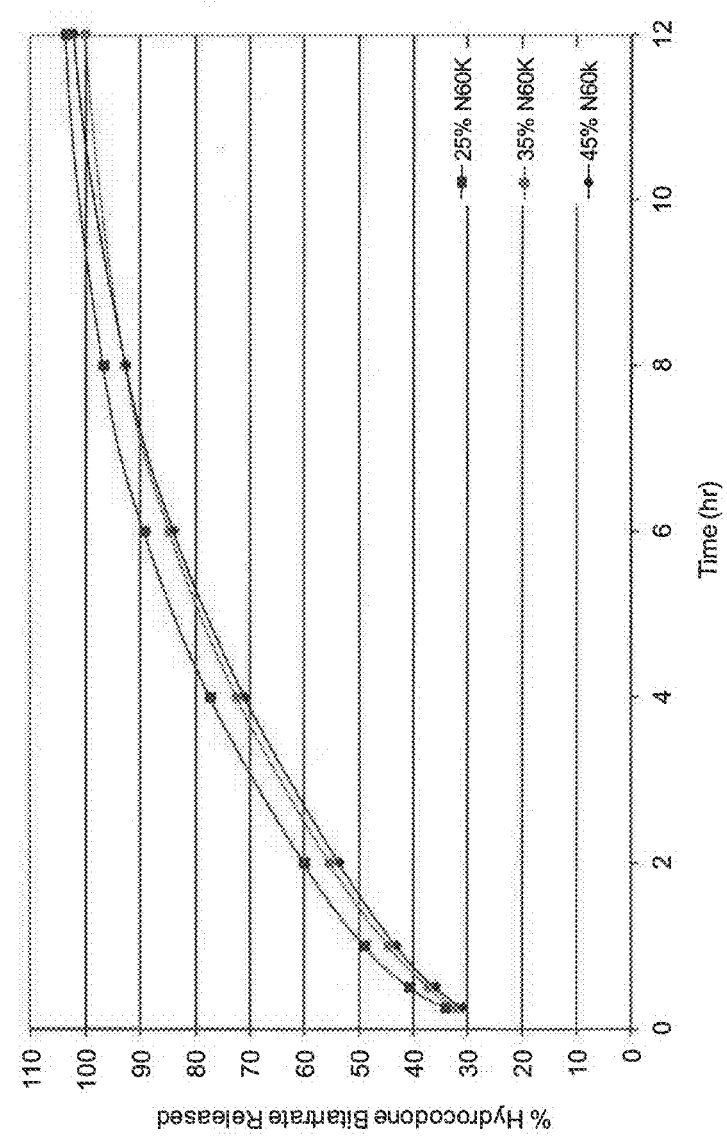

FIG. 58 presents hydrocodone bitartrate dissolution data for the three pharmaceutical formulations described in FIG. 57.

Figure 59:
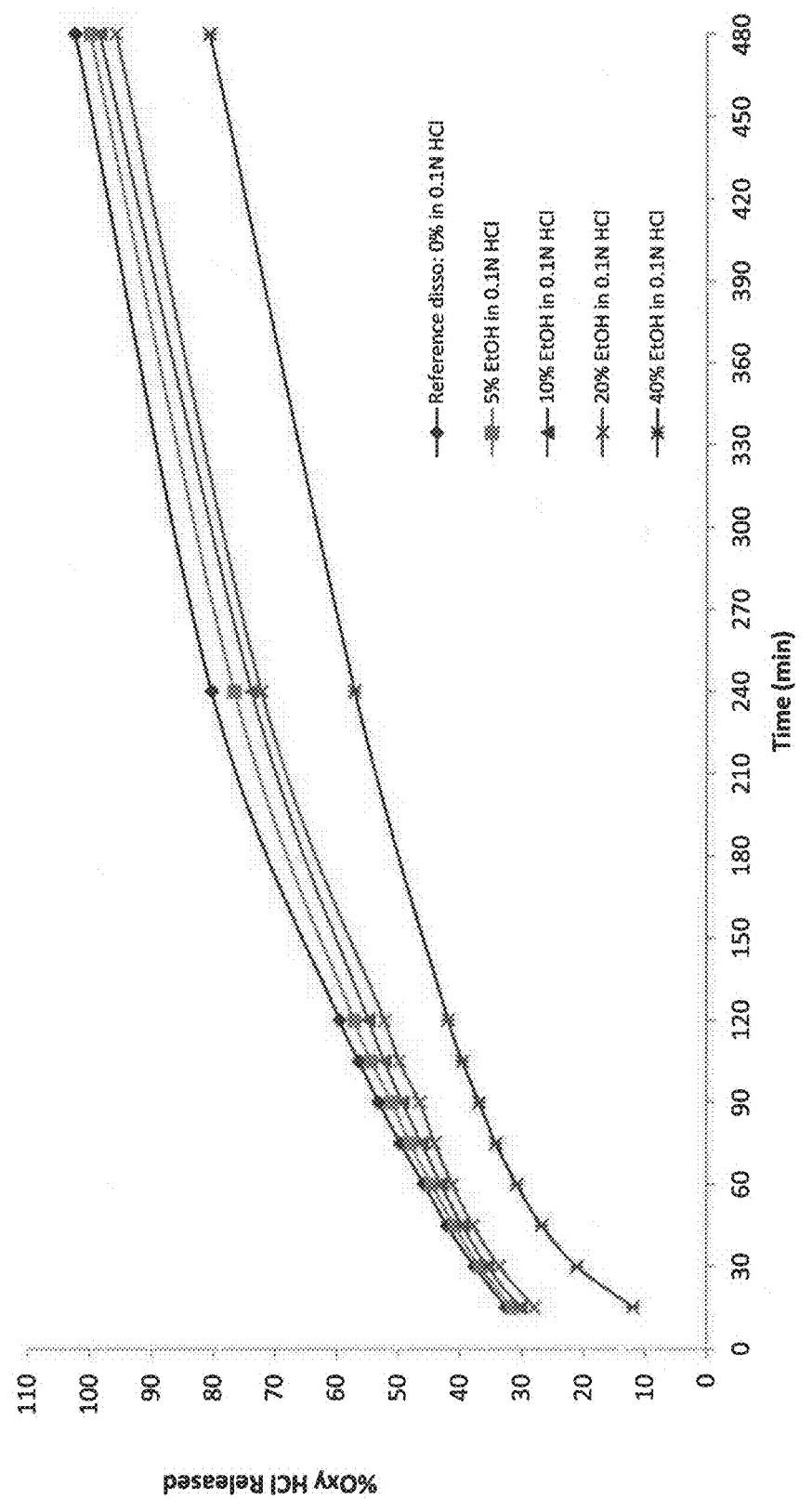

FIG. 59 presents the in vitro release of oxycodone from a bilayer tablet comprising 7.5 mg of oxycodone/325 mg of acetaminophen tested in 0.1 N HCl at a paddle speed of 100 rpm containing 0%, 5%, 20%, or 40% ethanol. Plotted is the percent of oxycodone released over a period of 8 hours.

Figure 60:
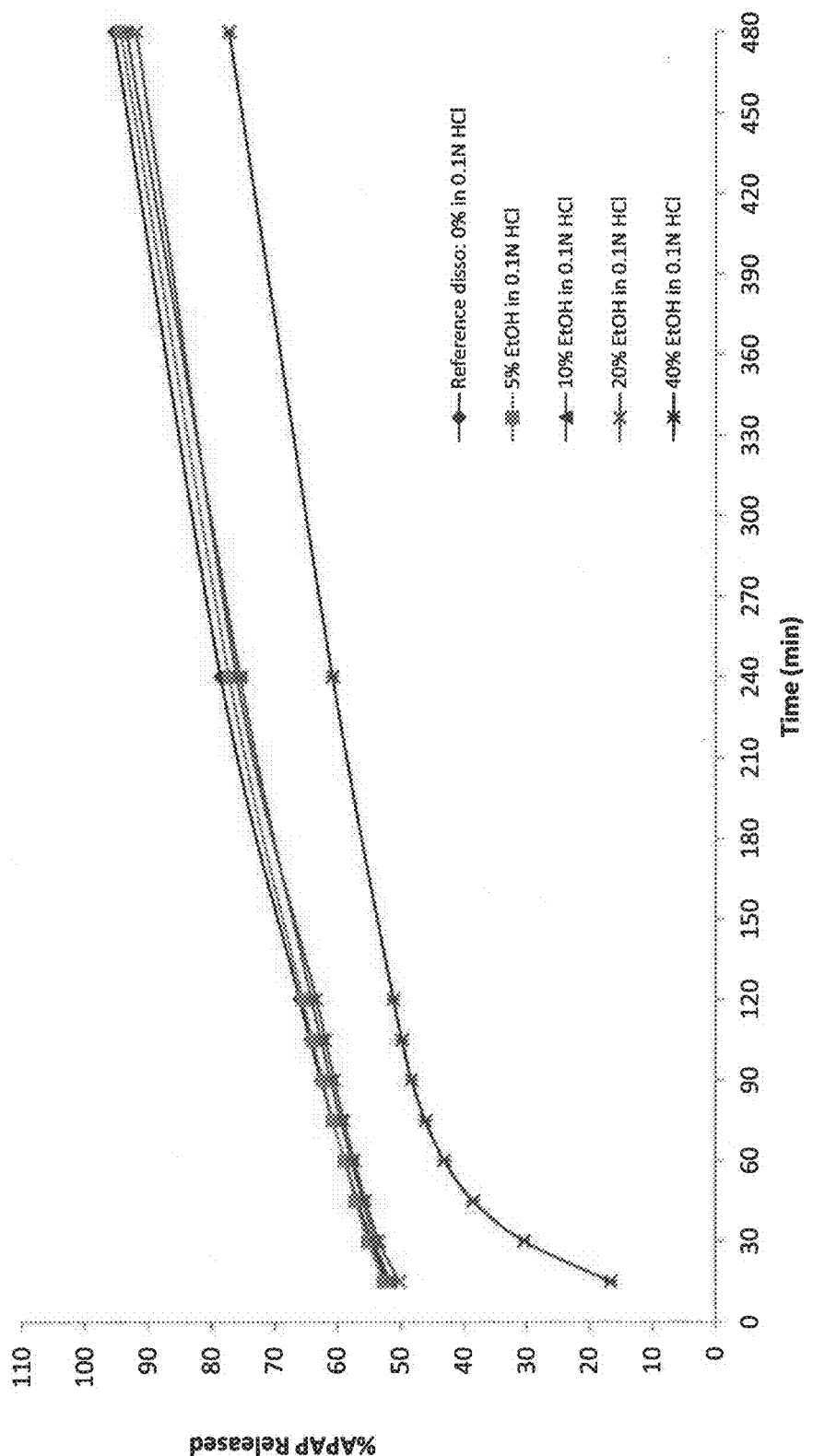

FIG. 60 presents the in vitro release of acetaminophen from a bilayer tablet comprising 7.5 mg of oxycodone/325 mg of acetaminophen tested in 0.1 N HCl at a paddle speed of 100 rpm containing 0%, 5%, 20%, or 40% ethanol. Plotted is the percent of acetaminophen released over a 8 hour period.

DETAILED DESCRIPTION OF THE INVENTION

Disclosed herein is a gastric retentive extended release pharmaceutical composition comprising at least one opioid wherein gastric retention of the composition is achieved by a combination of a physical property of the composition and release of the opioid. In particular, the opioid is released at a rate that is sufficient to delay gastric emptying but insufficient to cause serious adverse gastrointestinal effects. Because gastric retention of the composition is aided by release of the opioid, oral administration of the composition is independent of food intake. That is, the composition may be administered to a subject in either a fed state or a fasted state. It was discovered that, upon oral administration to a subject, the composition produces a plasma profile characterized by at least one pharmacokinetic parameter that differs by less than about 30% when the subject is in a fasted state as compared to a fed state. The food independence of this gastric retentive composition increases the convenience of administration of the composition in that it may be administered with or without food. Moreover, this property of the composition increases patient/subject compliance. The present disclosure also provides methods for administering the gastric retentive extended release composition disclosed herein, wherein the composition may be administered to a subject without regard to meals.

Headings included herein are simply for ease of reference, and are not intended to limit the disclosure in any way.

I. Definitions

Compounds useful in the compositions and methods include those described herein in any of their pharmaceutically acceptable forms, including isomers such as diastereomers and enantiomers, salts, solvates, and polymorphs, as well as racemic mixtures and pure isomers of the compounds described herein, where applicable.

When introducing elements of the various embodiment(s) of the present disclosure, the articles "a", "an", "the" and "said" are intended to mean that there are one or more of the elements. The terms "comprising", "including" and "having" are intended to be inclusive and mean that there may be additional elements other than the listed elements.

The use of individual numerical values are stated as approximations as though the values were preceded by the word "about" or "approximately." Similarly, the numerical values in the various ranges specified in this application, unless expressly indicated otherwise, are stated as approximations as though the minimum and maximum values within the stated ranges were both preceded by the word "about" or "approximately." In this manner, variations above and below the stated ranges can be used to achieve substantially the same results as values within the ranges. As used herein, the terms "about" and "approximately" when referring to a numerical value shall have their plain and ordinary meanings to a person of ordinary skill in the art to which the disclosed subject matter is most closely related or the art relevant to the range or element at issue. The amount of broadening from the strict numerical boundary depends upon many factors. For example, some of the factors which may be considered include the criticality of the element and/or the effect a given amount of variation will have on the performance of the claimed subject matter, as well as other considerations known to those of skill in the art. As used herein, the use of differing amounts of significant digits for different numerical values is not meant to limit how the use of the words "about" or "approximately" will serve to broaden a particular numerical value or range. Thus, as a general matter, "about" or "approximately" broaden the numerical value. Also, the disclosure of ranges is intended as a continuous range including every value between the minimum and maximum values plus the broadening of the range afforded by the use of the term "about" or "approximately." Consequently, recitation of ranges of values herein are merely intended to serve as a shorthand method of referring individually to each separate value falling within the range, unless otherwise indicated herein, and each separate value is incorporated into the specification as if it were individually recited herein.

The term "abuse quotient" for a pharmaceutical composition as used herein is the numerical value obtained via dividing the Cmax for a drug by the Tmax for the same drug. Generally speaking, the abuse quotient provides a means for predicting the degree of addictiveness of a given pharmaceutical composition. Pharmaceutical compositions with lower abuse quotients typically are less addictive compared to pharmaceutical compositions with higher abuse quotients.

The term "active agent" or "drug" is used herein to refer to any chemical that elicits a biochemical response when administered to a human or an animal. The drug may act as a substrate or product of a biochemical reaction, or the drug may interact with a cell receptor and elicit a physiological response, or the drug may bind with and block a receptor from eliciting a physiological response.

The term "bioequivalent," as used herein, refers to two compositions, products or methods where the 90% Confidence Intervals (CI) for AUC, partial AUC and Cmax are between 0.80 to 1.25.

The term "bulk density," as used herein, refers to a property of powders and is defined as the mass of many particles of the material divided by the total volume they occupy. The total volume includes particle volume, interparticle void volume and internal pore volume.

The term "content uniformity," as used herein refers to the testing of compressed tablets to provide an assessment of how uniformly the micronized or submicron active ingredient is dispersed in the powder mixture. Content uniformity is measured by use of USP Method (General Chapters, Uniformity of Dosage Forms), unless otherwise indicated. A plurality refers to five, ten or more tablet compositions.

The term "friability," as used herein, refers to the ease with which a tablet will break or fracture. The test for friability is a standard test known to one skilled in the art. Friability is measured under standardized conditions by weighing out a certain number of tablets (generally 20 tablets or less), placing them in a rotating Plexiglas drum in which they are lifted during replicate revolutions by a radial lever, and then dropped approximately 8 inches. After replicate revolutions (typically 100 revolutions at 25 rpm), the tablets are reweighed and the percentage of composition abraded or chipped is calculated.

The term "ER" as used herein refers to extended release. The phrases "extended release layer," "ER layer," "ER portion," and "extended release portion" are used interchangeably in this document. Further, as used herein the "extended release layer," "ER layer," "ER portion," and "extended release portion" can be either (i) a discrete part(s) of the pharmaceutical composition, (ii) integrated within the pharmaceutical composition, or (iii) a combination thereof.

The term "IR" as used herein refers to immediate release. The phrases "immediate release layer," "IR layer," "IR portion" and "immediate release portion" are used interchangeable in this document. In addition, as used herein the "immediate release layer," "IR layer," "IR portion" and "immediate release portion" can be either (i) a discrete part(s) of the pharmaceutical composition, (ii) integrated within the pharmaceutical composition, or (iii) a combination thereof.

The term "half life" as used herein refers to the time required for a drug's blood or plasma concentration to decrease by one half. This decrease in drug concentration is a reflection of its excretion or elimination after absorption is complete and distribution has reached an equilibrium or quasi equilibrium state. The half life of a drug in the blood may be determined graphically off of a pharmacokinetic plot of a drug's blood-concentration time plot, typically after intravenous administration to a sample population. The half life can also be determined using mathematical calculations that are well known in the art. Further, as used herein the term "half life" also includes the "apparent half-life" of a drug. The apparent half life may be a composite number that accounts for contributions from other processes besides elimination, such as absorption, reuptake, or enterohepatic recycling.

"Optional" or "optionally" means that the subsequently described element, component or circumstance may or may not occur, so that the description includes instances where the element, component, or circumstance occurs and instances where it does not.

"Partial AUC" means an area under the drug concentration-time curve (AUC) calculated using linear trapezoidal summation for a specified interval of time, for example, $AUC_{(0-1hr)}$, $AUC_{(0-2hr)}$, $AUC_{(0-4hr)}$, $AUC_{(0-6hr)}$, $AUC_{(0-8hr)}$, $AUC_{(0-(Tmax\ of\ IR\ product+2SD))}$, $AUC_{(0-(x)hr)}$, $AUC_{(x-yhr)}$, $AUC_{(Tmax-t)}$, $AUC(0-(t)hr)$, $AUC_{(Tmax\ of\ IR\ product+2SD)-t)}$, or $AUC_{(0-\infty)}$.

A drug "release rate," as used herein, refers to the quantity of drug released from a dosage form or pharmaceutical composition per unit time, e.g., milligrams of drug released per hour (mg/hr). Drug release rates for drug dosage forms are typically measured as an in vitro rate of dissolution, i.e., a quantity of drug released from the dosage form or pharmaceutical composition per unit time measured under appropriate conditions and in a suitable fluid. The specific results of dissolution tests claimed herein are performed on dosage forms or pharmaceutical compositions immersed in 900 mL of 0.1 N HCl using a USP Type II apparatus at a paddle speed of either about 100 rpm or about 150 rpm and a constant temperature of about 37° C. Suitable aliquots of the release rate solutions are tested to determine the amount of drug released from the dosage form or pharmaceutical composition. For example, the drug can be assayed or injected into a chromatographic system to quantify the amounts of drug released during the testing intervals.

The terms "subject" or "patient" are used interchangeably herein and refer to a vertebrate, preferably a mammal. Mammals include, but are not limited to, humans.

The term "tap density" or "tapped density," as used herein, refers to a measure of the density of a powder. The tapped density of a pharmaceutical powder is determined using a tapped density tester, which is set to tap the powder at a fixed impact force and frequency. Tapped density by the USP method is determined by a linear progression of the number of taps.

II. Gastric Retentive Extended Release Compositions

The present disclosure provides gastric retentive, extended release compositions comprising at least one opioid and at least one other active pharmaceutical ingredient (API) that is preferably absorbed in the upper gastrointestinal tract. In general, the gastric retentive, extended release composition comprises at least one extended release portion. The extended release portion(s) may comprise at least one opioid, at least one API, or combinations thereof. The gastric retentive, extended release composition disclosed herein may further comprise at least one immediate release portion. The immediate release portion(s) may comprise at least one opioid, at least one other API, or combinations thereof.

(a) Active Agents

The gastric retentive, extended release composition disclosed herein comprises at least one opioid and at least one additional API, each of which is discussed in more detail below. In one embodiment, the same opioid or combination of opioids is present in both the at least one immediate release portion and the at least one extended release portion of the composition; and the same API or combination of APIs is present in both the at least one immediate release portion and the at least one extended release portion of the composition.

(i) Opioids

The opioid(s) useful in the present invention include adulmine, alfentanil, allocryptopine, allylprodine, alphaprodine, anileridine, aporphine, benzylmorphine, berberine, bicuculine, bicucine, bezitramide, buprenorphine, bulbocaprine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, nalorphine, nalbuphene, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propoxyphene, sufentanil, tapentadol, tilidine, tramadol, and pharmaceutical salts of any of the foregoing. In various embodiments, the extended release dosage form may comprise one, two, three, four, or more than four opioids. In another embodiment, the opioid is selected from the group consisting of oxycodone, hydrocodone, tramadol, codeine, and pharmaceutical salts of any of the foregoing. In yet another embodiment, opioid is selected from the group consisting of adulmine, alfentanil, allocryptopine, allylprodine, alphaprodine, anileridine, aporphine, benzylmorphine, berberine, bicuculine, bicucine, bezitramide, buprenorphine, bulbocaprine, butorphanol, clonitazene, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydromorphone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, nalorphine, nalbuphene, normorphine, norpipanone, opium, oxymorphone, papaveretum, pentazocine, phenadoxone, phenomorphan, phenazocine, phenoperidine, piminodine, piritramide, propheptazine, promedol, properidine, propoxyphene, sufentanil, tapentadol, tilidine, and pharmaceutical salts of any of the foregoing. In one embodiment, the extended release dosage form comprises one opioid.

In one embodiment, the composition may comprise from about 1.0 mg to about 500 mg of the opioid. In another embodiment, the composition may comprise from about 1.4 mg to about 400 mg of the opioid. In yet another embodiment, the amount of opioid in the composition may range from about 5 mg to about 300 mg. In still another embodiment, the amount of opioid in the composition may range from about 4 mg to about 30 mg. In another embodiment, the amount of opioid in the composition may range from about 30 mg to about 60 mg. In yet another embodiment, the amount of opioid in the composition may range from about 60 mg to about 120 mg. In an alternate embodiment, the amount of opioid in the composition may range from about 120 mg to about 300 mg. In various embodiments, the amount of opioid in the composition may be about 4 mg, 4.5 mg, 5 mg, 5.5 mg, 6 mg, 6.5 mg, 7 mg, 7.5 mg, 8 mg, 8.5 mg, 9 mg, 9.5 mg, 10 mg, 11 mg, 12 mg, 13 mg, 14 mg, 15 mg, 16 mg, 17 mg, 18 mg, 19 mg, 20 mg, 22 mg, 24 mg, 26 mg, 28 mg, 30 mg, 32 mg, 34 mg, 36 mg, 38 mg, 40 mg, 42 mg, 44 mg, 46 mg, 48 mg, 50 mg, 52 mg, 54 mg, 56 mg, 58 mg, 60 mg, 62 mg, 64 mg, 66 mg, 68 mg, 70 mg, 80 mg, 90 mg, 100 mg, 110 mg, 120 mg, 130 mg, 140 mg, 150 mg, 160 mg, 170 mg, 180 mg, 190 mg, 200 mg, 220 mg, 240 mg, 260 mg, 280 mg, 300 mg, 320 mg, 340 mg, 360 mg, 380 mg, or 400 mg. In one embodiment, the amount of opioid in the composition may range from about 7.5 mg to about 30 mg. In another embodiment, the amount of opioid in the composition may range from about 7.5 mg to about 15 mg. In still another embodiment, the amount of opioid in the composition may range from about 15 mg to about 30 mg.

(ii) Other Active Pharmaceutical Ingredient (API)

The gastric retentive, extended release composition disclosed herein may also comprise at least one other active pharmaceutical ingredient (API). In general, the other API is preferentially absorbed in the upper gastrointestinal tract (GIT). Accordingly, optimal absorption of the API may occur in the upper GIT (i.e., duodenum, jejunum, and ileum of the small intestine), with little or no absorption in the lower GIT (i.e., cecum and colon of the large intestine).

In some embodiments, the other API may be a non-opioid analgesic. Suitable non-opioid analgesics include acetaminophen (also known as paracetamol), acetylsalicylic acid, diclofenac, diflunisol, ibuprofen, indomethacin, ketoprofen, ketorolac, naproxen, mefamanic acid, phenacetin, piroxicam, sulindac, and tolmetin. In other embodiments, the other API may be a steroidal anti-inflammatory agent such as celecoxib, deracoxib, ketoprofen, lumiracoxib, meloxicam, parecoxib, rofecoxib, or valdecoxib. In a further embodiment, the other API may be a steroidal anti-inflammatory agent such as alclometasone, dexamethasone, fluocinonide, hydrocortisone, methylprednisolone, prednisone, prednisolone, or triamcinolone. In further embodiments, the other API may be a norepinephrine transporter modulator such as tapentadol, a tricyclic antidepressant such as amitriptyline, an alpha-2 adrenergic agonist such as clonidine, a calcium channel blocker such as nimodipine, a GABA B agonist such as baclofen, a cannabinoid, a NMDA receptor antagonist, a CCK receptor antagonist, a beta blocker, or a serotonin receptor antagonist. Any of the aforementioned APIs may be in the form of a pharmaceutically acceptable salt. In various embodiments, the at least one extended release portion may comprise one, two, three, four, or more APIs. In one embodiment, one extended release portion may comprise one of the other APIs.

The amount of the other API in the gastric retentive, extended release composition can and will vary. In one embodiment, the composition may comprise from about 1.0 mg to about 1500 mg of the API. In another embodiment, the amount of API in the composition may range from about 100 mg to about 1000 mg. In another embodiment, the amount of API in the composition may range from about 50 mg to about 500 mg. In another embodiment, the amount of API in the composition may range from about 10 mg to about 100 mg. In yet another embodiment, the amount of API in the composition may range from about 1.0 mg to about 10 mg. In one embodiment, the amount of API in the composition may range from about 250 mg to about 1300 mg. In another embodiment, the amount of API in the composition may range from about 325 mg to about 650 mg. In still another embodiment, the amount of API in the composition may range from about 650 mg to about 1300 mg.

(b) Immediate Release Portion

The gastric retentive, extended release composition disclosed herein may comprise at least one immediate release portion. The at least one immediate release portion may comprise at least one opioid, at least one other API, or combinations thereof.

The at least one immediate release portion of the composition is designed to release more than 80%, more than 90%, or essentially all of the opioid(s) and/or the other API(s) in the at least one immediate release portion within about one hour. In one embodiment, more than 80%, more than 90%, or essentially all of the opioid(s) and/or the other API(s) in the at least one immediate release portion may be released in less than about 45 minutes. In another embodiment, more than 80%, more than 90%, or essentially all of the opioid(s) and/or the other API(s) in the at least one immediate release portion may be released in less that about 30 minutes. In a further embodiment, more than 80%, more than 90%, or essentially all of the opioid(s) and/or the other API(s) in the at least one immediate release portion may be released in less than about 20 minutes. In yet another embodiment, more than 80%, more than 90%, or essentially all of the opioid(s) and/or the other API(s) in the at least one immediate release portion may be released in less that about 15 minutes. In an alternate embodiment, more than 80%, more than 90%, or essentially all of the opioid(s) and/or the other API(s) in the at least one immediate release portion may be released in less that about 10 minutes. In yet another embodiment, more than 80%, more than 90%, or essentially all of the opioid(s) and/or the other API(s) in the at least one immediate release portion may be released in less that about 5 minutes.

In some embodiments, the immediate release portion may be part of or homogeneously mixed with the extended release portion.

(i) Opioid(s)

At least one immediate release portion of the gastric retentive, extended release composition may comprise at least one opioid. Suitable opioids are detailed above in section (II)(a)(i). In one embodiment, the opioid may be codeine or a salt thereof. In another embodiment, the opioid may be hydrocodone or a salt thereof. In yet another embodiment, the opioid may be hydromorphone or a salt thereof. In still another embodiment, the opioid may be morphine or a salt thereof. In a further embodiment, the opioid may be oxymorphone or a salt thereof. In an alternate embodiment, the opioid may be tramadol or a salt thereof. In another embodiment, the opioid may be oxycodone or a salt thereof.

The amount of opioid present in the at least one immediate release portion of the composition can and will vary. In one embodiment, the amount of opioid in the at least one immediate release portion may range from about 0.4 mg to about 100 mg. In another embodiment, the amount of opioid in the at least one immediate release portion may range from about 1.25 mg to about 75 mg. In another embodiment, the amount of opioid in the at least one immediate release portion may range from about 1 mg to about 20 mg. In still another embodiment, the amount of opioid in the at least one immediate release portion may range from about 0.5 mg to about 10 mg. In another embodiment, the amount of opioid in the at least one immediate release portion may range from about 7.5 mg to about 15 mg. In yet another embodiment, the amount of opioid in the at least one immediate release portion may range from about 15 mg to about 30 mg. In an alternate embodiment, the amount of opioid in the at least one immediate release portion may range from about 30 mg to about 75 mg. In various embodiments, the amount of opioid in the at least one immediate release portion may be about 1.5 mg, 1.525 mg, 1.55 mg, 1.575 mg, 1.6 mg, 1.625 mg, 1.65 mg, 1.675 mg, 1.7 mg, 1.725 mg, 1.75 mg, 1.775 mg, 1.8 mg, 1.825 mg, 1.85 mg, 1.875 mg, 1.9 mg, 1.925 mg, 1.95 mg, 1.975 mg, 2.0 mg, 2.25 mg, 2.5 mg, 2.75 mg, 3.0 mg, 3.25 mg, 3.5 mg, 3.75 mg, 4.0 mg, 4.25 mg, 4.5 mg, 4.75 mg, 5.0 mg, 5.25 mg, 5.5 mg, 5.75 mg, 6.0 mg, 6.25 mg, 6.5 mg, 6.75 mg, 7.0 mg, 7.25 mg, 7.5 mg, 7.75 mg, 8.0 mg, 8.25 mg, 8.5 mg, 8.75 mg, 9.0 mg, 9.25 mg, 9.5 mg, 9.75 mg, 10.0 mg, 12.5 mg, 15 mg, 16 mg, 17.5 mg, 20 mg, 22.5 mg, 25 mg, 27.5 mg, 30 mg, 40 mg, 75 mg, or 100 mg. In one embodiment, the amount of opioid in the at least one immediate release portion may range from about 1.0 mg and about 2.0 mg, for example, about 1.875 mg. In yet another embodiment, the amount of opioid in the at least one immediate release portion may range from about 2.0 mg and about 3.0 mg, for example, about 2.25 mg. In another embodiment, the amount of opioid in the at least one immediate release portion may range from about 3.0 mg and about 4.0 mg, for example, about 3.75 mg. In still another embodiment, the amount of opioid in the at least one immediate release portion may range from about 7.0 mg and about 8.0 mg, for example, about 7.5 mg.

The amount of opioid present in the at least one immediate release portion may be expressed as a percentage (w/w) of the total amount of opioid in the composition. At least one immediate release portion may comprise from about 20% to about 40% (w/w) of the total amount of opioid present in the composition. In certain embodiments, the percentage of opioid present in the at least one immediate release portion of the composition may be about 20%, 21%, 22%, 23%, 24%, 25%, 26%, 27%, 28%, 29%, 30%, 31%, 32%, 33%, 34%, 35%, 36%, 37%, 38%, 39%, or 40% (w/w) of the total amount of opioid present in the composition. In one embodiment, the percentage of opioid present in the at least one immediate release portion may range from about 20% to about 30% (w/w) of the total amount of opioid present in the composition. In another embodiment, the percentage of opioid present in the at least one immediate release portion may be about 25% (w/w) of the total amount of opioid present in the composition.

The amount of opioid in an immediate release portion also may be expressed as a percentage (w/w) of the total weight of such immediate release portion of the composition. In one embodiment, the amount of opioid in an immediate release portion may range from about 0.2% (w/w) to about 20% (w/w) of the total weight of such immediate release portion of the composition. In another embodiment, the amount of opioid in an immediate release portion may range from about 0.5% (w/w) to about 5% (w/w) of the total weight of such immediate release portion. In various embodiments, an immediate release portion may comprise an amount of opioid that is approximately 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.25%, 3.5%, 3.75%, 4.0%, 4.25%, 4.5%, 4.75%, 5.0%, 5.25%, 5.5%, 5.75%, 6.0%, 6.25%, 6.5%, 6.75%, 7.0%, 7.25%, 7.5%, 7.75%, 8.0%, 8.25%, 8.5%, 8.75%, 9.0%, 9.25%, 9.5%, 9.75%, 10%, 11%, 12%, 13%, 14%, 15%, 16%, 17%, 18%, 19%, or 20% (w/w) of the total weight of such immediate release portion of the composition. In one embodiment, the amount of opioid in an immediate release portion may be about 0.5% to about 1.0% (w/w) of the total weight of such immediate release portion of the composition.

In some embodiments, the opioid in the at least one immediate release portion of the dosage form may be in the form of particles comprising opioid and at least one excipient. The at least one immediate release portion, therefore, may comprise particles of opioid(s) that are admixed with other API(s) and optional excipient(s). Suitable oxycodone particles are described in co-pending application U.S. application Ser. No. 13/166,770, filed Jun. 22, 2011, which is incorporated herein by reference in its entirety. The opioid particles may be coated or uncoated. The average size or average diameter of the particles may vary. In general, the average diameter of the particles may range from about 50 microns to about 2000 microns, from about 100 microns to about 1000 microns, or from about 150 microns to about 200 microns. In one embodiment, the maximum diameter of about 50% of the particles (d50) may be about 40 microns, 50 microns, 100 microns, 150 microns, 200 microns, 250 microns, 300 microns, 400 microns, or 500 microns. In another embodiment, the maximum diameter of about 90% of the particles (d90) may be about 100 microns, 150 microns, 200 microns, 250 microns, 300 microns, 400 microns, or 500 microns.

(ii) Other API(s)

At least one immediate release portion of the composition may comprise at least one other API. Examples of suitable APIs that may be included in the at least one immediate release portion are presented above in section (II)(a)(ii). In one embodiment, the other API may be acetylsalicylic acid or a salt thereof. In another embodiment, the other API may be diclofenac or a salt thereof. In yet another embodiment, the other API may be ibuprofen or a salt thereof. In still another embodiment, the other API may be indomethacin or a salt thereof. In a further embodiment, the other API may be ketoprofen or a salt thereof. In an alternate embodiment, the other API may be naproxen or a salt thereof. In another embodiment, the other API may be piroxicam or a salt thereof. In still another embodiment, the other API may be prednisolone or a salt thereof. In one embodiment, the other API may be acetaminophen or salt thereof.

The amount of the other API in the at least one immediate release portion can and will vary. In one embodiment, the immediate release portion may comprise from about 0.5 mg to about 750 mg of the API. In another embodiment, the amount of API in the at least one immediate release portion may range from about 50 mg to about 500 mg. In another embodiment, the amount of API in the at least one immediate release portion may range from about 25 mg to about 250 mg. In another embodiment, the amount of API in the at least one immediate release portion may range from about 150 mg to about 500 mg. In yet another embodiment, the amount of API in the at least one immediate release portion may range from about 0.5 mg to about 5 mg. In one embodiment, the amount of API in the at least one immediate release portion may range from about 125 mg to about 650 mg. In another embodiment, the amount of API in the at least one immediate release portion may range from about 162.5 mg to about 325 mg. In still another embodiment, the amount of API in the at least one immediate release portion may range from about 325 mg to about 650 mg.

The amount of other API in the at least one immediate release portion of the gastric retentive, extended release composition can and will vary. In general, the amount of other API present in the at least one immediate release portion may range from about 30% to about 70% (w/w) of the total amount of other API in the composition. In one embodiment, the amount of other API present in the at least one immediate release portion ranges from about 40% to about 60% (w/w) of the total amount of API in the composition. In various embodiments, the at least one immediate release portion of the composition may comprise about 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, or 70% (w/w) of the total amount of API in the composition.

The amount of other API in an immediate release portion of the composition may range from about 15% to about 95% (w/w) of the total weight of such immediate release portion of the composition. In various embodiments, the amount of other API(s) in an immediate release portion may be about 15%, 20%, 25%, 30%, 35%, 40%, 45%, 50%, 55%, 60%, 65%, 68%, 69%, 70%, 71%, 72%, 73%, 74%, 75%, 76%, 77%, 78%, 79%, 80%, 82%, 84%, 86%, 88%, 90%, 92%, or 95% (w/w) of the total weight of such immediate release portion.

In embodiments in which the other API is acetaminophen, the amount of acetaminophen in the at least one immediate release portion may range from about 40 mg to about 800 mg. In another embodiment, the at least one immediate release portion of the composition may comprise from about 100 mg to about 600 mg of acetaminophen. In another embodiment, the at least one immediate release portion may comprise from about 150 mg to about 400 mg of acetaminophen. In a further embodiment, the amount of acetaminophen in the at least one immediate release portion may range from about 160 mg to about 325 mg. In yet another embodiment, the amount of acetaminophen in the at least one immediate release portion may be about 120 mg, 125 mg, 130 mg, 135 mg, 140 mg, 145 mg, 150 mg, 155 mg, 160 mg, 162.5 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 275 mg, 280 mg, 285 mg, 290 mg, 295 mg, 300 mg, 305 mg, 310 mg, 315 mg, 320 mg, 325 mg, 330 mg, 335 mg, 340 mg, 345 mg, 350 mg, 355 mg, 360 mg, 365 mg, 370 mg, 375 mg, 380 mg, 385 mg, 390 mg, 395 mg, 400 mg, 500 mg, 520 mg, 600 mg, 650 mg, 700 mg, 750 mg, or 780 mg. In one embodiment, the at least one immediate release portion may comprise about 325 mg of acetaminophen. In another embodiment, the amount of acetaminophen in the at least one immediate release portion may be about 250 mg. In yet another embodiment, the amount of acetaminophen in the at least one immediate release portion may be about 162.5 mg. In still another embodiment, the amount of acetaminophen in the at least one immediate release portion may be about 125 mg.

The at least one immediate release portion of the composition may comprise from about 40% to about 60% (w/w) of the total amount of acetaminophen present in the gastric retentive composition. The amount of acetaminophen in the at least one immediate release portion may be about 40%, 41%, 42%, 43%, 44%, 45%, 46%, 47%, 48%, 49%, 50%, 51%, 52%, 53%, 54%, 55%, 56%, 57%, 58%, 59%, or 60% (w/w) of the total amount of acetaminophen present in the composition. In one embodiment, the percentage of acetaminophen present in the at least one immediate release portion may be about 50% (w/w) of the total amount of acetaminophen present in the composition.

The amount of acetaminophen in an immediate release portion of the pharmaceutical composition may range from about 20% to about 95% (w/w) of the total weight of such immediate release portion of the composition. In various embodiments, an immediate release portion may comprise a dose of acetaminophen that is approximately about 20%, 25%, 30%, 35%, 40%, 45%, 50%, 55%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, or 95% (w/w) of the total weight of such immediate release portion. In one embodiment, the amount of acetaminophen in an immediate release portion may range from about 70% to about 80% (w/w) of the total weight of such immediate release portion of the composition.

(iii) Excipients

The at least one immediate release portion of the gastric retentive, extended release composition may further comprise at least one excipient. Suitable excipients include binders, fillers, disintegrants, lubricants, antioxidants, chelating agents, and color agents.

In one embodiment, the at least one immediate release portion of the composition may comprise at least one binder. Suitable binders include, without limit, starches (including corn starch and pregelatinized starch), gelatin, sugars (including sucrose, glucose, dextrose and lactose), polyethylene glycol, polyols, polyvinylalcohols, C12-C18 fatty acid alcohols, waxes, gums (e.g., guar gum, arabic gum, acacia gum, xantham gum, etc.), gelatin, pectin, sodium alginate, polyvinylpyrrolidone, cellulosic polymers (including hydroxypropyl cellulose, hydroxypropyl methylcellulose, hydroxylcellulose, methylcellulose, microcrystalline cellulose, ethylcellulose, hydroxyethyl cellulose, and the like), polyacrylamides, and polyvinyloxoazolidone. In one embodiment, the amount of binder or binders in an immediate release portion of the composition may range from about 5% to about 10% (w/w) of the total weight of such immediate release portion. In various embodiments, an immediate release portion of the composition may comprise at least one binder that is present in an amount that is about 6.0%, 6.25%, 6.5%, 6.75%, 7.0%, 7.1%, 7.2%, 7.3%, 7.4%, 7.5%, 7.6%, 7.7%, 7.8%, 7.9%, 8.0%, 8.2%, 8.4%, 8.6%, or 8.8% (w/w) of such immediate release portion of the composition.

In another embodiment, the at least one immediate release portion of the composition may comprise at least one filler. Suitable fillers include but are not limited to microcrystalline cellulose (MCC), dibasic calcium phosphate, tribasic calcium phosphate, magnesium carbonate, magnesium oxide, calcium silicate, magnesium aluminum silicate, silicon dioxide, titanium dioxide, alumina, talc, kaolin, polyvinylpyrrolidone, dibasic calcium sulfate, tribasic calcium sulfate, starch, calcium carbonate, magnesium carbonate, carbohydrates, modified starches, lactose, sucrose, dextrose, mannitol, sorbitol, and inorganic compounds. In one embodiment, the amount of filler or fillers in an immediate release portion may range from about 1.0% to about 10.0% (w/w) of the total weight of such immediate release portion. In various embodiments, an immediate release portion of the composition may comprise at least one filler that is present in an amount that is about 1.0%, 1.5%, 2.0%, 2.5%, 3.0%, 3.5%, 4.0%, 4.5%, 5.0%, 5.5%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.0%, 9.1%, 9.2%, 9.3%, 9.4%, 9.5%, 9.6%, 9.7%, 9.8%, 9.9%, or 10.0%, (w/w) of such immediate release portion of the composition.

In still another embodiment, the at least one immediate release portion of the composition may further comprise at least one disintegrant. The disintegrant may be selected from the group consisting of croscarmellose sodium, crospovidone, alginic acid, carboxymethylcellulose calcium, carboxymethylcellulose sodium, low substituted hydroxypropylcellulose, microcrystalline cellulose, and sodium starch glycolate. In one embodiment, the amount of disintegrant in an immediate release portion may range from about 2.0% to about 15.0% (w/w) of the total weight of such immediate release portion. In some embodiments, the amount of disintegrant in an immediate release portion may be about 4.0%, 4.2%, 4.4%, 4.6%, 4.8%, 5.0%, 5.2%, 5.4%, 5.6%, 5.8%, 6.0%, 6.2%, 6.4%. 6.6%, 6.8%, or 7.0% (w/w) of such immediate release portion of the composition.

In a further embodiment, the at least one immediate release portion of the composition may further comprise at least one lubricant. Useful lubricants include magnesium stearate, calcium stearate, stearic acid, and hydrogenated vegetable oil (preferably comprised of hydrogenated and refined triglycerides of stearic and palmitic acids). The lubricant may be present in an amount ranging from about 0.1% to about 3.0% (w/w) of the total weight of an immediate release portion. In certain embodiments, the amount of lubricant in an immediate release portion may be about 0.25%, 0.5%, 0.75%, 1.0%, 1.5%, 1.55%, 1.6%, 1.65%, 1.7%, 1.75%, 1.80%, 1.85%, 1.90%, 1.95%, or 2.0% (w/w) of the total weight of such immediate release portion.

In yet another embodiment, the at least one immediate release portion of the composition may comprise at least one antioxidant. Suitable antioxidants include, without limitation, ascorbic acid, citric acid, ascorbyl palmitate, butylated hydroxyanisole, a mixture of 2 and 3 tertiary-butyl-4-hydroxyanisole, butylated hydroxytoluene, sodium isoascorbate, dihydroguaretic acid, potassium sorbate, sodium bisulfate, sodium metabisulfate, sorbic acid, potassium ascorbate, vitamin E, 4-chloro-2,6-ditertiarybutylphenol, alphatocopherol, and propylgallate. The amount of antioxidant present in an immediate release portion of the composition may range from about 0.01% to about 4.0% (w/w), or from about 0.02% to about 0.10% (w/w) of the total weight of such immediate release portion. In various embodiments, the amount of antioxidant present in an immediate release portion of the composition may be about 0.01%, 0.02%, 0.03%, 0.04%, 0.05%, 0.06%, 0.07%, 0.08%, 0.09%, 0.10%, 0.12%, 0.14%, 0.16%, 0.18%, 0.20%, 0.25%, 0.50%, 0.75%, 1.00%, 1.50%, or 2.00% (w/w) of the total weight of such immediate release portion.

In still another embodiment, the at least one immediate release portion of the composition may comprise at least one chelating agent. Suitable chelating agents include ethylenediamine tetracetic acid (EDTA) and its salts, N-(hydroxyethyl)ethylenediaminetriacetic acid, nitrilotriacetic acid (NIA), ethylene-bis(oxyethylene-nitrilo)tetraacetic acid, 1,4,7,1-tetraazacyclodo-decane-N,N',N",N"'-tetraacetic acid, 1,4,7,10-tetraaza-cyclododecane-N,N',N"-triacetic acid, 1,4,7-tris(carboxymethyl)-10-(2'-hydroxypropyl)-1,4,7,1-tetraazocyclodecane, 1,4,7-triazacyclonane-N,N',N"-triacetic acid, 1,4,8,11-tetraazacyclotetra-decane-N,N',N",N"'-tetraacetic acid; diethylenetriamine-pentaacetic acid (DTPA), ethylenedicysteine, bis(aminoethanethiol)carboxylic acid, triethylenetetraamine-hexaacetic acid, and 1,2-diaminocyclohexane-N,N,N',N'-tetraacetic acid. In one embodiment, the chelating agent may be the sodium salt of EDTA. The amount of chelating agent present in an immediate release portion of the composition may range from about 0.001% to about 0.20% (w/w) of such immediate release portion. In some embodiments, the amount of chelating agent present in an immediate release portion of the composition may be about 0.001%, 0.002%, 0.003%, 0.004%, 0.005%, 0.01%, 0.02%, 0.03%, 0.04%, 0.05%, 0.06%, 0.07%, 0.08%, 0.09%, 0.10%, 0.11%, 0.12%, 0.13%, 0.14%, or 0.15% (w/w) of the total weight of such immediate release portion.

In an alternate embodiment, the at least one immediate release portion of the composition may comprise at least one color agent. Suitable color additives include, but are not limited to, food, drug and cosmetic colors (FD&C), drug and cosmetic colors (D&C), and external drug and cosmetic colors (Ext. D&C). In various embodiments, the amount of color agent present in an immediate release portion may range from about 2.0% to about 5.0% (w/w) of the total weight of such immediate release portion of the composition. In other embodiments, the amount of color agent present in an immediate release portion may be about 1.0%, 1.5%, 2.0%, 2.5%, 3.0%, 3.5%, 4.0%, 4.5%, or 5.0% (w/w) of the total weight of such immediate release portion.

(c) Extended Release Portion

The gastric retentive, extended release composition disclosed herein comprises at least one extended release portion. The at least one extended release portion may comprise at least one opioid, at least one other API, or combinations thereof. The at least one extended release portion further comprises at least one extended release component. The extended release component may comprise at least one extended release polymer.

The at least one extended release portion of the composition is designed to release the opioid(s) and the other API(s) over an extended period of time. In general, the at least one extended release portion provides release of the opioid(s) and/or the API(s) for a period of time ranging from at least about 4 hours (hrs) to at least about 12 hrs. In one embodiment, the opioid(s) and/or the other API(s) may be released from the at least one extended release portion composition over a period of time of at least about 5 hours, or over a period of at least about 6 hours. In another embodiment, the at least one extended release portion may release the opioid(s) and/or the other API(s) over a period of at least about 7 hours, or a period of at least about 8 hours. In still another embodiment, the opioid(s) and/or the other API(s) may be released from the at least one extended release portion over a period of at least about 9 hours, or over a period of at least about 10 hours. In a further embodiment, the at least one extended release portion may release the opioid(s) and/or the other API(s) over a period of at least about 11 hours, or over a period of at least about 12 hours.

(i) Opioids

At least one extended release portion of the gastric retentive, extended release composition comprises at least one opioid. Suitable opioids are detailed above in section (II)(a)(i). In one embodiment, the opioid may be codeine or a salt thereof. In another embodiment, the opioid may be hydrocodone or a salt thereof. In yet another embodiment, the opioid may be hydromorphone or a salt thereof. In still another embodiment, the opioid may be morphine or a salt thereof. In a further embodiment, the opioid may be oxymorphone or a salt thereof. In an alternate embodiment, the opioid may be tramadol or a salt thereof. In another embodiment, the opioid may be oxycodone or a salt thereof.

The amount of opioid present in the at least one extended release portion of the gastric retentive, extended release composition can and will vary. In one embodiment, the amount of opioid in the at least one extended release portion may range from about 1 mg to about 300 mg. In another embodiment, the amount of opioid in the at least one extended release portion may range from about 3.75 mg to about 225 mg. In a further embodiment, the at least one extended release portion of the composition may comprise from about 1 mg to about 22.5 mg of opioid. In another embodiment, the amount of opioid in the at least one extended release portion may be from about 22.5 mg to about 45 mg. In yet another embodiment, the amount opioid in the at least one extended release portion may be from about 45 mg to about 90 mg. In still another embodiment, the amount of opioid in the at least one extended release portion may be from about 90 mg to about 225 mg. In yet another embodiment, the amount of opioid in the at least one extended release portion may be about 1.5 mg, 2.0 mg, 2.5 mg, 3.0 mg, 3.5 mg, 4.0 mg, 4.5 mg, 5.0 mg, 5.5 mg, 5.625 mg, 6.0 mg, 6.5 mg, 7.0 mg, 7.5 mg, 8.0 mg, 8.5 mg, 9.0 mg, 9.5 mg, 10.0 mg, 10.5 mg, 11.0 mg, 11.25 mg, 11.5 mg, 12.0 mg, 12.5 mg, 13.0 mg, 13.5 mg, 14.0 mg, 14.5 mg, 15.0 mg, 15.5 mg, 16.0 mg, 16.5 mg, 17.0 mg, 17.5 mg, 18.0 mg, 18.5 mg, 19.0 mg, 19.5 mg, 20.0 mg, 22.5 mg, 25 mg, 27.5 mg, 30 mg, 35 mg, 40 mg, 45 mg, or 50 mg. In one embodiment, the amount of opioid in the at least one extended release portion may be from about 5 mg to about 6 mg, for example, about 5.625 mg. In another embodiment, the amount of opioid in the at least one extended release portion may be from about 10 mg to about 12 mg, for example, about 11.25 mg. In still another embodiment, the amount of opioid in the at least one extended release portion may be from about 22 mg to about 23 mg, for example, about 22.5 mg.

The amount of opioid present in the at least one extended release portion may be expressed as a percentage of the total amount of opioid in the gastric retentive, extended release composition. In one embodiment, the at least one extended release portion of the composition comprises from about 60% to about 80% (w/w) of the total amount of opioid present in the gastric retentive, extended release composition. In certain embodiments, the percentage of opioid present in the at least one extended release portion of the composition may be about 60%, 61%, 62%, 63%, 64%, 65%, 66%, 67%, 68%, 69% 70%, 71%, 72%, 73%, 74%, 75%, 76%, 77%, 78%, 79%, or 80% (w/w) of the total amount of opioid present in the composition. In one embodiment, the percentage of opioid present in the at least one extended release portion of the pharmaceutical composition may be about 75% of the total amount of opioid present in the composition.

The amount of opioid in an extended release portion also may be expressed as a percentage of the total weight of such extended release portion of the composition. In one embodiment, the amount of opioid in an extended release portion may range from about 0.3% to about 8.0% (w/w) of the total weight of such extended release portion of the composition. In various embodiments, an extended release portion may comprise an amount of opioid that is approximately 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.5%, 5%, 5.5%, 6%, 6.5%, 7%, 7.5%, or 8% (w/w) of the total weight of such extended release portion of the composition. In one embodiment, the amount of opioid in an extended release portion may comprise about 0.5% to about 2% (w/w) of the total weight of such extended release portion of the composition.

In some embodiments, the opioid of the at least one extended release portion of the composition may be in the form of particles comprising the opioid and at least one excipient. Thus, the at least one extended release portion may comprise particles of opioid(s) which are admixed with the additional API(s) and the extended release component, both of which are detailed below, as well as optional excipient(s). Suitable oxycodone particles are described in co-pending application U.S. application Ser. No. 13/166,770, filed Jun. 22, 2011, which is incorporated herein by reference in its entirety. The opioid particles may be coated or uncoated. The average size or average diameter of the particles may vary. In general, the average diameter of the particles may range from about 50 microns to about 2000 microns, from about 100 microns to about 1000 microns, or from about 150 microns to about 200 microns. In one embodiment, the d90 of the particles may be about 40 microns, 50 microns, 100 microns, 150 microns, 200 microns, 250 microns, 300 microns, 400 microns, or 500 microns. In another embodiment, the d90 of the particles may be about 100 microns, 150 microns, 200 microns, 250 microns, 300 microns, 400 microns, or 500 microns.

(ii) Other API(s)

The at least one extended release portion of the gastric retentive, extended release composition may comprise at least one other API. Examples of suitable APIs that may be included in the at least one extended release portion are presented above in section (I)(a)(ii). In one embodiment, the other API may be acetylsalicylic acid or a salt thereof. In another embodiment, the API may be diclofenac or a salt thereof. In yet another embodiment, the API may be ibuprofen or a salt thereof. In still another embodiment, the API may be indomethacin or a salt thereof. In a further embodiment, the API may be ketoprofen or a salt thereof. In an alternate embodiment, the API may be naproxen or a salt thereof. In another embodiment, the API may be piroxicam or a salt thereof. In still another embodiment, the API may be prednisolone or a salt thereof. In one embodiment, the API may be acetaminophen or salt thereof.

The amount of the other API in the at least one extended release portion can and will vary. In one embodiment, the at least one extended release portion may comprise from about 0.5 mg to about 750 mg of the API. In another embodiment, the amount of API in the at least one extended release portion may range from about 50 mg to about 500 mg. In another embodiment, the amount of API in the at least one extended release portion may range from about 25 mg to about 250 mg. In another embodiment, the amount of API in the at least one extended release portion may range from about 150 mg to about 500 mg. In yet another embodiment, the amount of API in the at least one extended release portion may range from about 0.5 mg to about 5 mg. In one embodiment, the amount of API in the at least one extended release portion may range from about 125 mg to about 650 mg. In another embodiment, the amount of API in the at least one extended release portion may range from about 162.5 mg to about 325 mg. In still another embodiment, the amount of API in the at least one extended release portion may range from about 325 mg to about 650 mg.

The amount of other API(s) in the at least one extended release portion of the gastric retentive, extended release composition can and will vary, depending upon the identity of the API(s). In general, the amount of other API present in the at least one extended release portion may range from about 30% to about 70% (w/w) of the total amount of other API in the composition. In one embodiment, the amount of other API present in the at least one extended release portion may range from about 40% to about 60% (w/w) of the total amount of other API in the composition. In various embodiments, the at least one extended release portion of the retentive, extended release composition may comprise about 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, or 70% (w/w) of the total amount of other API in the composition.

The amount of other API in an extended release portion also may be expressed as a percentage of the total weight of such extended release portion of the retentive, extended release composition. In various embodiments, the amount of other API in an extended release portion may range from about 10% to about 70% (w/w) of the total weight of such extended release portion of the composition. In various embodiments, the amount of other API in an extended release portion may be about 10%, 11%, 12%, 13%, 14%, 15%, 16%, 17%, 18%, 19%, 20%, 21%, 22%, 23%, 24%, 25%, 26%, 27%, 28%, 29%, 30%, 32%, 34%, 36%, 38%, 40%, 42%, 44%, 46%, 48%, 50%, 52%, 54%, 56%, 58%, 60%, 62%, 64%, 66%, 68%, or 70% (w/w) of the total weight of such extended release portion of the composition.

In embodiments in which the other API is acetaminophen, the amount of acetaminophen in the at least one extended release portion may range from about 40 mg to about 800 mg. In one embodiment, the at least one extended release portion of the composition may comprise from about 100 mg to about 600 mg of acetaminophen. In another embodiment, the at least one extended release portion may comprise from about 150 mg to about 400 mg of acetaminophen. In a further embodiment, the amount of acetaminophen in the at least one extended release portion may range from about 160 mg to about 325 mg. In yet another embodiment, the amount of acetaminophen in the at least one extended release portion may be about 100 mg, 110 mg, 120 mg, 125 mg, 130 mg, 135 mg, 140 mg, 145 mg, 150 mg, 155 mg, 160 mg, 162.5 mg, 165 mg, 170 mg, 175 mg, 180 mg, 185 mg, 190 mg, 195 mg, 200 mg, 210 mg, 220 mg, 230 mg, 240 mg, 250 mg, 260 mg, 270 mg, 280 mg, 290 mg, 300 mg, 310 mg, 320 mg, 325 mg, 330 mg, 340 mg, 350 mg, 360 mg, 370 mg, 380 mg, 390 mg, 400 mg, 450 mg, 500 mg, 550 mg, 600 mg, 650 mg, 700 mg, 750 mg, or 800 mg. In one embodiment, the at least one extended release portion may comprise about 325 mg of acetaminophen. In another embodiment, the amount of acetaminophen in the at least one extended release portion may be about 250 mg. In yet another embodiment, the amount of acetaminophen in the at least one extended release portion may be about 162.5 mg. In still another embodiment, the amount of acetaminophen in the at least one immediate release portion may be about 125 mg.

The amount of acetaminophen in the at least one extended release portion may range from about 40% to about 60% (w/w) of the total amount of acetaminophen present in the composition. In various embodiments, the amount of acetaminophen in the at least one extended release portion may be about 40%, 41%, 42%, 43%, 44%, 45%, 46%, 47%, 48%, 49%, 50%, 51%, 52%, 53%, 54%, 55%, 56%, 57%, 58%, 59%, or 60% (w/w) of the total amount of acetaminophen present in the gastric retentive, extended release composition. In one embodiment, the percentage of acetaminophen present in the at least one extended release portion of the composition may be about 50% (w/w) of the total amount of acetaminophen present in the composition.

The amount of acetaminophen in an extended release portion of the composition may range from about 15% to about 60% (w/w) of the total weight of such extended release portion of the composition. In various embodiments, the amount of acetaminophen in an extended release portion may be about 15%, 16%, 17%, 18%, 19%, 20%, 21%, 22%, 23%, 24%, 25%, 26%, 27%, 28%, 29%, 30%, 32%, 35%, 37%, 40%, 42%, 45%, 47%, 50%, 52%, 55%, 57%, or 60% (w/w) of the total weight of such extended release portion. In one embodiment, the amount of acetaminophen in an extended release portion may range from about 20% to about 40% (w/w) of the total weight of such extended release portion of the composition.

(iii) Extended Release Component

The at least one extended release portion of the gastric retentive, extended release composition also comprises at least one extended release component. Suitable extended release components include polymers, resins, hydrocolloids, hydrogels, and the like.

In one embodiment, the at least one extended release component comprises at least one extended release polymer. Suitable polymers for inclusion in the at least one extended release portion of the gastric retentive, extended release composition may be linear, branched, dendrimeric, or star polymers, and include synthetic hydrophilic polymers as well as semi-synthetic and naturally occurring hydrophilic polymers. The polymers may be homopolymers or copolymers, such as random copolymers, block copolymers, and graft copolymers. Suitable hydrophilic polymers include, but are not limited to: polyalkylene oxides, particularly poly(ethylene oxide), polyethylene glycol and poly(ethylene oxide)-poly(propylene oxide) copolymers; cellulosic polymers, such as methylcellulose, hydroxymethylcellulose, hydroxyethylcellulose, hydroxypropylcellulose, hydroxypropylmethylcellulose, and carboxymethylcellulose, microcrystalline cellulose, and polysaccharides and their derivatives; acrylic acid and methacrylic acid polymers, copolymers and esters thereof, preferably formed from acrylic acid, methacrylic acid, methyl acrylate, ethyl acrylate, methyl methacrylate, ethyl methacrylate, and copolymers thereof, with each other or with additional acrylate species such as aminoethyl acrylate; maleic anhydride copolymers; polymaleic acid; poly(acrylamides) such as polyacrylamide per se, poly(methacrylamide), poly(dimethylacrylamide), and poly(N-isopropyl-acrylamide); polyalkylene oxides; poly(olefinic alcohol)s such as poly(vinyl alcohol); poly(N-vinyl lactams) such as poly(vinyl pyrrolidone), poly(N-vinyl caprolactam), and copolymers thereof; polyols such as glycerol, polyglycerol (particularly highly branched polyglycerol), propylene glycol and trimethylene glycol substituted with one or more polyalkylene oxides, e.g., mono-, di- and tri-polyoxyethylated glycerol, mono- and di-polyoxyethylated propylene glycol, and mono- and di-polyoxyethylated trimethylene glycol; polyoxyethylated sorbitol and polyoxyethylated glucose; polyoxazolines, including poly(methyloxazoline) and poly(ethyloxazoline); polyvinylamines; polyvinylacetates, including polyvinylacetate per se as well as ethylene-vinyl acetate copolymers, polyvinyl acetate phthalate, and the like, polyimines, such as polyethyleneimine; starch and starch-based polymers; polyurethane hydrogels; chitosan; polysaccharide gums; xanthan gum; zein; and shellac, ammoniated shellac, shellac-acetyl alcohol, and shellac n-butyl stearate. The polymers may be used individually or in combination. Certain combinations may provide a more controlled release of opioid(s) and API(s) than their components when used individually. Suitable combinations include cellulose-based polymers combined with gums, such as hydroxyethyl cellulose or hydroxypropyl cellulose combined with xanthan gum, and poly(ethylene oxide) combined with xanthan gum.

In one embodiment, the at least one extended release polymer may be a cellulosic polymer, such as an alkyl substituted cellulose derivative as detailed above. In terms of their viscosities, one class of preferred alkyl substituted celluloses includes those whose viscosity is within the range of about 100 to about 110,000 centipoise as a 2% aqueous solution at 20° C. Another class includes those whose viscosity is within the range of about 1,000 to about 4,000 centipoise as a 1% aqueous solution at 20° C.

In one embodiment, the at least one extended release polymer may be a polyalkylene oxide. In another aspect, the polyalkylene oxide may be poly(ethylene) oxide. In a further embodiment, the poly(ethylene) oxide may have an approximate molecular weight between 500,000 Daltons (Da) to about 10,000,000 Da or about 900,000 Da to about 7,000,000 Da. In yet a further embodiment, the poly(ethylene) oxide may have a molecular weight of approximately about 600,000 Da, about 700,000 Da, about 800,000 Da, about 900,000 Da, about 1,000,000 Da, about 2,000,000 Da, about 3,000,000 Da, about 4,000,000 Da, about 5,000,000 Da, about 6,000,000 Da, about 7,000,000 Da, about 8,000,000 Da, 9,000,000 Da, or 10,000,000 Da.

In another embodiment, the polyethylene oxide may be any desirable grade of POLYOX™ or any combination thereof. By way of example and without limitation, the POLYOX™ grade may be WSR N-10, WSR N-80, WSR N-750, WSR 205, WSR 1105, WSR N-12K, WSR N-60K, WSR-301, WSR Coagulant, WSR-303, WSR-308, WSR N-3000, UCARFLOC Polymer 300, UCARFLOC Polymer 302, UCARFLOC Polymer 304, and UCARFLOC Polymer 309. In one embodiment, the polyethylene oxide may have an average molecular weight of from about 100,000 Da to about 8,000,000 Da. In another embodiment, the polyethylene oxide may have an average molecular weight of about 100,000 Da, about 200,000 Da, about 300,000 Da, about 400,000 Da, about 500,000 Da, about 600,000 Da, about 700,000 Da, about 800,000 Da, about 900,000 Da, about 1,000,000 Da, about 2,000,000 Da, about 3,000,000 Da, about 4,000,000 Da, about 5,000,000 Da, about 6,000,000 Da, about 7,000,000 Da, or about 8,000,000 Da. In still another embodiment, the polyethylene oxide may have an average number of repeating ethylene oxide units (—$CH_2CH_2O$—) of about 2,000 to about 160,000. In yet another embodiment, the polyethylene oxide may have an average number of repeating ethylene oxide units of about 2,275, about 4,500, about 6,800, about 9,100, about 14,000, about 20,000, about 23,000, about 45,000, about 90,000, about 114,000, or about 159,000.

The release profile of the extended release compositions disclosed herein will depend partially upon the molecular weight of the polymer. The polymers are preferably of a moderate to high molecular weight (900,000 Da to 4,000,000 Da) to provide control release of the opioid(s) and/or the API(s) from the composition via diffusion of the opioid(s) and/or other API(s) out of the polymer and/or erosion of the polymer. An example of suitable polyethylene oxide polymers are those having molecular weights (viscosity average) on the order of about 900,000 Da to about 2,000,000 Da. Using a lower molecular weight ("MW") polyethylene oxide, such as POLYOX® 1105 (900,000 MW), the release rates for all active agents generally will be higher. Using a higher molecular weight polyethylene oxide (such as POLYOX® N-60K (2,000,000 MW) or POLYOX®WSR-301 (4,000,000 MW) generally reduces the rate of release for all active agents. In another embodiment of the invention, a hydroxypropylmethylcellulose polymer of such molecular weight may be utilized such that the viscosity of a 2% aqueous solution may be about 4000 cps to greater than about 100,000 cps.

The release profile of the extended release pharmaceutical composition disclosed herein may also depend upon the amount of the extended release polymer(s) in the pharmaceutical composition. In general, the release rates for all active agents may be decreased by increasing the amount of the extended release polymer(s) in the pharmaceutical composition. By way of example and without limitation, the release profile of all active agents may be decreased by increasing the amount of POLYOX® 1105 from about 25% by weight of the ER portion to about 35% by weight of the ER portion.

The amount of polymer or polymers present in the at least one extended release portion of the composition can and will vary. In one embodiment, the polymer present in an extended release portion of the gastric retentive, extended release composition may range from about 15% to about 70% (w/w), or about 20% to about 60% (w/w), or about 25% to about 55% (w/w) of the total weight of such extended release portion of the composition. In another embodiment, the amount of polymer present in an extended release portion of the composition may range from about 30% to about 50% (w/w) of the total weight of such extended release portion. In still another embodiment, the amount of polymer present in an extended release portion of the pharmaceutical composition may range from about 35% to about 45% (w/w) of the total weight of such extended release portion. In yet another embodiment, the amount of polymer present in an extended release portion of the pharmaceutical composition may be about 30%, 35%, 40%, 45%, 50%, 55%, or 60% (w/w) of the total weight of such extended release portion. In still another embodiment, the amount of polymer present in an extended release portion of the pharmaceutical composition may be about 35% (w/w) of the total weight of such extended release portion. In another embodiment, the amount of polymer present in an extended release portion of the pharmaceutical composition may be about 45% (w/w) of the total weight of such extended release portion.

(iv) Excipients

The at least one extended release portion of the gastric retentive, extended release composition may further comprise at least one excipient. Suitable excipients include binders, fillers, lubricants, antioxidants, chelating agents, and color agents.

In one embodiment, the at least one extended release portion of the composition may comprise at least one binder. Suitable binders include, without limit, starches (including corn starch and pregelatinized starch), gelatin, sugars (including sucrose, glucose, dextrose and lactose), polyethylene glycol, polyols, polyvinylalcohols, C12-C18 fatty acid alcohols, waxes, gums (e.g., guar gum, arabic gum, acacia gum, xanthan gum, etc.), gelatin, pectin, sodium alginate, polyvinylpyrrolidone, cellulosic polymers (including hydroxypropyl cellulose, hydroxypropyl methylcellulose, hydroxylcellulose, methylcellulose, microcrystalline cellulose, ethylcellulose, hydroxyethyl cellulose, and the like), polyacrylamides, and polyvinyloxoazolidone. In one embodiment, the amount of binder or binders in an extended release portion of the composition may range from about 0.5% to about 8.0% (w/w) of such extended release portion. In various embodiments, an extended release portion of the composition may comprise at least one binder that is present in an amount that is about 0.5%, 1.0%, 1.1%, 1.2%, 1.3%, 1.4%, 1.5%, 1.6%, 1.7%, 1.8%, 1.9%, 2.0%, 2.5%, 3.0%, 3.5%, 4.0%, 4.5%, 5.0%, 5.5%, or 6.0% (w/w) of such extended release portion of the composition.

In another embodiment, the at least one extended release portion of the composition may comprise at least one filler. Suitable fillers include but are not limited to microcrystalline cellulose (MCC), dibasic calcium phosphate, tribasic calcium phosphate, magnesium carbonate, magnesium oxide, calcium silicate, magnesium aluminum silicate, silicon dioxide, titanium dioxide, alumina, talc, kaolin, polyvinylpyrrolidone, dibasic calcium sulfate, tribasic calcium sulfate, starch, calcium carbonate, magnesium carbonate, carbohydrates, modified starches, lactose, sucrose, dextrose, mannitol, sorbitol, and inorganic compounds. In one embodiment, the amount of filler or fillers in an extended release portion may range from about 2% to about 50% (w/w) of the total weight of such extended release portion. In various embodiments, an extended release portion of the dosage form may comprise at least one filler that is present in an amount that is about 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, or 50% (w/w) of such extended release portion of the composition.

In a further embodiment, the at least one extended release portion of the composition may further comprise at least one lubricant. Useful lubricants include magnesium stearate, calcium stearate, stearic acid, and hydrogenated vegetable oil (preferably comprised of hydrogenated and refined triglycerides of stearic and palmitic acids). The lubricant may be present in an amount ranging from about 0.1% to about 3.0% (w/w) of the total weight of an extended release portion. In certain embodiments, the amount of lubricant in an extended release portion may be about 0.25%, 0.5%, 0.75%, 1.0%, 1.5%, 1.75%, 1.80%, 1.85%, 1.90%, or 2.0% (w/w) of the total weight of such extended release portion of the composition.

In yet another embodiment, the at least one extended release portion of the composition may comprise at least one antioxidant. Suitable antioxidants include, without limit, ascorbic acid, citric acid, ascorbyl palmitate, butylated hydroxyanisole, a mixture of 2 and 3 tertiary-butyl-4-hydroxyanisole, butylated hydroxytoluene, sodium isoascorbate, dihydroguaretic acid, potassium sorbate, sodium bisulfate, sodium metabisulfate, sorbic acid, potassium ascorbate, vitamin E, 4-chloro-2,6-ditertiarybutylphenol, alphatocopherol, and propylgallate. The amount of antioxidant present in an extended release portion of the composition may range from about 0.01% to about 4.0% (w/w), or from about 0.02% to about 0.10% (w/w). In various embodiments, the amount of antioxidant present in an extended release portion of the composition may be about 0.01%, 0.02%, 0.03%, 0.04%, 0.05%, 0.06%, 0.07%, 0.08%, 0.09%, 0.10%, 0.12%, 0.14%, 0.16%, 0.18%. 0.20%, 0.25%, 0.50%, 0.75%, 1.00%, 1.50%, or 2.00% (w/w) of the total weight of such extended release portion.

In still another embodiment, the at least one extended release portion of the composition may comprise at least one chelating agent. Suitable chelating agents include ethylenediamine tetracetic acid (EDTA) and its salts, N-(hydroxyethyl)ethylenediaminetriacetic acid, nitrilotriacetic acid (NIA), ethylene-bis(oxyethylene-nitrilo)tetraacetic acid, $1,4,7,1_0$-tetraazacyclodo-decane-N,N',N'',N'''-tetraacetic acid, $1,4,7,1_0$-tetraaza-cyclododecane-N,N',N''-triacetic acid, 1,4,7-tris(carboxymethyl)-10-(2'-hydroxypropyl)-1,4, $7,1_0$-tetraazocyclodecane, 1,4,7-triazacyclonane-N,N',N''-triacetic acid, 1,4,8,11-tetraazacyclotetra-decane-N,N',N'', N'''-tetraacetic acid; diethylenetriamine-pentaacetic acid (DTPA), ethylenedicysteine, bis(aminoethanethiol)carboxylic acid, triethylenetetraamine-hexaacetic acid, and 1,2-diaminocyclohexane-N,N,N',N'-tetraacetic acid. In one embodiment, the chelating agent may be the sodium salt of EDTA. The amount of chelating agent present in an extended release portion of the composition may range from about 0.001% to about 0.20% (w/w) of such extended release portion. In some embodiments, the amount of chelating agent present in an extended release portion may be about 0.001%, 0.002%, 0.003%, 0.004%, 0.005%, 0.006%, 0.007%, 0.008%, 0.009%, 0.01%, 0.02%, 0.03%, 0.04%, 0.05%, 0.06%, 0.07%, 0.08%, 0.09%, 0.10%, 0.11%, 0.12%, 0.13%, 0.14%, or 0.15% of the total weight of such extended release portion.

In an alternate embodiment, the at least one extended release portion of the composition may comprise at least one color agent. Suitable color additives include, but are not limited to, food, drug and cosmetic colors (FD&C), drug and cosmetic colors (D&C), and external drug and cosmetic colors (Ext. D&C). In various embodiments, the amount of color agent present in an extended release portion may range from about 2.0% to about 5.0% (w/w) of such extended release portion of the composition. In other embodiments, the amount of color agent present in an extended release portion may be about 1.0%, 1.5%, 2.0%, 2.5%, 3.0%, 3.5%, 4.0%, 4.5%, or 5.0% (w/w) of such extended release portion.

(d) Gastric Retention

The opioid containing extended release composition disclosed herein has gastric retentive properties. In general, the gastric retentive properties of the composition are due to a combination of a physical property of the composition and release of the opioid.

(i) Physical Properties

A. Size of the Composition

The physical property of the composition that leads to gastric retention can and will vary. In one embodiment, the physical property of the composition that results in gastric retention may be the physical size of the composition. That is, the composition may have a size that is small enough to be orally ingested and enter the stomach, but large enough to prevent passage through the pyloric sphincter into the small intestine. In some embodiments in which the composition is designed for humans, the composition may have a length (or diameter) of more than about 7 mm, 8 mm, 9 mm, or 10 mm. In other embodiments in which the composition is designed for humans, the composition may have a length (or diameter) of more than about 11 mm, 12 mm, or 13 mm, 14 mm, 15 mm, 16 mm, 17 mm, 18 mm, 19 mm, 20 mm or longer. In still other embodiments, the composition may have (i) a length of approximately 19 mm, 19.1 mm, 19.2 mm, 19.3 mm, 19.4 mm, 19.5 mm, 19.6 mm, 19.7 mm, 19.8 mm, 19.9 mm, or 20 mm as measured on the major axis, (ii) a width of approximately 12 mm, 12.1 mm, 12.2 mm, 12.3 mm, 12.4 mm, 12.5 mm, 12.6 mm, 12.7 mm, 12.8 mm, 12.9 mm, or 13 mm as measured on the minor axis, and (iii) a height or thickness of approximately 5 mm, 5.1 mm, 5.2 mm, 5.3 mm, 5.4 mm, 5.5 mm, 5.6 mm, 5.7 mm, 5.8 mm, 5.9 mm, or 6 mm. In yet another embodiment, the composition may have (i) a length of approximately 19.1 mm, 19.11 mm, 19.12 mm, 19.13 mm, 19.14 mm, 19.15 mm, 19.16 mm, 19.17 mm, 19.18 mm, 19.19 mm, 19.2 mm, 19.21 mm, 19.22 mm, 19.23 mm, 19.24 mm, 19.25 mm, 19.26 mm, 19.27 mm, 19.28 mm, 19.29 mm, or 19.3 mm as measured on the major axis, (ii) a width of approximately 12.4 mm, 12.41 mm, 12.42 mm, 12.43 mm, 12.44 mm, 12.45 mm, 12.46 mm, 12.47 mm, 12.48 mm, 12.49 mm, or 12.5 mm as measured on the minor axis, and (iii) a height or thickness of approximately 5.6 mm, 5.61 mm, 5.62 mm, 5.63 mm, 5.64 mm, 5.65 mm, 5.66 mm, 5.67 mm, 5.68 mm, 5.69 mm, 5.7 mm, 5.71 mm, 5.72 mm, 5.73 mm, 5.74 mm, 5.75 mm, 5.76 mm, 5.77 mm, 5.78 mm, 5.79 mm, or 5.8 mm. In general, such compositions are designed to degrade, disintegrate, decrease in size, or collapse in a specified time interval (e.g., dosing interval) such that they may pass through the pyloric valve or be evacuated from the stomach by a housekeeper wave of gastric contractions.

In still other embodiments, prior to administration to a patient or immersion in fluid, the pharmaceutical composition may have (i) a length of approximately 18 mm, 18.01 mm, 18.02 mm, 18.03 mm, 18.04 mm, 18.05 mm, 18.06 mm, 18.07 mm, 18.08 mm, 18.09 mm, 18.1 mm, 18.11 mm, 18.12 mm, 18.13 mm, 18.14 mm, 18.15 mm, 18.16 mm, 18.17 mm, 18.18 mm, 18.19 mm, 18.2 mm, 18.21 mm, 18.22 mm, 18.23 mm, 18.24 mm, 18.25 mm, 18.26 mm, 18.27 mm, 18.28 mm, 18.29 mm, 18.3 mm, 18.31 mm, 18.32 mm, 18.33 mm, 18.34 mm, 18.35 mm, 18.36 mm, 18.37 mm, 18.38 mm, 18.39 mm, 18.4 mm, 18.41 mm, 18.42 mm, 18.43 mm, 18.44 mm, 18.45 mm, 18.46 mm, 18.47 mm, 18.48 mm, 18.49 mm, 18.5 mm, 18.51 mm, 18.52 mm, 18.53 mm, 18.54 mm, 18.55 mm, 18.56 mm, 18.57 mm, 18.58 mm, 18.59 mm, 18.6 mm, 18.61 mm, 18.62 mm, 18.63 mm, 18.64 mm, 18.65 mm, 18.66 mm, 18.67 mm, 18.68 mm, 18.69 mm, 18.7 mm, 18.71 mm, 18.72 mm, 18.73 mm, 18.74 mm, 18.75 mm, 18.76 mm, 18.77 mm, 18.78 mm, 18.79 mm, 18.8 mm, 18.81 mm, 18.82 mm, 18.83 mm, 18.84 mm, 18.85 mm, 18.86 mm, 18.87 mm, 18.88 mm, 18.89 mm, 18.9 mm, 18.91 mm, 18.92 mm, 18.93 mm, 18.94 mm, 18.95 mm, 18.96 mm, 18.97 mm, 18.98 mm, 18.99 mm, 19 mm, 19.01 mm, 19.02 mm, 19.03 mm, 19.04 mm, 19.05 mm, 19.06 mm, 19.07 mm, 19.08 mm, 19.09 mm, 19.1 mm, 19.11 mm, 19.12 mm, 19.13 mm, 19.14 mm, 19.15 mm, 19.16 mm, 19.17 mm, 19.18 mm, 19.19 mm, 19.2 mm, 19.21 mm, 19.22 mm, 19.23 mm, 19.24 mm, 19.25 mm, 19.26 mm, 19.27 mm, 19.28 mm, 19.29 mm, 19.3 mm, 19.31 mm, 19.32 mm, 19.33 mm, 19.34 mm, 19.35 mm, 19.36 mm, 19.37 mm, 19.38 mm, 19.39 mm, 19.4 mm, 19.41 mm, 19.42 mm, 19.43 mm, 19.44 mm, 19.45 mm, 19.46 mm, 19.47 mm, 19.48 mm, 19.49 mm, 19.5 mm, 19.51 mm, 19.52 mm, 19.53 mm, 19.54 mm, 19.55 mm, 19.56 mm, 19.57 mm, 19.58 mm, 19.59 mm 19.6 mm, 19.61 mm, 19.62 mm, 19.63 mm, 19.64 mm, 19.65 mm, 19.66 mm, 19.67 mm, 19.68 mm, 19.69 mm, 19.7 mm, 19.71 mm, 19.72 mm, 19.73 mm, 19.74 mm, 19.75 mm, 19.76 mm, 19.77 mm, 19.78 mm, 19.79 mm, 19.8 mm, 19.81 mm, 19.82 mm, 19.83 mm, 19.84 mm, 19.85 mm, 19.86 mm, 19.87 mm, 19.88 mm, 19.89 mm, 19.9 mm, 19.91 mm, 19.92 mm, 19.93 mm, 19.94 mm, 19.95 mm, 19.96 mm, 19.97 mm, 19.98 mm, 19.99 mm, or 20 mm as measured on the major axis, (ii) a width of approximately 11 mm, 11.01 mm, 11.02 mm, 11.03 mm, 11.04 mm, 11.05 mm, 11.06 mm, 11.07 mm, 11.08 mm, 11.09 mm, 11.1 mm, 11.11 mm, 11.12 mm, 11.13 mm, 11.14 mm, 11.15 mm, 11.16 mm, 11.17 mm, 11.18 mm, 11.19 mm, 11.2 mm, 11.21 mm, 11.22 mm, 11.23 mm, 11.24 mm, 11.25 mm, 11.26 mm, 11.27 mm, 11.28 mm, 11.29 mm, 11.3 mm, 11.31 mm, 11.32 mm, 11.33 mm, 11.34 mm, 11.35 mm, 11.36 mm, 11.37 mm, 11.38 mm, 11.39 mm, 11.4 mm, 11.41 mm, 11.42 mm, 11.43 mm, 11.44 mm, 11.45 mm, 11.46 mm, 11.47 mm, 11.48 mm, 11.49 mm, 11.5 mm, 11.51 mm, 11.52 mm, 11.53 mm, 11.54 mm, 11.55 mm, 11.56 mm, 11.57 mm, 11.58 mm, 11.59 mm, 11.6 mm, 11.61 mm, 11.62 mm, 11.63 mm, 11.64 mm, 11.65 mm, 11.66 mm, 11.67 mm, 11.68 mm, 11.69 mm, 11.7 mm, 11.71 mm, 11.72 mm, 11.73 mm, 11.74 mm, 11.75 mm, 11.76 mm, 11.77 mm, 11.78 mm, 11.79 mm, 11.8 mm, 11.81 mm, 11.82 mm, 11.83 mm, 11.84 mm, 11.85 mm, 11.86 mm, 11.87 mm, 11.88 mm, 11.89 mm, 11.9 mm, 11.91 mm, 11.92 mm, 11.93 mm, 11.94 mm, 11.95 mm, 11.96 mm, 11.97 mm, 11.98 mm, 11.99 mm, 12 mm, 12.01 mm, 12.02 mm, 12.03 mm, 12.04 mm, 12.05 mm, 12.06 mm, 12.07 mm, 12.08 mm, 12.09 mm, 12.1 mm, 12.11 mm, 12.12 mm, 12.13 mm, 12.14 mm, 12.15 mm, 12.16 mm, 12.17 mm, 12.18 mm, 12.19 mm, 12.2 mm, 12.21 mm, 12.22 mm, 12.23 mm, 12.24 mm, 12.25 mm, 12.26 mm, 12.27 mm, 12.28 mm, 12.29 mm, 12.3 mm, 12.31 mm, 12.32 mm, 12.33 mm, 12.34 mm, 12.35 mm, 12.36 mm, 12.37 mm, 12.38 mm, 12.39 mm, 12.4 mm, 12.41 mm, 12.42 mm, 12.43 mm, 12.44 mm, 12.45 mm, 12.46 mm, 12.47 mm, 12.48 mm, 12.49 mm, 12.5 mm, 12.51 mm, 12.52 mm, 12.53 mm, 12.54 mm, 12.55 mm, 12.56 mm, 12.57 mm, 12.58 mm, 12.59 mm, 12.6 mm, 12.61 mm, 12.62 mm, 12.63 mm, 12.64 mm, 12.65 mm, 12.66 mm, 12.67 mm, 12.68 mm, 12.69 mm, 12.7 mm, 12.71 mm, 12.72 mm, 12.73 mm, 12.74 mm, 12.75 mm, 12.76 mm, 12.77 mm, 12.78 mm, 12.79 mm, 12.8 mm, 12.81 mm, 12.82 mm, 12.83 mm, 12.84 mm, 12.85 mm, 12.86 mm, 12.87 mm, 12.88 mm, 12.89 mm, 12.9 mm, 12.91 mm, 12.92 mm, 12.93 mm, 12.94 mm, 12.95 mm, 12.96 mm, 12.97 mm, 12.98 mm, 12.99 mm, or 13 mm, and (iii) a height or thickness of approximately 5 mm, 5.01 mm, 5.02 mm, 5.03 mm, 5.04 mm, 5.05 mm, 5.06 mm, 5.07 mm, 5.08 mm, 5.09 mm, 5.1 mm, 5.11 mm, 5.12 mm, 5.13 mm, 5.14 mm, 5.15 mm, 5.16 mm, 5.17 mm, 5.18 mm, 5.19 mm, 5.2 mm, 5.21 mm, 5.22 mm, 5.23 mm, 5.24 mm, 5.25 mm, 5.26 mm, 5.27 mm, 5.28 mm, 5.29 mm, 5.3 mm, 5.31 mm, 5.32 mm, 5.33 mm, 5.34 mm, 5.35 mm, 5.36 mm, 5.37 mm, 5.38 mm, 5.39 mm, 5.4 mm, 5.41 mm, 5.42 mm, 5.43 mm, 5.44 mm, 5.45 mm, 5.46 mm, 5.47 mm, 5.48 mm, 5.49 mm, 5.5 mm, 5.51 mm, 5.52 mm, 5.53 mm, 5.54 mm, 5.55 mm, 5.56 mm, 5.57 mm, 5.58 mm, 5.59 mm, 5.6 mm, 5.61 mm, 5.62 mm, 5.63 mm, 5.64 mm, 5.65 mm, 5.66 mm, 5.67 mm, 5.68 mm, 5.69 mm, 5.7 mm, 5.71 mm, 5.72 mm, 5.73 mm, 5.74 mm, 5.75 mm, 5.76 mm, 5.77 mm, 5.78 mm, 5.79 mm, 5.8 mm, 5.81 mm, 5.82 mm, 5.83 mm, 5.84 mm, 5.85 mm, 5.86 mm, 5.87 mm, 5.88 mm, 5.89 mm, 5.9 mm, 5.91 mm, 5.92 mm, 5.93 mm, 5.94 mm, 5.95 mm, 5.96 mm, 5.97 mm, 5.98 mm, 5.99 mm, or 6 mm. In yet another embodiment, the pharmaceutical composition may have (i) a length of approximately 19.1 mm, 19.11 mm, 19.12 mm, 19.13 mm, 19.14 mm, 19.15 mm, 19.16 mm, 19.17 mm, 19.18 mm, 19.19 mm, or 19.2 mm, 19.21 mm, 19.22 mm, 19.23 mm, 19.24 mm, 19.25 mm, 19.26 mm, 19.27 mm, 19.28 mm, 19.29 mm, or 19.3 mm as measured on the major axis, (ii) a width of approximately 12.4 mm, 12.41 mm, 12.42 mm, 12.43 mm, 12.44 mm, 12.45 mm, 12.46 mm, 12.47 mm, 12.48 mm, 12.49 mm, or 12.5 mm, and (iii) a height or thickness of approximately 5.6 mm, 5.61 mm, 5.62 mm, 5.63 mm, 5.64 mm, 5.65 mm, 5.66 mm, 5.67 mm, 5.68 mm, 5.69 mm, 5.7 mm, 5.71 mm, 5.72 mm, 5.73 mm, 5.74 mm, 5.75 mm, 5.76 mm, 5.77 mm, 5.78 mm, 5.79 mm, or 5.8 mm.

In another embodiment, the composition may be expandable. That is, the composition has size that is small enough for oral intake, but the composition absorbs water from the gastric fluid and swells to a size that prevents its passage through the pylorus. Such a composition comprises at least one swellable, expandable material, such as a polymer, resin, hydrocolloid, hydrogel, or the like. In various embodiments, the composition may swell to a size that is about 110% to about 200% of the original volume within about 30 minutes of administration. For example, the composition may swell to approximately 115% of it original volume within 30 minutes of administration, and at a later time may swell to a volume that is 130% or more of the original volume. In other embodiments, the composition may exhibit a volume increase of two-fold or more. Additionally, the composition may become slippery upon absorption of water, which provides resistance to peristalsis and further promotes gastric retention. The swellable material degrades or erodes over a specified period of time (e.g., the dosing interval) such that the composition is no longer retained in the stomach. In one embodiment, the ER layer swells upon imbibition of fluid to a size which is about 15%, 20%, 25%, 30%, 35% 40%, 45%, 50%, 55%, 60%, 65%, 70%, 75%, 80%, 85%, 90%, 95% or 100% larger than the size of the ER layer prior to imbibition of fluid. In another embodiment, the ER layer swells upon imbibition of fluid to a size at least about 25% larger than the size of the ER layer prior to imbibition of fluid within about 15 minutes of the start of fluid imbibition. In still another embodiment, the ER layer swells upon imbibition of fluid to a size at least about 100% larger than the size of the ER layer prior to imbibition of fluid within about 45 min, 50 min, 60 min, 75 min, or 90 min of the start of fluid imbibitions.

In yet another embodiment, the length of the composition increases by about 4%, 4.25%, 4.5% 4.75%, 5%, 5.25%, 5.5%, 5.75%, 6%, 6.25%, 6.5%, 6.75%, 7%, 7.25%, 7.5%, 7.75%, 8%, 8.25%, 8.5%, 8.75%, 9%, 9.25%, 9.5%, 9.75%, 10%, 10.25%, 10.5%, 10.75%, 11%, 11.25%, 11.5%, 11.75%, 12%, 12.25%, 12.5%, 12.75%, or 13% within about 10 minutes of the start of fluid imbibition. In still another embodiment, the length of the composition increases by about 5%, 5.25%, 5.5%, 5.75%, 6%, 6.25%, 6.5%, 6.75%, 7%, 7.25%, 7.5%, 7.75%, 8%, 8.25%, 8.5%, 8.75%, 9%, 9.25%, 9.5%, 9.75%, 10%, 10.25%, 10.5%, 10.75%, 11%, 11.25%, 11.5%, 11.75%, 12%, 12.25%, 12.5%, 12.75%, 13%, 13.25%, 13.5%, 13.75%, 14%, 14.25%, 14.5%, 14.75%, or 15% within about 15 minutes of the start of fluid imbibition. In yet another embodiment, the length of the composition increases by about 5%, 5.25%, 5.5%, 5.75%, 6%, 6.25%, 6.5%, 6.75%, 7%, 7.25%, 7.5%, 7.75%, 8%, 8.25%, 8.5%, 8.75%, 9%, 9.25%, 9.5%, 9.75%, 10%, 10.25%, 10.5%, 10.75%, 11%, 11.25%, 11.5%, 11.75%, 12%, 12.25%, 12.5%, 12.75%, 13%, 13.25%, 13.5%, 13.75%, 14%, 14.25%, 14.5%, 14.75%, or 15% within about 20 minutes of the start of fluid imbibition. In a further embodiment, the length of the composition increases by about 7%, 7.25%, 7.5%, 7.75%, 8%, 8.25%, 8.5%, 8.75%, 9%, 9.25%, 9.5%, 9.75%, 10%, 10.25%, 10.5%, 10.75%, 11%, 11.25%, 11.5%, 11.75%, 12%, 12.25%, 12.5%, 12.75%, 13%, 13.25%, 13.5%, 13.75%, 14%, 14.25%, 14.5%, 14.75%, 15%, 15.25%, 15.5%, 15.75%, 16%, 16.25%, 16.5%, 16.75%, 17%, 17.25%, 17.5%, 17.75%, or 18% within about 30 minutes of the start of fluid imbibition. In another embodiment, the length of the composition increases by about 8%, 8.25%, 8.5%, 8.75%, 9%, 9.25%, 9.5%, 9.75%, 10%, 10.25%, 10.5%, 10.75%, 11%, 11.25%, 11.5%, 11.75%, 12%, 12.25%, 12.5%, 12.75%, 13%, 13.25%, 13.5%, 13.75%, 14%, 14.25%, 14.5%, 14.75%, 15%, 15.25%, 15.5%, 15.75%, 16%, 16.25%, 16.5%, 16.75%, 17%, 17.25%, 17.5%, 17.75%, 18%, 18.25%, 18.5%, 18.75%, or 19% within about 45 minutes of the start of fluid imbibition. In yet another embodiment, the length of the composition increases by about 8%, 8.25%, 8.5%, 8.75%, 9%, 9.25% 9.5%, 9.75%, 10%, 10.25%, 10.5%, 10.75%, 11%, 11.25%, 11.5%, 11.75%, 12%, 12.25%, 12.5%, 12.75%, 13%, 13.25%, 13.5%, 13.75%, 14%, 14.25%, 14.5%, 14.75%, 15%, 15.25%, 15.5%, 15.75%, 16%, 16.25%, 16.5%, 16.75%, 17%, 17.25%, 17.5%, 17.75%, 18%, 18.25%, 18.5%, 18.75%, or 19% within about 55 minutes of the start of fluid imbibition. In still another embodiment, the length of the composition increases by about 8%, 8.25%, 8.5%, 8.75%, 9%, 9.25%, 9.5%, 9.75%, 10%, 10.25%, 10.5%, 10.75%, 11%, 11.25%, 11.5%, 11.75%, 12%, 12.25%, 12.5%, 12.75%, 13%, 13.25%, 13.5%, 13.75%, 14%, 14.25%, 14.5%, 14.75%, 15%, 15.25%, 15.5%, 15.75%, 16%, 16.25%, 16.5%, 16.75%, 17%, 17.25%, 17.5%, 17.75%, 18%, 18.25%, 18.5%, 18.75%, 19%, 19.25%, 19.5%, 19.75%, or 20% within about 60 minutes of the start of fluid imbibition.

In a further embodiment, the width of the composition increases by about 6%, 6.25%, 6.5%, 6.75%, 7%, 7.25%, 7.5%, 7.75%, 8%, 8.25%, 8.5%, 8.75%, 9%, 9.25%, 9.5%, 9.75%, 10%, 10.25%, 10.5%, 10.75%, 11%, 11.25%, 11.5%, 11.75%, 12%, 12.25%, 12.5%, 12.75%, 13%, 13.25%, 13.5%, 13.75%, 14%, 14.25%, 14.5%, 14.75%, or 15% within about 10 minutes of the start of fluid imbibition. In still another embodiment, the width of the composition increases by about 6%, 6.25%, 6.5%, 6.75%, 7%, 7.25%, 7.5%, 7.75%, 8%, 8.25%, 8.5%, 8.75%, 9%, 9.25%, 9.5%, 9.75%, 10%, 10.25%, 10.5%, 10.75%, 11%, 11.25%, 11.5%, 11.75%, 12%, 12.25%, 12.5%, 12.75%, 13%, 13.25%, 13.5%, 13.75%, 14%, 14.25%, 14.5%, 14.75%, 15%, 15.25%, 15.5%, 15.75%, 16%, 16.25%, 16.5%, 16.75%, 17%, 17.25%, 17.5%, 17.75%, or 18%, within about 15 minutes of the start of fluid imbibition. In yet another embodiment, the width of the composition increases by about 6%, 6.25%, 6.5% 6.75%, 7%, 7.25%, 7.5% 7.75%, 8%, 8.25%, 8.5%, 8.75%, 9%, 9.25%, 9.5%, 9.75%, 10%, 10.25%, 10.5%, 10.75%, 11%, 11.25%, 11.5%, 11.75%, 12%, 12.25%, 12.5%, 12.75%, 13%, 13.25%, 13.5%, 13.75%, 14%, 14.25%, 14.5%, 14.75%, 15%, 15.25%, 15.5%, 15.75%, 16% 16.25%, 16.5%, 16.75%, 17%, 17.25%, 17.5%, 17.75%, or 18%, within about 20 minutes of the start of fluid imbibition. In a further embodiment, the width of the composition increases by about 10%, 10.25%, 10.5%, 10.75%, 11%, 11.25%, 11.5%, 11.75%, 12%, 12.25%, 12.5%, 12.75%, 13%, 13.25%, 13.5%, 13.75%, 14%, 14.25%, 14.5%, 14.75%, 15%, 15.25%, 15.5%, 15.75%, 16%, 16.25%, 16.5%, 16.75%, 17%, 17.25%, 17.5%, 17.75%, 18%, 18.25%, 18.5%, 18.75%, 19%, 19.25%, 19.5%, 19.75%, 20%, 20.25%, 20.5%, 20.75%, 21%, 21.25%, 21.5%, 21.75%, 22%, 22.25%, 22.5%, 22.75%, 23%, 23.25%, 23.5%, 23.75%, or 24% within about 30 minutes of the start of fluid imbibition. In another embodiment, the width of the composition increases by about 12%, 12.25%, 12.5%, 12.75%, 13%, 13.25%, 13.5%, 13.75%, 14%, 14.25%, 14.5%, 14.75%, 15%, 15.25%, 15.5%, 15.75%, 16%, 16.25%, 16.5%, 16.75%, 17%, 17.25%, 17.5%, 17.75%, 18%, 18.25%, 18.5%, 18.75%, 19%, 19.25%, 19.5%, 19.75%, 20.0%, 20.25%, 20.5%, 20.75%, 21%, 21.25%, 21.5%, 21.75%, 22%, 22.25%, 22.5%, 22.75%, 23%, 23.25%, 23.5%, 23.75%, 24%, 24.25%, 24.5%, 24.75%, or 25% within about 45 minutes of the start of fluid imbibition. In yet another embodiment, the width of the composition increases by about 12%, 12.25%, 12.5%, 12.75%, 13%, 13.25%, 13.5%, 13.75%, 14%, 14.25%, 14.5%, 14.75%, 15%, 15.25%, 15.5%, 15.75%, 16%, 16.25%, 16.5%, 16.75%, 17%, 17.25%, 17.5%, 17.75%, 18%, 18.25%, 18.5%, 18.75%, 19%, 19.25%, 19.5%, 19.75%, 20.25%, 20.5%, 20.75%, 21%, 21.25%, 21.5%, 21.75%, 22%, 22.25%, 22.5%, 22.75%, 23%, 23.25%, 23.5%, 23.75%, 24%, 24.25%, 24.5%, 24.75%, or 25% within about 55 minutes of the start of fluid imbibition. In still another embodiment, the width of the composition increases by about 14%, 14.25%, 14.5%, 14.75%, 15%, 15.25%, 15.5%, 15.75%, 16%, 16.25%, 16.5%, 16.75%, 17%, 17.25%, 17.5%, 17.75%, 18%, 18.25%, 18.5%, 18.75%, 19%, 19.25%, 19.5%, 19.75%, 20%, 20.25%, 20.5%, 20.75%, 21%, 21.25%, 21.5%, 21.75%, 22%, 22.25%, 22.5%, 22.75%, 23%, 23.25%, 23.5%, 23.75%, 24%, 24.25%, 24.5%, 24.75%, 25%, 25.25%, 25.5%, 25.75%, or 26% within about 60 minutes of the start of fluid imbibition.

In additional embodiments, the pharmaceutical composition may have (i) a length of about 18.5 mm, 18.6 mm, 18.7 mm, 18.8 mm, 18.9 mm, 19 mm, 19.1 mm, 19.2 mm, 19.3 mm, 19.4 mm, 19.5 mm, 19.6 mm, 19.7 mm, 19.8 mm, 19.9 mm, 20 mm, 20.1 mm, 20.2 mm, 20.3 mm, 20.4 mm, 20.5 mm, 20.6 mm, 20.7 mm, 20.8 mm, 20.9 mm, or 21 mm; and (ii) a width of about 11 mm, 11.1 mm, 11.2 mm, 11.3 mm, 11.4 mm, 11.5 mm, 11.6 mm, 11.7 mm, 11.8 mm, 11.9 mm, 12 mm, 12.1 mm, 12.2 mm, 12.3 mm, 12.4 mm, 12.5 mm, 12.6 mm, 12.7 mm, 12.8 mm, 12.9 mm, 13 mm, 13.1 mm, 13.2 mm, 13.3 mm, 13.4 mm, 13.5 mm, 13.6 mm, 13.7 mm, 13.8 mm, 13.9 mm, or 14 mm within about 5 minutes of the start of fluid imbibition. In other embodiments, the pharmaceutical composition may have (i) a length of about 18.5 mm, 18.6 mm, 18.7 mm, 18.8 mm, 18.9 mm, 19 mm, 19.1 mm, 19.2 mm, 19.3 mm, 19.4 mm, 19.5 mm, 19.6 mm, 19.7 mm, 19.8 mm, 19.9 mm, 20 mm, 20.1 mm, 20.2 mm, 20.3 mm, 20.4 mm, 20.5 mm, 20.6 mm, 20.7 mm, 20.8 mm, 20.9 mm, 21 mm, 21.1 mm, 21.2 mm, 21.3 mm, 21.4 mm, 21.5 mm, 21.6 mm, 21.7 mm, 21.8 mm, 21.9 mm, or 22 mm; and (ii) a width of about 11 mm, 11.1 mm, 11.2 mm, 11.3 mm, 11.4 mm, 11.5 mm, 11.6 mm, 11.7 mm, 11.8 mm, 11.9 mm, 12 mm, 12.1 mm, 12.2 mm, 12.3 mm, 12.4 mm, 12.5 mm, 12.6 mm, 12.7 mm, 12.8 mm, 12.9 mm, 13 mm, 13.1 mm, 13.2 mm, 13.3 mm, 13.4 mm, 13.5 mm, 13.6 mm, 13.7 mm, 13.8 mm, 13.9 mm, 14 mm, 14.1 mm, 14.2 mm, 14.3 mm, 14.4 mm, 14.5 mm, 14.6 mm, 14.7 mm, 14.8 mm, 14.9 mm, or 15 mm within about 10 minutes to about 15 minutes of the start of fluid imbibition. In still other embodiments, the pharmaceutical composition may have (i) a length of about 19 mm, 19.1 mm, 19.2 mm, 19.3 mm, 19.4 mm, 19.5 mm, 19.6 mm, 19.7 mm, 19.8 mm, 19.9 mm, 20 mm, 20.1 mm, 20.2 mm, 20.3 mm, 20.4 mm, 20.5 mm, 20.6 mm, 20.7 mm, 20.8 mm, 20.9 mm, 21 mm, 21.1 mm, 21.2 mm, 21.3 mm, 21.4 mm, 21.5 mm, 21.6 mm, 21.7 mm, 21.8 mm, 21.9 mm, 22 mm, 22.1 mm, 22.2 mm, 22.3 mm, 22.4 mm, or 22.5 mm; and (ii) a width of about 12 mm, 12.1 mm, 12.2 mm, 12.3 mm, 12.4 mm, 12.5 mm, 12.6 mm, 12.7 mm, 12.8 mm, 12.9 mm, 13 mm, 13.1 mm, 13.2 mm, 13.3 mm, 13.4 mm, 13.5 mm, 13.6 mm, 13.7 mm, 13.8 mm, 13.9 mm, 14 mm, 14.1 mm, 14.2 mm, 14.3 mm, 14.4 mm, 14.5 mm, 14.6 mm, 14.7 mm, 14.8 mm, 14.9 mm, or 15 mm within about 20 minutes to about 25 minutes of the start of fluid imbibition. In additional embodiments, the pharmaceutical composition may have (i) a length of about 19 mm, 19.1 mm, 19.2 mm, 19.3 mm, 19.4 mm, 19.5 mm, 19.6 mm, 19.7 mm, 19.8 mm, 19.9 mm, 20 mm, 20.1 mm, 20.2 mm, 20.3 mm, 20.4 mm, 20.5 mm, 20.6 mm, 20.7 mm, 20.8 mm, 20.9 mm, 21 mm, 21.1 mm, 21.2 mm, 21.3 mm, 21.4 mm, 21.5 mm, 21.6 mm, 21.7 mm, 21.8 mm, 21.9 mm, 22 mm, 22.1 mm, 22.2 mm, 22.3 mm, 22.4 mm, 22.5 mm, 22.6 mm, 22.7 mm, 22.8 mm, 22.9 mm, or 23 mm; and (ii) a width of about 12.5 mm, 12.6 mm, 12.7 mm, 12.8 mm, 12.9 mm, 13 mm, 13.1 mm, 13.2 mm, 13.3 mm, 13.4 mm, 13.5 mm, 13.6 mm, 13.7 mm, 13.8 mm, 13.9 mm, 14 mm, 14.1 mm, 14.2 mm, 14.3 mm, 14.4 mm, 14.5 mm, 14.6 mm, 14.7 mm, 14.8 mm, 14.9 mm, or 15 mm within about 30 minutes to about 35 minutes of the start of fluid imbibition. In still other embodiments, the pharmaceutical composition may have (i) a length of about 19.5 mm, 19.6 mm, 19.7 mm, 19.8 mm, 19.9 mm, 20 mm, 20.1 mm, 20.2 mm, 20.3 mm, 20.4 mm, 20.5 mm, 20.6 mm, 20.7 mm, 20.8 mm, 20.9 mm, 21 mm, 21.1 mm, 21.2 mm, 21.3 mm, 21.4 mm, 21.5 mm, 21.6 mm, 21.7 mm, 21.8 mm, 21.9 mm, 22 mm, 22.1 mm, 22.2 mm, 22.3 mm, 22.4 mm, 22.5 mm, 22.6 mm, 22.7 mm, 22.8 mm, 22.9 mm, 23 mm, 23.1 mm, 23.2 mm, 23.3 mm, 23.4 mm, or 23.5; (ii) a width of about 13 mm, 13.1 mm, 13.2 mm, 13.3 mm, 13.4 mm, 13.5 mm, 13.6 mm, 13.7 mm, 13.8 mm, 13.9 mm, 14 mm, 14.1 mm, 14.2 mm, 14.3 mm, 14.4 mm, 14.5 mm, 14.6 mm, 14.7 mm, 14.8 mm, 14.9 mm, 15 mm, 15.1 mm, 15.2 mm, 15.3 mm, 15.4 mm, 15.5 mm, 15.6 mm, 15.7 mm, 15.8 mm, 15.9 mm, or 16 mm; and (iii) a height of about 5.5 mm, 5.6 mm, 5.7 mm, 5.8 mm, 5.9 mm, 6 mm, 6.1 mm, 6.2 mm, 6.3 mm, 6.4 mm, 6.5 mm, 6.6 mm, 6.7 mm, 6.8 mm, 6.9 mm, or 7 mm within about 50 minutes to about 55 minutes of the start of fluid imbibition. In yet another embodiment, the pharmaceutical composition may have (i) a length of about 19.5 mm, 19.6 mm, 19.7 mm, 19.8 mm, 19.9 mm, 20 mm, 20.1 mm, 20.2 mm, 20.3 mm, 20.4 mm, 20.5 mm, 20.6 mm, 20.7 mm, 20.8 mm, 20.9 mm, 21 mm, 21.1 mm, 21.2 mm, 21.3 mm, 21.4 mm, 21.5 mm, 21.6 mm, 21.7 mm, 21.8 mm, 21.9 mm, 22 mm, 22.1 mm, 22.2 mm, 22.3 mm, 22.4 mm, 22.5 mm, 22.6 mm, 22.7 mm, 22.8 mm, 22.9 mm, 23 mm, 23.1 mm, 23.2 mm, 23.3 mm, 23.4 mm, or 23.5; (ii) a width of about 13 mm, 13.1 mm, 13.2 mm, 13.3 mm, 13.4 mm, 13.5 mm, 13.6 mm, 13.7 mm, 13.8 mm, 13.9 mm, 14 mm, 14.1 mm, 14.2 mm, 14.3 mm, 14.4 mm, 14.5 mm, 14.6 mm, 14.7 mm, 14.8 mm, 14.9 mm, 15 mm, 15.1 mm, 15.2 mm, 15.3 mm, 15.4 mm, 15.5 mm, 15.6 mm, 15.7 mm, 15.8 mm, 15.9 mm, or 16 mm; and (iii) a height of about 5.5 mm, 5.6 mm, 5.7 mm, 5.8 mm, 5.9 mm, 6 mm, 6.1 mm, 6.2 mm, 6.3 mm, 6.4 mm, 6.5 mm, 6.6 mm, 6.7 mm, 6.8 mm, 6.9 mm, or 7 mm within about 60 minutes of the start of fluid imbibition.

In a further embodiment, the composition contains at least one swellable polymer. For example, the composition may include chitosan, methylcellulose, polyvinyl acetate, purified shellac, or an expansive polymeric film, such as one composed of polyvinyl acetate and shellac.

In still another embodiment, the physical property of the composition that imparts gastric retention may be the shape of the composition. For example, the composition may have a ring, tetrahedron, spiral, coil, planar disc, planar multilobe, continuous stick, sheet, oval, parallelogram, or string geometric configuration, wherein the composition is unable to pass through the pyloric sphincter. In some iterations, the composition may be folded into a pharmaceutical carrier (e.g., a gelatin capsule) or secured by readily dissolvable (e.g., gelatin) strips such that, upon dissolution of the carrier or strips, the composition unfolds in the stomach. In general, unfoldable compositions comprise biodegradable polymers such that the composition is degraded and/or reduced in size over a specified period of time (e.g., the dosing interval). In another embodiment, the composition has a diameter of greater than or equal to 7.5 mm.

In yet another embodiment, the physical property of the composition that imparts gastric retention may be the adhesivity of the composition. Bio-mucoadhesive compositions bind to the gastric epithelial cell surface, or mucin, and increase gastric retention time by increasing the intimacy and duration of contact between the composition and the biological membrane. Bio-mucoadhesive compositions generally comprise a natural or synthetic polymer that is capable of adhering to a biological membrane (e.g., a bioadhesive polymer) or the mucus lining of the stomach or intestinal tract (e.g., a mucoadhesive polymer). Certain hydrophilic polymers tend to imbibe large amounts of water and become sticky, thereby acquiring bioadhesive properties. The adhesion of polymers to a mucus or epithelial cell surface may involve various bonding mechanisms, including physical-mechanical bonding and chemical bonding. Physical-mechanical bonding may result from the insertion of the adhesive material into the crevices or folds of the mucosa. Chemical bonds may be either covalent or non-covalent (e.g., ionic bonds, hydrogen bonds, van der Waals interactions, etc). Moreover, certain polymers may bind to specific receptor sites on the surface of cells, thereby enhancing the gastric retention. For example, certain plant lectins interact specifically with the sugar groups present in mucus or on the glycocalyx.

In still another embodiment, the physical property of the composition that imparts gastric retention may be the density of the composition. In one iteration, the composition may have a low density with sufficient buoyancy such that the composition floats over the gastric contents and remains in the stomach for a prolonged period. Floating compositions may be effervescent or noneffervescent. Effervescent compositions generally comprise matrices prepared with swellable polymers and an effervescent component. For example, the effervescent component can be either a carbonate or bicarbonate salt (e.g., sodium bicarbonate, calcium bicarbonate), an organic acid (e.g., citric acid, tartaric acid), or any combination thereof. The effervescent component can also be a floating chamber filled with vacuum, air, an inert gas, or a liquid that gasifies at body temperature. Floatability is generally achieved by generation of gas bubbles. Gas may be introduced into the floating chamber by the volatilization of an organic solvent, or by an effervescent reaction between a carbonate-bicarbonate salt and an organic acid. The matrices may be fabricated so that upon arrival in the stomach, carbon dioxide is liberated by the acidity of the gastric contents and is entrapped in the gellified matrix. This maintains the buoyancy of the composition, causing it to float. In another embodiment, the composition may also contain a polymer which exhibits floating characteristics, such as hydroxypropyl cellulose, hydroxypropyl methylcellulose, crospovidone, sodium carboxymethyl cellulose, or ethyl cellulose. In a further embodiment, the composition may comprise a device having a hollow deformable unit that converts from a collapsed to expanded form and vise versa. The unit is supported by a housing that is internally divided into two chambers separated by a pressure-sensitive movable bladder. The first chamber contains the therapeutic agent and the second contains a volatile liquid (e.g., cyclopentane, ether) that vaporizes at body temperature and imparts buoyancy to the system. The system also contains a bioerodible plug to aid in the exit from the body. Further embodiments of this two chamber system are disclosed in U.S. Pat. Nos. 3,901,232 and 3,786,813, which are hereby incorporated by reference. In still a further embodiment, the composition may contain hollow microspheres or microballoons, which cause the composition to float. The composition may also comprise floating microparticles such as polypropylene foam, Eudragit, ethyl cellulose, or polymethyl metha acylate (PMMA).

Noneffervescent compositions incorporate a high level of one or more gel-forming, highly swellable, cellulosic hydrocolloids. Upon contact with the gastric contents, these hydrocolloids hydrate and forms a colloidal gel barrier, wherein air trapped by the swollen hydrocolloid confers buoyancy to this composition. In another iteration, the composition may have a density that exceeds the density of normal gastric contents such the composition sinks to the bottom of the stomach (i.e., the antrum) where it is entrapped in the folds of the antrum and withstands the peristaltic waves of the gastric wall. In yet another iteration, the composition has a density that is greater than or equal to 1.3 g/mL.

In one embodiment, the composition is retained in the stomach due to the presence of an extended release polymer that absorbs water from the gastric contents and swells or expands to a size that cannot pass through the pyloric sphincter. As a consequence, the opioid and the other API are slowly released from the composition in the stomach and absorbed in the upper gastrointestinal tract.

In still another embodiment, the composition may contain an agent which delays the passage of the composition through the pyloric sphincter. For example, the composition may include triethanol amine myristate or propantheline.

(ii) Opioid Release

Because opioids reduce gastric motility, the erosion time of the dosage form can be increased (thus, hindering drug release) if the opioid is not properly dosed. The gastric retentive extended release composition disclosed herein is engineered to release the opioid(s) at a rate that is sufficient to delay gastric emptying such that the composition is retained in the stomach for a longer period of time than a comparable composition that is not gastric retentive. For example, the composition may be designed to release the opioid(s) at a rate that delays gastric emptying by about 15 minutes, 30 minutes, 60 minutes, 90 minutes, 2.0 hours, 2.5 hours, 3.0 hours, 3.5 hours, 4.0 hours, 4.5 hours, or 5.0 hours. The rate of release of the opioid(s) may be manipulated by selecting a suitable extended release component for inclusion in an extended release portion of the composition. For example, in embodiments in which the extended release component is an extended release polymer, the extended release polymer generally is selected such that the composition releases the opioid(s) at a rate that delays gastric emptying by the desired amount. Additionally, the rate of release of the opioid(s) from the composition may be adjusted by selecting the proper ratio of opioid present in the at least one immediate release and the at least one extended release portions of the composition. For instance, the proportion of the opioid(s) in the at least one immediate release portion and the at least one extended release portion may be about 20:80, 21;79, 22:78, 23;77; 24:76, 25;75, 26:74, 27:73, 28;72, 29;71, 30:70, 31:69, 32:68, 33:67, 34:66, 35:65, 34:66, 35:65, 36:64, 37:63, 38:62, 39:61, or 40:60.

Additionally, the gastric retentive extended release composition is engineered to release the opioid(s) at a rate that is insufficient to cause any serious adverse gastrointestinal effects. Adverse gastrointestinal effects include, but are not limited to, intestinal hypomotility, intestinal blockage, intestinal pseudo-obstruction, abdominal distention, bloating, constipation, intestinal distress, severe intestinal contractions, colon spasms, hypoactive bowel, and increased anal sphincter tone.

(iii) Overall Composition

With the knowledge of the preferred dissolution and pharmacokinetic profiles for the opioid and the additional API, and the pharmacodynamics effects of the opioid and the additional API, a composition under the present invention can be developed using any of the gastric retentive dosage forms discussed above. Moreover, a composition under the present invention can be developed using another gastric retentive dosage form that achieves the same dissolution, pharmacokinetic, and pharmacodynamic profiles as the compositions disclosed herein. A composition could also be developed that is a sustained release formulation which lacks one of the specific gastric retentive dosage forms discussed above, yet, achieves the same dissolution and pharmacokinetic profiles, and exhibits the pharmacodynamic effects.

(e) Administration of the Gastric Retentive Extended Release Composition

The gastric retentive extended release composition may be administered to a subject in need thereof, wherein the subject may be either in a fed state or a fasted state. In general, a fed state is defined as having consumed food within about 30 min prior to administration of the composition. The food may be a high fat meal, a low fat meal, a high calorie meal, or a low calorie meal. A fasted state may be defined as not having ingested food for at least 10 hours prior to administration of the composition. In some embodiments, the subject may have fasted for at least 10 hours prior to the first dose and refrains from ingesting food for at least one hour prior to administration of subsequent doses. In other embodiments, the fasted subject may not have ingested food for at least 1 hour, 2 hours, 3 hours, 4 hours, 5 hours, 6 hours, 7 hours, 8 hours, 9 hours, or 10 hours prior to administration of each dose of the composition.

Upon oral administration of the composition, the other API(s) in the composition produce a plasma profile characterized by at least one pharmacokinetic parameter that differs by less than about 30% under fed and fasted conditions. In various embodiments, the pharmacokinetic parameter may vary by less than about 25%, 20%, 15%, 10%, or 5% under fed and fasted conditions. The pharmacokinetic parameter of the other API(s) that is independent of food may be, but is not limited to, Cmax, C1hr, C2hr, AUC, partial AUC, Tmax, and Tlag. Additionally, the opioid(s) in the composition produce a plasma profile characterized by at least one pharmacokinetic parameter that differs by less than about 30% under fed and fasted conditions. In various embodiments, the pharmacokinetic parameter may vary by less than about 25%, 20%, 15%, 10%, or 5% under fed and fasted conditions. In one embodiment, the pharmacokinetic parameter of the opioid that is independent of food may be, but is not limited to, $C_{max}$, $C_{1hr}$, C2 hr, AUC, partial AUC, $T_{max}$, and $T_{lag}$. In a further embodiment, the compositions disclosed herein may by administered to a subject in need thereof without regard to food.

(f) Dosage Forms

The physical form of the pharmaceutical compositions disclosed herein can and will vary. In one embodiment, the composition is provided as a solid dosage form comprising at least one extended release portion and, optionally, at least one immediate release portion. Suitable solid dosage forms include tablets, caplets, capsules, encapsulated beads, and gelcaps. Non-limiting types of tablets include coated tablets, uncoated tablets, bilayer tablets, multi-particle tablets, monolithic tablets, matrix tablets, compressed tablets, and molded tablets. Non-limiting types of capsules include hard capsules and multi-layer capsules.

In one embodiment, the dosage form may be a capsule. Non-limiting examples of suitable hard capsules include hard starch capsules, hard gelatin capsules, hard cellulose capsules, and hydrogel capsules. In one example, the core of the capsule may comprise one extended release portion comprising the opioid(s) and other API(s) and the shell of the capsule may comprise one immediate release portion of the composition comprising the opioid(s) and other API(s). In another example, the core of the capsule may comprise two extended release portions, each comprising one of the opioid or the other API, and the shell of the capsule may comprise the immediate release portion of the composition comprising both the opioid and the other API. In yet another example, the core of the capsule may comprise multiple extended release portions, each comprising one of the opioid or the other API, and the shell of the capsule may comprise the immediate release portion of the composition comprising both the opioid and the other API. In still another example, the core of the capsule may comprise one extended release portion, comprising either the opioid or the other API, and the shell of the capsule may comprise the immediate release portion of the composition comprising either the opioid and the other API. In an additional example, the core of the capsule may comprise multiple extended release and immediate release portions, each comprising one of the opioid or the other API. In still another embodiment, the dosage form may be a sustained release capsule comprising the opioid or the other API and exhibiting immediate release and/or extended release properties.

In another embodiment, the dosage form may be a tablet comprising at least one extended release portion and at least one immediate release portion. The at least one immediate release portion may be adjacent to, abutting, or surrounding the at least one extended release portion. In one embodiment, the dosage form may be a bilayer tablet comprising one extended release portion comprising both the opioid and the other API and one immediate release portion comprising both the opioid and the other API. In still another embodiment, the dosage form may be a sustained release tablet comprising the opioid and/or the other API and exhibiting immediate release and/or extended release properties. The bilayer tablet may comprise a coating.

In another embodiment, the dosage form may be a multilayer tablet comprising two extended release portions, each comprising one of the opioid or the other API, and one immediate release portion comprising both the opioid and the other API. In yet another embodiment, the dosage form may be a multilayer tablet comprising two extended release portions, each comprising one of the opioid or the other API, and two immediate release portions, each comprising one of the opioid or the other API. In a further embodiment, the dosage form may be a multilayer tablet comprising multiple extended release portions, each comprising one of the opioid, the other API, or both, and one immediate release portion comprising both the opioid and the other API. In yet another embodiment, the dosage form may be a multilayer tablet comprising multiple extended release portions, each comprising one of the opioid, the other API, or both, and multiple immediate release portions comprising the opioid, the other API, or both. In still another embodiment, the dosage form may be a sustained release tablet comprising the opioid In yet another embodiment, the immediate release portion may be part of or homogeneously mixed with the extended release portion.

In certain embodiment, the tablet may have a friability of no greater than about 0.1%, 0.2%, 0.3%, 0.4%, 0.5%, 0.7% or 1.0%. In another embodiment, the tablet may have a friability of greater than 0 but less that about 1.0%, greater than 0 but less than about 0.5%, greater than 0 but less than about 0.3%, or greater than 0 but less than about 0.2%. In still another embodiment, the tablet may have a friability of zero.

In one embodiment, the tablet may have a hardness of at least about 10 Kilopond (also known as kilopons) (kp). In some embodiments, the tablet may have a hardness of about 9 kp to about 25 kp, or about 12 kp to about 20 kp. In further embodiments, the tablet may have a hardness of about 11 kp, 12 kp, 13 kp, 14 kp, 15 kp, or 16 kp.

In additional embodiments, the tablet may have a content uniformity of from about 85 to about 115 percent by weight or from about 90 to about 110 percent by weight, or from about 95 to about 105 percent by weight. In other embodiments, the content uniformity may have a relative standard deviation (RSD) equal to or less than about 3.5%, 3.0%, 2.5%, 2.0%, 1.5%, 1.0%, or 0.5%.

(g) Abuse and Tamper Resistant Properties of the Composition

Extended release pain medications have provided many benefits to patients in the management of their chronic pain by providing a sustained release over time of a larger quantity of drug than is typically contained in an immediate release formulation. Consequently, these dosage forms (especially if they contain opioids) are attractive targets for drug abusers looking to defeat the extended release formulation to allow immediate bolus administration or "dose-dumping" of the entire drug contents of the dosage form.

Dosage forms of the pharmaceutical composition disclosed herein may be more resistant to crushing, grinding, pulverizing, or other common means used to produce a powder than an immediate release product. Accordingly, some embodiment forms are tamper resistant and less prone to abuse or misuse. For example, certain embodiments may not be crushed into a powder and snorted. Additionally, some embodiments comprising an extended release polymer may not be crushed, mixed with an aqueous solution, and injected (i.e., the resultant mixture becomes extremely viscous and cannot be effectively drawn into a syringe.)

For example, dosage forms of the pharmaceutical composition disclosed herein form a pasty semi-solid mixture when dissolved. Thus, the pharmaceutical composition is difficult to draw into a syringe and inject intravenously. The yield of active pharmaceutical ingredient(s) obtained from the pharmaceutical composition is also low (less than 20%).

Further, dosage forms of the pharmaceutical composition disclosed herein cannot easily be snorted. In order for a drug abuser to successfully snort a drug obtained from a dosage form, he must prepare a crushed, finely divided powder form of the dosage form for insufflating the powder into the nasal cavity. However, the pharmaceutical compositions disclosed herein form a clumpy, solid mass and do not allow acceptable absorption through the nasal tissue.

Dosage forms of the pharmaceutical composition disclosed herein also do not allow "dose dumping" caused by the deliberate introduction of alcohol into a drug abuser's stomach which accelerates the release of active ingredient(s) from the time-release formulation. The pharmaceutical compositions disclosed herein are resistant to the accelerated release of active ingredient(s).

In addition, dosage forms of the pharmaceutical composition disclosed herein do not allow for "free basing." Successful free basing by a drug abuser requires the generation of a salt free form of the active pharmaceutical ingredient(s). This requires physical and chemical manipulation to release the active pharmaceutical ingredient(s) from its salt(s) and selective extraction from other matrix excipients. The pharmaceutical composition disclosed herein cannot be easily manipulated to generate a free base preparation.

Moreover, the tamper resistance properties of the pharmaceutical compositions disclosed herein may be increased by increasing the average molecular weight of the extended release polymer used in the pharmaceutical composition. In another embodiment, the tamper resistance properties of the pharmaceutical compositions disclosed herein may be increased by increasing the amount of the extended release polymer used in the pharmaceutical composition.

In further embodiments, the solid oral dosage forms of the pharmaceutical compositions disclosed herein exhibit substantial differences in the release profiles of oxycodone and acetaminophen when the dosage forms are crushed or ground. Indeed, the intact solid oral dosage forms surprisingly exhibit a higher release rate of both active ingredients than one that is crushed or ground. This suggests that upon grinding or crushing the solid oral dosage forms disclosed herein, the oxycodone and acetaminophen in the immediate release portion are incorporated into the extended release portion, and the pharmaceutical composition loses its immediate release characteristics. This feature may effectively negate a drug abuser's purpose for crushing the solid oral dosage form in the first place—to obtain an early onset of analgesia. Thus, this is an unexpected tamper resistant property of the pharmaceutical compositions disclosed herein.

In another embodiment, as the amount of oxycodone in the pharmaceutical composition increases, so does the duration of gastric retention after administration to a subject. Consequently, if a subject either intentionally or accidentally ingests a larger dose of the pharmaceutical composition than prescribed, the pharmaceutical composition will be retained in the stomach for a longer time period than an IR or traditional ER pharmaceutical composition, thereby giving a medical provider additional time to perform gastric lavage, induce vomiting, or administer activated charcoal to prevent the body from absorbing the oxycodone. In a further embodiment, the pharmaceutical composition provides a medical provider with about an additional 15 minutes, 30 minutes, 45 minutes, 60 minutes, 75 minutes, 90 minutes, 105 minutes, 2.0 hours, 2.25 hours, 2.5 hours, 2.75 hours, 3.0 hours, 3.25 hours, 3.5 hours, 3.75 hours, or 4 hours in which to prevent the absorption of oxycodone in the subject. In another embodiment, the pharmaceutical composition provides a medical provider with sufficient time to treat a subject who has overdosed on oxycodone so that death, difficulty breathing, cardiac arrest, and limp muscles do not occur in the subject.

In yet another embodiment, if vomiting is induced or naturally occurs as a result of an increased dose of oxycodone, the entire pharmaceutical composition is expelled from the subject. Thus, toxic concentrations of the oxycodone due to absorption into the subject's blood are prevented by removing the further release of oxycodone. In still another embodiment, if vomiting is induced or naturally occurs as a result of the increased dose of oxycodone about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% of the pharmaceutical composition is expelled from the subject. In yet another embodiment, if vomiting is induced or naturally occurs within about 30 minutes to about 60 minutes after ingestion of the increased dose of oxycodone about 50% to about 65% of the oxycodone dose is expelled from the subject.

(h) Exemplary Compositions

In one embodiment, the opioid of the gastric retentive extended release composition is oxycodone and the other API is acetaminophen. In another embodiment, the at least one immediate release portion of the composition comprises oxycodone, acetaminophen, or a combination thereof, and the at least one extended release portion of the composition comprises an extended release component and oxycodone, acetaminophen, or a combination thereof. In yet another embodiment, the gastric retentive extended release composition comprises an immediate release portion comprising oxycodone and acetaminophen and an extended release portion comprising oxycodone, acetaminophen and an extended release component. In still yet another embodiment, the compositions comprises two extended release portions, each comprising an extended release component and one of oxycodone or acetaminophen, and an immediate release portion comprising oxycodone and acetaminophen. In another embodiment, the composition comprises two extended release portions, each comprising an extended release component and one of oxycodone or acetaminophen, and two immediate release portions, each comprising one of oxycodone or acetaminophen. In one embodiment, the extended release component comprise at least one extended release polymer. In one exemplary embodiment, the at least one extended release polymer comprises a polyethylene oxide. The molecular weight of the polyethylene oxide may be from about 500,000 Daltons to about 10,000,000 Daltons.

In another embodiment, the composition may comprise from about 5 mg to about 30 mg of oxycodone and from about 250 mg to about 1300 mg of acetaminophen. In one embodiment, the composition may comprise about 15 mg of oxycodone and about 650 mg of acetaminophen. In another embodiment, the composition may comprise about 15 mg of oxycodone and about 500 mg of acetaminophen. In a further embodiment, the composition may comprise about 30 mg of oxycodone and about 500 mg of acetaminophen. In still another embodiment, the composition may comprise about 15 mg of oxycodone and about 325 mg of acetaminophen. In yet another exemplary embodiment, the composition may comprise about 7.5 mg of oxycodone and about 325 mg of acetaminophen. In still another exemplary embodiment, the pharmaceutical composition may comprise about 10 mg of oxycodone and about 325 mg of acetaminophen. In a further exemplary embodiment, the pharmaceutical composition may comprise about 20 mg of oxycodone and about 650 mg of acetaminophen. In another exemplary embodiment, the composition may comprise about 30 mg of oxycodone and about 650 mg of acetaminophen.

In another embodiment, the composition may comprise from about 5 mg to about 30 mg of hydrocodone and from about 250 mg to about 1300 mg of acetaminophen. In one embodiment, the composition may comprise about 15 mg of hydrocodone and about 650 mg of acetaminophen. In another embodiment, the composition may comprise about 15 mg of hydrocodone and about 500 mg of acetaminophen. In a further embodiment, the composition may comprise about 30 mg of hydrocodone and about 500 mg of acetaminophen. In still another embodiment, the composition may comprise about 15 mg of hydrocodone and about 325 mg of acetaminophen. In yet another exemplary embodiment, the composition may comprise about 7.5 mg of hydrocodone and about 325 mg of acetaminophen. In still another exemplary embodiment, the pharmaceutical composition may comprise about 10 mg of hydrocodone and about 325 mg of acetaminophen. In a further exemplary embodiment, the pharmaceutical composition may comprise about 20 mg of hydrocodone and about 650 mg of acetaminophen. In another exemplary embodiment, the composition may comprise about 30 mg of hydrocodone and about 650 mg of acetaminophen.

In another embodiment, the composition may comprise from about 5 mg to about 30 mg of opioid and from about 250 mg to about 1300 mg of at least one other API. In one embodiment, the composition may comprise about 15 mg of opioid and about 650 mg of at least one other API. In another embodiment, the composition may comprise about 15 mg of opioid and about 500 mg of at least one other API. In a further embodiment, the composition may comprise about 30 mg of opioid and about 500 mg of at least one other API. In still another embodiment, the composition may comprise about 15 mg of opioid and about 325 mg of at least one other API. In yet another exemplary embodiment, the composition may comprise about 7.5 mg of opioid and about 325 mg of at least one other API. In still another exemplary embodiment, the pharmaceutical composition may comprise about 10 mg of opioid and about 325 mg of at least one other API. In a further exemplary embodiment, the pharmaceutical composition may comprise about 20 mg of opioid and about 650 mg of at least one other API. In another exemplary embodiment, the composition may comprise about 30 mg of opioid and about 650 mg of at least one other API. In yet another exemplary embodiment, the composition may comprise about 22.5 mg of opioid and about 925 mg of at least one other API.

In a further embodiment, a single dosage form of the pharmaceutical composition disclosed herein (e.g., one tablet) will provide a subject with approximately the same therapeutic benefit and pharmacokinetic profile as either two dosage forms (e.g., two tablets) of the composition formulated at half the strength, or three dosage forms (e.g., three tablets) of the composition formulated at a third of the strength. In yet another exemplary embodiment, the pharmaceutical composition comprising 15 mg of oxycodone and 650 mg of acetaminophen in a single dosage form (e.g., one tablet) will provide a subject with approximately the same therapeutic benefit and pharmacokinetic profile as two dosage forms of the pharmaceutical composition formulated at half the strength (e.g., each tablet comprising 7.5 mg of oxycodone and 325 mg of acetaminophen). In still another exemplary embodiment, the pharmaceutical composition comprising 15 mg of oxycodone and 650 mg of acetaminophen in a single dosage form (e.g., one tablet) will provide a subject with approximately the same therapeutic benefit and pharmacokinetic profile as three dosage forms of the pharmaceutical composition formulated at a third of the strength (e.g., each tablet comprising 5 mg of oxycodone and about 216.7 mg of acetaminophen). In yet another embodiment, the pharmaceutical composition comprising 15 mg of oxycodone and 325 mg of acetaminophen in a single dosage form (e.g., one tablet) taken together with another tablet comprising 7.5 mg of oxycodone and 325 mg of acetaminophen in a single dosage form will provide a subject with approximately the same therapeutic benefit and pharmacokinetic profile as a single tablet comprising 22.5 mg of oxycodone and 650 mg of acetaminophen. In still another exemplary embodiment, the pharmaceutical composition comprising 15 mg of oxycodone and 325 mg of acetaminophen in a single dosage form (e.g., one tablet) taken together with another tablet comprising 15 mg of oxycodone and 325 mg of acetaminophen in a single dosage form will provide a subject with approximately the same therapeutic benefit and pharmacokinetic profile as a single tablet configuration totaling 30 mg of oxycodone and 650 mg of acetaminophen. In yet a further exemplary embodiment, a pharmaceutical composition comprising 21 mg of oxycodone and 650 mg of acetaminophen in a single dosage form (e.g., one tablet) will provide a subject with approximately the same therapeutic benefit and pharmacokinetic profile as two dosage forms of the pharmaceutical composition formulated at half the strength (e.g., each tablet comprising 10.5 mg of oxycodone and 325 mg of acetaminophen). In yet another exemplary embodiment, a pharmaceutical composition comprising 22.5 mg of oxycodone and 925 mg of acetaminophen in a single dosage form (e.g., one tablet) will provide a subject with approximately the same therapeutic benefit and pharmacokinetic profile as three dosage forms of the pharmaceutical composition formulated at a third of the strength (e.g., each tablet comprising 7.5 mg of oxycodone and 325 mg of acetaminophen).

In a further embodiment, a single dosage form of the pharmaceutical composition disclosed herein (e.g., one tablet) will provide a subject with approximately the same therapeutic benefit and pharmacokinetic profile as either two dosage forms (e.g., two tablets) of the composition formulated at half the strength, or three dosage forms (e.g., three tablets) of the composition formulated at a third of the strength. In yet another exemplary embodiment, the pharmaceutical composition comprising 15 mg of hydrocodone and 650 mg of acetaminophen in a single dosage form (e.g., one tablet) will provide a subject with approximately the same therapeutic benefit and pharmacokinetic profile as two dosage forms of the pharmaceutical composition formulated at half the strength (e.g., each tablet comprising 7.5 mg of hydrocodone and 325 mg of acetaminophen). In still another exemplary embodiment, the pharmaceutical composition comprising 15 mg of hydrocodone and 650 mg of acetaminophen in a single dosage form (e.g., one tablet) will provide a subject with approximately the same therapeutic benefit and pharmacokinetic profile as three dosage forms of the pharmaceutical composition formulated at a third of the strength (e.g., each tablet comprising 5 mg of hydrocodone and about 216.7 mg of acetaminophen). In yet another embodiment, the pharmaceutical composition comprising 15 mg of hydrocodone and 325 mg of acetaminophen in a single dosage form (e.g., one tablet) taken together with another tablet comprising 7.5 mg of hydrocodone and 325 mg of acetaminophen in a single dosage form will provide a subject with approximately the same therapeutic benefit and pharmacokinetic profile as a single tablet comprising 22.5 mg of hydrocodone and 650 mg of acetaminophen. In still another exemplary embodiment, the pharmaceutical composition comprising 15 mg of hydrocodone and 325 mg of acetaminophen in a single dosage form (e.g., one tablet) taken together with another tablet comprising 15 mg of hydrocodone and 325 mg of acetaminophen in a single dosage form will provide a subject with approximately the same therapeutic benefit and pharmacokinetic profile as a single tablet configuration totaling 30 mg of hydrocodone and 650 mg of acetaminophen. In yet a further exemplary embodiment, a pharmaceutical composition comprising 21 mg of hydrocodone and 650 mg of acetaminophen in a single dosage form (e.g., one tablet) will provide a subject with approximately the same therapeutic benefit and pharmacokinetic profile as two dosage forms of the pharmaceutical composition formulated at half the strength (e.g., each tablet comprising 10.5 mg of hydrocodone and 325 mg of acetaminophen). In yet another exemplary embodiment, a pharmaceutical composition comprising 22.5 mg of hydrocodone and 925 mg of acetaminophen in a single dosage form (e.g., one tablet) will provide a subject with approximately the same therapeutic benefit and pharmacokinetic profile as three dosage forms of the pharmaceutical composition formulated at a third of the strength (e.g., each tablet comprising 7.5 mg of hydrocodone and 325 mg of acetaminophen).

In another embodiment, the at least one immediate release portion may comprise from about 40% to about 60% (w/w) of the total amount of acetaminophen present in the composition and from about 20% to about 30% (w/w) of the total amount of oxycodone present in the composition, whereas the at least one extended release portion may comprise from about 40% to about 60% (w/w) of the total amount of acetaminophen present in the composition and from about 70% to about 80% (w/w) of the total amount of oxycodone present in the composition. In an exemplary embodiment, the at least one immediate release portion may comprise about 50% of the total amount of acetaminophen and about 25% (w/w) of the total amount of oxycodone present in the composition, and the at least one extended release portion may comprise about 50% of the total amount of acetaminophen and about 75% (w/w) of the total amount of oxycodone present in the composition.

In yet another embodiment, an immediate release portion of the composition may comprise, by weight of such immediate release portion, from about 70% to about 80% acetaminophen and from about 0.5% to about 1% of oxycodone, and an extended release portion of the composition may comprise, by weight of such extended release portion, from about 30% to about 50% of the extended release polymer, from about 20% to about 40% of acetaminophen, and from about 0.5% to about 2% of oxycodone.

In another embodiment, the composition may comprise from about 7.5 mg to about 30 mg of oxycodone and from about 325 mg to about 650 mg of acetaminophen, wherein the at least one immediate release portion may comprise about 25% of the total amount of oxycodone and about 50% of the total amount of acetaminophen present in the composition, and the at least one extended release portion may comprise about 75% of the total amount of oxycodone and about 50% of the total amount of acetaminophen present in the composition, and each extend release portion further comprises from about 35% to about 45%, by weight of each extended release portion, of an extended release polymer comprising a polyethylene oxide. Other exemplary formulations are set forth in Charts 1-3 below.

CHART 1

Representative hydrocodone formulations.*

| | | Formulation No. | | | | | | | | | |
|---|---|---|---|---|---|---|---|---|---|---|---|
| | | 1 | 2 | 3 | 4 | 5 | 6 | 7 | 8 | 9 | 10 |
| Immediate Release Layer | APAP | 185.3 | 175.0 | 180.0 | 160.4 | 200.0 | 193.4 | 118.8 | 162.5 | 139.0 | 150.0 |
| | Hydrocodone bitartrate | 1.100 | 1.75 | 2.00 | 2.50 | 1.25 | 1.00 | 2.75 | 1.875 | 1.75 | 1.875 |
| | Microcrystalline cellulose | 23.0 | 17.0 | 19.0 | 27.0 | 16.0 | 18.0 | 18.0 | 14.0 | 21.0 | 24.0 |
| | Pregelatinized starch | 0.05 | 0.15 | 0.25 | 0.10 | 0.05 | 0.30 | 0.20 | 0.25 | 0.15 | 0.20 |
| | Citric Acid Anhydrous | 0.08 | 0.08 | 0.08 | 0.11 | 0.11 | 0.14 | 0.07 | 0.13 | 0.15 | 0.17 |
| | EDTA disodium salt, dihydrate | 0.087 | 0.106 | 0.075 | 0.03 | 0.050 | 0.055 | 0.033 | 0.025 | 0.045 | 0.018 |
| | Hydroxypropyl cellulose | 14.1 | 17.8 | — | — | 17.3 | — | 16.7 | 16.1 | 21.5 | — |
| | Hypromellose | 2.5 | — | 3.2 | — | — | — | — | — | 8.9 | 19.5 |
| | Hydroxypropyl methyl cellulose | — | — | 21.7 | 18.3 | — | 19.3 | — | — | — | 3.0 |
| | Croscarmellose sodium | 10.0 | 11.0 | 11.5 | 11.5 | 13.0 | 14.5 | 14.5 | 12.5 | 14.0 | 12.5 |
| | Silicon dioxide | 0.97 | 0.75 | 1.14 | 1.02 | 1.10 | 1.03 | 0.88 | 1.05 | 0.93 | 2.30 |
| | Magnesium stearate | 1.5 | 1.0 | 1.0 | 0.5 | 0.5 | 2.0 | 2.0 | 0.5 | 1.5 | 2.5 |
| Extended Release Layer | APAP | 185.3 | 150.0 | 145.0 | 155.2 | 125.0 | 100.5 | 146.9 | 162.5 | 207.4 | 150.0 |
| | Hydrocodone bitartrate | 6.900 | 5.75 | 5.50 | 5.00 | 6.25 | 6.50 | 7.25 | 5.625 | 4.75 | 6.625 |
| | Microcrystalline cellulose | 175.4 | 180.0 | 302.2 | 275.0 | 214.8 | 250.0 | 245.7 | 203.6 | 288.3 | 200.5 |
| | Pregelatinized starch | 0.60 | 0.60 | 0.70 | 0.70 | 0.70 | 0.75 | 0.75 | 0.75 | 0.85 | 0.85 |
| | Citric Acid Anhydrous | 0.24 | 0.16 | 0.24 | 0.22 | 0.33 | 0.28 | 0.07 | 0.38 | 0.45 | 0.34 |
| | EDTA disodium salt, dihydrate | 0.160 | 0.085 | 0.095 | 0.055 | 0.130 | 0.065 | 0.065 | 0.075 | 0.130 | 0.125 |
| | Hydroxypropyl cellulose | 30.0 | 275.8 | 95.5 | 210.6 | 13.2 | 40.7 | 32.9 | 9.6 | — | — |
| | Polyox N12K | 292.8 | — | — | — | 287.7 | — | — | 321.8 | 155.5 | — |
| | Polyox 303 | — | — | 244.2 | — | — | — | 275.5 | — | — | 189.2 |
| | Hydroxypropyl methyl cellulose | — | 103.2 | — | 134.2 | — | 182.2 | — | — | 155.5 | 210.2 |
| | Silicon Dioxide | 1.8 | 1.3 | 1.5 | 2.3 | 2.4 | 3.0 | 3.5 | 3.6 | 2.0 | 2.5 |
| | Magnesium Stearate | 7.5 | 8.0 | 7.4 | 8.1 | 7.5 | 10.2 | 9.9 | 7.2 | 10.3 | 10.3 |

| | | Formulation No. | | | | | | | | | |
|---|---|---|---|---|---|---|---|---|---|---|---|
| | | 11 | 12 | 13 | 14 | 15 | 16 | 17 | 18 | 19 | 20 |
| Immediate Release Layer | APAP | 300.0 | 150.0 | 200.0 | 150.0 | 100.0 | 160.0 | 190.0 | 75.0 | 90.0 | 125.0 |
| | Hydrocodone bitartrate | 2.00 | 1.00 | 1.50 | 3.50 | 2.75 | 1.25 | 1.25 | 2.50 | 1.75 | 3.00 |
| | Microcrystalline cellulose | 21.5 | 18.5 | 25.3 | 35.0 | 15.7 | 27.1 | 9.9 | 13.9 | 24.2 | 16.9 |
| | Pregelatinized starch | 0.03 | 0.30 | 0.25 | 0.27 | 0.08 | 0.35 | 0.75 | 0.09 | 0.15 | 0.26 |
| | Citric Acid Anhydrous | 0.12 | 0.08 | 0.09 | 0.16 | 0.07 | 0.24 | 0.14 | 0.26 | 0.15 | 0.20 |
| | EDTA disodium salt, dihydrate | 0.04 | 0.175 | 0.1 | 0.06 | 0.1 | 0.09 | 0.06 | 0.08 | 0.063 | 0.09 |
| | Hydroxypropyl cellulose | — | 21.5 | 1.8 | 9.8 | 14.8 | — | 20.8 | 19.2 | 25.4 | — |

CHART 1-continued

Representative hydrocodone formulations.*

| | | | | | | | | | | | |
|---|---|---|---|---|---|---|---|---|---|---|---|
| | Hypromellose | 2.5 | — | — | — | — | — | — | — | 10.3 | 22.5 |
| | Hydroxypropyl methyl cellulose | 16.3 | 11.4 | 17.5 | 8.7 | — | 29.3 | — | — | — | 4.4 |
| | Croscarmellose sodium | 6.8 | 11.0 | 12.8 | 7.9 | 19.0 | 9.6 | 13.3 | 15.6 | 15.1 | 14.7 |
| | Silicon dioxide | 0.86 | 0.80 | 2.25 | 1.24 | .95 | 1.34 | 0.80 | 1.66 | 0.79 | 2.37 |
| | Magnesium stearate | 1.75 | 1.0 | 0.75 | 0.6 | 0.5 | 2.5 | 1.9 | 0.8 | 1.2 | 2.8 |
| Extended Release Layer | APAP | 150.0 | 150.0 | 125.0 | 75.0 | 100.0 | 165.0 | 135.0 | 225.0 | 210.0 | 150.0 |
| | Hydrocodone bitartrate | 8.00 | 6.50 | 6.00 | 6.50 | 3.25 | 6.25 | 6.25 | 5.00 | 6.25 | 5.50 |
| | Microcrystalline cellulose | 182.2 | 197.6 | 300.4 | 269.6 | 210.0 | 275.5 | 283.2 | 310.2 | 240.8 | 210.0 |
| | Pregelatinized starch | 0.75 | 0.73 | 0.46 | 0.89 | 0.55 | 0.78 | 0.55 | 0.65 | 0.67 | 0.64 |
| | Citric Acid Anhydrous | 0.25 | 0.36 | 0.38 | 0.34 | 0.37 | 0.23 | 0.14 | 0.40 | 0.70 | 0.70 |
| | EDTA disodium salt, dihydrate | 0.23 | 0.09 | 0.14 | 0.06 | 0.183 | 0.035 | 0.049 | 0.03 | 0.105 | 0.075 |
| | Hydroxypropyl cellulose | 34.7 | 321.9 | 88.4 | 212.9 | 11.9 | 37.7 | 34.2 | 17.4 | — | — |
| | Polyox N12K | — | — | 252.4 | — | 290.3 | — | 248.2 | 279.2 | 175.2 | — |
| | Polyox 303 | 275.8 | — | — | — | — | — | — | — | — | 224.5 |
| | Hydroxypropyl methyl cellulose | — | 101.1 | — | 110.5 | — | 192.1 | — | — | 140.9 | 185.6 |
| | Silicon Dioxide | 1.3 | 1.3 | 1.2 | 2.4 | 2.1 | 3.2 | 4.0 | 4.0 | 2.0 | 3.8 |
| | Magnesium Stearate | 5.7 | 9.4 | 6.6 | 5.5 | 7.7 | 9.4 | 6.4 | 5.2 | 9.9 | 7.2 |

| | | Formulation No. | | | | | | | | | |
|---|---|---|---|---|---|---|---|---|---|---|---|
| | | 21 | 22 | 23 | 24 | 25 | 26 | 27 | 28 | 29 | 30 |
| Immediate Release Layer | APAP | 185.3 | 175.0 | 180.0 | 160.4 | 200.0 | 193.4 | 118.8 | 162.5 | 139.0 | 150.0 |
| | Hydrocodone bitartrate | 1.100 | 1.75 | 2.00 | 2.50 | 1.25 | 1.00 | 2.75 | 1.875 | 1.75 | 1.875 |
| | Microcrystalline cellulose | 23.0 | 17.0 | 19.0 | 27.0 | 16.0 | 18.0 | 18.0 | 14.0 | 21.0 | 24.0 |
| | Pregelatinized starch | 0.05 | 0.15 | 0.25 | 0.10 | 0.05 | 0.30 | 0.20 | 0.25 | 0.15 | 0.20 |
| | Citric Acid Anhydrous | 0.08 | 0.08 | 0.08 | 0.11 | 0.11 | 0.14 | 0.07 | 0.13 | 0.15 | 0.17 |
| | EDTA disodium salt, dihydrate | 0.087 | 0.106 | 0.075 | 0.03 | 0.050 | 0.055 | 0.033 | 0.025 | 0.045 | 0.018 |
| | Hydroxypropyl cellulose | 14.1 | 17.8 | — | — | 17.3 | — | 16.7 | 16.1 | 21.5 | — |
| | Hypromellose | 2.5 | — | 3.2 | — | — | — | — | — | 8.9 | 19.5 |
| | Hydroxypropyl methyl cellulose | — | — | 21.7 | 18.3 | — | 19.3 | — | — | — | 3.0 |
| | Croscarmellose sodium | 10.0 | 11.0 | 11.5 | 11.5 | 13.0 | 14.5 | 14.5 | 12.5 | 14.0 | 12.5 |
| | Silicon dioxide | 0.97 | 0.75 | 1.14 | 1.02 | 1.10 | 1.03 | 0.88 | 1.05 | 0.93 | 2.30 |
| | Magnesium stearate | 1.5 | 1.0 | 1.0 | 0.5 | 0.5 | 2.0 | 2.0 | 0.5 | 1.5 | 2.5 |
| Extended Release Layer | APAP | 185.3 | 150.0 | 145.0 | 155.2 | 125.0 | 100.5 | 146.9 | 162.5 | 207.4 | 150.0 |
| | Hydrocodone bitartrate | 6.900 | 5.75 | 5.50 | 5.00 | 6.25 | 6.50 | 7.25 | 5.625 | 4.75 | 6.625 |
| | Microcrystalline cellulose | 175.4 | 180.0 | 302.2 | 275.0 | 214.8 | 250.0 | 245.7 | 203.6 | 288.3 | 200.5 |
| | Pregelatinized starch | 0.60 | 0.60 | 0.70 | 0.70 | 0.70 | 0.75 | 0.75 | 0.75 | 0.85 | 0.85 |
| | Citric Acid Anhydrous | 0.24 | 0.16 | 0.24 | 0.22 | 0.33 | 0.28 | 0.07 | 0.38 | 0.45 | 0.34 |
| | EDTA disodium salt, dihydrate | 0.160 | 0.085 | 0.095 | 0.055 | 0.130 | 0.065 | 0.065 | 0.075 | 0.130 | 0.125 |
| | Hydroxypropyl cellulose | 30.0 | 275.8 | 95.5 | 210.6 | 13.2 | 40.7 | 32.9 | 9.6 | — | — |
| | Polyox N60K | 292.8 | — | — | — | 287.7 | — | — | 321.8 | 155.5 | — |
| | Polyox 205 | — | — | 244.2 | — | — | — | 275.5 | — | — | 189.2 |
| | Hydroxypropyl methyl cellulose | — | 103.2 | — | 134.2 | — | 182.2 | — | — | 155.5 | 210.2 |
| | Silicon Dioxide | 1.8 | 1.3 | 1.5 | 2.3 | 2.4 | 3.0 | 3.5 | 3.6 | 2.0 | 2.5 |
| | Magnesium Stearate | 7.5 | 8.0 | 7.4 | 8.1 | 7.5 | 10.2 | 9.9 | 7.2 | 10.3 | 10.3 |

| | | Formulation No. | | | | | | | | | |
|---|---|---|---|---|---|---|---|---|---|---|---|
| | | 31 | 32 | 33 | 34 | 35 | 36 | 37 | 38 | 39 | 40 |
| Immediate Release Layer | APAP | 300.0 | 150.0 | 200.0 | 150.0 | 100.0 | 160.0 | 190.0 | 75.0 | 90.0 | 125.0 |
| | Hydrocodone bitartrate | 2.00 | 1.00 | 1.50 | 3.50 | 2.75 | 1.25 | 1.25 | 2.50 | 1.75 | 3.00 |
| | Microcrystalline cellulose | 21.5 | 18.5 | 25.3 | 35.0 | 15.7 | 27.1 | 9.9 | 13.9 | 24.2 | 16.9 |
| | Pregelatinized starch | 0.03 | 0.30 | 0.25 | 0.27 | 0.08 | 0.35 | 0.75 | 0.09 | 0.15 | 0.26 |
| | Citric Acid Anhydrous | 0.12 | 0.08 | 0.09 | 0.16 | 0.07 | 0.24 | 0.14 | 0.26 | 0.15 | 0.20 |
| | EDTA disodium salt, dihydrate | 0.04 | 0.175 | 0.1 | 0.06 | 0.1 | 0.09 | 0.06 | 0.08 | 0.063 | 0.09 |
| | Hydroxypropyl cellulose | — | 21.5 | 1.8 | 9.8 | 14.8 | — | 20.8 | 19.2 | 25.4 | — |
| | Hypromellose | 2.5 | — | — | — | — | — | — | — | 10.3 | 22.5 |
| | Hydroxypropyl methyl cellulose | 16.3 | 11.4 | 17.5 | 8.7 | — | 29.3 | — | — | — | 4.4 |
| | Croscarmellose sodium | 6.8 | 11.0 | 12.8 | 7.9 | 19.0 | 9.6 | 13.3 | 15.6 | 15.1 | 14.7 |
| | Silicon dioxide | 0.86 | 0.80 | 2.25 | 1.24 | .95 | 1.34 | 0.80 | 1.66 | 0.79 | 2.37 |
| | Magnesium stearate | 1.75 | 1.0 | 0.75 | 0.6 | 0.5 | 2.5 | 1.9 | 0.8 | 1.2 | 2.8 |
| Extended Release Layer | APAP | 150.0 | 150.0 | 125.0 | 75.0 | 100.0 | 165.0 | 135.0 | 225.0 | 210.0 | 150.0 |
| | Hydrocodone bitartrate | 8.00 | 6.50 | 6.00 | 6.50 | 3.25 | 6.25 | 6.25 | 5.00 | 6.25 | 5.50 |
| | Microcrystalline cellulose | 182.2 | 197.6 | 300.4 | 269.6 | 210.0 | 275.5 | 283.2 | 310.2 | 240.8 | 210.0 |
| | Pregelatinized starch | 0.75 | 0.73 | 0.46 | 0.89 | 0.55 | 0.78 | 0.55 | 0.65 | 0.67 | 0.64 |
| | Citric Acid Anhydrous | 0.25 | 0.36 | 0.38 | 0.34 | 0.37 | 0.23 | 0.14 | 0.40 | 0.70 | 0.70 |
| | EDTA disodium salt, | 0.23 | 0.09 | 0.14 | 0.06 | 0.183 | 0.035 | 0.049 | 0.03 | 0.105 | 0.075 |

CHART 1-continued

Representative hydrocodone formulations.*

| | | | | | | | | | | |
|---|---|---|---|---|---|---|---|---|---|---|
| | dihydrate | | | | | | | | | |
| | Hydroxypropyl cellulose | 34.7 | 321.9 | 88.4 | 212.9 | 11.9 | 37.7 | 34.2 | 17.4 | — | — |
| | Polyox N60K | — | — | 252.4 | — | 290.3 | — | 248.2 | 279.2 | 175.2 | — |
| | Polyox 205 | 275.8 | — | — | — | — | — | — | — | — | 224.5 |
| | Hydroxypropyl methyl cellulose | — | 101.1 | — | 110.5 | — | 192.1 | — | — | 140.9 | 185.6 |
| | Silicon Dioxide | 1.3 | 1.3 | 1.2 | 2.4 | 2.1 | 3.2 | 4.0 | 4.0 | 2.0 | 3.8 |
| | Magnesium Stearate | 5.7 | 9.4 | 6.6 | 5.5 | 7.7 | 9.4 | 6.4 | 5.2 | 9.9 | 7.2 |

| | | Formulation No. | | | | | | | | | |
|---|---|---|---|---|---|---|---|---|---|---|---|
| | | 41 | 42 | 43 | 44 | 45 | 46 | 47 | 48 | 49 | 50 |
| Immediate Release Layer | APAP | 185.3 | 175.0 | 180.0 | 160.4 | 200.0 | 193.4 | 118.8 | 162.5 | 139.0 | 150.0 |
| | Hydrocodone bitartrate | 1.100 | 1.75 | 2.00 | 2.50 | 1.25 | 1.00 | 2.75 | 1.875 | 1.875 | 1.875 |
| | Microcrystalline cellulose | 23.0 | 17.0 | 19.0 | 27.0 | 16.0 | 18.0 | 18.0 | 14.0 | 21.0 | 24.0 |
| | Pregelatinized starch | 0.05 | 0.15 | 0.25 | 0.10 | 0.05 | 0.30 | 0.20 | 0.25 | 0.15 | 0.20 |
| | Citric Acid Anhydrous | 0.08 | 0.08 | 0.08 | 0.11 | 0.11 | 0.14 | 0.07 | 0.13 | 0.15 | 0.17 |
| | EDTA disodium salt, dihydrate | 0.087 | 0.106 | 0.075 | 0.03 | 0.050 | 0.055 | 0.033 | 0.025 | 0.045 | 0.018 |
| | Hydroxypropyl cellulose | 14.1 | 17.8 | — | — | 17.3 | — | 16.7 | 16.1 | 21.5 | — |
| | Hypromellose | 2.5 | — | 3.2 | — | — | — | — | — | 8.9 | 19.5 |
| | Hydroxypropyl methyl cellulose | — | — | 21.7 | 18.3 | — | 19.3 | — | — | — | 3.0 |
| | Croscarmellose sodium | 10.0 | 11.0 | 11.5 | 11.5 | 13.0 | 14.5 | 14.5 | 12.5 | 14.0 | 12.5 |
| | Silicon dioxide | 0.97 | 0.75 | 1.14 | 1.02 | 1.10 | 1.03 | 0.88 | 1.05 | 0.93 | 2.30 |
| | Magnesium stearate | 1.5 | 1.0 | 1.0 | 0.5 | 0.5 | 2.0 | 2.0 | 0.5 | 1.5 | 2.5 |
| Extended Release Layer | APAP | 185.3 | 150.0 | 145.0 | 155.2 | 125.0 | 100.5 | 146.9 | 162.5 | 207.4 | 150.0 |
| | Hydrocodone bitartrate | 6.900 | 5.75 | 5.50 | 5.00 | 6.25 | 6.50 | 7.25 | 5.625 | 4.75 | 6.625 |
| | Microcrystalline cellulose | 175.4 | 180.0 | 302.2 | 275.0 | 214.8 | 250.0 | 245.7 | 203.6 | 288.3 | 200.5 |
| | Pregelatinized starch | 0.60 | 0.60 | 0.70 | 0.70 | 0.70 | 0.75 | 0.75 | 0.75 | 0.85 | 0.85 |
| | Citric Acid Anhydrous | 0.24 | 0.16 | 0.24 | 0.22 | 0.33 | 0.28 | 0.07 | 0.38 | 0.45 | 0.34 |
| | EDTA disodium salt, dihydrate | 0.160 | 0.085 | 0.095 | 0.055 | 0.130 | 0.065 | 0.065 | 0.075 | 0.130 | 0.125 |
| | Hydroxypropyl cellulose | 30.0 | 275.8 | 95.5 | 210.6 | 13.2 | 40.7 | 32.9 | 9.6 | — | — |
| | Polyox 1105 | 262.2 | — | — | — | 301.6 | — | — | 250.3 | 188.3 | — |
| | Polyox N-750 | — | — | 244.2 | — | — | — | 275.5 | — | — | 189.2 |
| | Hydroxypropyl methyl cellulose | — | 103.2 | — | 134.2 | — | 182.2 | — | — | 155.5 | 210.2 |
| | Silicon Dioxide | 1.8 | 1.3 | 1.5 | 2.3 | 2.4 | 3.0 | 3.5 | 3.6 | 2.0 | 2.5 |
| | Magnesium Stearate | 7.5 | 8.0 | 7.4 | 8.1 | 7.5 | 10.2 | 9.9 | 7.2 | 10.3 | 10.3 |

| | | Formulation No. | | | | | | | | | |
|---|---|---|---|---|---|---|---|---|---|---|---|
| | | 51 | 52 | 53 | 54 | 55 | 56 | 57 | 58 | 59 | 60 |
| Immediate Release Layer | APAP | 300.0 | 150.0 | 200.0 | 150.0 | 100.0 | 160.0 | 190.0 | 75.0 | 90.0 | 125.0 |
| | Hydrocodone bitartrate | 2.00 | 1.00 | 1.50 | 3.50 | 2.75 | 1.25 | 1.25 | 2.50 | 1.75 | 3.00 |
| | Microcrystalline cellulose | 21.5 | 18.5 | 25.3 | 35.0 | 15.7 | 27.1 | 9.9 | 13.9 | 24.2 | 16.9 |
| | Pregelatinized starch | 0.03 | 0.30 | 0.25 | 0.27 | 0.08 | 0.35 | 0.75 | 0.09 | 0.15 | 0.26 |
| | Citric Acid Anhydrous | 0.12 | 0.08 | 0.09 | 0.16 | 0.07 | 0.24 | 0.14 | 0.26 | 0.15 | 0.20 |
| | EDTA disodium salt, dihydrate | 0.04 | 0.175 | 0.1 | 0.06 | 0.1 | 0.09 | 0.06 | 0.08 | 0.063 | 0.09 |
| | Hydroxypropyl cellulose | — | 21.5 | 1.8 | 9.8 | 14.8 | — | 20.8 | 19.2 | 25.4 | — |
| | Hypromellose | 2.5 | — | — | — | — | — | — | — | 10.3 | 22.5 |
| | Hydroxypropyl methyl cellulose | 16.3 | 11.4 | 17.5 | 8.7 | — | 29.3 | — | — | — | 4.4 |
| | Croscarmellose sodium | 6.8 | 11.0 | 12.8 | 7.9 | 19.0 | 9.6 | 13.3 | 15.6 | 15.1 | 14.7 |
| | Silicon dioxide | 0.86 | 0.80 | 2.25 | 1.24 | .95 | 1.34 | 0.80 | 1.66 | 0.79 | 2.37 |
| | Magnesium stearate | 1.75 | 1.0 | 0.75 | 0.6 | 0.5 | 2.5 | 1.9 | 0.8 | 1.2 | 2.8 |
| Extended Release Layer | APAP | 150.0 | 150.0 | 125.0 | 75.0 | 100.0 | 165.0 | 135.0 | 225.0 | 210.0 | 150.0 |
| | Hydrocodone bitartrate | 8.00 | 6.50 | 6.00 | 6.50 | 3.25 | 6.25 | 6.25 | 5.00 | 6.25 | 5.50 |
| | Microcrystalline cellulose | 182.2 | 197.6 | 300.4 | 269.6 | 210.0 | 275.5 | 283.2 | 310.2 | 240.8 | 210.0 |
| | Pregelatinized starch | 0.75 | 0.73 | 0.46 | 0.89 | 0.55 | 0.78 | 0.55 | 0.65 | 0.67 | 0.64 |
| | Citric Acid Anhydrous | 0.25 | 0.36 | 0.38 | 0.34 | 0.37 | 0.23 | 0.14 | 0.40 | 0.70 | 0.70 |
| | EDTA disodium salt, dihydrate | 0.23 | 0.09 | 0.14 | 0.06 | 0.183 | 0.035 | 0.049 | 0.03 | 0.105 | 0.075 |
| | Hydroxypropyl cellulose | 34.7 | 321.9 | 88.4 | 212.9 | 11.9 | 37.7 | 34.2 | 17.4 | — | — |
| | Polyox 1105 | — | — | 252.4 | — | 290.3 | — | 248.2 | 279.2 | 175.2 | — |
| | Polyox N-750 | 275.8 | — | — | — | — | — | — | — | — | 224.5 |
| | Hydroxypropyl methyl cellulose | — | 101.1 | — | 110.5 | — | 192.1 | — | — | 140.9 | 185.6 |
| | Silicon Dioxide | 1.3 | 1.3 | 1.2 | 2.4 | 2.1 | 3.2 | 4.0 | 4.0 | 2.0 | 3.8 |
| | Magnesium Stearate | 5.7 | 9.4 | 6.6 | 5.5 | 7.7 | 9.4 | 6.4 | 5.2 | 9.9 | 7.2 |

CHART 1-continued

Representative hydrocodone formulations.*

| | | \multicolumn{10}{c|}{Formulation No.} | | | | | | | | | |
| --- | --- | --- | --- | --- | --- | --- | --- | --- | --- | --- | --- |
| | | 61 | 62 | 63 | 64 | 65 | 66 | 67 | 68 | 69 | 70 |
| Immediate Release Layer | APAP | 185.3 | 175.0 | 180.0 | 160.4 | 200.0 | 193.4 | 118.8 | 162.5 | 139.0 | 150.0 |
| | Hydrocodone bitartrate | 1.100 | 1.75 | 2.00 | 2.50 | 1.25 | 1.00 | 2.75 | 1.875 | 1.75 | 1.875 |
| | Microcrystalline cellulose | 23.0 | 17.0 | 19.0 | 27.0 | 16.0 | 18.0 | 18.0 | 14.0 | 21.0 | 24.0 |
| | Pregelatinized starch | 0.05 | 0.15 | 0.25 | 0.10 | 0.05 | 0.30 | 0.20 | 0.25 | 0.15 | 0.20 |
| | Citric Acid Anhydrous | 0.08 | 0.08 | 0.08 | 0.11 | 0.11 | 0.14 | 0.07 | 0.13 | 0.15 | 0.17 |
| | EDTA disodium salt, dihydrate | 0.087 | 0.106 | 0.075 | 0.03 | 0.050 | 0.055 | 0.033 | 0.025 | 0.045 | 0.018 |
| | Hydroxypropyl cellulose | 14.1 | 17.8 | — | — | 17.3 | — | 16.7 | 16.1 | 21.5 | — |
| | Hypromellose | 2.5 | — | 3.2 | — | — | — | — | — | 8.9 | 19.5 |
| | Hydroxypropyl methyl cellulose | — | — | 21.7 | 18.3 | — | 19.3 | — | — | — | 3.0 |
| | Croscarmellose sodium | 10.0 | 11.0 | 11.5 | 11.5 | 13.0 | 14.5 | 14.5 | 12.5 | 14.0 | 12.5 |
| | Silicon dioxide | 0.97 | 0.75 | 1.14 | 1.02 | 1.10 | 1.03 | 0.88 | 1.05 | 0.93 | 2.30 |
| | Magnesium stearate | 1.5 | 1.0 | 1.0 | 0.5 | 0.5 | 2.0 | 2.0 | 0.5 | 1.5 | 2.5 |
| Extended Release Layer | APAP | 185.3 | 150.0 | 145.0 | 155.2 | 125.0 | 100.5 | 146.9 | 162.5 | 207.4 | 150.0 |
| | Hydrocodone bitartrate | 6.900 | 5.75 | 5.50 | 5.00 | 6.25 | 6.50 | 7.25 | 5.625 | 4.75 | 6.625 |
| | Microcrystalline cellulose | 175.4 | 180.0 | 302.2 | 275.0 | 214.8 | 250.0 | 245.7 | 203.6 | 288.3 | 200.5 |
| | Pregelatinized starch | 0.60 | 0.60 | 0.70 | 0.70 | 0.70 | 0.75 | 0.75 | 0.75 | 0.85 | 0.85 |
| | Citric Acid Anhydrous | 0.24 | 0.16 | 0.24 | 0.22 | 0.33 | 0.28 | 0.07 | 0.38 | 0.45 | 0.34 |
| | EDTA disodium salt, dihydrate | 0.160 | 0.085 | 0.095 | 0.055 | 0.130 | 0.065 | 0.065 | 0.075 | 0.130 | 0.125 |
| | Hydroxypropyl cellulose | 30.0 | 275.8 | 95.5 | 210.6 | 13.2 | 40.7 | 32.9 | 9.6 | — | — |
| | Polyox 301 | 292.8 | — | — | — | 287.7 | — | — | 321.8 | 155.5 | — |
| | Polyox N-80 | — | — | 244.2 | — | — | — | 275.5 | — | — | 189.2 |
| | Hydroxypropyl methyl cellulose | — | 103.2 | — | 134.2 | — | 182.2 | — | — | 155.5 | 210.2 |
| | Silicon Dioxide | 1.8 | 1.3 | 1.5 | 2.3 | 2.4 | 3.0 | 3.5 | 3.6 | 2.0 | 2.5 |
| | Magnesium Stearate | 7.5 | 8.0 | 7.4 | 8.1 | 7.5 | 10.2 | 9.9 | 7.2 | 10.3 | 10.3 |

| | | \multicolumn{10}{c|}{Formulation No.} | | | | | | | | | |
| --- | --- | --- | --- | --- | --- | --- | --- | --- | --- | --- | --- |
| | | 71 | 72 | 73 | 74 | 75 | 76 | 77 | 78 | 79 | 80 |
| Immediate Release Layer | APAP | 300.0 | 150.0 | 200.0 | 150.0 | 100.0 | 160.0 | 190.0 | 75.0 | 90.0 | 125.0 |
| | Hydrocodone bitartrate | 2.00 | 1.00 | 1.50 | 3.50 | 2.75 | 1.25 | 1.25 | 2.50 | 1.75 | 3.00 |
| | Microcrystalline cellulose | 21.5 | 18.5 | 25.3 | 35.0 | 15.7 | 27.1 | 9.9 | 13.9 | 24.2 | 16.9 |
| | Pregelatinized starch | 0.03 | 0.30 | 0.25 | 0.27 | 0.08 | 0.35 | 0.75 | 0.09 | 0.15 | 0.26 |
| | Citric Acid Anhydrous | 0.12 | 0.08 | 0.09 | 0.16 | 0.07 | 0.24 | 0.14 | 0.26 | 0.15 | 0.20 |
| | EDTA disodium salt, dihydrate | 0.04 | 0.175 | 0.1 | 0.06 | 0.1 | 0.09 | 0.06 | 0.08 | 0.063 | 0.09 |
| | Hydroxypropyl cellulose | — | 21.5 | 1.8 | 9.8 | 14.8 | — | 20.8 | 19.2 | 25.4 | — |
| | Hypromellose | 2.5 | — | — | — | — | — | — | — | 10.3 | 22.5 |
| | Hydroxypropyl methyl cellulose | 16.3 | 11.4 | 17.5 | 8.7 | — | 29.3 | — | — | — | 4.4 |
| | Croscarmellose sodium | 6.8 | 11.0 | 12.8 | 7.9 | 19.0 | 9.6 | 13.3 | 15.6 | 15.1 | 14.7 |
| | Silicon dioxide | 0.86 | 0.80 | 2.25 | 1.24 | .95 | 1.34 | 0.80 | 1.66 | 0.79 | 2.37 |
| | Magnesium stearate | 1.75 | 1.0 | 0.75 | 0.6 | 0.5 | 2.5 | 1.9 | 0.8 | 1.2 | 2.8 |
| Extended Release Layer | APAP | 150.0 | 150.0 | 125.0 | 75.0 | 100.0 | 165.0 | 135.0 | 225.0 | 210.0 | 150.0 |
| | Hydrocodone bitartrate | 8.00 | 6.50 | 6.00 | 6.50 | 3.25 | 6.25 | 6.25 | 5.00 | 6.25 | 5.50 |
| | Microcrystalline cellulose | 182.2 | 197.6 | 300.4 | 269.6 | 210.0 | 275.5 | 283.2 | 310.2 | 240.8 | 210.0 |
| | Pregelatinized starch | 0.75 | 0.73 | 0.46 | 0.89 | 0.55 | 0.78 | 0.55 | 0.65 | 0.67 | 0.64 |
| | Citric Acid Anhydrous | 0.25 | 0.36 | 0.38 | 0.34 | 0.37 | 0.23 | 0.14 | 0.40 | 0.70 | 0.70 |
| | EDTA disodium salt, dihydrate | 0.23 | 0.09 | 0.14 | 0.06 | 0.183 | 0.035 | 0.049 | 0.03 | 0.105 | 0.075 |
| | Hydroxypropyl cellulose | 34.7 | 321.9 | 88.4 | 212.9 | 11.9 | 37.7 | 34.2 | 17.4 | — | — |
| | Polyox 301 | — | — | 252.4 | — | 290.3 | — | 248.2 | 279.2 | 175.2 | — |
| | Polyox N-80 | 275.8 | — | — | — | — | — | — | — | — | 224.5 |
| | Hydroxypropyl methyl cellulose | — | 101.1 | — | 110.5 | — | 192.1 | — | — | 140.9 | 185.6 |
| | Silicon Dioxide | 1.3 | 1.3 | 1.2 | 2.4 | 2.1 | 3.2 | 4.0 | 4.0 | 2.0 | 3.8 |
| | Magnesium Stearate | 5.7 | 9.4 | 6.6 | 5.5 | 7.7 | 9.4 | 6.4 | 5.2 | 9.9 | 7.2 |

*All weights in mg.

CHART 2

Representative oxycodone formulations.*

| | | \multicolumn{10}{c}{Formulation No.} |
| | | 81 | 82 | 83 | 84 | 85 | 86 | 87 | 88 | 89 | 90 |
|---|---|---|---|---|---|---|---|---|---|---|---|
| Immediate Release Layer | APAP | 185.3 | 175.0 | 180.0 | 160.4 | 200.0 | 193.4 | 118.8 | 162.5 | 139.0 | 150.0 |
| | Oxycodone hydrochloride | 1.100 | 1.75 | 2.00 | 2.50 | 1.25 | 1.00 | 2.75 | 1.875 | 1.75 | 1.875 |
| | Microcrystalline cellulose | 23.0 | 17.0 | 19.0 | 27.0 | 16.0 | 18.0 | 18.0 | 14.0 | 21.0 | 24.0 |
| | Pregelatinized starch | 0.05 | 0.15 | 0.25 | 0.10 | 0.05 | 0.30 | 0.20 | 0.25 | 0.15 | 0.20 |
| | Citric Acid Anhydrous | 0.08 | 0.08 | 0.08 | 0.11 | 0.11 | 0.14 | 0.07 | 0.13 | 0.15 | 0.17 |
| | EDTA disodium salt, dihydrate | 0.087 | 0.106 | 0.075 | 0.03 | 0.050 | 0.055 | 0.033 | 0.025 | 0.045 | 0.018 |
| | Hydroxypropyl cellulose | 14.1 | 17.8 | — | — | 17.3 | — | 16.7 | 16.1 | 21.5 | — |
| | Hypromellose | 2.5 | — | 3.2 | — | — | — | — | — | 8.9 | 19.5 |
| | Hydroxypropyl methyl cellulose | — | — | 21.7 | 18.3 | — | 19.3 | — | — | — | 3.0 |
| | Croscarmellose sodium | 10.0 | 11.0 | 11.5 | 11.5 | 13.0 | 14.5 | 14.5 | 12.5 | 14.0 | 12.5 |
| | Silicon dioxide | 0.97 | 0.75 | 1.14 | 1.02 | 1.10 | 1.03 | 0.88 | 1.05 | 0.93 | 2.30 |
| | Magnesium stearate | 1.5 | 1.0 | 1.0 | 0.5 | 0.5 | 2.0 | 2.0 | 0.5 | 1.5 | 2.5 |
| Extended Release Layer | APAP | 185.3 | 150.0 | 145.0 | 155.2 | 125.0 | 100.5 | 146.9 | 162.5 | 207.4 | 150.0 |
| | Oxycodone hydrochloride | 6.900 | 5.75 | 5.50 | 5.00 | 6.25 | 6.50 | 7.25 | 5.625 | 4.75 | 6.625 |
| | Microcrystalline cellulose | 175.4 | 180.0 | 302.2 | 275.0 | 214.8 | 250.0 | 245.7 | 203.6 | 288.3 | 200.5 |
| | Pregelatinized starch | 0.60 | 0.60 | 0.70 | 0.70 | 0.70 | 0.75 | 0.75 | 0.75 | 0.85 | 0.85 |
| | Citric Acid Anhydrous | 0.24 | 0.16 | 0.24 | 0.22 | 0.33 | 0.28 | 0.07 | 0.38 | 0.45 | 0.34 |
| | EDTA disodium salt, dihydrate | 0.160 | 0.085 | 0.095 | 0.055 | 0.130 | 0.065 | 0.065 | 0.075 | 0.130 | 0.125 |
| | Hydroxypropyl cellulose | 30.0 | 275.8 | 95.5 | 210.6 | 13.2 | 40.7 | 32.9 | 9.6 | — | — |
| | Polyox N12K | 292.8 | — | — | — | 287.7 | — | — | — | 155.5 | — |
| | Polyox 1105 | — | — | 244.2 | — | — | — | 275.5 | 321.8 | — | 189.2 |
| | Hydroxypropyl methyl cellulose | — | 103.2 | — | 134.2 | — | 182.2 | — | — | 155.5 | 210.2 |
| | Silicon Dioxide | 1.8 | 1.3 | 1.5 | 2.3 | 2.4 | 3.0 | 3.5 | 3.6 | 2.0 | 2.5 |
| | Magnesium Stearate | 7.5 | 8.0 | 7.4 | 8.1 | 7.5 | 10.2 | 9.9 | 7.2 | 10.3 | 10.3 |

| | | \multicolumn{10}{c}{Formulation No.} |
| | | 91 | 92 | 93 | 94 | 95 | 96 | 97 | 98 | 99 | 100 |
|---|---|---|---|---|---|---|---|---|---|---|---|
| Immediate Release Layer | APAP | 300.0 | 150.0 | 200.0 | 150.0 | 100.0 | 160.0 | 190.0 | 75.0 | 90.0 | 125.0 |
| | Oxycodone hydrochloride | 2.00 | 1.00 | 1.50 | 3.50 | 2.75 | 1.25 | 1.25 | 2.50 | 1.75 | 3.00 |
| | Microcrystalline cellulose | 21.5 | 18.5 | 25.3 | 35.0 | 15.7 | 27.1 | 9.9 | 13.9 | 24.2 | 16.9 |
| | Pregelatinized starch | 0.03 | 0.30 | 0.25 | 0.27 | 0.08 | 0.35 | 0.75 | 0.09 | 0.15 | 0.26 |
| | Citric Acid Anhydrous | 0.12 | 0.08 | 0.09 | 0.16 | 0.07 | 0.24 | 0.14 | 0.26 | 0.15 | 0.20 |
| | EDTA disodium salt, dihydrate | 0.04 | 0.175 | 0.1 | 0.06 | 0.1 | 0.09 | 0.06 | 0.08 | 0.063 | 0.09 |
| | Hydroxypropyl cellulose | — | 21.5 | 1.8 | 9.8 | 14.8 | — | 20.8 | 19.2 | 25.4 | — |
| | Hypromellose | 2.5 | — | — | — | — | — | — | — | 10.3 | 22.5 |
| | Hydroxypropyl methyl cellulose | 16.3 | 11.4 | 17.5 | 8.7 | — | 29.3 | — | — | — | 4.4 |
| | Croscarmellose sodium | 6.8 | 11.0 | 12.8 | 7.9 | 19.0 | 9.6 | 13.3 | 15.6 | 15.1 | 14.7 |
| | Silicon dioxide | 0.86 | 0.80 | 2.25 | 1.24 | .95 | 1.34 | 0.80 | 1.66 | 0.79 | 2.37 |
| | Magnesium stearate | 1.75 | 1.0 | 0.75 | 0.6 | 0.5 | 2.5 | 1.9 | 0.8 | 1.2 | 2.8 |
| Extended Release Layer | APAP | 150.0 | 150.0 | 125.0 | 75.0 | 100.0 | 165.0 | 135.0 | 225.0 | 210.0 | 150.0 |
| | Oxycodone hydrochloride | 8.00 | 6.50 | 6.00 | 6.50 | 3.25 | 6.25 | 6.25 | 5.00 | 6.25 | 5.50 |
| | Microcrystalline cellulose | 182.2 | 197.6 | 300.4 | 269.6 | 210.0 | 275.5 | 283.2 | 310.2 | 240.8 | 210.0 |
| | Pregelatinized starch | 0.75 | 0.73 | 0.46 | 0.89 | 0.55 | 0.78 | 0.55 | 0.65 | 0.67 | 0.64 |
| | Citric Acid Anhydrous | 0.25 | 0.36 | 0.38 | 0.34 | 0.37 | 0.23 | 0.14 | 0.40 | 0.70 | 0.70 |
| | EDTA disodium salt, dihydrate | 0.23 | 0.09 | 0.14 | 0.06 | 0.183 | 0.035 | 0.049 | 0.03 | 0.105 | 0.075 |
| | Hydroxypropyl cellulose | 34.7 | 321.9 | 88.4 | 212.9 | 11.9 | 37.7 | 34.2 | 17.4 | — | — |
| | Polyox N12K | — | — | 252.4 | — | 290.3 | — | 248.2 | 279.2 | 175.2 | — |
| | Polyox 1105 | 275.8 | — | — | — | — | — | — | — | — | 224.5 |
| | Hydroxypropyl methyl cellulose | — | 101.1 | — | 110.5 | — | 192.1 | — | — | 140.9 | 185.6 |
| | Silicon Dioxide | 1.3 | 1.3 | 1.2 | 2.4 | 2.1 | 3.2 | 4.0 | 4.0 | 2.0 | 3.8 |
| | Magnesium Stearate | 5.7 | 9.4 | 6.6 | 5.5 | 7.7 | 9.4 | 6.4 | 5.2 | 9.9 | 7.2 |

| | | \multicolumn{10}{c}{Formulation No.} |
| | | 101 | 102 | 103 | 104 | 105 | 106 | 107 | 108 | 109 | 110 |
|---|---|---|---|---|---|---|---|---|---|---|---|
| Immediate Release Layer | APAP | 185.3 | 175.0 | 180.0 | 160.4 | 200.0 | 193.4 | 118.8 | 162.5 | 139.0 | 150.0 |
| | Oxycodone hydrochloride | 1.100 | 1.75 | 2.00 | 2.50 | 1.25 | 1.00 | 2.75 | 1.875 | 1.75 | 1.875 |
| | Microcrystalline cellulose | 23.0 | 17.0 | 19.0 | 27.0 | 16.0 | 18.0 | 18.0 | 14.0 | 21.0 | 24.0 |
| | Pregelatinized starch | 0.05 | 0.15 | 0.25 | 0.10 | 0.05 | 0.30 | 0.20 | 0.25 | 0.15 | 0.20 |
| | Citric Acid Anhydrous | 0.08 | 0.08 | 0.08 | 0.11 | 0.11 | 0.14 | 0.07 | 0.13 | 0.15 | 0.17 |
| | EDTA disodium salt, dihydrate | 0.087 | 0.106 | 0.075 | 0.03 | 0.050 | 0.055 | 0.033 | 0.025 | 0.045 | 0.018 |
| | Hydroxypropyl cellulose | 14.1 | 17.8 | — | — | 17.3 | — | 16.7 | 16.1 | 21.5 | — |

CHART 2-continued

Representative oxycodone formulations.*

|  |  |  |  |  |  |  |  |  |  |  |
|---|---|---|---|---|---|---|---|---|---|---|
|  | Hypromellose | 2.5 | — | 3.2 | — | — | — | — | — | 8.9 | 19.5 |
|  | Hydroxypropyl methyl cellulose | — | — | 21.7 | 18.3 | — | 19.3 | — | — | — | 3.0 |
|  | Croscarmellose sodium | 10.0 | 11.0 | 11.5 | 11.5 | 13.0 | 14.5 | 14.5 | 12.5 | 14.0 | 12.5 |
|  | Silicon dioxide | 0.97 | 0.75 | 1.14 | 1.02 | 1.10 | 1.03 | 0.88 | 1.05 | 0.93 | 2.30 |
|  | Magnesium stearate | 1.5 | 1.0 | 1.0 | 0.5 | 0.5 | 2.0 | 2.0 | 0.5 | 1.5 | 2.5 |
| Extended Release Layer | APAP | 185.3 | 150.0 | 145.0 | 155.2 | 125.0 | 100.5 | 146.9 | 162.5 | 207.4 | 150.0 |
|  | Oxycodone hydrochloride | 6.900 | 5.75 | 5.50 | 5.00 | 6.25 | 6.50 | 7.25 | 5.625 | 4.75 | 6.625 |
|  | Microcrystalline cellulose | 175.4 | 180.0 | 302.2 | 275.0 | 214.8 | 250.0 | 245.7 | 203.6 | 288.3 | 200.5 |
|  | Pregelatinized starch | 0.60 | 0.60 | 0.70 | 0.70 | 0.70 | 0.75 | 0.75 | 0.75 | 0.85 | 0.85 |
|  | Citric Acid Anhydrous | 0.24 | 0.16 | 0.24 | 0.22 | 0.33 | 0.28 | 0.07 | 0.38 | 0.45 | 0.34 |
|  | EDTA disodium salt, dihydrate | 0.160 | 0.085 | 0.095 | 0.055 | 0.130 | 0.065 | 0.065 | 0.075 | 0.130 | 0.125 |
|  | Hydroxypropyl cellulose | 30.0 | 275.8 | 95.5 | 210.6 | 13.2 | 40.7 | 32.9 | 9.6 | — | — |
|  | Polyox N60K | 292.8 | — | — | — | 287.7 | — | — | — | 155.5 | — |
|  | Polyox 205 | — | — | 244.2 | — | — | — | 275.5 | 321.8 | — | 189.2 |
|  | Hydroxypropyl methyl cellulose | — | 103.2 | — | 134.2 | — | 182.2 | — | — | 155.5 | 210.2 |
|  | Silicon Dioxide | 1.8 | 1.3 | 1.5 | 2.3 | 2.4 | 3.0 | 3.5 | 3.6 | 2.0 | 2.5 |
|  | Magnesium Stearate | 7.5 | 8.0 | 7.4 | 8.1 | 7.5 | 10.2 | 9.9 | 7.2 | 10.3 | 10.3 |

|  |  | Formulation No. | | | | | | | | | |
|---|---|---|---|---|---|---|---|---|---|---|---|
|  |  | 111 | 112 | 113 | 114 | 115 | 116 | 117 | 118 | 119 | 120 |
| Immediate Release Layer | APAP | 300.0 | 150.0 | 200.0 | 150.0 | 100.0 | 160.0 | 190.0 | 75.0 | 90.0 | 125.0 |
|  | Oxycodone hydrochloride | 2.00 | 1.00 | 1.50 | 3.50 | 2.75 | 1.25 | 1.25 | 2.50 | 1.75 | 3.00 |
|  | Microcrystalline cellulose | 21.5 | 18.5 | 25.3 | 35.0 | 15.7 | 27.1 | 9.9 | 13.9 | 24.2 | 16.9 |
|  | Pregelatinized starch | 0.03 | 0.30 | 0.25 | 0.27 | 0.08 | 0.35 | 0.75 | 0.09 | 0.15 | 0.26 |
|  | Citric Acid Anhydrous | 0.12 | 0.08 | 0.09 | 0.16 | 0.07 | 0.24 | 0.14 | 0.26 | 0.15 | 0.20 |
|  | EDTA disodium salt, dihydrate | 0.04 | 0.175 | 0.1 | 0.06 | 0.1 | 0.09 | 0.06 | 0.08 | 0.063 | 0.09 |
|  | Hydroxypropyl cellulose | — | 21.5 | 1.8 | 9.8 | 14.8 | — | 20.8 | 19.2 | 25.4 | — |
|  | Hypromellose | 2.5 | — | — | — | — | — | — | — | 10.3 | 22.5 |
|  | Hydroxypropyl methyl cellulose | 16.3 | 11.4 | 17.5 | 8.7 | — | 29.3 | — | — | — | 4.4 |
|  | Croscarmellose sodium | 6.8 | 11.0 | 12.8 | 7.9 | 19.0 | 9.6 | 13.3 | 15.6 | 15.1 | 14.7 |
|  | Silicon dioxide | 0.86 | 0.80 | 2.25 | 1.24 | .95 | 1.34 | 0.80 | 1.66 | 0.79 | 2.37 |
|  | Magnesium stearate | 1.75 | 1.0 | 0.75 | 0.6 | 0.5 | 2.5 | 1.9 | 0.8 | 1.2 | 2.8 |
| Extended Release Layer | APAP | 150.0 | 150.0 | 125.0 | 75.0 | 100.0 | 165.0 | 135.0 | 225.0 | 210.0 | 150.0 |
|  | Oxycodone hydrochloride | 8.00 | 6.50 | 6.00 | 6.50 | 3.25 | 6.25 | 6.25 | 5.00 | 6.25 | 5.50 |
|  | Microcrystalline cellulose | 182.2 | 197.6 | 300.4 | 269.6 | 210.0 | 275.5 | 283.2 | 310.2 | 240.8 | 210.0 |
|  | Pregelatinized starch | 0.75 | 0.73 | 0.46 | 0.89 | 0.55 | 0.78 | 0.55 | 0.65 | 0.67 | 0.64 |
|  | Citric Acid Anhydrous | 0.25 | 0.36 | 0.38 | 0.34 | 0.37 | 0.23 | 0.14 | 0.40 | 0.70 | 0.70 |
|  | EDTA disodium salt, dihydrate | 0.23 | 0.09 | 0.14 | 0.06 | 0.183 | 0.035 | 0.049 | 0.03 | 0.105 | 0.075 |
|  | Hydroxypropyl cellulose | 34.7 | 321.9 | 88.4 | 212.9 | 11.9 | 37.7 | 34.2 | 17.4 | — | — |
|  | Polyox N60K | — | 45.5 | 249.9 | 24.3 | 282.0 | 49.8 | 200.1 | 240.1 | 186.8 | — |
|  | Polyox 205 | 268.4 | — | 53.6 | 70.2 | — | — | 36.3 | 10.4 | — | 259.3 |
|  | Hydroxypropyl methyl cellulose | — | 90.5 | — | 65.4 | — | 192.1 | — | — | 127.3 | 142.0 |
|  | Silicon Dioxide | 1.3 | 1.3 | 1.2 | 2.4 | 2.1 | 3.2 | 4.0 | 4.0 | 2.0 | 3.8 |
|  | Magnesium Stearate | 5.7 | 9.4 | 6.6 | 5.5 | 7.7 | 9.4 | 6.4 | 5.2 | 9.9 | 7.2 |

|  |  | Formulation No. | | | | | | | | | |
|---|---|---|---|---|---|---|---|---|---|---|---|
|  |  | 121 | 122 | 123 | 124 | 125 | 126 | 127 | 128 | 129 | 130 |
| Immediate Release Layer | APAP | 185.3 | 175.0 | 180.0 | 160.4 | 200.0 | 193.4 | 118.8 | 162.5 | 139.0 | 150.0 |
|  | Oxycodone hydrochloride | 1.100 | 1.75 | 2.00 | 2.50 | 1.25 | 1.00 | 2.75 | 1.875 | 1.75 | 1.875 |
|  | Microcrystalline cellulose | 23.0 | 17.0 | 19.0 | 27.0 | 16.0 | 18.0 | 18.0 | 14.0 | 21.0 | 24.0 |
|  | Pregelatinized starch | 0.05 | 0.15 | 0.25 | 0.10 | 0.05 | 0.30 | 0.20 | 0.25 | 0.15 | 0.20 |
|  | Citric Acid Anhydrous | 0.08 | 0.08 | 0.08 | 0.11 | 0.11 | 0.14 | 0.07 | 0.13 | 0.15 | 0.17 |
|  | EDTA disodium salt, dihydrate | 0.087 | 0.106 | 0.075 | 0.03 | 0.050 | 0.055 | 0.033 | 0.025 | 0.045 | 0.018 |
|  | Hydroxypropyl cellulose | 14.1 | 17.8 | — | — | 17.3 | — | 16.7 | 16.1 | 21.5 | — |
|  | Hypromellose | 2.5 | — | 3.2 | — | — | — | — | — | 8.9 | 19.5 |
|  | Hydroxypropyl methyl cellulose | — | — | 21.7 | 18.3 | — | 19.3 | — | — | — | 3.0 |
|  | Croscarmellose sodium | 10.0 | 11.0 | 11.5 | 11.5 | 13.0 | 14.5 | 14.5 | 12.5 | 14.0 | 12.5 |
|  | Silicon dioxide | 0.97 | 0.75 | 1.14 | 1.02 | 1.10 | 1.03 | 0.88 | 1.05 | 0.93 | 2.30 |
|  | Magnesium stearate | 1.5 | 1.0 | 1.0 | 0.5 | 0.5 | 2.0 | 2.0 | 0.5 | 1.5 | 2.5 |

CHART 2-continued

Representative oxycodone formulations.*

| | | | | | | | | | | | |
|---|---|---|---|---|---|---|---|---|---|---|---|
| Extended Release Layer | APAP | 185.3 | 150.0 | 145.0 | 155.2 | 125.0 | 100.5 | 146.9 | 162.5 | 207.4 | 150.0 |
| | Oxycodone hydrochloride | 6.900 | 5.75 | 5.50 | 5.00 | 6.25 | 6.50 | 7.25 | 5.625 | 4.75 | 6.625 |
| | Microcrystalline cellulose | 175.4 | 180.0 | 302.2 | 275.0 | 214.8 | 250.0 | 245.7 | 203.6 | 288.3 | 200.5 |
| | Pregelatinized starch | 0.60 | 0.60 | 0.70 | 0.70 | 0.70 | 0.75 | 0.75 | 0.75 | 0.85 | 0.85 |
| | Citric Acid Anhydrous | 0.24 | 0.16 | 0.24 | 0.22 | 0.33 | 0.28 | 0.07 | 0.38 | 0.45 | 0.34 |
| | EDTA disodium salt, dihydrate | 0.160 | 0.085 | 0.095 | 0.055 | 0.130 | 0.065 | 0.065 | 0.075 | 0.130 | 0.125 |
| | Hydroxypropyl cellulose | 30.0 | 275.8 | 95.5 | 210.6 | 13.2 | 40.7 | 32.9 | 9.6 | — | — |
| | Polyox N-750 | 292.8 | — | — | — | 287.7 | — | — | — | 155.5 | — |
| | Polyox 301 | — | — | 244.2 | — | — | — | 275.5 | 321.8 | — | 189.2 |
| | Hydroxypropyl methyl cellulose | — | 103.2 | — | 134.2 | — | 182.2 | — | — | 155.5 | 210.2 |
| | Silicon Dioxide | 1.8 | 1.3 | 1.5 | 2.3 | 2.4 | 3.0 | 3.5 | 3.6 | 2.0 | 2.5 |
| | Magnesium Stearate | 7.5 | 8.0 | 7.4 | 8.1 | 7.5 | 10.2 | 9.9 | 7.2 | 10.3 | 10.3 |

| | | Formulation No. | | | | | | | | | |
|---|---|---|---|---|---|---|---|---|---|---|---|
| | | 131 | 132 | 133 | 134 | 135 | 136 | 137 | 138 | 139 | 140 |
| Immediate Release Layer | APAP | 300.0 | 150.0 | 200.0 | 150.0 | 100.0 | 160.0 | 190.0 | 75.0 | 90.0 | 125.0 |
| | Oxycodone hydrochloride | 2.00 | 1.00 | 1.50 | 3.50 | 2.75 | 1.25 | 1.25 | 2.50 | 1.75 | 3.00 |
| | Microcrystalline cellulose | 21.5 | 18.5 | 25.3 | 35.0 | 15.7 | 27.1 | 9.9 | 13.9 | 24.2 | 16.9 |
| | Pregelatinized starch | 0.03 | 0.30 | 0.25 | 0.27 | 0.08 | 0.35 | 0.75 | 0.09 | 0.15 | 0.26 |
| | Citric Acid Anhydrous | 0.12 | 0.08 | 0.09 | 0.16 | 0.07 | 0.24 | 0.14 | 0.26 | 0.15 | 0.20 |
| | EDTA disodium salt, dihydrate | 0.04 | 0.175 | 0.1 | 0.06 | 0.1 | 0.09 | 0.06 | 0.08 | 0.063 | 0.09 |
| | Hydroxypropyl cellulose | — | 21.5 | 1.8 | 9.8 | 14.8 | — | 20.8 | 19.2 | 25.4 | — |
| | Hypromellose | 2.5 | — | — | — | — | — | — | — | 10.3 | 22.5 |
| | Hydroxypropyl methyl cellulose | 16.3 | 11.4 | 17.5 | 8.7 | — | 29.3 | — | — | — | 4.4 |
| | Croscarmellose sodium | 6.8 | 11.0 | 12.8 | 7.9 | 19.0 | 9.6 | 13.3 | 15.6 | 15.1 | 14.7 |
| | Silicon dioxide | 0.86 | 0.80 | 2.25 | 1.24 | .95 | 1.34 | 0.80 | 1.66 | 0.79 | 2.37 |
| | Magnesium stearate | 1.75 | 1.0 | 0.75 | 0.6 | 0.5 | 2.5 | 1.9 | 0.8 | 1.2 | 2.8 |
| Extended Release Layer | APAP | 150.0 | 150.0 | 125.0 | 75.0 | 100.0 | 165.0 | 135.0 | 225.0 | 210.0 | 150.0 |
| | Oxycodone hydrochloride | 8.00 | 6.50 | 6.00 | 6.50 | 3.25 | 6.25 | 6.25 | 5.00 | 6.25 | 5.50 |
| | Microcrystalline cellulose | 182.2 | 197.6 | 300.4 | 269.6 | 210.0 | 275.5 | 283.2 | 310.2 | 240.8 | 210.0 |
| | Pregelatinized starch | 0.75 | 0.73 | 0.46 | 0.89 | 0.55 | 0.78 | 0.55 | 0.65 | 0.67 | 0.64 |
| | Citric Acid Anhydrous | 0.25 | 0.36 | 0.38 | 0.34 | 0.37 | 0.23 | 0.14 | 0.40 | 0.70 | 0.70 |
| | EDTA disodium salt, dihydrate | 0.23 | 0.09 | 0.14 | 0.06 | 0.183 | 0.035 | 0.049 | 0.03 | 0.105 | 0.075 |
| | Hydroxypropyl cellulose | 34.7 | 321.9 | 88.4 | 212.9 | 11.9 | 37.7 | 34.2 | 17.4 | — | — |
| | Polyox N-750 | 63.4 | 30.1 | 125.9 | 100.3 | 149.2 | 63.2 | 150.5 | 140.3 | 94.3 | — |
| | Polyox 301 | 210.4 | — | 175.8 | 60.7 | 175.8 | — | 160.5 | 149.7 | 100.8 | 194.6 |
| | Hydroxypropyl methyl cellulose | — | 128.3 | — | 65.4 | — | 227.7 | — | — | 127.3 | 142.0 |
| | Silicon Dioxide | 1.3 | 1.3 | 1.2 | 2.4 | 2.1 | 3.2 | 4.0 | 4.0 | 2.0 | 3.8 |
| | Magnesium Stearate | 5.7 | 9.4 | 6.6 | 5.5 | 7.7 | 9.4 | 6.4 | 5.2 | 9.9 | 7.2 |

*All weights in mg.

CHART 3

Additional opioid formulations.*

| | | Formulation No. | | | | | | | | | |
|---|---|---|---|---|---|---|---|---|---|---|---|
| | | 141 | 142 | 143 | 144 | 145 | 146 | 147 | 148 | 149 | 150 |
| Immediate Release Layer | APAP | 250.0 | 250.0 | 250.0 | 250.0 | 250.0 | 250.0 | 325.0 | 325.0 | 325.0 | 325.0 |
| | Oxycodone hydrochloride | 3.75 | 3.75 | 3.75 | 7.5 | 7.5 | 7.5 | 3.75 | — | — | — |
| | Hydrocodone bitartrate | — | — | — | — | — | — | — | 3.75 | 3.75 | 3.75 |
| | Microcrystalline cellulose | 23.72 | 23.72 | 23.72 | 32.42 | 32.42 | 32.42 | 28.10 | 28.1 | 28.1 | 28.1 |
| | Pregelatinized starch | 0.50 | 0.50 | 0.50 | 1.00 | 1.00 | 1.00 | 0.50 | 0.50 | 0.50 | 0.50 |
| | Citric Acid Anhydrous | 0.25 | 0.25 | 0.25 | 0.50 | 0.50 | 0.50 | 0.25 | 0.25 | 0.25 | 0.25 |
| | EDTA disodium salt, dihydrate | 0.05 | 0.05 | 0.05 | 0.10 | 0.10 | 0.10 | 0.05 | 0.05 | 0.05 | 0.05 |
| | Hydroxypropyl cellulose | 25.23 | 25.23 | 25.23 | 26.43 | 26.43 | 26.43 | 32.24 | 32.24 | 32.24 | 32.24 |
| | Croscarmellose sodium | 19.21 | 19.21 | 19.21 | 20.13 | 20.13 | 20.13 | 12.09 | 25.09 | 25.09 | 25.09 |
| | Silicon dioxide | 1.63 | 1.63 | 1.63 | 1.70 | 1.70 | 1.70 | 2.09 | 2.09 | 2.09 | 2.09 |
| | Magnesium stearate | 0.81 | 0.81 | 0.81 | 0.85 | 0.85 | 0.85 | 1.045 | 1.045 | 1.045 | 1.045 |
| Extended Release Layer | APAP | 250.0 | 250.0 | 250.0 | 250.0 | 250.0 | 250.0 | 325.0 | 325.0 | 325.0 | 325.0 |
| | Hydrocodone bitartrate | — | — | — | — | — | — | — | 11.25 | 11.25 | 11.25 |
| | Oxycodone hydrochloride | 11.25 | 11.25 | 11.25 | 22.5 | 22.5 | 22.5 | 11.25 | — | — | — |
| | Microcrystalline cellulose | 175.24 | 103.74 | 103.74 | 159.62 | 88.12 | 88.12 | 23.85 | 95.19 | 23.85 | 23.85 |
| | Pregelatinized starch | 1.50 | 1.50 | 1.50 | 3.00 | 3.00 | 3.00 | 1.5 | 1.5 | 1.5 | 1.5 |
| | Citric Acid Anhydrous | 0.75 | 0.75 | 0.75 | 1.50 | 1.50 | 1.50 | 0.75 | 0.75 | 0.75 | 0.75 |

CHART 3-continued

Additional opioid formulations.*

| | | | | | | | | | | |
|---|---|---|---|---|---|---|---|---|---|---|
| EDTA disodium salt, dihydrate | 0.15 | 0.15 | 0.15 | 0.30 | 0.30 | 0.30 | 0.15 | 0.15 | 0.15 | 0.15 |
| Hydroxypropyl cellulose | 15.13 | 15.13 | 15.13 | 17.11 | 17.11 | 17.11 | — | 19.16 | 19.16 | 19.16 |
| Polyox 1105 | 250.25 | 321.75 | — | 250.25 | 321.75 | — | 321.02 | 249.68 | 321.02 | — |
| Polyox N60K | — | — | 321.75 | — | — | 321.75 | — | — | — | 321.02 |
| Silicon Dioxide | 3.58 | 3.58 | 3.58 | 3.58 | 3.58 | 3.58 | 3.57 | 3.57 | 3.57 | 3.57 |
| Magnesium Stearate | 7.15 | 7.15 | 7.15 | 7.15 | 7.15 | 7.15 | 7.13 | 7.13 | 7.13 | 7.13 |

| | | Formulation No. | | | | | | | | | | |
|---|---|---|---|---|---|---|---|---|---|---|---|---|
| | | 151 | 152 | 153 | 154 | 155 | 156 | 157 | 158 | 159 | 160 | 161 | 162 |
| Immediate Release Layer | APAP | 325.0 | 325.0 | 325 | 325 | 325 | 325 | 325 | 325.0 | 325.0 | 325.0 | 162.5 | 162.5 |
| | Oxycodone hydrochloride | 3.75 | — | — | 3.75 | — | — | 3.75 | — | 3.75 | 3.75 | 2.5 | 3.75 |
| | Hydrocodone bitartrate | — | 3.75 | 3.75 | — | 3.75 | 3.75 | — | 3.75 | — | — | — | — |
| | Microcrystalline cellulose | 28.10 | 28.10 | 28.10 | 28.10 | 28.10 | 28.10 | 28.10 | 28.1 | 28.1 | 28.10 | 15.50 | 18.40 |
| | Pregelatinized starch | 0.50 | 0.50 | 0.50 | 0.50 | 0.50 | 0.50 | 0.50 | 0.50 | 0.50 | 0.50 | 0.33 | 0.50 |
| | Citric Acid Anhydrous | 0.25 | 0.25 | 0.25 | 0.25 | 0.25 | 0.25 | 0.25 | 0.25 | 0.25 | 0.25 | 0.17 | 0.25 |
| | EDTA disodium salt, dihydrate | 0.05 | 0.05 | 0.05 | 0.05 | 0.05 | 0.05 | 0.05 | 0.05 | 0.05 | 0.05 | 0.033 | 0.05 |
| | Hydroxypropyl cellulose | 32.23 | 32.23 | 32.24 | 32.24 | 32.24 | 32.24 | 32.24 | 32.24 | 32.24 | 32.23 | 16.32 | 16.72 |
| | Croscarmellose sodium | 25.087 | 25.087 | 25.09 | 25.09 | 25.09 | 25.09 | 25.09 | 25.09 | 25.09 | 25.087 | 12.70 | 13.01 |
| | Silicon dioxide | 2.09 | 2.09 | 2.09 | 2.09 | 2.09 | 2.09 | 2.09 | 2.09 | 2.09 | 2.09 | 1.06 | 1.08 |
| | Magnesium stearate | 1.045 | 1.045 | 1.05 | 1.05 | 1.05 | 1.05 | 1.05 | 1.045 | 1.045 | 1.045 | 0.53 | 0.54 |
| Extended Release Layer | APAP | 325.0 | 325.0 | 325 | 325 | 325 | 325 | 325 | 325.0 | 325.0 | 325.0 | 162.5 | 162.5 |
| | Hydrocodone bitartrate | — | 11.25 | 11.25 | — | 11.25 | 11.25 | — | 11.25 | 11.25 | — | — | — |
| | Oxycodone hydrochloride | 11.25 | — | — | 11.25 | — | — | 11.25 | — | — | 11.25 | 7.5 | 11.25 |
| | Microcrystalline cellulose | 23.85 | 23.85 | 95.19 | 95.19 | 23.85 | 23.85 | 23.85 | 23.85 | 23.85 | 23.85 | 201.02 | 195.80 |
| | Pregelatinized starch | 1.50 | 1.50 | 1.50 | 1.50 | 1.50 | 1.50 | 1.50 | 1.5 | 1.5 | 1.50 | 1.00 | 1.50 |
| | Citric Acid Anhydrous | 0.75 | 0.75 | 0.75 | 0.75 | 0.75 | 0.75 | 0.75 | 0.75 | 0.75 | 0.75 | 0.50 | 0.75 |
| | EDTA disodium salt, dihydrate | 0.15 | 0.15 | 0.15 | 0.15 | 0.15 | 0.15 | 0.15 | 0.15 | 0.15 | 0.15 | 0.10 | 0.15 |
| | Hydroxypropyl cellulose | 19.16 | 19.16 | 19.16 | 19.16 | 19.16 | 19.16 | 19.16 | 19.16 | 19.16 | 19.16 | 9.91 | 10.57 |
| | Polyox 1105 | 321.02 | 321.02 | 249.68 | 249.68 | — | 321.02 | — | — | — | — | 321.75 | 321.75 |
| | Polyox N12K | — | — | — | — | 321.02 | — | 321.02 | — | — | 321.02 | — | — |
| | Polyox N60K | — | — | — | — | — | — | — | 321.02 | 321.02 | — | — | — |
| | Silicon Dioxide | 3.57 | 3.57 | 3.57 | 3.57 | 3.57 | 3.57 | 3.57 | 3.57 | 3.57 | 3.57 | 3.58 | 3.58 |
| | Magnesium Stearate | 7.13 | 7.13 | 7.13 | 7.13 | 7.13 | 7.13 | 7.13 | 7.13 | 7.13 | 7.13 | 7.15 | 7.15 |

*All weights in mg.

(i) In Vitro Release Properties of the Exemplary Compositions

In one embodiment, the composition comprises at least one immediate release portion and at least one extended release portion, each of which comprise either oxycodone or hydrocodone, acetaminophen, or a combination thereof. The in vitro release rates of oxycodone, hydrocodone, and acetaminophen may be measured in 900 mL of 0.1 N HCl using a USP type II paddle apparatus and at paddle speed of either about 100 rpm or about 150 rpm and at a constant temperature of 37° C.

In one embodiment, the at least one immediate release portion of the composition may have in vitro release rate of oxycodone and acetaminophen as follows: more than about 90% of the oxycodone and/or the acetaminophen present in the at least one immediate release portion is released in about 15 minutes, or essentially 100% of the oxycodone and/or the acetaminophen present in the at least one immediate release portion may be released within about 15 minutes. In another embodiment, more than about 90% of the oxycodone and/or the acetaminophen present in the at least one immediate release portion may be released within about 5 min. In yet another embodiment, essentially 100% of the oxycodone and/or the acetaminophen present in the at least one immediate release portion may be released within about 5 min.

In one embodiment, the at least one extended release portion of the composition may have in vitro release rates of oxycodone as follows: from about 1% to about 20% of the oxycodone present in the at least one extended release portion may be released within about 15 min, from about 35% to about 60% of the oxycodone present in the at least one extended release portion is released within about 2 hours, from about 60% to about 90% of the oxycodone present in the at least one extended release portion is released in about 4 hours, and at least about 90% of the oxycodone present in the at least one extended release portion is released within about 8 hours.

In still another embodiment, the at least one extended release portion may have in vitro release rates of oxycodone as follows: from about 1% to about 20% of the oxycodone present in the extended release portion may be released within about 15 min, from about 35% to about 60% of the oxycodone present in the extended release portion may be released within about 2 hours, from about 60% to about 90% of the oxycodone present in the extended release portion may be released within about 4 hours, and from about 90% to about 100% of the oxycodone present in the extended release portion may be released within about 8 hours.

In yet another embodiment, the at least one extended release portion may have in vitro release rates of oxycodone as follows: from about 1% to about 10% of the oxycodone present in the extended release portion may be released within about 15 min, from about 40% to about 50% of the oxycodone present in the extended release portion may be released within about 2 hours, from about 70% to about 80% of the oxycodone present in the extended release portion may be released within about 4 hours, and from about 90% to about 100% of the oxycodone present in the extended release portion may be released within about 8 hours.

In one embodiment, the at least one extended release portion of the composition may have in vitro release rates of acetaminophen as follows: from about 1% to about 15% of the acetaminophen present in the at least one extended release portion may be released within about 15 min, from about 20% to about 50% of the acetaminophen present in the at least one extended release portion may be released within about 2 hours, from about 35% to about 75% of the acetaminophen present in the at least one extended release portion may be released within about 4 hours, and from about 65% to about 100% of the acetaminophen present in the at least one extended release portion may be released within about 8 hours.

In another embodiment, the at least one extended release portion of the composition may have in vitro release rates of acetaminophen as follows: from about 1% to about 15% of the acetaminophen present in the at least one extended release portion may be released within about 15 min, from about 20% to about 50% of the acetaminophen present in the at least one extended release portion may be released within about 2 hours, from about 35% to about 75% of the acetaminophen present in the at least one extended release portion may be released within about 4 hours, and from about 65% to about 100% of the acetaminophen present in the at least one extended release portion may be released within about 8 hours.

In one embodiment, the in vitro release rates of oxycodone from the composition may be as follows: about 20% to about 45% of oxycodone may be released from the composition within about 15 minutes, from about 50% to about 75% of oxycodone may be released from the composition in about 2 hours, from about 70% to about 95% of oxycodone may be released from the composition within about 4 hours, and from about 90% to about 100% of oxycodone may be released from the composition within about 8 hours.

In another embodiment, the in vitro release rates of oxycodone from the composition may be as follows: about 20% to about 45% of oxycodone may be released from the pharmaceutical composition within about 15 minutes, from about 50% to about 75% of oxycodone may be released from the pharmaceutical composition within about 2 hours, from about 70% to about 95% of oxycodone may be released from the pharmaceutical composition within about 4 hours, and from about 90% to about 100% of oxycodone may be released from the pharmaceutical composition within about 8 hours.

In one embodiment, the in vitro release rates of acetaminophen from the composition may be as follows: from about 40% to about 65% of acetaminophen may be released from the composition in about 15 minutes, from about 55% to about 80% of acetaminophen may be released from the composition in about 2 hours, from about 65% to about 95% of acetaminophen may be released from the composition in about 4 hours, and from about 80% to about 100% of acetaminophen may be released from the composition in about 8 hours.

In another embodiment, the in vitro release rates of acetaminophen from the pharmaceutical composition disclosed herein may be as follows: from about 40% to about 65% of acetaminophen may be released from the pharmaceutical composition within about 15 minutes, from about 55% to about 80% of acetaminophen may be released from the pharmaceutical composition within about 2 hours, from about 65% to about 95% of acetaminophen may be released from the pharmaceutical composition within about 4 hours, and from about 80% to about 100% of acetaminophen may be released from the pharmaceutical composition within about 8 hours. In another embodiment, about 90% to about 100% of the IR dose of acetaminophen is released within about 15 minutes, 30 minutes, 45 minutes or 60 minutes after oral administration. In one embodiment, the dosage form provides a dissolution profile wherein about 20% to about 65%, about 35% to about 55% or about 40% to about 50% of the ER dose of acetaminophen remains in the ER layer between about 1 and 2 hours after administration. In yet another embodiment, the dosage form provides a dissolution profile wherein about 50% to about 95% of the ER dose of acetaminophen remains in the ER layer between about 1 and 2 hours after administration. In another embodiment, the dosage form provides a dissolution profile wherein about 15% to about 40% of the ER dose of acetaminophen is released from the ER layer between about 1 and 2 hours after administration. In one embodiment, not more than 50% of the ER dose of acetaminophen is released within about the first hour. In a further embodiment, not more than 45% or not more than 40% of the ER dose of acetaminophen is released within about the first hour. In another embodiment, not more than 85% of the ER dose of acetaminophen is released within about 4 hours. In yet another embodiment, not less than 50% is released after about 6 hours. In yet another embodiment, not less than 55% is released after about 6 hours. In one embodiment, the ER dose of acetaminophen is released over a time period of about 6 to 12, about 8 to 10, or about 9 to 10 hours in vitro. In another embodiment, the ER dose of acetaminophen is released over a time period of about 7 hours, 8 hours, 9 hours, 10 hours, 11 hours or 12 hours in vitro. In one embodiment, at least 80% or 85% of the ER dose of acetaminophen is released over a time period of about 7 hours, 8 hours, 9 hours, 10 hours, 11 hours or 12 hours in vitro. In another embodiment, at least 90% or 95% of the ER dose of acetaminophen is released over a time period of about 7 hours, 8 hours, 9 hours, 10 hours, 11 hours or 12 hours in vitro.

In one embodiment, the at least one immediate release portion of the composition may have in vitro release rate of hydrocodone and acetaminophen as follows: more than about 90% of the hydrocodone and/or the acetaminophen present in the at least one immediate release portion is released in about 15 minutes, or essentially 100% of the hydrocodone and/or the acetaminophen present in the at least one immediate release portion may be released within about 15 minutes. In another embodiment, more than about 90% of the hydrocodone and/or the acetaminophen present in the at least one immediate release portion may be released within about 5 min. In yet another embodiment, essentially 100% of the hydrocodone and/or the acetaminophen present in the at least one immediate release portion may be released within about 5 min.

In one embodiment, the at least one extended release portion of the composition may have in vitro release rates of hydrocodone as follows: from about 1% to about 20% of the hydrocodone present in the at least one extended release portion may be released within about 15 min, from about 30% to about 50% of the hydrocodone present in the at least one extended release portion is released within about 2 hours, from about 50% to about 75% of the hydrocodone present in the at least one extended release portion is released in about 4 hours, at least about 80% of the hydrocodone present in the at least one extended release portion is released within about 8 hours, and at least about 90% of the hydrocodone present in the at least one extended release portion is released within about 12 hours.

In yet another embodiment, the at least one extended release portion may have in vitro release rates of hydrocodone as follows: from about 1% to about 20% of the hydrocodone present in the extended release portion may be released within about 15 min, from about 30% to about 50% of the hydrocodone present in the extended release portion may be released within about 2 hours, from about 50% to about 75% of the hydrocodone present in the extended release portion may be released within about 4 hours, and from about 80% to about 100% of the hydrocodone present in the extended release portion may be released within about 8 hours.

In one embodiment, the in vitro release rates of hydrocodone from the composition may be as follows: about 20% to about 50% of hydrocodone may be released from the composition within about 15 minutes, from about 25% to about 55% of hydrocodone may be released from the composition within about 30 minutes, from about 35% to about 65% of hydrocodone may be released within about 1 hour, from about 40% to about 80% of hydrocodone may be released from the composition in about 2 hours, from about 60% to about 100% of hydrocodone may be released from the composition within about 4 hours, from about 70% to about 100% of hydrocodone may be released from the composition within about 6 hours, from about 80% to about 100% of hydrocodone may be released from the composition within about 8 hours, from about 90% to about 100% of hydrocodone may be released from the composition within about 12 hours, and from about 90% to about 100% of hydrocodone may be released from the composition within about 18 hours.

In another embodiment, the in vitro release rates of hydrocodone from the composition may be as follows: about 20% to about 40% of hydrocodone may be released from the composition within about 15 minutes, from about 25% to about 45% of hydrocodone may be released from the composition within about 30 minutes, from about 35% to about 55% of hydrocodone may be released within about 1 hour, from about 45% to about 65% of hydrocodone may be released from the composition in about 2 hours, from about 60% to about 85% of hydrocodone may be released from the composition within about 4 hours, from about 70% to about 100% of hydrocodone may be released from the composition within about 6 hours, from about 80% to about 100% of hydrocodone may be released from the composition within about 8 hours, from about 85% to about 100% of hydrocodone may be released from the composition within about 12 hours, and from about 90% to about 100% of hydrocodone may be released from the composition within about 18 hours.

In another embodiment, the in vitro release rates of hydrocodone from the composition may be as follows: about 30% to about 35% of hydrocodone may be released from the composition within about 15 minutes, from about 35% to about 40% of hydrocodone may be released from the composition within about 30 minutes, from about 40% to about 50% of hydrocodone may be released within about 1 hour, from about 50% to about 60% of hydrocodone may be released from the composition in about 2 hours, from about 65% to about 75% of hydrocodone may be released from the composition within about 4 hours, from about 80% to about 90% of hydrocodone may be released from the composition within about 6 hours, from about 90% to about 100% of hydrocodone may be released from the composition within about 8 hours, and from about 95% to about 100% of hydrocodone may be released from the composition within about 12 hours.

In one embodiment, the in vitro release rates of acetaminophen from the composition may be as follows: about 40% to about 65% of acetaminophen may be released from the composition within about 15 minutes, from about 45% to about 65% of acetaminophen may be released from the composition with about 30 minutes, from about 50% to about 70% of acetaminophen may be released from the composition within about 1 hour, from about 55% to about 80% of acetaminophen may be released from the composition within about 2 hours, from about 65% to about 95% of acetaminophen may be released from the composition within about 4 hours, from about 75% to about 100% of acetaminophen may be released from the composition within about 6 hours, from about 80% to about 100% of acetaminophen may be released from the composition within about 8 hours, from about 85% to about 100% of acetaminophen may be released from the composition within about 12 hours, and from about 90% to about 100% of acetaminophen may be released from the composition within about 18 hours.

In a further embodiment, the in vitro release rates of acetaminophen from the composition may be as follows: about 50% to about 55% of acetaminophen may be released from the composition within about 15 minutes, from about 52% to about 58% of acetaminophen may be released from the composition within about 30 minutes, from about 55% to about 60% of acetaminophen may be released from the composition within about 1 hour, from about 60% to about 65% of acetaminophen may be released from the composition within about 2 hours, from about 70% to about 75% of acetaminophen may be released from the composition within about 4 hours, from about 80% to about 85% of acetaminophen may be released from the composition within about 6 hours, from about 90% to about 95% of acetaminophen may be released from the composition with about 8 hours, and from about 95% to about 100% of acetaminophen may be released from the composition within about 12 hours.

Additionally, the in vitro release rates of oxycodone and acetaminophen from the composition generally are not affected by low concentrations of ethanol (i.e., from about 5% v/v to about 20% v/v) when measured in 900 mL of 0.1 N HCl containing the desired percentage of ethanol using a USP type II paddle apparatus and at a constant temperature of 37° C. and about 150 rpm. For example, from about 25% to about 35% of oxycodone and about 50% to about 55% of acetaminophen may be released from the composition within about 15 minutes when measured in the presence of 5% to 20% ethanol, and from about 50% to about 65% of oxycodone and from about 60% to about 70% of acetaminophen may be released from the composition within about 2 hours when measured in the presence of 5% to 20% ethanol.

The in vitro release rates of oxycodone and acetaminophen from the composition generally are reduced, however, in the presence of 40% ethanol. For example, from about 5% to about 15% of the oxycodone and from about 15% to about 25% of the acetaminophen may be released from the composition within about 15 minutes when measured in the presence of 40% ethanol, and from about 35% to about 45% of oxycodone and from about 45% to about 55% of acetaminophen may be released from the composition within about 2 hours when measured in the presence of 40% ethanol.

Stated another way, less oxycodone is extracted from the composition by a solution of 0.1 N HCl and 40% ethanol than is extracted by a solution of 0.1 N HCl. In some embodiments, less than about 75% of the oxycodone that is released in the presence of 0.1N HCl is released in the presence 0.1N HCl containing 40% ethanol. In additional embodiments, less than about 70%, 65%, 60%, 55%, 50%, 45%, or 40% of the oxycodone that may be released in the presence of 0.1N HCl is released in the presence 0.1N HCl and 40% ethanol. For example, less than about 40% of the oxycodone that is released in the presence of 0.1N HCl within about 15 minutes may be released in the presence 0.1N HCl and 40% ethanol within about 15 minutes. In other embodiments, less than about 60% of the oxycodone that is released in the presence of 0.1N HCl within about 30 minutes may be released in the presence of 0.1N HCl and 40% ethanol within about 30 minutes. In additional embodiments, less than about 75% of the oxycodone that is released in the presence of 0.1N HCl within about 2 hours may be released in the presence 0.1N HCl and 40% ethanol within about 2 hours.

Further, the in vitro release rates of hydrocodone and acetaminophen from the composition generally are not affected by low concentrations of ethanol (e.g., 5% v/v or 20% v/v) when measured in 900 mL of 0.1 N HCl containing the desired percentage of ethanol using a USP type II paddle apparatus and at a constant temperature of 37° C. and about 150 rpm. For example, from about 25% to about 35% of hydrocodone and about 50% to about 55% of acetaminophen may be released from the composition within about 15 minutes when measured in the presence of 5% to 20% ethanol, and from about 50% to about 65% of hydrocodone and from about 60% to about 70% of acetaminophen may be released from the composition within about 2 hours when measured in the presence of 5% to 20% ethanol.

The in vitro release rates of hydrocodone and acetaminophen from the composition generally are reduced, however, in the presence of 40% ethanol. For example, from about 5% to about 15% of the hydrocodone and from about 15% to about 30% of the acetaminophen may be released from the composition within about 15 minutes when measured in the presence of 40% ethanol, and from about 30% to about 45% of hydrocodone and from about 45% to about 55% of acetaminophen may be released from the composition within about 2 hours when measured in the presence of 40% ethanol.

Stated another way, less hydrocodone is extracted from the composition by a solution of 0.1 N HCl and 40% ethanol than is extracted by a solution of 0.1 N HCl. In some embodiments, less than about 75% of the hydrocodone that is released in the presence of 0.1N HCl is released in the presence 0.1N HCl containing 40% ethanol. In additional embodiments, less than about 70%, 65%, 60%, 55%, 50%, 45%, or 40% of the hydrocodone that may be released in the presence of 0.1N HCl is released in the presence 0.1N HCl and 40% ethanol. For example, less than about 40% of the hydrocodone that is released in the presence of 0.1N HCl within about 15 minutes may be released in the presence 0.1N HCl and 40% ethanol within about 15 minutes. In other embodiments, less than about 60% of the hydrocodone that is released in the presence of 0.1 N HCl within about 30 minutes may be released in the presence of 0.1N HCl and 40% ethanol within about 30 minutes. In additional embodiments, less than about 75% of the hydrocodone that is released in the presence of 0.1N HCl within about 2 hours may be released in the presence 0.1N HCl and 40% ethanol within about 2 hours.

(ii) Stability Data for the Pharmaceutical Composition

In one embodiment, p-aminophenol may be present in the pharmaceutical composition as a degradation product of acetaminophen in any amount up to and including, but no more than, about 100 ppm. In other embodiments, p-aminophenol may be present in the pharmaceutical composition as a degradation product of acetaminophen in an amount of about 0.2 ppm to about 6.0 ppm after storage for about 1, 2, or 3 months at a temperature of about 25° C. to about 40° C. and at about 60% to about 75% relative humidity. In still another embodiment, p-aminophenol may be present in the pharmaceutical composition as a degradation product of acetaminophen in an amount of about 0.6 ppm to about 6.0 ppm after storage for about 1, 2, or 3 months at a temperature of about 25° C. to about 40° C. and at about 60% to about 75% relative humidity. In still another embodiments, p-aminophenol may be present in the pharmaceutical composition as a degradation product of acetaminophen in an amount of about 0.2 ppm, 0.3 ppm, 0.4 ppm, 0.5 ppm, 0.6 ppm, 0.7 ppm, 0.8 ppm, 0.9 ppm, 1.0 ppm, 1.1 ppm, 1.2 ppm, 1.3 ppm, 1.4 ppm, 1.5 ppm, 1.6 ppm, 1.7 ppm, 1.8 ppm, 1.9 ppm, 2.0 ppm, 2.1 ppm, 2.2 ppm, 2.3 ppm, 2.4 ppm, 2.5 ppm, 2.6 ppm, 2.7 ppm, 2.8 ppm, 2.9 ppm, 3.0 ppm, 3.1 ppm, 3.2 ppm, 3.3 ppm, 3.4 ppm, 3.5 ppm, 3.6 ppm, 3.7 ppm, 3.8 ppm, 3.9 ppm, 4.0 ppm, 4.1 ppm, 4.2 ppm, 4.3 ppm, 4.4 ppm, 4.5 ppm, 4.6 ppm, 4.7 ppm, 4.8 ppm, 4.9 ppm, 5.0 ppm, 5.1 ppm, 5.2 ppm, 5.3 ppm, 5.4 ppm, 5.5 ppm, 5.6 ppm, 5.7 ppm, 5.8 ppm, 5.9 ppm, and 6.0 ppm after storage for about 1, 2, or 3 months at a temperature of 25° C. to about 40° C. and at about 60% to about 75% relative humidity In one embodiment, oxycodone N-oxide may be present in the pharmaceutical composition as a degradation product of oxycodone in any amount up to and including about 0.5% by weight of the oxycodone. In other embodiments, oxycodone N-oxide may be present in the pharmaceutical composition as a degradation product of oxycodone in an amount of about 0.01% to about 0.5% by weight of the oxycodone after storage for about 1, 2, or 3 months at a constant temperature of about 25° C. to 40° C. and at about 60% to 75% relative humidity. In still another embodiment, oxycodone N-oxide may be present in the pharmaceutical composition as a degradation product of oxycodone in an amount of about 0.05% to about 0.5% by weight of the oxycodone after storage for about 1, 2, or 3 months at a constant temperature of about 25° C. to 40° C. and at about 60% to 75% relative humidity. In additional embodiments, oxycodone N-oxide may be present in the pharmaceutical composition as a degradation product of oxycodone in an amount of about 0.01%, 0.02%, 0.03%, 0.04%, 0.05%, 0.06%, 0.07%, 0.08%, 0.09%, 0.1%, 0.11%, 0.12%, 0.13%, 0.14%, 0.15%, 0.16%, 0.17%, 0.18%, 0.19%, 0.2%, 0.21%, 0.22%, 0.23%, 0.24%, 0.25%, 0.26%, 0.27%, 0.28%, 0.29%, 0.3%, 0.31%, 0.32%, 0.33%, 0.34%, 0.35%, 0.36%, 0.37%, 0.38%, 0.39%, 0.4%, 0.41%, 0.42%, 0.43%, 0.44%, 0.45%, 0.46%, 0.47%, 0.48%, 0.49%, and 0.5% by weight of the oxycodone after storage for about 1, 2, or 3 months at a constant temperature of about 25° C. to about 40° C. and at about 60% to about 75% relative humidity.

In one embodiment, Related Substance A (i.e., C-Nor-morphinan-6-carboxylic acid, 4,5-epoxy-6,14-dihydroxy-3-methoxy-17-methyl-, (5α,6α)-) may be present in the pharmaceutical composition as a degradation product of oxycodone in a maximum amount of about 0.5% by weight of the oxycodone. In other embodiments, Related Substance A may be present in the pharmaceutical composition as a degradation product of oxycodone in an amount of about 0.01% to about 0.5% by weight of the oxycodone after storage for about 1, 2, or 3 months at a temperature of about 25° C. to about 40° C. and at about 60% to about 75% relative humidity. In other embodiments, Related Substance A may be present in the pharmaceutical composition as a degradation product of oxycodone in an amount of about 0.01%, 0.02%, 0.03%, 0.04%, 0.05%, 0.06%, 0.07%, 0.08%, 0.09%, 0.1%, 0.11%, 0.12%, 0.13%, 0.14%, 0.15%, 0.16%, 0.17%, 0.18%, 0.19%, 0.2%, 0.21%, 0.22%, 0.23%, 0.24%, 0.25%, 0.26%, 0.27%, 0.28%, 0.29%, 0.3%, 0.31%, 0.32%, 0.33%, 0.34%, 0.35%, 0.36%, 0.37%, 0.38%, 0.39%, 0.4%, 0.41%, 0.42%, 0.43%, 0.44%, 0.45%, 0.46%, 0.47%, 0.48%, 0.49%, and 0.5% by weight of the oxycodone after storage for about 1, 2, or 3 months at a temperature of about 25° C. to about 40° C. and at about 60% to about 75% relative humidity.

In one embodiment, each unspecified acetaminophen degradation product may be present in the pharmaceutical composition in any amount up to about 0.15% by weight of the acetaminophen. In another embodiment, each unspecified acetaminophen degradation product may be present in the pharmaceutical composition as a degradation product of acetaminophen in an amount of about 0.01% and about 0.15% by weight of the acetaminophen after storage for about 1, 2, or 3 months at a temperature of about 25° C. to about 40° C. and at about 60% to about 75% relative humidity. In other embodiments, each unspecified acetaminophen degradation product may be present in the pharmaceutical composition as a degradation product of acetaminophen in an amount of about 0.01%, 0.02%, 0.03%, 0.04%, 0.05%, 0.06%, 0.07%, 0.08%, 0.09%, 0.1%, 0.11%, 0.12%, 0.13%, 0.14%, and 0.15% by weight of the acetaminophen after storage for about 1, 2, or 3 months at a temperature of about 25° C. to about 40° C. and at about 60% to about 75% relative humidity.

In one embodiment, each unspecified oxycodone HCl degradation product may be present in the pharmaceutical composition in a maximum amount of about 0.2% by weight of the oxycodone. In other embodiments, each unspecified oxycodone HCl degradation product may be present in the pharmaceutical composition in an amount of about 0.01% to about 0.2% by weight of the oxycodone after storage for about 1, 2, or 3 months at a temperature of about 25° C. to about 40° C. and at about 60% to about 75% relative humidity. In further embodiments, each unspecified oxycodone HCl degradation product may be present in the pharmaceutical composition in an amount of about 0.01%, 0.02%, 0.03%, 0.04%, 0.05%, 0.06%, 0.07%, 0.08%, 0.09%, 0.10%, 0.11%, 0.12%, 0.13%, 0.14%, 0.15%, 0.16%, 0.17%, 0.18%, 0.19%, and 0.2% by weight of the oxycodone after storage for about 1, 2, or 3 months at a temperature of about 25° C. to about 40° C. and at about 60% to about 75% relative humidity.

In one embodiment, the total acetaminophen degradation products may be present in the pharmaceutical composition in a maximum amount of about 1.0% by weight of the acetaminophen. In other embodiments, the total acetaminophen degradation products may be present in the pharmaceutical composition in an amount of about 0.05% to about 1.0% by weight of the acetaminophen after storage for about 1, 2, or 3 months at a temperature of about 25° C. to about 40° C. and at about 60% to about 75% relative humidity. In further embodiments, the total acetaminophen degradation products may be present in the pharmaceutical composition in an amount of about 0.05%, 0.1%, 0.15%, 0.2%, 0.25%, 0.3%, 0.35%, 0.4%, 0.45%, 0.5%, 0.55%, 0.6%, 0.65%, 0.7%, 0.75%, 0.8%, 0.85%, 0.9%, 0.95%, and 1.0% by weight of the acetaminophen after storage for about 1, 2, or 3 months at a temperature of about 25° C. to about 40° C. and at about 60% to about 75% relative humidity.

In one embodiment, the total oxycodone degradation products may be present in the pharmaceutical composition in a maximum amount of about 1.0% by weight of the oxycodone. In further embodiments, the total oxycodone degradation products may be present in the pharmaceutical composition in an amount of about 0.05% to about 1.0% by weight of the oxycodone after storage for about 1, 2, or 3 months at a temperature of about 25° C. to about 40° C. and at about 60% to about 75% relative humidity. In yet other embodiments, the total oxycodone degradation products may be present in the pharmaceutical composition in an amount of about 0.05% 0.1%, 0.15%, 0.2%, 0.25%, 0.3%, 0.35%, 0.4%, 0.45%, 0.5%, 0.55%, 0.6%, 0.65%, 0.7%, 0.75%, 0.8%, 0.85%, 0.9%, 0.95%, and 1.0% by weight of the oxycodone after storage for about 1, 2, or 3 months at a temperature of about 25° C. to about 40° C. and at about 60% to about 75% relative humidity.

(iii) In Vivo and Pharmacokinetic Properties of the Exemplary Compositions

The composition comprises at least one immediate release portion for immediate release of either oxycodone or hydrocodone and acetaminophen such that therapeutic plasma concentrations are quickly attained (i.e., within one hour) upon oral administration to a subject. The composition also comprises at least one extended release portion for sustained release of either oxycodone or hydrocodone and acetaminophen over an extended period of time, e.g., about 3 to about 12 hours, or about 4 to about 9 hours, or at least about 6 hours, or at least about 8 hours, to the upper gastrointestinal tract where acetaminophen, and potentially oxycodone and hydrocodone, are best absorbed.

The composition may be orally administered to a subject once in a 24 hour period (q.d. or once-daily), two times in a 24 hour period (b.i.d. or twice-daily), or three times in a 24 hour period (t.i.d. or three times daily). In one embodiment, the composition may be orally administered to the subject twice a day (i.e., every 12 hours). The subject may be a mammal, and preferably the subject is a human.

In another embodiment, the subject may be administered a first or loading dose of the pharmaceutical composition. This first or loading dose may assist the subject in more quickly attaining steady state blood levels of the active drugs. In a further embodiment, the subject may be administered a first or loading dose of the pharmaceutical composition comprising about 22.5 mg of opioid and about 975 mg of an additional active ingredient. In yet another embodiment, the subject may be administered a first or loading dose of the pharmaceutical composition comprising 2 tablets, each tablet comprising about 11.25 mg of opioid and about 462.5 mg of an additional active ingredient. In yet another embodiment, the subject may be administered a first or loading dose of the pharmaceutical composition comprising 3 tablets, each tablet comprising about 7.5 mg of opioid and about 325 mg of an additional active ingredient. In still another embodiment, the subject may be administered a first or loading dose of the pharmaceutical composition comprising 4 tablets, each tablet comprising about 5.625 mg of opioid and about 231.25 mg of an additional active ingredient. In one embodiment, the opioid contained in the tablet is either oxycodone or hydrocodone, and the additional active ingredient is acetaminophen. In yet another embodiment, the subject may be administered a first or loading dose of the pharmaceutical composition comprising 2 capsules, each capsule comprising about 11.25 mg of opioid and about 462.5 mg of an additional active ingredient. In yet another embodiment, the subject may be administered a first or loading dose of the pharmaceutical composition comprising 3 capsules, each capsules comprising about 7.5 mg of opioid and about 325 mg of an additional active ingredient. In still another embodiment, the subject may be administered a first or loading dose of the pharmaceutical composition comprising 4 capsules, each capsules comprising about 5.625 mg of opioid and about 231.25 mg of an additional active ingredient. In one embodiment, the opioid contained in the capsule is either oxycodone or hydrocodone, and the additional active ingredient is acetaminophen.

Upon oral administration to a subject, the composition disclosed herein may maintain a therapeutic blood plasma concentration of oxycodone of at least about 5 ng/mL from about 0.75 hours to about 12 hours after administration of the composition. In another embodiment, the plasma concentration of oxycodone may be maintained at a concentration of at least about 5 ng/mL from about 0.75 hour to about 10 hours after administration of the composition. In still another embodiment, the plasma concentration of oxycodone may be maintained at a concentration of at least about 7.5 ng/mL from about 1 hour to about 12 hours after administration of the composition. In a further embodiment, the plasma concentration of oxycodone may be maintained at a concentration of at least about 10 ng/mL from about 2 hours to about 10 hours after administration of the composition. In yet another embodiment, the plasma concentration of oxycodone may be maintained at a concentration of at least about 10 ng/mL from about 1 hour to about 10 hours after administration of the composition. In still another embodiment, the plasma concentration of oxycodone may be maintained at a concentration of at least about 10 ng/mL from about 0.75 hour to about 10 hours after administration of the composition.

In another embodiment, the composition, when orally administered to a subject, may produce a plasma profile characterized by a mean Cmax (peak plasma concentration) for oxycodone from about 0.9 ng/mL/mg to about 1.6 ng/mL/mg. In another embodiment, the mean Cmax for oxycodone may range from about 1.0 ng/mL/mg to about 1.5 ng/mL/mg. In an additional embodiment, the mean Cmax for oxycodone may be 0.9, 1.0, 1.1, 1.2, 1.3, 1.4, 1.5, or 1.6 ng/mL/mg. Moreover, the mean Cmax for oxycodone at steady state may range from about 1.5 ng/mL/mg to about 2.0 ng/mL/mg, from about 1.6 ng/mL/mg to about 1.95 ng/mL/mg, or from about 1.7 ng/mL/mg to about 1.85 ng/mL/mg.

In a further embodiment, the pharmaceutical composition, when orally administered to a subject, surprisingly may produce a plasma profile characterized by a biphasic absorption of oxycodone. Deconvolution of the pharmaceutical composition and the target plasma profiles can be done in WinNonLin (version 5.2, Pharsight Corp., Mountain View, Calif.). The results of such a deconvolution analysis for oxycodone is depicted in FIG. 23. The biphasic absorption of oxycodone may be characterized by an initial rapid absorption resulting in a first peak in plasma concentrations between about 1 hour and 2 hours, which contributes to the early onset of action, and a second peak in plasma concentrations between about 3 hours and 7 hours as a result of slower absorption taking place from the at least one extended release portion after administration of the composition, which contributes to the duration or maintenance of analgesia. In some instances, the second peak may correspond to the overall Cmax of the composition. The biphasic absorption of oxycodone may be characterized by a plasma concentration-time profile for oxycodone in which the slope of a line drawn between 0 hour and 2 hour is greater than the slope of a line drawn between about 2 hours and 5 hours. See FIG. 23.

This biphasic increase in oxycodone levels resulting from the composition has several benefits. For example, providing rapid but not too high concentrations of oxycodone for quick onset of analgesia followed by maintenance of oxycodone levels over an extended time period could prevent a human subject from developing liking or dependence (abuse) for oxycodone. Further fluctuations in the oxycodone plasma levels could also prevent development of tolerance at the active site. Thus, the biphasic increase in oxycodone levels helps to prevent this acute tolerance.

In an additional embodiment, the pharmaceutical composition, when orally administered to a subject, may produce a plasma profile characterized by a mean AUC for oxycodone from about 9.0 ng·hr/mL/mg to about 18.5 ng·hr/mL/mg. In a further embodiment, the mean AUC for oxycodone may be from about 12.0 ng·hr/mL/mg to about 16.0 ng·hr/mL/mg. In another embodiment, the mean AUC for oxycodone may be about 9.0, 9.5, 10.0, 10.5, 11.0, 11.5, 12.0, 12.5, 13.0, 13.5, 14.0, 14.5, 15.0, 15.5, or 16.0 ng·hr/mL/mg. Additionally, the mean AUC for oxycodone at steady state may range from about 11.0 ng·hr/mL/mg to about 17.0 ng·hr/mL/mg, from about 12.0 ng·hr/mL/mg to about 16.0 ng·hr/mL/mg, or from about 13.0 ng·hr/mL/mg to about 15.0 ng·hr/mL/mg.

In a further embodiment, the pharmaceutical composition, when orally administered to a subject, may produce a plasma profile characterized by a median Tmax (time to peak plasma concentration) for oxycodone from about 2.0 hours to about 7.0 hours. In an alternate embodiment, the median Tmax for oxycodone may be from about 3.0 hours to about 6.0 hours. In another embodiment, the median Tmax for oxycodone may be about 2.0, 2.5, 3.0, 3.5, 4.0, 4.5, 5.0, 5.5 or 6.0 hours. Moreover, the median Tmax for oxycodone at steady state may range from about 1.5 hours to about 3.5 hours, or from about 2 hours to about 3 hours.

In still another embodiment, the pharmaceutical composition, when orally administered to a subject, may produce a plasma profile characterized by a median tlag for oxycodone from about 0 hours to about 0.5 hours. In an alternate embodiment, the median tlag for oxycodone may be from about 0 hours to about 0.25 hours.

Rates of absorption are often assessed by comparing standard pharmacokinetic parameters such as Tmax and Cmax. The extent of absorption is assessed by the AUC. A short $T_{max}$ has been used to indicate rapid absorption. The U.S. FDA, *Guidance for Industry: Bioavailability and Bioequivalence Studies for Orally Administered Drug Products—General Considerations* (March 2003) and related publications (Chen et al, Clin. Pharmacokinet. 40(8):565-72, 2001) also recommends the use of partial AUC for some modified-release drugs ("MR drugs"), such as the pharmaceutical compositions disclosed herein. A partial AUC calculation may be used to measure early exposure to a drug, which may signify an initial onset of pain relief and/or to measure prolonged exposure of a drug in achieving sustained relief. Partial AUC calculations can also demonstrate whether two MR drugs are truly bioequivalent by comparing, for example, an early partial AUC, which will be associated with a drug's response onset, and a late partial AUC, which will be associated with a drug's sustained response. The parameters for compositions vary greatly between subjects. The parameters also vary depending on aspects of the study protocol such as the sampling scheduling, subject posture and general subject health. Values quoted in this specification are given as mean±standard deviation unless otherwise noted.

For partial AUC calculations, the standard linear trapezoidal summation over each time interval is used. The partial AUCs are calculated from the mean pharmacokinetic profile. For time 0 to 1 hour the partial AUC is $AUC_{(0-1hr)}$; for time 0 to 2 hours the partial AUC is $AUC_{(0-2hr)}$; for time 0-4 hours the partial AUC is $AUC_{(0-4hr)}$; for time 0 to 6 hour the partial AUC is $AUC_{(0-6hr)}$; for time 0 to 8 hours the partial AUC is $AUC_{(0-8hr)}$; and for time 0 to the last measurable time point ("x") the partial AUC is $AUC_{(0-(x)hr)}$ where each partial AUC is calculated according to standard pharmaceutical industry pharmacokinetic calculation methodologies as given by:

$AUC_{(0-1hr)}$—Area under the drug concentration-time curve calculated using linear trapezoidal summation from time zero to time 1 hour.

$AUC_{(0-2hr)}$—Area under the drug concentration-time curve calculated using linear trapezoidal summation from time zero to time 2 hours.

$AUC_{(0-4hr)}$—Area under the drug concentration-time curve calculated using linear trapezoidal summation from time zero to time 4 hours.

$AUC_{(0-6hr)}$—Area under the drug concentration-time curve calculated using linear trapezoidal summation from time zero to time 6 hour.

$AUC_{(0-8hr)}$—Area under the drug concentration-time curve calculated using linear trapezoidal summation from time zero to time 8 hours.

$AUC_{(0-(t)hr)}$—Area under the drug concentration-time curve calculated using linear trapezoidal summation from time zero to the last measurable time point.

$AUC_{(0-(Tmax\ of\ IR\ product+2SD))}$—Area under the drug concentration-time curve calculated using linear trapezoidal summation from time zero to the time of the mean peak (Tmax) for the immediate release version of the drug plus two standard deviations ("2SD") for the immediate release drug. The FDA has identified this calculation in association with an early onset of response for modified-release dosage forms. (See supra March 2003 Guidance; Draft Guidance on Dexmethylphenidate Hydrochloride (March 2012); Draft Guidance on Methylphenidate Hydrocholoride (November 2011)).

$AUC_{((Tmax\ of\ IR\ product+2SD)-t)}$—Area under the drug concentration-time curve calculated using linear trapezoidal summation from the time of the mean peak (Tmax) for the immediate release version of the drug plus two standard deviations ("2SD") for the immediate release drug to the last measurable time point. The FDA has identified this parameter in association with sustaining the response for modified-release dosage forms. (See March 2003 Guidance supra; Draft Guidance on Dexmethylphenidate Hydrochloride (March 2012); Draft Guidance on Methylphenidate Hydrocholoride (November 2011)).

$AUC_{(x-(y)hr)}$—Area under the drug concentration-time curve calculated using linear trapezoidal summation from time "x" (e.g., any measurable time point, such as 8 hours) to time "y" (e.g., any other measurable time point later than "x", such as 12 hours).

$AUC_{(0-\infty)}$—Area under the drug concentration-time curve calculated using linear trapezoidal summation from time 0 to infinity.

Further, partial AUC may be calculated using trapezoidal summation from time Tmax to time t (the last measured time point of plasma concentration profile).

In one embodiment, the pharmaceutical composition, when orally administered to a subject, may produce a plasma profile characterized by an $AUC_{0-1hr}$ for oxycodone from about 0.10 ng·hr/mL/mg to about 0.45 ng·hr/mL/mg, from about 0.15 ng·hr/mL/mg to about 0.25 ng·hr/mL/mg, or from about 0.25 ng·hr/mL/mg to about 0.35 ng·hr/mL/mg. In another embodiment, the $AUC_{0-1hr}$ for oxycodone may be about 0.10, 0.15, 0.20, 0.25, 0.30, 0.35, 0.40, or 0.45 ng·hr/mL/mg.

In an additional embodiment, the pharmaceutical composition, when orally administered to a subject, may produce a plasma profile characterized by an $AUC_{0-2hr}$ for oxycodone from about 0.65 ng·hr/mL/mg to about 1.35 ng·hr/mL/mg, from about 0.80 ng·hr/mL/mg to about 1.0 ng·hr/mL/mg, or from about 1.0 ng·hr/mL/mg to about 1.2 ng·hr/mL/mg. In another embodiment, the $AUC_{0-2hr}$ for oxycodone may be about 0.65, 0.70, 0.75, 0.80, 0.85, 0.90, 0.95, 1.0, 1.05, 1.10, 1.15, 1.20, 1.25, 1.30 or 1.35 ng·hr/mL/mg.

In a further embodiment, the pharmaceutical composition, when orally administered to a subject, may produce a plasma profile characterized by an $AUC_{0-4hr}$ for oxycodone from about 2.0 ng·hr/mL/mg to about 4.0 ng·hr/mL/mg, from about 2.5 ng·hr/mL/mg to about 3.0 ng·hr/mL/mg, or from about 3.0 ng·hr/mL/mg to about 3.5 ng·hr/mL/mg. In another embodiment, the $AUC_{0-4hr}$ for oxycodone may be about 2.0, 2.5, 3.0, 3.5, or 4.0 ng·hr/mL/mg.

In yet another embodiment, the pharmaceutical composition, when orally administered to a subject, may produce a plasma profile characterized by an $AUC_{Tmax-t}$ for oxycodone from about 5.0 ng·hr/mL/mg to about 16.0 ng·hr/mL/mg, from about 8.0 ng·hr/mL/mg to about 10.5 ng·hr/mL/mg, or from about 10.5 ng·hr/mL/mg to about 14.0 ng·hr/mL/mg. In another embodiment, the $AUC_{Tmax-t}$ for oxycodone may be about 5.0, 6.0, 7.0, 8.0, 9.0, 10.0, 11.0, 12.0, 12.5, 13.0, 13.5, 14.0, 14.5, 15.0 or 16.0 ng·hr/mL/mg.

In still another embodiment, the pharmaceutical composition, when orally administered to a subject, may produce a plasma profile characterized by an $AUC_{(0-(Tmax\ of\ IR\ product+2SD))}$ for oxycodone after a single dose from about 1.0 ng·hr/mL/mg to about 3.0 ng·hr/mL/mg, from about 1.50 ng·hr/mL/mg to about 2.5 ng·hr/mL/mg, or from about 1.75 ng·hr/mL/mg to about 2.25 ng·hr/mL/mg. In another embodiment, the $AUC_{(0-(Tmax\ of\ IR\ product+2SD))}$ for oxycodone may be about 1.0, 1.25, 1.3, 1.35, 1.4, 1.45, 1.5, 1.55, 1.6, 1.65, 1.7, 1.75, 1.8, 1.85, 1.9, 1.95, 2.0, 2.05, 2.1, 2.15, 2.2, 2.25, 2.3, 2.35, 2.4, 2.45, 2.5, 2.55, 2.6, 2.65, 2.7, or 2.75 ng·hr/mL/mg.

In one embodiment, the immediate release product referenced for the Partial AUC calculations is Percocet in the fasted state and the following calculation was used to determine $AUC_{(0-(Tmax\ of\ IR\ product+2SD))}$:

oxycodone mean±SD=1.0h±0.89h; $Tmax+2SD=2.8$ hours

In such embodiment, the pharmaceutical composition, when orally administered to a subject, may produce a plasma profile characterized by an $AUC_{(0-2.8)}$ for oxycodone after a single dose from about 1.0 ng·hr/mL/mg to about 3.0 ng·hr/ mL/mg, from about 1.50 ng·hr/mL/mg to about 2.5 ng·hr/mL/mg, or from about 1.75 ng·hr/mL/mg to about 2.25 ng·hr/mL/mg. In another embodiment, the $AUC_{(0-2.8)}$ for oxycodone may be about 1.25, 1.3, 1.35, 1.4, 1.45, 1.5, 1.55, 1.6, 1.65, 1.7, 1.75, 1.8, 1.85, 1.9, 1.95, 2.0, 2.05, 2.1, 2.15, 2.2, 2.25, 2.3, 2.35, 2.4, 2.45, 2.5, 2.55, 2.6, 2.65, 2.7, or 2.75 ng·hr/mL/mg.

In yet another embodiment, the pharmaceutical composition, when orally administered to a subject, may produce a plasma profile characterized by an $AUC_{(2.8-48)}$ for oxycodone after a single dose from about 7.5 ng·hr/mL/mg to about 15.0 ng·hr/mL/mg, from about 8.45 ng·hr/mL/mg to about 13.7 ng·hr/mL/mg, or from about 9.5 ng·hr/mL/mg to about 11.5 ng·hr/mL/mg. In another embodiment, the $AUC_{(2.8-48)}$ for oxycodone may be about 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, or 12.5 ng·hr/mL/mg.

In one embodiment, the immediate release product referenced for the Partial AUC calculations is Percocet in the fed state and the following calculation was used to determine $AUC_{(0-(Tmax\ of\ IR\ product+2SD))}$:

oxycodone mean±SD=1.9h±1.2h; $T$max+2SD=4.3 hours

In such embodiment, the pharmaceutical composition, when orally administered to a subject, may produce a plasma profile characterized by an $AUC_{(0-4.3)}$ for oxycodone after a single dose from about 1.5 ng·hr/mL/mg to about 5.5 ng·hr/mL/mg, from about 2.0 ng·hr/mL/mg to about 5.0 ng·hr/mL/mg, from about 2.5 ng·hr/mL/mg to about 4.5 ng·hr/mL/mg, or from about 3.0 ng·hr/mL/mg to about 4.0 ng·hr/mL/mg. In another embodiment, the $AUC_{(0-4.3)}$ for oxycodone may be about 1.5, 1.55, 1.6, 1.65, 1.7, 1.75, 1.8, 1.85, 1.9, 1.95, 2.0, 2.05, 2.1, 2.15, 2.2, 2.25, 2.3, 2.35, 2.4, 2.45, 2.5, 2.55, 2.6, 2.65, 2.7, 2.75, 2.8, 2.85, 2.9, 2.95, 3.0, 3.05, 3.1, 3.15, 3.2, 3.25, 3.3, 3.35, 3.4, 3.45, 3.5, 3.55, 3.6, 3.65, 3.7, 3.75, 3.8, 3.85, 3.9, 3.95, 4.0, 4.05, 4.1, 4.15, 4.2, 4.25, 4.3, 4.35, 4.4, 4.45, 4.5, 4.55, 4.6, 4.65, 4.7, 4.75, 4.8, 4.85, 4.9, 4.95, 5.0, 5.05, 5.1, 5.15, 5.2, 5.25, 5.3, 5.35, 5.4, 5.45, or 5.5 ng·hr/mL/mg.

In yet another embodiment, the pharmaceutical composition, when orally administered to a subject, may produce a plasma profile characterized by an $AUC_{(4.3-48)}$ for oxycodone after a single dose from about 5.0 ng·hr/mL/mg to about 15.0 ng·hr/mL/mg, from about 7.5 ng·hr/mL/mg to about 13.5 ng·hr/mL/mg, from about 9.0 ng·hr/mL/mg to about 12.0 ng·hr/mL/mg, or from about 9.5 ng·hr/mL/mg to about 11.5 ng·hr/mL/mg. In another embodiment, the $AUC_{(4.3-48)}$ for oxycodone may be about 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, 13.0, 13.1, 13.2, 13.3, 13.4, 13.5, 13.6, 13.7, 13.8, 13.9, 14.0, 14.1, 14.2, 14.3, 14.4, 14.5, 14.6, 14.7, 14.8, 14.9, or 15.0 ng·hr/mL/mg.

In one embodiment, the pharmaceutical composition, when orally administered to a subject in a fasted state, may produce a plasma profile characterized by an $AUC_{8-12hr}$ for oxycodone from about 3% to about 33% of the $AUC_{0-t}$, from about 10% to about 27% of the $AUC_{0-t}$, or from about 15% to about 22% of the $AUC_{0-t}$. In another embodiment, the pharmaceutical composition, when orally administered to a subject in a fed state, may produce a plasma profile characterized by an $AUC_{8-12hr}$ for oxycodone from about 5% to about 35% of the $AUC_{0-t}$, from about 12% to about 30% of the $AUC_{0-t}$, or from about 15% to about 25% of the $AUC_{0-t}$.

In an alternate embodiment, the pharmaceutical composition, when orally administered to a subject, may provide a mean half-life of oxycodone that ranges from about 3.5 hours to about 5.5 hours, or more preferably from about 4 hours to about 5 hours. In various embodiments, the mean half-life of oxycodone may be about 3.8, 4.0, 4.2, 4.4, 4.6, 4.8, 5.0, or 5.2 hours.

In yet another embodiment, the pharmaceutical composition, when orally administered to a subject, may produce a plasma profile characterized by an abuse quotient for oxycodone from about 3 to about 5. In other embodiments, the abuse quotient for oxycodone may be about 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0.

Further, upon oral administration to a subject, the composition disclosed herein may maintain a therapeutic blood plasma concentration of hydrocodone of at least about 5 ng/mL from about 0.75 hours to about 20 hours after administration of the composition. In another embodiment, the plasma concentration of hydrocodone may be maintained at a concentration of at least about 7.5 ng/mL from about 1 hour to about 12 hours after administration of the composition. In a further embodiment, the plasma concentration of hydrocodone may be maintained at a concentration of at least about 10 ng/mL from about 2 hour to about 10 hours after administration of the composition. In yet another embodiment, the plasma concentration of hydrocodone may be maintained at a concentration of at least about 10 ng/mL from about 1 hour to about 10 hours after administration of the composition. In still another embodiment, the plasma concentration of hydrocodone may be maintained at a concentration of at least about 10 ng/mL from about 0.75 hour to about 10 hours after administration of the composition.

In another embodiment, the composition, when orally administered to a subject, may produce a plasma profile characterized by a mean Cmax (peak plasma concentration) for hydrocodone from about 0.9 ng/mL/mg to about 2.0 ng/mL/mg. In another embodiment, the mean Cmax for hydrocodone may range from about 1.0 ng/mL/mg to about 1.6 ng/mL/mg. In an additional embodiment, the mean Cmax for hydrocodone may be 0.9, 1.0, 1.1, 1.2, 1.3, 1.4, 1.5, 1.6, 1.7, 1.8, 1.9, or 2.0 ng/mL/mg. Moreover, the mean Cmax for hydrocodone at steady state may range from about 1.3 ng/mL/mg to about 2.0 ng/mL/mg, from about 1.5 ng/mL/mg to about 1.95 ng/mL/mg, or from about 1.6 ng/mL/mg to about 1.85 ng/mL/mg.

In a further embodiment, the pharmaceutical composition, when orally administered to a subject, surprisingly may produce a plasma profile characterized by a biphasic absorption of hydrocodone. Deconvolution of the pharmaceutical composition and the target plasma profiles can be done in WinNonLin (version 5.2, Pharsight Corp., Mountain View, Calif.). The biphasic absorption of hydrocodone may be characterized by an initial rapid absorption resulting in a first peak in plasma concentrations between about 1 hour and 2 hours, which contributes to the early onset of action, and a second peak in plasma concentrations between about 3 hours and 7 hours as a result of slower absorption taking place from the at least one extended release portion after administration of the composition, which contributes to the duration or maintenance of analgesia. In some instances, the second peak may correspond to the overall Cmax of the composition. The biphasic absorption of hydrocodone may be characterized by a plasma concentration-time profile for hydrocodone in which the slope of a line drawn between 0 hour and 2 hour is greater than the slope of a line drawn between about 2 hours and 5 hours.

This biphasic increase in hydrocodone levels resulting from the composition has several benefits. For example, providing rapid but not too high concentrations of hydrocodone for quick onset of analgesia followed by maintenance of hydrocodone levels over an extended time period could prevent a human subject from developing liking or dependence (abuse) for hydrocodone. Further fluctuations in the hydrocodone plasma levels could also prevent development of tolerance at the active site. Thus, the biphasic increase in hydrocodone levels helps to prevent this acute tolerance.

In an additional embodiment, the pharmaceutical composition, when orally administered to a subject, may produce a plasma profile characterized by a mean AUC for hydrocodone from about 9.0 ng·hr/mL/mg to about 24.0 ng·hr/mL/mg. In a further embodiment, the mean AUC for hydrocodone may be from about 10.0 ng·hr/mL/mg to about 22.0 ng·hr/mL/mg. In another embodiment, the mean AUC for hydrocodone may be about 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 23.5, or 24.0 ng·hr/mL/mg. Additionally, the mean AUC for hydrocodone at steady state may range from about 10.0 ng·hr/mL/mg to about 20.0 ng·hr/mL/mg, from about 12.0 ng·hr/mL/mg to about 19.0 ng·hr/mL/mg, or from about 13.0 ng·hr/mL/mg to about 18.0 ng·hr/mL/mg.

In a further embodiment, the pharmaceutical composition, when orally administered to a subject, may produce a plasma profile characterized by a median Tmax (time to peak plasma concentration) for hydrocodone from about 2.0 hours to about 8.0 hours. In an alternate embodiment, the median Tmax for hydrocodone may be from about 3.0 hours to about 6.0 hours. In another embodiment, the median Tmax for hydrocodone may be about 2.0, 2.5, 3.0, 3.5, 4.0, 4.5, 5.0, 5.5, 6.0, 6.5, 7.0, 7.5, or 8.0 hours. Moreover, the median Tmax for hydrocodone at steady state may range from about 1.5 hours to about 5.0 hours, or from about 2 hours to about 4 hours.

In still another embodiment, the pharmaceutical composition, when orally administered to a subject, may produce a plasma profile characterized by a median tlag for hydrocodone from about 0 hours to about 0.5 hours. In an alternate embodiment, the median tlag for hydrocodone may be from about 0 hours to about 0.33 hours.

In one embodiment, the pharmaceutical composition, when orally administered to a subject, may produce a plasma profile characterized by an $AUC_{(0-(Tmax\ of\ IR\ product+2SD))}$ for hydrocodone after a single dose from about 1.0 ng·hr/mL/mg to about 5.0 ng·hr/mL/mg, from about 1.50 ng·hr/mL/mg to about 4.25 ng·hr/mL/mg, or from about 2.0 ng·hr/mL/mg to about 3.0 ng·hr/mL/mg. In another embodiment, the $AUC_{0-(Tmax+2SD\ of\ IR\ product)}$ for hydrocodone may be about 1.0, 1.25, 1.45, 1.5, 1.55, 1.6, 1.65, 1.7, 1.75, 1.8, 1.85, 1.9, 1.95, 2.0, 2.05, 2.1, 2.15, 2.2, 2.25, 2.3, 2.35, 2.4, 2.45, 2.5, 2.55, 2.6, 2.65, 2.7, 2.75, 2.8, 2.85, 2.9, 2.95, 3.0, 3.05, 3.1, 3.15, 3.2, 3.25, 3.3, 3.35, 3.4, 3.45, or 3.5 ng·hr/mL/mg.

In one embodiment, the pharmaceutical composition, when orally administered to a subject, may produce a plasma profile characterized by an $AUC_{(0-3hr)}$ for hydrocodone after a single dose from about 1.0 ng·hr/mL/mg to about 5.0 ng·hr/mL/mg, from about 1.50 ng·hr/mL/mg to about 4.25 ng·hr/mL/mg, or from about 2.0 ng·hr/mL/mg to about 3.0 ng·hr/mL/mg. In another embodiment, the $AUC_{(0-3hr)}$ for hydrocodone may be about 1.0, 1.25, 1.45, 1.5, 1.55, 1.6, 1.65, 1.7, 1.75, 1.8, 1.85, 1.9, 1.95, 2.0, 2.05, 2.1, 2.15, 2.2, 2.25, 2.3, 2.35, 2.4, 2.45, 2.5, 2.55, 2.6, 2.65, 2.7, 2.75, 2.8, 2.85, 2.9, 2.95, 3.0, 3.05, 3.1, 3.15, 3.2, 3.25, 3.3, 3.35, 3.4, 3.45, or 3.5 ng·hr/mL/mg.

In another embodiment, the pharmaceutical composition, when orally administered to a subject, may produce a plasma profile characterized by an $AUC_{(0-2.44hr)}$ for hydrocodone after a single dose from about 0.5 ng·hr/mL/mg to about 5.0 ng·hr/mL/mg, from about 1.0 ng·hr/mL/mg to about 4.25 ng·hr/mL/mg, or from about 1.5 ng·hr/mL/mg to about 3.0 ng·hr/mL/mg. In another embodiment, the $AUC_{(0-2.44hr)}$ for hydrocodone may be about 0.5, 0.55, 0.6, 0.65, 0.7, 0.75, 0.8, 0.85, 0.9, 0.95, 1.0, 1.05, 1.1, 1.15, 1.2, 1.25, 1.3, 1.35, 1.4, 1.45, 1.5, 1.55, 1.6, 1.65, 1.7, 1.75, 1.8, 1.85, 1.9, 1.95, 2.0, 2.05, 2.1, 2.15, 2.2, 2.25, 2.3, 2.35, 2.4, 2.45, 2.5, 2.55, 2.6, 2.65, 2.7, 2.75, 2.8, 2.85, 2.9, 2.95, 3.0, 3.05, 3.1, 3.15, 3.2, 3.25, 3.3, 3.35, 3.4, 3.45, or 3.5 ng·hr/mL/mg.

In one embodiment, the pharmaceutical composition, when orally administered to a subject, may produce a plasma profile characterized by an $AUC_{0-12hr}$ for hydrocodone from about 5 ng·hr/mL/mg to about 25 ng·hr/mL/mg, from about 7.5 ng·hr/mL/mg to about 15.5 ng·hr/mL/mg, or from about 8.5 ng·hr/mL/mg to about 12.5 ng·hr/mL/mg. In other embodiments, the pharmaceutical composition, when orally administered to a subject, may produce a plasma profile characterized by an $AUC_{0-12hr}$ for hydrocodone from about 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, 13.0, 13.1, 13.2, 13.3, 13.4, 13.5, 13.6, 13.7, 13.8, 13.9, 14.0, 14.1, 14.2, 14.3, 14.4, 14.5, 14.6, 14.7, 14.8, 14.9, 15.0, 15.1, 15.2, 15.3, 15.4, 15.5, 15.6, 15.7, 15.8, 15.9, 16.0, 16.1, 16.2, 16.3, 16.4, 16.5, 16.6, 16.7, 16.8, 16.9, 17.0, 17.1, 17.2, 17.3, 17.4, 17.5, 17.6, 17.7, 17.8, 17.9, 18.0, 18.1, 18.2, 18.3, 18.4, 18.5, 18.6, 18.7, 18.8, 18.9, 19.0, 19.1, 19.2, 19.3, 19.4, 19.5, 19.6, 19.7, 19.8, 19.9, or 20.0 ng·hr/mL/mg.

In one embodiment, the pharmaceutical composition, when orally administered to a subject, may produce a plasma profile characterized by an $AUC_{1-12hr}$ for hydrocodone from about 3 ng·hr/mL/mg to about 20 ng·hr/mL/mg, from about 7.5 ng·hr/mL/mg to about 15.0 ng·hr/mL/mg, or from about 8 ng·hr/mL/mg to about 12.5 ng·hr/mL/mg. In other embodiments, the pharmaceutical composition, when orally administered to a subject, may produce a plasma profile characterized by an $AUC_{1-12hr}$ for hydrocodone from about 3.0, 4.0, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, 13.0, 13.1, 13.2, 13.3, 13.4, 13.5, 13.6, 13.7, 13.8, 13.9, 14.0, 14.1, 14.2, 14.3, 14.4, 14.5, 14.6, 14.7, 14.8, 14.9, 15.0, 15.1, 15.2, 15.3, 15.4, 15.5, 15.6, 15.7, 15.8, 15.9, 16.0, 16.1, 16.2, 16.3, 16.4, 16.5, 16.6, 16.7, 16.8, 16.9, 17.0, 17.1, 17.2, 17.3, 17.4, 17.5, 17.6, 17.7, 17.8, 17.9, 18.0, 18.1, 18.2, 18.3, 18.4, 18.5, 18.6, 18.7, 18.8, 18.9, 19.0, 19.1, 19.2, 19.3, 19.4, 19.5, 19.6, 19.7, 19.8, 19.9, or 20.0 ng·hr/mL/mg.

In one embodiment, the pharmaceutical composition, when orally administered to a subject, may produce a plasma profile characterized by an $AUC_{12-36hr}$ for hydrocodone from about 2 ng·hr/mL/mg to about 10 ng·hr/mL/mg, from about 4 ng·hr/mL/mg to about 8 ng·hr/mL/mg, and from about 6 ng·hr/mL/mg to about 7 ng·hr/mL/mg. In other embodiments, the pharmaceutical composition, when orally administered to a subject, may produce a plasma profile characterized by an $AUC_{12-36hr}$ for hydrocodone from about 2.0, 2.5, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, or 12.0 ng·hr/mL/mg.

In one embodiment, the pharmaceutical composition, when orally administered to a subject, may produce a plasma profile characterized by an $AUC_{8-12hr}$ for hydrocodone from about 1 ng·hr/mL/mg to about 6 ng·hr/mL/mg, from about 2 ng·hr/mL/mg to about 5 ng·hr/mL/mg, or from about 3 ng·hr/mL/mg to about 4 ng·hr/mL/mg. In other embodiments, the pharmaceutical composition, when orally administered to a subject, may produce a plasma profile characterized by an $AUC_{8-12hr}$ for hydrocodone from about 1.25, 1.3, 1.35, 1.4, 1.45, 1.5, 1.55, 1.6, 1.65, 1.7, 1.75, 1.8, 1.85, 1.9, 1.95, 2.0, 2.05, 2.1, 2.15, 2.2, 2.25, 2.3, 2.35, 2.4, 2.45, 2.5, 2.55, 2.6, 2.65, 2.7, 2.75, 2.8, 2.85, 2.9, 2.95, 3.0, 3.05, 3.1, 3.15, 3.2, 3.25, 3.3, 3.35, 3.4, 3.45, 3.5, 3.55, 3.6, 3.65, 3.7, 3.75, 3.8, 3.85, 3.9, 3.95, 4.0, 4.05, 4.1, 4.15, 4.2, 4.25, 4.3, 4.35, 4.4, 4.45, 4.5, 4.55, 4.6, 4.65, 4.7, 4.75, 4.8, 4.85, 4.9, 4.95, 5.0, 5.05, 5.1, 5.15, 5.2, 5.25, 5.3, 5.35, 5.4, 5.45, 5.5, 5.55, 5.6, 5.65, 5.7, or 5.75 ng·hr/mL/mg.

In one embodiment, the pharmaceutical composition, when orally administered to a subject, may produce a plasma profile characterized by an $AUC_{Tmax+2SD-36hr}$ for hydrocodone from about 5 ng·hr/mL/mg to about 25 ng·hr/mL/mg, from about 10 ng·hr/mL/mg to about 20 ng·hr/mL/mg, or from about 13 ng·hr/mL/mg to about 17 ng·hr/mL/mg. In other embodiments, the pharmaceutical composition, when orally administered to a subject, may produce a plasma profile characterized by an $AUC_{3-36hr}$ for hydrocodone from about 5.0, 5.25, 5.50, 5.75, 6.0, 6.25, 6.5, 6.75, 7.0, 7.25, 7.5, 7.75, 8.0, 8.25, 8.5, 8.75, 9.0, 9.25, 9.5, 9.75, 10.0, 10.25, 10.5, 10.75, 11.0, 11.25, 11.5, 11.75, 12.0, 12.25, 12.5, 12.75, 13.0, 13.25, 13.5, 13.75, 14.0, 14.25, 14.5, 14.75, 15.0, 15.25, 15.5, 15.75, 16.0, 16.25, 16.50, 16.75, 17.0, 17.25, 17.5, 17.75, 18.0, 18.25, 18.5, 18.75, 19.0, 19.25, 19.5, 19.75, 20.0, 20.25, 20.5, 20.75, 21.0, 21.25, 21.5, 21.75, 22.0, 22.25, 22.5, 22.75, 23.0, 23.25, 23.5, 23.75, 24.0, 24.25, 24.5, 24.75, or 25.0 ng·hr/mL/mg.

In one embodiment, the pharmaceutical composition, when orally administered to a subject, may produce a plasma profile characterized by an $AUC_{2.44-36hr}$ for hydrocodone from about 5 ng·hr/mL/mg to about 25 ng·hr/mL/mg, from about 10 ng·hr/mL/mg to about 20 ng·hr/mL/mg, or from about 13 ng·hr/mL/mg to about 17 ng·hr/mL/mg. In other embodiments, the pharmaceutical composition, when orally administered to a subject, may produce a plasma profile characterized by an $AUC_{2.44-36hr}$ for hydrocodone from about 5.0, 5.25, 5.50, 5.75, 6.0, 6.25, 6.5, 6.75, 7.0, 7.25, 7.5, 7.75, 8.0, 8.25, 8.5, 8.75, 9.0, 9.25, 9.5, 9.75, 10.0, 10.25, 10.5, 10.75, 11.0, 11.25, 11.5, 11.75, 12.0, 12.25, 12.5, 12.75, 13.0, 13.25, 13.5, 13.75, 14.0, 14.25, 14.5, 14.75, 15.0, 15.25, 15.5, 15.75, 16.0, 16.25, 16.50, 16.75, 17.0, 17.25, 17.5, 17.75, 18.0, 18.25, 18.5, 18.75, 19.0, 19.25, 19.5, 19.75, 20.0, 20.25, 20.5, 20.75, 21.0, 21.25, 21.5, 21.75, 22.0, 22.25, 22.5, 22.75, 23.0, 23.25, 23.5, 23.75, 24.0, 24.25, 24.5, 24.75, or 25.0 ng·hr/mL/mg.

In one embodiment, the pharmaceutical composition, when orally administered to a subject, may produce a plasma profile characterized by an $AUC_{0-12hr}$ for hydrocodone from about 50% to about 90% of the $AUC_{0-t}$, from about 55% to about 80% of the $AUC_{0-t}$, or from about 60% to about 70% of the $AUC_{0-t}$. In other embodiments, the pharmaceutical composition, when orally administered to a subject, may produce a plasma profile characterized by an $AUC_{0-12hr}$ for hydrocodone that is about 50%, about 53%, about 55%, about 58%, about 60%, about 63%, about 65%, about 68%, about 70%, about 73%, about 75%, about 78%, about 80%, about 83%, about 85%, about 88%, or about 90% of the $AUC_{0-t}$.

In one embodiment, the pharmaceutical composition, when orally administered to a subject, may produce a plasma profile characterized by an $AUC_{1-12hr}$ for hydrocodone from about 40% to about 90% of the $AUC_{0-t}$, from about 55% to about 80% of the $AUC_{0-t}$, or from about 60% to about 70% of the $AUC_{0-t}$. In other embodiments, the pharmaceutical composition, when orally administered to a subject, may produce a plasma profile characterized by an $AUC_{1-12hr}$ for hydrocodone of about 40%, about 43%, about 45%, about 48%, about 50%, about 53%, about 55%, about 58%, about 60%, about 63%, about 65%, about 68%, about 70%, about 73%, about 75%, about 78%, about 80%, about 83%, about 85%, about 88%, or about 90% of the $AUC_{0-t}$.

In one embodiment, the pharmaceutical composition, when orally administered to a subject, may produce a plasma profile characterized by an $AUC_{12-36hr}$ for hydrocodone from about 20% to about 50% of the $AUC_{0-t}$, from about 25% to about 45% of the $AUC_{0-t}$, or from about 30% to about 40% of the $AUC_{0-t}$. In other embodiments, the pharmaceutical composition, when orally administered to a subject, may produce a plasma profile characterized by an $AUC_{1-12hr}$ for hydrocodone of about 20%, about 23%, about 25%, about 28%, about 30%, about 33%, about 35%, about 38%, about 40%, about 43%, about 45%, about 48%, about 50%, or about 53% of the $AUC_{0-t}$.

In one embodiment, the pharmaceutical composition, when orally administered to a subject, may produce a plasma profile characterized by an $AUC_{8-12hr}$ for hydrocodone from about 5% to about 30% of the $AUC_{0-t}$, from about 10% to about 25% of the $AUC_{0-t}$, or from about 15% to about 20% of the $AUC_{0-t}$. In other embodiments, the pharmaceutical composition, when orally administered to a subject, may produce a plasma profile characterized by an $AUC_{1-12hr}$ for hydrocodone of about 5%, about 8%, about 10%, about 13%, about 15%, about 18%, about 20%, about 23%, about 25%, about 28%, or about 30% of the $AUC_{0-t}$.

Moreover, upon oral administration, the pharmaceutical composition disclosed herein may maintain a therapeutic plasma concentration of acetaminophen of at least about 2 mg/mL from about 1 hour to about 6 hours after administration. In another embodiment, the pharmaceutical composition may maintain a therapeutic plasma concentration of acetaminophen of at least about 2 mg/mL from about 0.75 hour to about 6.5 hours after administration. In yet another embodiment, the composition may maintain a plasma concentration of acetaminophen of at least about 1 mg/mL from about 0.5 hour to about 12 hours after administration.

In another embodiment, the composition, when orally administered to a subject, may produce a plasma profile characterized by a mean Cmax for acetaminophen from about 4.0 ng/mL/mg to about 11.0 ng/mL/mg. In other embodiments, the mean Cmax for acetaminophen may be from about 4.0, 4.5, 5.0, 5.5, 6.0, 6.5, 7.0, 7.5, 8.0, 8.5, 9.0, 9.5, 10.0, 10.5, or 11.0 ng/mL/mg. Moreover, the mean Cmax for acetaminophen at steady state may range from about 6.0 ng/mL/mg to about 9.0 ng/mL/mg, from about 6.5 ng/mL/mg to about 8.5 ng/mL/mg, or from about 7.0 ng/mL/mg to about 8.0 ng/mL/mg.

In a further embodiment, the pharmaceutical composition, when orally administered to a subject, surprisingly may produce a plasma profile characterized by a biphasic absorption of acetaminophen. The biphasic absorption of acetaminophen may characterized by an initial rapid absorption resulting in first peak in plasma concentrations between about 0.5 hour and 2 hours, which contributes to the early onset of action, and a second peak in plasma concentrations between about 3 hours and 7 hours after administration of the composition, which contributes to the duration or maintenance of analgesia. In some instances, the second peak may correspond to the overall Cmax of the composition. The biphasic absorption of acetaminophen. may be characterized by a plasma concentration-time profile for acetaminophen in which the slope of a line drawn between 0 hour and 2 hour is greater than the slope of a line drawn between about 2 hours and 5 hours. See FIG. 24.

This biphasic increase in acetaminophen levels resulting from the composition has several benefits. For example, the initial rapid rise in plasma levels produce quick onset of analgesia and the slower absorption provides maintenance of analgesia for an extended period of time.

In a further embodiment, the pharmaceutical composition, when orally administered to a subject, may produce a plasma profile characterized by a mean AUC for acetaminophen from about 35.0 ng·hr/mL/mg to about 80.0 ng·hr/mL/mg. In a further embodiment, the mean AUC for acetaminophen from about 35.0 ng·hr/mL/mg to about 60.0 ng·hr/mL/mg. In other embodiments, the mean AUC for acetaminophen may be about 35.0, 40.0, 45.0, 50.0, 55.0, 60.0, 65.0, 70.0, 75.0, or 80.0 ng·hr/mL/mg. Additionally, the mean AUC for acetaminophen at steady state may range from about 40.0 ng·hr/mL/mg to about 50.0 ng·hr/mL/mg, from about 35.0 ng·hr/mL/mg to about 45.0 ng·hr/mL/mg, or from about 37.0 ng·hr/mL/mg to about 42.0 ng·hr/mL/mg.

In yet another embodiment, the pharmaceutical composition when orally administered to a subject, may produce a plasma profile characterized by a median $T_{max}$ for acetaminophen from about 0.5 hours to about 6.0 hours. In another embodiment, the median $T_{max}$ for acetaminophen may range from about 1.0 hour to about 5.0 hours. In a further embodiment, the median $T_{max}$ for acetaminophen may range from about 0.5 hour to about 4.0 hours. In still another embodiment, the median $T_{max}$ for acetaminophen may range from about 0.75 to about 1.5 hours. In other embodiments, the median $T_{max}$ may be about 0.5, 0.6, 0.7, 0.8, 0.9, 1.0, 1.1, 1.2, 1.3, 1.4, 1.5, 1.6, 1.7, 1.8, 1.9, 2.0, 2.2, 2.4, 2.6, 2.8, 3.0, 3.2, 3.4, 3.6, 3.8, 4.0, 4.2, 4.4, 4.6, 4.8, or 5.0 hours. Moreover, the median $T_{max}$ for acetaminophen at steady state may range from about 0.5 hours to about 1.0 hour, or from about 0.5 hours to about 0.75 hours.

In a further embodiment, the pharmaceutical composition, when orally administered to a subject, may produce a plasma profile characterized by a median tlag for acetaminophen from about 0 hours to about 0.5 hours. In an alternate embodiment, the median tlag for acetaminophen may be from about 0 hours to about 0.25 hours. In one embodiment, the median tlag for acetaminophen may be 0 hour. In another embodiment, the median tlag for acetaminophen may be 0.25 hour.

In one embodiment, the pharmaceutical composition, when orally administered to a subject, surprisingly may produce a plasma profile characterized by various partial AUCs for acetaminophen. The partial AUCs for acetaminophen are calculated as described above for oxycodone. The pharmaceutical composition, when orally administered to a subject, may produce a plasma profile characterized by an $AUC_{0-1hr}$ for acetaminophen from about 1.25 ng·hr/mL/mg to about 3.25 ng·hr/mL/mg, from about 1.60 ng·hr/mL/mg to about 2.0 ng·hr/mL/mg, or from about 2.0 ng·hr/mL/mg to about 2.75 ng·hr/mL/mg. In another embodiment, the $AUC_{0-1hr}$ for acetaminophen may be about 1.50, 1.55, 1.60, 1.65, 1.70, 1.75, 1.80, 1.85, 1.90, 1.95, 2.0, 2.05, 2.10, 2.15, 2.20, 2.25, 2.30, 2.35, 2.40, 2.45, 2.50, 2.55, 2.60, 2.65, 2.70, 2.75, 2.80, 2.85, or 2.90 ng·hr/mL/mg.

In an additional embodiment, the pharmaceutical composition, when orally administered to a subject, may produce a plasma profile characterized by an $AUC_{0-2hr}$ for acetaminophen from about 4.25 ng·hr/mL/mg to about 8.75 ng·hr/mL/mg, from about 5.50 ng·hr/mL/mg to about 6.0 ng·hr/mL/mg, or from about 6.0 ng·hr/mL/mg to about 7.25 ng·hr/mL/mg. In another embodiment, the $AUC_{0-2hr}$ for acetaminophen may be about 5.0, 5.25, 5.5, 5.75, 6.0, 6.25, 6.5, 6.75, 7.0, 7.25, 7.50, 7.75 or 8.0 ng·hr/mL/mg.

In a further embodiment, the pharmaceutical composition, when orally administered to a subject, may produce a plasma profile characterized by an $AUC_{0-4hr}$ for acetaminophen from about 10.0 ng·hr/mL/mg to about 20.0 ng·hr/mL/mg, from about 13.0 ng·hr/mL/mg to about 14.5 ng·hr/mL/mg, or from about 14.5 ng·hr/mL/mg to about 16.5 ng·hr/mL/mg. In another embodiment, the $AUC_{0-4hr}$ for acetaminophen may be about 13.0, 13.5, 14.0, 14.5, 15.0, 15.5, 16.0, 16.5, or 17.0 ng·hr/mL/mg.

In yet another embodiment, the pharmaceutical composition, when orally administered to a subject, may produce a plasma profile characterized by an $AUC_{Tmax-t}$ for acetaminophen from about 20.0 ng·hr/mL/mg to about 40.0 ng·hr/mL/mg, from about 23.5 ng·hr/mL/mg to about 36.0 ng·hr/mL/mg, or from about 29.0 ng·hr/mL/mg to about 31.0 ng·hr/mL/mg. In another embodiment, the $AUC_{Tmax-t}$ for acetaminophen may be about 23.0, 23.5, 24.0, 24.5, 25.0, 25.5, 26.0, 26.5, 27.0, 27.5, 28.0, 28.5, 29.0, 29.5, 30.0, 30.5, 31.0, 31.5, 32.0, 32.5, 33.0, 33.5, 34.0, 34.5, 35.0, 35.5 or 36.0 ng·hr/mL/mg.

In yet another embodiment, the pharmaceutical composition, when orally administered to a subject, may produce a plasma profile characterized by an $AUC_{(0-(Tmax\ of\ IR\ product+2SD))}$ for acetaminophen after a single dose from about 5.0 ng·hr/mL/mg to about 13.0 ng·hr/mL/mg, from about 7.2 ng·hr/mL/mg to about 11.6 ng·hr/mL/mg, or from about 8.5 ng·hr/mL/mg to about 10.0 ng·hr/mL/mg. In another embodiment, the $AUC_{(0-(Tmax\ of\ IR\ product+2SD))}$ for acetaminophen may be about 5.0, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, or 12.0 ng·hr/mL/mg.

In one embodiment, the immediate release product referenced for the Partial AUC calculations is Percocet in the fasted state and the following calculation was used to determine $AUC_{(0-(Tmax\ of\ IR\ product+2SD))}$:

acetaminophen mean±SD=0.596h±0.529h; Tmax+2SD=1.65 hour

In a further embodiment, the pharmaceutical composition, when orally administered to a subject, may produce a plasma profile characterized by an $AUC_{(0-1.7)}$ for acetaminophen after a single dose from about 5.0 ng·hr/mL/mg to about 13.0 ng·hr/mL/mg, from about 7.2 ng·hr/mL/mg to about 11.6 ng·hr/mL/mg, or from about 8.5 ng·hr/mL/mg to about 10.0 ng·hr/mL/mg. In another embodiment, the $AUC_{(0-1.7)}$ for acetaminophen may be about 5.0, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, or 12.0 ng·hr/mL/mg.

In still a further embodiment, the pharmaceutical composition, when orally administered to a subject, may produce a plasma profile characterized by an $AUC_{(1.7-48)}$ for acetaminophen after a single dose from about 25.0 ng·hr/mL/mg to about 75.0 ng·hr/mL/mg, from about 31.5 ng·hr/mL/mg to about 55.0 ng·hr/mL/mg, or from about 35.0 ng·hr/mL/mg to about 50.0 ng·hr/mL/mg. In another embodiment, the $AUC_{(1.7-48)}$ for acetaminophen may be about 25, 26, 27, 28, 29, 30.0, 30.5, 31.0, 31.5, 32.0, 32.5, 33.0, 33.5, 34.0, 34.5, 35.0, 35.5, 36.0, 36.5, 37.0, 37.5, 38.0, 38.5, 39.0, 39.5, 40.0, 40.5, 41.0, 41.5, 42.0, 42.5, 43.0, 43.5, 44.0, 44.5, 45.0, 45.5, 46.0, 46.5, 47.0, 47.5, 48.0, 48.5, 49.0, 49.5, 50.0, 50.5, 51.0, 51.5, 52.0, 52.5, 53.0, 53.5, 54.0, 54.5, or 55.0 ng·hr/mL/mg.

In one embodiment, the immediate release product referenced for the Partial AUC calculations is Percocet in the fed state and the following calculation was used to determine $AUC_{(0-(Tmax\ of\ IR\ product+2SD))}$:

acetaminophen mean±SD=1.48h±0.875h; Tmax+2SD=3.2 hour

In such embodiment, the pharmaceutical composition, when orally administered to a subject, may produce a plasma profile characterized by an $AUC_{(0-3.2)}$ for acetaminophen after a single dose from about 7.0 ng·hr/mL/mg to about 21.0 ng·hr/mL/mg, from about 9.0 ng·hr/mL/mg to about 18.0 ng·hr/mL/mg, from about 10.0 ng·hr/mL/mg to about 16.0 ng·hr/mL/mg, or from about 12.0 ng·hr/mL/mg to about 15.0 ng·hr/mL/mg. In another embodiment, the $AUC_{(0-3.2)}$ for acetaminophen may be about 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, 13.0, 13.1, 13.2, 13.3, 13.4, 13.5, 13.6, 13.7, 13.8, 13.9, 14.0, 14.1, 14.2, 14.3, 14.4, 14.5, 14.6, 14.7, 14.8, 14.9, 15.0, 15.1, 15.2, 15.3, 15.4, 15.5, 15.6, 15.7, 15.8, 15.9, 16.0, 16.1, 16.2, 16.3, 16.4, 16.5, 16.6, 16.7, 16.8, 16.9, 17.0, 17.1, 17.2, 17.3, 17.4, 17.5, 17.6, 17.7, 17.8, 17.9, 18.0, 18.1, 18.2, 18.3, 18.4, 18.5, 18.6, 18.7, 18.8, 18.9, 19.0, 19.1, 19.2, 19.3, 19.4, 19.5, 19.6, 19.7, 19.8, 19.9, 20.0, 20.1, 20.2, 20.3, 20.4, 20.5, 20.6, 20.7, 20.8, 20.9, or 21.0 ng·hr/mL/mg.

In still a further embodiment, the pharmaceutical composition, when orally administered to a subject, may produce a plasma profile characterized by an $AUC_{(3.2-48)}$ for acetaminophen after a single dose from about 15.0 ng·hr/mL/mg to about 75.0 ng·hr/mL/mg, from about 25.0 ng·hr/mL/mg to about 55.0 ng·hr/mL/mg, from about 27.5 ng·hr/mL/mg to about 45.0 ng·hr/mL/mg, or from about 30.0 ng·hr/mL/mg to about 40.0 ng·hr/mL/mg. In another embodiment, the $AUC_{(3.2-48)}$ for acetaminophen may be about 15.0, 15.5, 16.0, 16.5, 17.0, 17.5, 18.0, 18.5, 19.0, 19.5, 20.0, 20.5, 21.0, 21.5, 22.0, 22.5, 23.0, 23.5, 24.0, 24.5, 25.0, 25.5, 26.0, 26.5, 27.0, 27.5, 28.0, 28.5, 29.0, 29.5, 30.0, 30.5, 31.0, 31.5, 32.0, 32.5, 33.0, 33.5, 34.0, 34.5, 35.0, 35.5, 36.0, 36.5, 37.0, 37.5, 38.0, 38.5, 39.0, 39.5, 40.0, 40.5, 41.0, 41.5, 42.0, 42.5, 43.0, 43.5, 44.0, 44.5, 45.0, 45.5, 46.0, 46.5, 47.0, 47.5, 48.0, 48.5, 49.0, 49.5, 50.0, 50.5, 51.0, 51.5, 52.0, 52.5, 53.0, 53.5, 54.0, 54.5, 55.0, 55.5, 56.0, 56.5, 57.0, 57.5, 58.0, 58.5, 59.0, 59.5, 60.0, 60.5, 61.0, 61.5, 62.0, 62.5, 63.0, 63.5, 64.0, 64.5, 65.0, 65.5, 66.0, 66.5, 67.0, 67.5, 68.0, 68.5, 69.0, 69.5, 70.0, 70.5, 71.0, 71.5, 72.0, 72.5, 73.0, 73.5, 74.0, 74.5, or 75.0 ng·hr/mL/mg.

In another embodiment, the pharmaceutical composition, when orally administered to a subject, may produce a plasma profile characterized by an $AUC_{(0-1.27)}$ for acetaminophen after a single dose from about 3.0 ng·hr/mL/mg to about 13.0 ng·hr/mL/mg, from about 4.0 ng·hr/mL/mg to about 11.6 ng·hr/mL/mg, or from about 5.0 ng·hr/mL/mg to about 10.0 ng·hr/mL/mg. In another embodiment, the $AUC_{(0-1.27)}$ for acetaminophen may be about 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, or 13 ng·hr/mL/mg.

In still a further embodiment, the pharmaceutical composition, when orally administered to a subject, may produce a plasma profile characterized by an $AUC_{(1.27-36)}$ for acetaminophen after a single dose from about 20.0 ng·hr/mL/mg to about 75.0 ng·hr/mL/mg, from about 25.0 ng·hr/mL/mg to about 65.0 ng·hr/mL/mg, or from about 30.0 ng·hr/mL/mg to about 50.0 ng·hr/mL/mg. In another embodiment, the $AUC_{(1.27-36)}$ for acetaminophen may be about 20.0, 20.5, 21.0, 21.5, 22.0, 22.5, 23.0, 23.5, 24.0, 24.5, 25.0, 25.5, 26.0, 26.5, 27.0, 27.5, 28.0, 28.5, 29.0, 29.5, 30.0, 30.5, 31.0, 31.5, 32.0, 32.5, 33.0, 33.5, 34.0, 34.5, 35.0, 35.5, 36.0, 36.5, 37.0, 37.5, 38.0, 38.5, 39.0, 39.5, 40.0, 40.5, 41.0, 41.5, 42.0, 42.5, 43.0, 43.5, 44.0, 44.5, 45.0, 45.5, 46.0, 46.5, 47.0, 47.5, 48.0, 48.5, 49.0, 49.5, 50.0, 50.5, 51.0, 51.5, 52.0, 52.5, 53.0, 53.5, 54.0, 54.5, 55.0, 55.5, 56.0, 56.5, 57.0, 57.5, 58.0, 58.5, 59.0, 59.5, 60.0, 60.5, 61.0, 61.5, 62.0, 62.5, 63.0, 63.5, 64.0, 64.5, 65.0, 65.5, 66.0, 66.5, 67.0, 67.5, 68.0, 68.5, 69.0, 69.5, 70.0, 70.5, 71.0, 71.5, 72.0, 72.5, 73.0, 73.5, 74.0, 74.5, or 75.0 ng·hr/mL/mg.

In one embodiment, the pharmaceutical composition, when orally administered to a subject, may produce a plasma profile characterized by an $AUC_{0-12hr}$ for acetaminophen from about 20.0 ng·hr/mL/mg to about 60.0 ng·hr/mL/mg, from about 30 ng·hr/mL/mg to about 50 ng·hr/mL/mg, from about 35 to about 45 ng·hr/mL/mg, or from about 37.5 ng·hr/mL/mg to about 42.5 ng·hr/mL/mg. In another embodiment, the pharmaceutical composition, when orally administered to a subject, may produce a plasma profile characterized by an $AUC_{0-12hr}$ for acetaminophen from about 20.0, 20.5, 21.0, 21.5, 22.0, 22.5, 23.0, 23.5, 24.0, 24.5, 25.0, 25.5, 26.0, 26.5, 27.0, 27.5, 28.0, 28.5, 29.0, 29.5, 30.0, 30.5, 31.0, 31.5, 32.0, 32.5, 33.0, 33.5, 34.0, 34.5, 35.0, 35.5, 36.0, 36.5, 37.0, 37.5, 38.0, 38.5, 39.0, 39.5, 40.0, 40.5, 41.0, 41.5, 42.0, 42.5, 43.0, 43.5, 44.0, 44.5, 45.0, 45.5, 46.0, 46.5, 47.0, 47.5, 48.0, 48.5, 49.0, 49.5, 50.0, 50.5, 51.5, 52.0, 52.5, 53.0, 53.5, 54.0, 54.5, or 55.0. In a further embodiment, at $AUC_{0-12hr}$ between about 70%-95%, about 75%-92%, or about 77%-90% of the acetaminophen has been cleared. In still another embodiment, about 80% of the acetaminophen has been cleared.

In another embodiment, the pharmaceutical composition, when orally administered to a subject, may produce a plasma profile characterized by an $AUC_{1-12hr}$ for acetaminophen from about 15.0 ng·hr/mL/mg to about 55.0 ng·hr/mL/mg, from about 25.0 ng·hr/mL/mg to about 45.0 ng·hr/mL/mg, or from about 30.0 to about 40.0 ng·hr/mL/mg. In another embodiment, the pharmaceutical composition, when orally administered to a subject, may produce a plasma profile characterized by an $AUC_{1-12hr}$ for acetaminophen from about 15, 15.5, 16, 16.5, 17, 17.5, 18, 18.5, 19, 19.5, 20.0, 20.5, 21.0, 21.5, 22.0, 22.5, 23.0, 23.5, 24.0, 24.5, 25.0, 25.5, 26.0, 26.5, 27.0, 27.5, 28.0, 28.5, 29.0, 29.5, 30.0, 30.5, 31.0, 31.5, 32.0, 32.5, 33.0, 33.5, 34.0, 34.5, 35.0, 35.5, 36.0, 36.5, 37.0, 37.5, 38.0, 38.5, 39.0, 39.5, 40.0, 40.5, 41.0, 41.5, 42.0, 42.5, 43.0, 43.5, 44.0, 44.5, 45.0, 45.5, 46.0, 46.5, 47.0, 47.5, 48.0, 48.5, 49.0, 49.5, or 50.0 ng·hr/mL/mg.

In yet another embodiment, the pharmaceutical composition, when orally administered to a subject, may produce a plasma profile characterized by an $AUC_{12-36hr}$ for acetaminophen from about 5.0 ng·hr/mL/mg to about 25.0 ng·hr/mL/mg, from about 7.5 ng·hr/mL/mg to about 20.0 ng·hr/mL/mg, or from about 10.0 ng·hr/mL/mg to about 15.0. In other embodiments, the pharmaceutical composition, when orally administered to a subject, may produce a plasma profile characterized by an $AUC_{12-36hr}$ for acetaminophen from about 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, 13.0, 13.1, 13.2, 13.3, 13.4, 13.5, 13.6, 13.7, 13.8, 13.9, 14.0, 14.1, 14.2, 14.3, 14.4, 14.5, 14.6, 14.7, 14.8, 14.9, 15.0, 15.1, 15.2, 15.3, 15.4, 15.5, 15.6, 15.7, 15.8, 15.9, 16.0, 16.1, 16.2, 16.3, 16.4, 16.5, 16.6, 16.7, 16.8, 16.9, or 17.0 ng·hr/mL/mg.

In another embodiment, the pharmaceutical composition, when orally administered to a subject, may produce a plasma profile characterized by an $AUC_{8-12hr}$ for acetaminophen from about 1.5 ng·hr/mL/mg to about 15.5 ng·hr/mL/mg, from about 2 ng·hr/mL/mg to about 12.25 ng·hr/mL/mg, from about 3.5 ng·hr/mL/mg to about 10 ng·hr/mL/mg, or from about 4.5 ng·hr/mL/mg to about 6.5 ng·hr/mL/mg. In other embodiments, the pharmaceutical composition, when orally administered to a subject, may produce a plasma profile characterized by an $AUC_{8-12hr}$ for acetaminophen from about 1.5, 1.75, 2.0, 2.25, 2.5, 2.75, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, or 12.0 ng·hr/mL/mg.

In still another embodiment, the pharmaceutical composition, when orally administered to a subject, may produce a plasma profile characterized by an $AUC_{0-1hr}$ for acetaminophen from about 1.5 ng·hr/mL/mg to about 15.5 ng·hr/mL/mg, from about 2 ng·hr/mL/mg to about 12.25 ng·hr/mL/mg, from about 3.5 ng·hr/mL/mg to about 10 ng·hr/mL/mg, or from about 4.5 to about 6.5 ng·hr/mL/mg. In other embodiments, the pharmaceutical composition, when orally administered to a subject, may produce a plasma profile characterized by an $AUC_{0-1hr}$ for acetaminophen from about 1.5, 1.75, 2.0, 2.25, 2.5, 2.75, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, or 12.0 ng·hr/mL/mg.

In a further embodiment, the pharmaceutical composition, when orally administered to a subject, may produce a plasma profile characterized by an $AUC_{0-1.27hr}$ for acetaminophen from about 15.0 ng·hr/mL/mg to about 75.0 ng·hr/mL/mg, from about 25.0 ng·hr/mL/mg to about 55.0 ng·hr/mL/mg, or from about 30.0 to about 45.0 ng·hr/mL/mg. In another embodiment, the pharmaceutical composition, when orally administered to a subject, may produce a plasma profile characterized by an $AUC_{O-1.27hr}$ for acetaminophen from about 15, 15.5, 16, 16.5, 17, 17.5, 18, 18.5, 19, 19.5, 20.0, 20.5, 21.0, 21.5, 22.0, 22.5, 23.0, 23.5, 24.0, 24.5, 25.0, 25.5, 26.0, 26.5, 27.0, 27.5, 28.0, 28.5, 29.0, 29.5, 30.0, 30.5, 31.0, 31.5, 32.0, 32.5, 33.0, 33.5, 34.0, 34.5, 35.0, 35.5, 36.0, 36.5, 37.0, 37.5, 38.0, 38.5, 39.0, 39.5, 40.0, 40.5, 41.0, 41.5, 42.0, 42.5, 43.0, 43.5, 44.0, 44.5, 45.0, 45.5, 46.0, 46.5, 47.0, 47.5, 48.0, 48.5, 49.0, 49.5, or 50.0 ng·hr/mL/mg.

In yet another embodiment, the pharmaceutical composition, when orally administered to a subject, may produce a plasma profile characterized by an $AUC_{1.27-36hr}$ for acetaminophen from about 1.5 ng·hr/mL/mg to about 15.5 ng·hr/mL/mg, from about 2 ng·hr/mL/mg to about 12.25 ng·hr/mL/mg, from about 3.5 ng·hr/mL/mg to about 10 ng·hr/mL/mg, or from about 4.5 to about 7.5 ng·hr/mL/mg. In other embodiments, the pharmaceutical composition, when orally administered to a subject, may produce a plasma profile characterized by an $AUC_{1.27-36hr}$ for acetaminophen from about 1.5, 1.75, 2.0, 2.25, 2.5, 2.75, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, or 12.0 ng·hr/mL/mg.

In one embodiment, the pharmaceutical composition, when orally administered to a subject, may produce a plasma profile characterized by an $AUC_{(0-3hr)}$ for acetaminophen from about 5 ng·hr/mL/mg to about 30 ng·hr/mL/mg, from about 10 ng·hr/mL/mg to about 20 ng·hr/mL/mg, or from about 13 ng·hr/mL/mg to about 17 ng·hr/mL/mg. In other embodiments, the pharmaceutical composition, when orally administered to a subject, may produce a plasma profile characterized by an $AUC_{(0-3hr)}$ for acetaminophen from about 5.0, 6.0, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, 13.0, 13.1, 13.2, 13.3, 13.4, 13.5, 13.6, 13.7, 13.8, 13.9, 14.0, 14.1, 14.2, 14.3, 14.4, 14.5, 14.6, 14.7, 14.8, 14.9, 15.0, 15.1, 15.2, 15.3, 15.4, 15.5, 15.6, 15.7, 15.8, 15.9, 16.0, 16.1, 16.2, 16.3, 16.4, 16.5, 16.6, 16.7, 16.8, 16.9, 17.0, 17.1, 17.2, 17.3, 17.4, 17.5, 17.6, 17.7, 17.8, 17.9, 18.0, 18.1, 18.2, 18.3, 18.4, 18.5, 18.6, 18.7, 18.8, 18.9, 19.0, 19.1, 19.2, 19.3, 19.4, 19.5, 19.6, 19.7, 19.8, 19.9, or 20.0 ng·hr/mL/mg.

In another embodiment, the pharmaceutical composition, when orally administered to a subject, may produce a plasma profile characterized by an $AUC_{(3-36hr)}$ for acetaminophen from about 20 ng·hr/mL/mg to about 50 ng·hr/mL/mg, from about 20 ng·hr/mL/mg to about 40 ng·hr/mL/mg, or from about 25 ng·hr/mL/mg to about 35 ng·hr/mL/mg. In other embodiments, the pharmaceutical composition, when orally administered to a subject, may produce a plasma profile characterized by an $AUC_{(3-36hr)}$ for acetaminophen from about 20, 20.5, 21, 21.5, 22, 22.5, 23, 23.5, 24, 24.5, 25, 25.5, 26, 26.5, 27, 27.5, 28, 28.5, 29, 29.5, 30, 30.5, 31, 31.5, 32, 32.5, 33, 33.5, 34, 34.5, 35, 35.5, 36, 36.5, 37, 37.5, 38, 38.5, 39, 39.5, 40, 40.5, 41, 41.5, 42, 42.5, 43, 43.5, 44, 44.5, 45, 45.5, 46, 46.5, 47, 47.5, 48, 48.5, 49, 49.5, or 50 ng·hr/mL/mg.

In one embodiment, the pharmaceutical composition, when orally administered to a subject, may produce a plasma profile characterized by an $AUC_{0-12hr}$ for acetaminophen from about 50% to about 90% of the $AUC_{0-t}$, from about 55% to about 85% of the $AUC_{0-t}$, or from about 75% to about 85% of the $AUC_{0-t}$. In other embodiments, the pharmaceutical composition, when orally administered to a subject, may produce a plasma profile characterized by an $AUC_{0-12hr}$ for acetaminophen that is about 50%, 55%, 60%, 65%, 70%, 75%, 76%, 77%, 78%, 79%, 80%, 81%, 82%, 83%, 84% or 85% of the $AUC_{0-t}$.

In one embodiment, the pharmaceutical composition, when orally administered to a subject, may produce a plasma profile characterized by an $AUC_{1-12hr}$ for acetaminophen from about 40% to about 90% of the $AUC_{0-t}$, from about 55% to about 85% of the $AUC_{0-t}$, or from about 60% to about 75% of the $AUC_{0-t}$. In other embodiments, the pharmaceutical composition, when orally administered to a subject, may produce a plasma profile characterized by an $AUC_{1-12hr}$ for acetaminophen of about 40%, 45%, 50%, 55%, 60%, 61%, 62%, 63%, 64%, 65%, 66%, 67%, 68%, 69%, 70%, 71%, 72%, 73%, 74%, 75%, 76%, 77%, 78%, 79%, or 80% of the $AUC_{0-t}$.

In one embodiment, the pharmaceutical composition, when orally administered to a subject, may produce a plasma profile characterized by an $AUC_{12-36hr}$ for acetaminophen from about 10% to about 40% of the $AUC_{0-t}$, from about 15% to about 35% of the $AUC_{0-t}$, or from about 20% to about 30% of the $AUC_{0-t}$. In other embodiments, the pharmaceutical composition, when orally administered to a subject, may produce a plasma profile characterized by an $AUC_{12-36hr}$ for acetaminophen of about 10%, 12%, 14%, 16%, 18%, 20%, 21%, 22%, 23%, 24%, 25%, 26%, 27%, 28%, 29%, or 30% of the $AUC_{0-t}$.

In one embodiment, the pharmaceutical composition, when orally administered to a subject, may produce a plasma profile characterized by an $AUC_{8-12hr}$ for acetaminophen from about 5% to about 30% of the $AUC_{0-t}$, from about 7% to about 25% of the $AUC_{0-t}$, or from about 10% to about 20% of the $AUC_{0-t}$. In other embodiments, the pharmaceutical composition, when orally administered to a subject, may produce a plasma profile characterized by an $AUC_{8-12hr}$ for acetaminophen of about 5%, 6%, 7%, 8%, 9%, 10%, 11%, 12%, 13%, 14%, 15%, 16%, 17%, 18%, 19%, 20%, 21%, 22%, 23%, 24%, or 25% of the $AUC_{0-t}$.

In an alternate embodiment, the pharmaceutical composition, when orally administered to a subject, may have a mean half-life of acetaminophen that ranges from about 2 hours to about 10 hours, or more preferably from about 3 hours to about 6 hours. In another embodiment, the pharmaceutical composition, when orally administered to a subject, may have a mean half-life of acetaminophen that ranges from about 3 hours to about 5 hours. In still another embodiment, the pharmaceutical composition, when orally administered to a subject, may have a mean half-life of acetaminophen that ranges from about 4 hours to about 5 hours. In various embodiments, the mean half-life of acetaminophen may be about 2.5, 3.0, 3.5, 4.0, 4.5, 5.0, 5.5, 6.0, 6.5, 7.0, 7.5, or 8 hours. In additional embodiments, the pharmaceutical composition, when orally administered to a subject, has a mean observed half-life of acetaminophen that is more than the mean half-life of commercially available immediate release acetaminophen products.

In another embodiment, upon administration of the pharmaceutical composition to a subject, the composition may provide at least about 4 hours to about 12 hours of drug delivery to the upper gastrointestinal tract, which includes the duodenum, jejunum, and ileum of the small intestine. In another embodiment, the composition may provide at least about 6 hours of drug delivery to the upper gastrointestinal tract. In yet a further embodiment, the composition may provide at least about 8 hours of drug delivery to the upper gastrointestinal tract. In yet a further embodiment, the composition may provide at least about 9 hours, or at least about 10 hours of drug delivery to the upper gastrointestinal tract.

In yet another embodiment, upon administration of the pharmaceutical composition to a subject, the additional API undergoes presystemic metabolism in the gut and/or liver allowing only a fraction of the drug to reach the systemic circulation. The fraction of drug that is originally absorbed prior to presystemic metabolism is referred to as the fraction absorbed and denoted "Fab." This is different from the fraction bioavailable "F," which is the fraction that reaches the systemic circulation after the metabolism in the gut and liver.

In another embodiment, 60-90% of the acetaminophen in the pharmaceutical composition, which is available for absorption into the systemic circulation, is absorbed in the upper gastrointestinal tract. In still another embodiment, 60-85% of acetaminophen in the pharmaceutical composition, which is available for absorption into the systemic circulation, is absorbed in the duodenum and jejunum. See FIG. 27. Greater than 50% absorption of acetaminophen in the upper gastrointestinal tract is beneficial to a human subject because acetaminophen is poorly absorbed in the stomach and well absorbed in the small intestine and particularly, the upper segment of the gastrointestinal tract. It is therefore critical that acetaminophen is available in upper small intestine for its absorption. In one embodiment acetaminophen is released in stomach and reaches quickly into upper GIT for the absorption to take place.

In another embodiment, when about 60% to about 75% of the acetaminophen is released from the dosage form in the stomach within 2 hours following oral administration, about 10% to about 25% of the total amount of the acetaminophen in the dosage form, which is available for absorption into the systemic circulation, is absorbed in the duodenum, about 25% to about 40% is absorbed in the proximal jejunum (noted as "jejunum 1" in FIG. 27), about 15% to about 20% is absorbed in the distal jejunum (noted as "jejunum 2" in FIG. 27), and about 5% to about 15% is absorbed in the ileum.

In another embodiment, when about 70% to about 90% of the acetaminophen is released from the dosage form in the stomach within 4 hours following oral administration, about 10% to about 25% of the total amount of the acetaminophen in the dosage form, which is available for absorption into the systemic circulation, is absorbed in the duodenum, about 25% to about 40% is absorbed in the proximal jejunum (noted as "jejunum 1" in FIG. 27), about 15% to about 20% is absorbed in the distal jejunum (noted as "jejunum 2" in FIG. 27), and about 5% to about 15% is absorbed in the ileum.

In yet another embodiment, when at least about 55% of the total amount of the acetaminophen is released from the dosage form in the stomach within 1 hour after oral administration and when at least about 60% of the acetaminophen is released in the stomach after 2 hours, about 15% to about 20% of the total amount of the acetaminophen in the dosage form, which is available for absorption into the systemic circulation, is absorbed in the duodenum, about 30% to about 37% is absorbed in the proximal jejunum, about 15% to about 18% is absorbed in the distal jejunum, and about 8% to about 10% is absorbed in the ileum.

In still another embodiment, upon administration of the pharmaceutical composition to a subject, the opioid undergoes presystemic metabolism in the gut and/or liver allowing only a fraction of the drug absorbed into the systemic circulation. This is referred to as the fraction absorbed and denoted "Fab." In one embodiment, the opioid is oxycodone. In another embodiment, the opioid is hydrocodone.

In a further embodiment, 70-95% of the oxycodone in the pharmaceutical composition, which is available for absorption into the systemic circulation, is absorbed in the upper gastrointestinal tract. In still another embodiment, 80-95% of oxycodone in the pharmaceutical composition, which is available for absorption into the systemic circulation, is absorbed in the duodenum and jejunum. See FIG. 28.

In one embodiment, the composition releases the opioid and other API in the stomach to optimize drug absorption in the duodenum and jejunum. For example, when about 25% to about 50% of oxycodone is released from the dosage form in the stomach within 1 hour following oral administration, about 10% to about 45% of the total amount of the oxycodone in the dosage form, which is available for absorption into the systemic circulation, is absorbed in the duodenum, about 25% to about 50% is absorbed in the proximal jejunum (noted as "jejunum 1" in FIG. 28), about 7% to about 20% is absorbed in the distal jejunum (noted as "jejunum 2" in FIG. 28), and about 2% to about 15% is absorbed in the ileum.

In another embodiment, when about 45% to about 65% of oxycodone is released from the dosage form in the stomach within 2 hours following oral administration, about 10% to about 50% of the total amount of the oxycodone in the dosage form, which is available for absorption into the systemic circulation, is absorbed in the duodenum, about 25% to about 55% is absorbed in the proximal jejunum (noted as "jejunum 1" in FIG. 28), about 5% to about 25% is absorbed in the distal jejunum (noted as "jejunum 2" in FIG. 28), and about 2% to about 15% is absorbed in the ileum.

In another embodiment, when about 60% to about 85% of oxycodone is released from the dosage form in the stomach within 4 hours following oral administration, about 10% to about 55% of the total amount of the oxycodone in the dosage form, which is available for absorption into the systemic circulation, is absorbed in the duodenum, about 30% to about 60% is absorbed in the proximal jejunum (noted as "jejunum 1" in FIG. 28), about 10% to about 30% is absorbed in the distal jejunum (noted as "jejunum 2" in FIG. 28), and about 2% to about 20% is absorbed in the ileum.

In yet another embodiment, when at least 25% of the total amount of the oxycodone is released from the dosage form in the stomach within 1 hour after oral administration and when at least 45% of the oxycodone is released in the stomach after 2 hours, about 30% to about 45% of the total amount of oxycodone in the dosage form, which is available for absorption into the systemic circulation, is absorbed in the duodenum, about 37% to about 43% is absorbed in the proximal jejunum (noted as "jejunum 1" in FIG. 28), about 10% to about 15% is absorbed in the distal jejunum (noted as "jejunum 2" in FIG. 28), and about 2% to about 8% is absorbed in the ileum.

Under U.S. FDA guidelines, two pharmaceutical products or methods are bioequivalent if the 90% Confidence Intervals (CI) for AUC and Cmax are between 0.80 to 1.25. U.S. FDA, *Guidance for Industry: Bioavailability and Bioequivalence Studies for Orally Administered Drug Products— General Considerations* (March 2003). In one embodiment, a common characteristic of the inventive pharmaceutical compositions include bioequivalence established by a 90% Confidence Interval of between 0.80 and 1.25 for both Cmax and AUC.

In one embodiment, the pharmaceutical formulations disclosed herein rapidly achieve therapeutic plasma drug levels of oxycodone and acetaminophen similar to an immediate release product, which provides an early onset of action within about 5 minutes, 10 minutes, 15 minutes, 20 minutes, 25 minutes, 30 minutes, 35 minutes, 40 minutes, 45 minutes, 50 minutes, 55 minutes, or 60 minutes after administration of the formulation, but unlike an immediate release product, the pharmaceutical composition is able to maintain those therapeutic plasma drug levels of oxycodone and acetaminophen over an extended period of time (e.g., up to 12 hours). Currently, there is no pharmaceutical composition available comprising oxycodone and acetaminophen, which is able to provide a patient with quick onset of analgesia and maintenance of analgesia for an extended period of time.

In still another embodiment, the pharmaceutical composition rapidly achieves therapeutic plasma drug levels of hydrocodone and acetaminophen similar to an immediate release product, but unlike an immediate release product, the pharmaceutical composition is able to maintain those therapeutic plasma drug levels of hydrocodone and acetaminophen over an extended period of time (e.g., 12 hours). Currently, there is no pharmaceutical composition available comprising hydrocodone and acetaminophen, which is able to provide a patient with quick onset of analgesia and maintenance of analgesia for an extended period of time.

In a further embodiment, the pharmaceutical composition rapidly achieves therapeutic plasma drug levels of opioid and an additional API similar to an immediate release product, but unlike an immediate release product, the pharmaceutical composition is able to maintain those therapeutic plasma drug levels of opioid and the additional API over an extended period of time (e.g., 12 hours).

In yet another embodiment, upon average, within one hour of administration to a subject, the pharmaceutical composition achieves a Cmax for acetaminophen. The Cmax achieved by the pharmaceutical composition disclosed herein is comparable to the Cmax obtained from a commercially-available immediate release product containing acetaminophen formulated at half the strength of the commercially-available immediate release product. The acetaminophen continues to be released from the pharmaceutical composition at a rate less than the clearance rate for the acetaminophen, so that the acetaminophen levels fall smoothly until all of the acetaminophen is absorbed. Stated another way, the acetaminophen released by the pharmaceutical composition is eliminated by the body faster than it is being absorbed. The absorption of the acetaminophen released from the pharmaceutical composition is complete in about 8 to about 10 hours so that for one half life of acetaminophen the blood supply reaching the subject's liver via the portal vein contains no additional amounts of acetaminophen beyond the amounts present in the subject's general circulation.

These additional amounts of acetaminophen delivered to the liver from the subject's portal vein are frequently caused by the absorption of acetaminophen in the subject's gastrointestinal tract. Indeed, blood from the subject's intestines passes through the liver and then on to the general circulation. When acetaminophen is undergoing absorption, blood containing acetaminophen from the absorption process passes through the subject's liver prior to entering the general circulation where the acetaminophen is diluted by the distribution and clearance processes. The metabolism of these higher acetaminophen concentrations in blood coming into the subject's liver is termed the "first pass effect." Hence, the absorption process for acetaminophen taxes a subject's metabolic systems in the liver due to these higher "first pass" concentrations. Once the absorption process is complete, the concentration of acetaminophen in the blood reaching the subject's liver through the portal vein will be the same concentration of acetaminophen as found in blood throughout the rest of the subject's body. Thus, the pharmaceutical compositions disclosed herein provide a Cmax comparable to a commercially-available immediate-release acetaminophen product (dosed at half strength) while providing a less taxing burden on the subject's metabolic systems in the liver because the acetaminophen released by the pharmaceutical composition is eliminated by the subject's body faster than it is being absorbed. This results in decreased levels of acetaminophen in a subject's liver as compared to an immediate release dosage form of acetaminophen dosed every 6 hours.

(iv) the Pharmacokinetic Profiles of the Pharmaceutical Compositions of the Invention are not Affected by the Fed or Fasted State of the Subject Food can play a significant role in both the rate and extent of absorption of a drug. As is known, the primary function of the small intestine is to absorb food. During and after a meal, the intestine normally shows very irregular or unsynchronized contractions that move the food content back and forth and mix it with the digestive enzymes that are secreted into the intestine. However, these contractions are not entirely unsynchronized; they move the contents of the intestine slowly towards the large intestine. It normally takes about 90-120 minutes for the first part of a meal to reach the large intestine, and the last portion of the meal may not reach the large intestine for five (5) hours. Between meals, the intestine shows cycles of activity that repeat about every 90-120 minutes. The cycle consists of a short period of very few contractions (Phase I), followed by a long period of unsynchronized contractions that appear similar to the fed pattern (pre-burst, Phase II), and then a burst of strong, regular contractions that move down the intestine in a peristaltic fashion (Phase III). Phase III represents a continuation of the "housekeeper waves" that start in the stomach; its function is to sweep undigested food particles and bacteria out of the small intestine and ultimately into the large intestine.

Because non-opioid GR dosage forms of the prior art, as well as prior art extended release opioid formulations, demonstrate food effects, Applicants expected to likewise see a food effect with the pharmaceutical compositions of the present invention. Here, however, Applicants have surprisingly discovered that the pharmacokinetic profiles of the oxycodone and acetaminophen, and the hydrocodone and acetaminophen, are not substantially affected by the fed or fasted state of a human subject ingesting the composition. This means that there is no substantial difference in the quantity of drug absorbed or the rate of drug absorption when the oxycodone/acetaminophen compositions are administered in the fed versus the fasted state. Without being bound to theory, Applicants believe that in a fasted state the opioid acts to reduce gastric motility in an amount sufficient to retain the dosage form in the stomach thereby mitigating the "housekeeper waves" described above.

As shown in Examples 6 and 9, the pharmacokinetic parameters of the compositions of the invention are similar when the composition is administered in the fed and fasted states. Benefits of a dosage form, which substantially eliminates the effect of food, include an increase in convenience, thereby increasing patient compliance, as the patient does not need to ensure that they are taking a dose either with or without food. This is significant because poor patient compliance can lead to adverse therapeutic outcomes.

The invention also encompasses an oxycodone/APAP pharmaceutical composition in which administration of the composition to a human subject in a fasted state is bioequivalent to administration of the composition to a human subject in a fed state wherein bioequivalence is established by: (1) a 90% Confidence Interval (CI) for AUC which is between 80% and 125%, and (2) a 90% CI for $C_{max}$, which is 80% and 125%. In other embodiments, the difference in absorption of the APIs of the invention, when administered in the fed versus the fasted state, is less than about 35%, less than about 30%, less than about 25%, less than about 20%, less than about 15%, less than about 10%, less than about 5%, or less than about 3%.

III. Methods for Preparing Solid Dosage Forms

Another aspect of the disclosure provides methods for preparing solid dosage forms of the extended release pharmaceutical composition that provides extended release of oxycodone and acetaminophen. Solid dosage pharmaceutical compositions in the form of tablets may be produced using any suitable method known in the art including but not limited to wet granulation, dry granulation, direct compression, and combinations thereof.

Granulation is a manufacturing process which increases the size and homogeneity of active pharmaceutical ingredients and excipients that comprise a solid dose formulation. The granulation process, which is often referred to as agglomeration, changes important physical characteristics of the dry formulation, with the aim of improving manufacturability and, thereby, product quality, as well as providing desired release kinetics. Wet granulation is by far the more prevalent agglomeration process utilized within the pharmaceutical industry. Most wet granulation procedures follow some basic steps; the active agent(s) and excipients are mixed together, and a binder solution is prepared and added to the powder mixture to form a wet mass. The moist particles are then dried and sized by milling or by screening through a sieve. In some cases, the wet granulation is "wet milled" or sized through screens before the drying step. The wet granulation process may be a high shear granulation process or a fluid bed granulation process. Several methods of granulation are described in co-pending application U.S. application Ser. No. 13/166,770, filed Jun. 22, 2011, which is incorporated herein by reference in its entirety.

After granulation and drying of the resultant particles, batches are characterized with respect to properties such as final Loss on Drying (LOD), bulk density, tap density, and particle size. LOD typically is determined after each granulation using the Moisture Analyzer. Several 1 g samples may be taken and loaded into the moisture analyzer. The samples may be run for 5 minutes at a temperature of 105° C. In another embodiment, samples are run at 105° C. until there is no weight fluctuation in order to determine the LOD.

Bulk and tap densities may be determined as follows. A graduated cylinder is filled with a certain amount of material (30-40 g or 82-88 g), and the volume recorded to determine the material bulk density. Tap density can be determined with a help of a Tap Density Tester by exposing the material to 100 taps per test and recording the new volume.

Particle size determination generally is performed immediately after granulation, after sieving through 20 mesh screen to remove agglomerates. Particle diameter may be determined with a sieve-type particle diameter distribution gauge using sieves with openings of 30, 40, 60, 80, 120, and 325 mesh. Fractions may be weighed on a Mettler balance to estimate size distribution. This provides determination of the quantitative ratio by particle diameter of composition comprising extended release particles. Sieve analysis according to standard United States Pharmacopoeia methods (e.g., USP-23 NF 18), may be done such as by using a Meinzer II Sieve Shaker.

In one embodiment, the method for preparing dosage forms of the pharmaceutical composition may comprise wet granulating a first mixture comprising the opioid, the API, and a binder to produce a first granulation mixture. The wet granulation process may be a fluid bed granulation process. In additional embodiments, the first mixture may further comprise at least one additional excipient selected from the group consisting of fillers, lubricants, antioxidants, chelating agents, and color agents. The first granulation mixture may be blended with an extended release polymer and one or more excipients, as listed above, to form at least one extended release portion of a dosage form. In another embodiment, the extended release polymer may be a polyethylene oxide.

In another embodiment, the method further comprises wet granulating a second mixture comprising the opioid, the API, and a binder to form a second granulation mixture. The wet granulation process may be a fluid bed granulation process. In some embodiments, the second mixture may further comprise at least one additional excipient selected from the group consisting of fillers, lubricants, disintegrants, antioxidants, chelating agents, and color agents. The second granulation mixture may be blended with one or more excipients, as listed above, to form at least one immediate release portion of a dosage form.

In an additional embodiment, the method may further comprise compressing the at least one extended release portion and the at least one immediate release portion into a tablet. The tablet may be a bilayer tablet. The tablet may be coated with a tablet coating.

In another embodiment, the method may comprise granulating via a high shear wet granulation process a mixture comprising the opioid and at least one excipient to form opioid particles. The opioid particles may be dried at a suitable temperature. The opioid particles may be granulated via a fluid bed granulation process with the API, a binder, and an optional excipient to form a first granulation mixture. The first granulation mixture may be blended with an extended release polymer and at least one excipient to form an extended release portion of a solid dosage form.

In a further embodiment, the method may further comprise granulating via a fluid bed granulation process opioid particles with the API, a binder, and an optional excipient to form a second granulation mixture. The second granulation mixture may be blended with one or more excipients to form an immediate release portion of a solid dosage form.

In an additional embodiment, the method may further comprise compressing the at least one extended release portion comprising opioid particles and the at least one immediate release portion comprising opioid particles into a tablet. In one embodiment, the method comprises compressing one extended release portion comprising opioid particle and one immediate release portion comprising opioid particles into a bilayer tablet. The tablet may be coated with a tablet coating.

In another embodiment, wet granulation of either mixture may produce particles with a bulk density ranging from about 0.30 to 0.40 grams/milliliter (g/mL). In other aspects, the wet granulation may produce particles with a tap density ranging from about 0.35 g/mL to about 0.45 g/mL. In other embodiments, the wet granulation may produce particles, wherein at least about 50% of the particles have a size greater than 125 microns. In still other embodiments, the wet granulation may produce particles wherein about 20% to about 65% of the particles have a size greater than about 125 microns and less than about 250 microns.

Tablets generally are characterized with respect to disintegration and dissolution release profiles as well as tablet hardness, friability, and content uniformity.

In vitro dissolution profiles for the tablets may be determined using a USP Type II apparatus, at a paddle speed of about 150 rpm, in 0.1 N HCl, at 37° C. Samples of 5 mL at each time-point, may be taken without media replacement at 0.8, 0.25, 0.5, 1, 2, 4, 6, 8 and 12 hours, for example. In some embodiments, the dissolution profiles may be determined at varying pH values, such as at a pH of about 3.0, 3.5, 4.0, 4.5, 5.0, 5.5, 6.0 or 6.5. The fluid used may be, for example, HCl, phosphate buffer, or simulated gastric fluid. The resulting cumulative dissolution profiles for the tablets are based upon a theoretical percent active added to the pharmaceutical compositions.

A tablet preferably disintegrates before it dissolves. A disintegration tester measures the time it takes a tablet to break apart in solution. The tester suspends tablets in a solution bath for visual monitoring of the disintegration rate. Both the time to disintegration and the disintegration consistency of all tablets may be measured. The disintegration profile may be determined in a USP Disintegration Tester in pH 5.8 phosphate buffer or 0.1 N HCl of pH 1.2. The fluid used may be, for example, HCl, phosphate buffer, or simulated gastric fluid. Samples, 1-5 mL at each time-point, may be taken, for example, without media replacement at 0.5, 1, 2, 3, 4, 5, 6, 7 and 8 hours. The resulting cumulative disintegration profiles are based upon a theoretical percent active added to the pharmaceutical compositions.

After tablets are formed by compression, it is desired that the tablets have a strength of at least 9-25 Kiloponds (kp), preferably at least about 12-20 (kp). A hardness tester generally is used to determine the load required to diametrically break the tablets (crushing strength) into two equal halves. The fracture force may be measured using a Venkel Tablet Hardness Tester, using standard USP protocols.

Friability is a well-known measure of a tablet's resistance to surface abrasion that measures weight loss in percentage after subjecting the tablets to a standardized agitation procedure. Friability properties are especially important during any transport of the dosage form as any fracturing of the final dosage form may result in a subject receiving less than the prescribed medication. Friability may be determined using a Roche Friability Drum according to standard USP guidelines which specifies the number of samples, the total number of drum revolutions, and the drum rpm to be used. Friability values of from 0.8 to 1.0% are regarded as constituting the upper limit of acceptability.

The prepared tablets generally are tested for content uniformity to determine if they meet the pharmaceutical requirement of an acceptance value of 15 or less. Each tablet is placed in a solution of 60% methanol/40% isopropanol and stirred at room temperature until the tablet disintegrates.

The solution containing the dissolved tablet generally is further diluted in 90% water/10% isopropanol/0.1% heptafluorobutyric acid and analyzed by HPLC.

IV. Methods for Administering a Gastric Retentive Pharmaceutical Composition

A further aspect of the disclosure encompasses a method for administering a gastric retentive pharmaceutical composition comprising at least one opioid disclosed herein to a subject in need thereof. The method comprises orally administering an effective amount of the gastric retentive pharmaceutical composition to the subject, wherein the subject is in a fasted state. Moreover, upon administration of the pharmaceutical composition, the opioid in the composition produces a plasma profile characterized by at least one pharmacokinetic parameter that differs by less than about 30% when the subject is in a fasted state as compared to a fed state.

The subject in need thereof may be suffering from pain or diagnosed with a condition associated with pain. Suitable pain conditions are detailed below. In some embodiments, the subject may be suffering from or diagnosed with chronic pain. In yet another embodiment, the subject may be suffering from or diagnosed with acute pain. In yet other embodiments, the subject may be suffering from or diagnosed with both chronic and acute pain. The subject may be a mammal, and preferably the subject may be a human.

The gastric retentive pharmaceutical composition generally is administered to a subject in a fasted state. A fasted state may be defined as not having ingested food for at least 10 hours prior to administration of the pharmaceutical composition. In some embodiments, the subject may have fasted for at least 10 hours prior to the first dose and refrains from ingesting food for at least one hour prior to administration of subsequent doses. In other embodiments, the fasted subject may not have ingested food for at least 1 hour, 2 hours, 3 hours, 4 hours, 5 hours, 6 hours, 7 hours, 8 hours, 9 hours, or 10 hours prior to administration of each dose of the pharmaceutical composition.

An effective amount of the pharmaceutical composition may comprise from about 5 mg to about 300 mg of the opioid and from about 100 mg to about 1300 mg of the other API. In embodiments in which the opioid is oxycodone and the API is acetaminophen, the pharmaceutical composition may comprise from about 7.5 mg to about 30 mg of oxycodone and from about 250 mg to about 1300 mg of acetaminophen. In one exemplary embodiment, an effective amount of the pharmaceutical composition may comprise 15 mg of oxycodone and 650 mg of acetaminophen, wherein one solid dosage form comprising 15 mg of oxycodone and 650 mg of acetaminophen is administered. In another exemplary embodiment, effective amount of the pharmaceutical composition may comprise about 15 mg of oxycodone and about 650 mg of acetaminophen, wherein two solid dosage forms each comprising 7.5 mg of oxycodone and 325 mg of acetaminophen is administered. In still another exemplary embodiment, an effective amount of the pharmaceutical composition may comprise 7.5 mg of oxycodone and 325 mg of acetaminophen, wherein one solid dosage form comprising 7.5 mg of oxycodone and 325 mg of acetaminophen is administered. In yet another embodiment, the effective amount of a pharmaceutical composition may be 20 mg of oxycodone and 650 mg of acetaminophen. For example, one solid dosage form comprising 20 mg of oxycodone and 650 mg of acetaminophen may be administered. Alternatively, two solid dosage forms with each comprising 10 mg of oxycodone and 325 mg of acetaminophen may be administered. In another embodiment, the effective amount of a pharmaceutical composition may be 10 mg of oxycodone and 325 mg of acetaminophen, wherein one solid dosage form comprising 10 mg of oxycodone and 325 mg of acetaminophen may be administered. In still yet another embodiment, the effective amount of a pharmaceutical composition may be 30 mg of oxycodone and 650 mg of acetaminophen. For example, one solid dosage form comprising 30 mg of oxycodone and 650 mg of acetaminophen may be administered. Alternatively, two solid dosage forms with each comprising 15 mg of oxycodone and 325 mg of acetaminophen may be administered. In another embodiment, the effective amount of a pharmaceutical composition may be 15 mg of oxycodone and 325 mg of acetaminophen, wherein one solid dosage form comprising 15 mg of oxycodone and 325 mg of acetaminophen may be administered.

The dosing intervals of the effective amount of the pharmaceutical composition can and will vary. For example, an effective amount of the pharmaceutical composition may be administered once a day, twice a day, or three times a day. In one embodiment, an effective amount of the pharmaceutical composition may be administered twice a day.

The pharmacokinetic parameter of the active agent(s) of the pharmaceutical composition that differs by less that about 30% under fed and fasted conditions may be, but is not limited to, Cmax, C1hr, C2hr, AUC, partial AUC, $T_{max}$, and Tlag. In various embodiments, the pharmacokinetic parameter may vary by less than about 25%, 20%, 15%, 10%, or 5% under fed and fasted conditions.

In embodiments in which the pharmaceutical composition comprises oxycodone and acetaminophen, the Cmax or AUC of oxycodone and the Cmax or AUC of acetaminophen may each individually vary by less than about 30%, 29%, 28%, 27%, 26%, 25%, 24%, 23%, 22%, 21%, 20%, 19%, 18%, 17%, 16%, 15%, 14%. 13%, 12%, 11%, 10%, 9%, 8%, 7%, 6%, 5%, 4%, 3%, 2%, or 1% under fed and fasted conditions.

Suitable pain conditions for which the subject in need may be suffering from or diagnosed with include without limitation headache pain, pain associated with migraine, neuropathic pain selected from the group consisting of diabetic neuropathy, HIV sensory neuropathy, post-herpetic neuralgia, post-thoracotomy pain, trigeminal neuralgia, radiculopathy, neuropathic pain associated with chemotherapy, reflex sympathetic dystrophy, back pain, peripheral neuropathy, entrapment neuropathy, phantom limb pain, and complex regional pain syndrome, dental pain, pain associated with a surgical procedure and or other medical intervention, bone cancer pain, joint pain associated with psoriatic arthritis, osteoarthritic pain, rheumatoid arthritic pain, juvenile chronic arthritis associated pain, juvenile idiopathic arthritis associated pain, Spondyloarthropathies (such as ankylosing spondylitis (Mb Bechterew) and reactive arthritis (Reiter's syndrome) associated pain), pain associated with psoriatic arthritis, gout pain, pain associated with pseudogout (pyrophosphate arthritis), pain associated with systemic lupus erythematosus (SLE), pain associated with systemic sclerosis (scleroderma), pain associated with Behcet's disease, pain associated with relapsing polychondritis, pain associated with adult Still's disease, pain associated with transient regional osteoporosis, pain associated with neuropathic arthropathy, pain associated with sarcoidosis, arthritic pain, rheumatic pain, joint pain, osteoarthritic joint pain, rheumatoid arthritic joint pain, juvenile chronic arthritis associated joint pain, juvenile idiopathic arthritis associated joint pain, Spondyloarthropathies (such as ankylosing spondylitis (Mb Bechterew) and reactive arthritis (Reiter's syndrome) associated joint pain), gout joint pain, joint pain associated with pseudogout (pyrophosphate arthritis), joint pain associated with systemic lupus erythematosus (SLE), joint pain associated with systemic sclerosis (scleroderma), joint pain associated with Behcet's disease, joint pain associated with relapsing polychondritis, joint pain associated with adult Still's disease, joint pain associated with transient regional osteoporosis, joint pain associated with neuropathic arthropathy, joint pain associated with sarcoidosis, arthritic joint pain, rheumatic joint pain, acute pain, acute joint pain, chronic pain, chronic joint pain, inflammatory pain, inflammatory joint pain, mechanical pain, mechanical joint pain, pain associated with the fibromyalgia syndrome (FMS), pain associated with polymyalgia rheumatica, monarticular joint pain, polyarticular joint pain, nociceptive pain, psychogenous pain, pain of unknown etiology, pain mediated by IL-6, IL-6 soluble receptor, or IL-6 receptor, pain associated with a surgical procedure in a patient with a clinical diagnosis of OA, pain like static allodynia, pain like dynamic allodynia, and/or pain associated with Crohn's disease.

It is to be understood that any ranges, ratios and ranges of ratios that can be formed by, or derived from, any of the data disclosed herein represent further embodiments of the present disclosure and are included as part of the disclosure as though they were explicitly set forth. This includes ranges that can be formed that do or do not include a finite upper and/or lower boundary. Accordingly, a person of ordinary skill in the art most closely related to a particular range, ratio or range of ratios will appreciate that such values are unambiguously derivable from the data presented herein.

Having described the invention in detail, it will be apparent that modifications and variations are possible without departing from the scope of the invention defined in the appended claims.

EXAMPLES

The following examples are included to demonstrate certain embodiments of the invention. Those of skill in the art should, however, in light of the present disclosure, appreciate that modifications can be made in the specific embodiments that are disclosed and still obtain a like or similar result without departing from the spirit and scope of the invention, therefore all matter set forth is to be interpreted as illustrative and not in a limiting sense.

Example 1

In Vitro Dissolution of Controlled-Release Bilayer Tablets

Controlled-release bilayer tablets were prepared containing 15 mg of oxycodone and 500 mg of acetaminophen (APAP), or 30 mg of oxycodone and 500 mg APAP. (See selected examples from Chart No. 3.) The ER layer contained 75% of the total amount of oxycodone in the tablet, 50% of the total amount of APAP in the tablet, and either 35% w/w POLYOX® 1105 (for fast release), 45% w/w POLYOX® 1105 (for medium release), or 45% w/w POLYOX® N60K (for slow release). The IR layer contained 25% of the total amount of oxycodone in the tablet and 50% of the total amount of APAP in the tablet.

Dissolution profiles for the three above-described compositions were determined in USP Type II apparatus. Six tablets of each composition were weighed, placed in a sinker, and dropped into an equilibrated dissolution bath vessel that contained 900 mL of (helium sparged) 0.1 N HCl that was heated to 37° C.±0.5° C. The mixture was stirred at 150±6 rpm and the temperature was maintained at 37° C.±0.5° C. for 12 hr. The bath vessel was covered with a low evaporation vessel cover. Samples (5 mL) were removed at 0.25, 0.5, 1, 2, 4, 6, 8, and 12 hours. Each sample was filtered through a 0.45 µm filter and analyzed by HPLC using standard procedures.

The cumulative release of oxycodone and APAP from 15 mg oxycodone/500 mg APAP tablets is presented in Table 1. Table 2 presents the cumulative release of oxycodone and APAP from 30 mg oxycodone/500 mg APAP (30/500) tablets. FIG. 1 presents the release profile of oxycodone from the 15/500 and 30/500 tablets. The dissolution profile of APAP from the 15/500 and 30/500 tablets is shown in FIG. 2. The release of oxycodone and APAP from the fast release and medium release tablets was essentially linear during the first half of the 12 hour time period but then plateaued during the last half of the 12 hour time period. The release of oxycodone and APAP from the slow release tablets was essentially linear during the entire 12 hour time period.

TABLE 1

Cumulative Release - 15 mg oxycodone/500 mg APAP Tablets

| Time (hr) | Oxycodone (%) | | | APAP (%) | | |
| --- | --- | --- | --- | --- | --- | --- |
| | Fast | Medium | Slow | Fast | Medium | Slow |
| 0.25 | 27.56 | 25.70 | 25.68 | 54.78 | 53.06 | 53.01 |
| 0.5 | 34.33 | 31.31 | 30.39 | 57.55 | 55.73 | 54.89 |
| 1.0 | — | 40.85 | 37.81 | — | 60.03 | 58.03 |
| 2.0 | 59.88 | 55.67 | 49.50 | 71.42 | 68.16 | 63.27 |
| 4.0 | 83.46 | 77.94 | 67.43 | 86.17 | 81.55 | 72.31 |
| 6.0 | 97.48 | 92.12 | 80.53 | 96.19 | 91.62 | 79.97 |
| 8.0 | 101.26 | 99.26 | 90.20 | 100.16 | 96.96 | 86.06 |
| 12.0 | 101.57 | 101.23 | 99.36 | 100.10 | 99.16 | 94.41 |

TABLE 2

Cumulative Release - 30 mg oxycodone/500 mg APAP Tablets

| Time (hr) | Oxycodone (%) | | | APAP (%) | | |
| --- | --- | --- | --- | --- | --- | --- |
| | Fast | Medium | Slow | Fast | Medium | Slow |
| 0.25 | 31.65 | 30.27 | 29.78 | 54.17 | 52.97 | 52.97 |
| 0.5 | 37.55 | 35.91 | 34.42 | 56.96 | 55.64 | 54.97 |
| 1.0 | 47.18 | 45.21 | 41.12 | 61.81 | 60.19 | 58.15 |
| 2.0 | 62.51 | 59.63 | 52.40 | 70.60 | 68.04 | 63.61 |
| 4.0 | 84.72 | 80.44 | 70.01 | 85.28 | 81.56 | 73.04 |
| 6.0 | 96.97 | 93.98 | 82.49 | 94.57 | 91.42 | 80.94 |
| 8.0 | 100.23 | 99.63 | 91.78 | 97.91 | 96.48 | 87.26 |
| 12.0 | 100.57 | 101.13 | 99.60 | 98.09 | 98.14 | 95.25 |

The cumulative in vitro release of oxycodone and APAP from 7.5 mg oxycodone/325 mg APAP medium release tablets is presented in Table 3. The ER layer of these tablets contained 5.625 mg of oxycodone, 162.5 mg of APAP, and 45% (w/w) POLYOX® 1105, and the IR layer contained 1.875 mg of oxycodone and 162.5 mg of APAP. (See selected example from Chart 2.) The dissolution profile was determined essentially as described above, except that samples were collected at 0.08 hour (~5 min) in addition to the later time points.

TABLE 3

Cumulative Release
7.5 mg oxycodone/325 mg APAP Tablets

| Time (hr) | Oxycodone (%) Mean (%) | % RSD (%) | APAP (%) Mean (%) | % RSD (%) |
|---|---|---|---|---|
| 0.08 | 26.6 | 4.3 | 49.0 | 3.4 |
| 0.25 | 31.5 | 4.2 | 51.3 | 3.1 |
| 0.5 | 37.5 | 2.7 | 53.8 | 2.9 |
| 1.0 | 45.9 | 1.6 | 58.2 | 2.5 |
| 2.0 | 60.1 | 1.7 | 66.0 | 2.3 |
| 4.0 | 81.4 | 1.1 | 78.7 | 1.7 |
| 6.0 | 95.4 | 1.4 | 88.4 | 1.9 |
| 8.0 | 101.8 | 0.9 | 93.9 | 1.4 |
| 12.0 | 103.2 | 1.2 | 94.9 | 1.1 |

FIG. 3 and FIG. 4 present the percentage of oxycodone and APAP, respectively, released from two different lots of 7.5/325 tablets as compared to 15/650 tablets (see Example 30 for the dissolution data of the 15 mg oxycodone/650 acetaminophen tablets). The dissolution profiles were similar among all the tablets.

The release of oxycodone and APAP from each layer was analyzed by determining the calculated release from the ER layer and actual release from the total composition. For this, the tablets contained 7.5 mg of oxycodone HCl and 325 mg of APAP (i.e., the ER layer contained 5.625 mg of oxycodone HCl, 162.5 mg of APAP, and 45% (w/w) POLYOX® 1105; and the IR layer contained 1.875 mg of oxycodone HCl and 162.5 mg of APAP). The dissolution profile was determined essentially as described above. The calculated cumulative release of oxycodone HCl from the ER layer and the total tablet is presented in Table 4, and the calculated cumulative release of APAP from the ER layer and the total tablet is presented in Table 5. These data show that essentially all of the 1.875 mg of oxycodone HCl in the IR layer was released within about 5 minutes and essentially all of the 162.5 mg of APAP in the IR layer was released within about 15 minutes.

TABLE 4

Split Release of Oxycodone
7.5 mg oxycodone/325 mg APAP Tablets

| Time (hr) | Total (%) | Total (mg) | ER (%) | ER (mg) |
|---|---|---|---|---|
| 0.08 | 26.6 | 2.00 | 2.1 | 0.12 |
| 0.25 | 31.5 | 2.36 | 8.7 | 0.49 |
| 0.5 | 37.5 | 2.81 | 16.7 | 0.94 |
| 1.0 | 45.9 | 3.44 | 27.9 | 1.57 |
| 2.0 | 60.1 | 4.51 | 46.8 | 2.63 |
| 4.0 | 81.4 | 6.11 | 75.2 | 4.23 |
| 6.0 | 95.4 | 7.16 | 93.9 | 5.28 |
| 8.0 | 101.8 | 7.64 | 102.4 | 5.76 |
| 12.0 | 103.2 | 7.74 | 104.3 | 5.87 |

TABLE 5

Split Release of APAP
7.5 mg oxycodone/325 mg APAP Tablets

| Time (hr) | Total (%) | Total (mg) | ER (%) | ER (mg) |
|---|---|---|---|---|
| 0.08 | 49.0 | 159.25 | 0.0 | 0.00 |
| 0.25 | 51.3 | 166.73 | 2.6 | 4.22 |
| 0.5 | 53.8 | 174.85 | 7.6 | 12.35 |
| 1.0 | 58.2 | 189.15 | 16.4 | 26.65 |
| 2.0 | 66.0 | 214.50 | 32.0 | 52.00 |
| 4.0 | 78.7 | 255.78 | 57.4 | 93.28 |
| 6.0 | 88.4 | 287.30 | 76.8 | 124.80 |
| 8.0 | 93.9 | 305.18 | 87.8 | 142.68 |
| 12.0 | 94.9 | 308.43 | 89.8 | 145.93 |

Example 2

Clinical Pharmacokinetic Analysis of Controlled-Release 15 mg Oxycodone/500 Mg Acetaminophen Bilayer Tablets—Single Dose An open-label, single dose, four-period crossover study was conducted to evaluate the pharmacokinetics (PK) and bioavailability of three controlled-release bilayer tablets comprising 15 mg oxycodone (OC) and 500 mg APAP as compared to a commercially available immediate-release tablet containing 7.5 mg oxycodone/325 mg acetaminophen. The three controlled release formulations—fast, medium, and slow—described above. (See selected examples from Chart No. 3.) One tablet of each of the controlled-release bilayer formulations was administered to the test subjects under fed conditions. One tablet of the commercially available immediate-release tablet containing 7.5 mg oxycodone/ 325 mg acetaminophen was administered every 6 hours (Q6h) for two doses under fed conditions. The test subjects were about 40 normal, healthy male subjects between 21-45 years of age.

Subjects were randomly assigned to Treatments A, B, C, and D using a four-period, eight-sequence, crossover design as follows:

Treatment A: One (1) tablet of 15 mg OC/500 mg APAP, Fast Release administered orally under fed conditions.

Treatment B: One (1) tablet of 15 mg OC/500 mg APAP, Medium Release administered orally under fed conditions.

Treatment C: One (1) tablet of 15 mg OC/500 mg APAP, Slow Release administered orally under fed conditions.

Treatment D: One (1) tablet of a commercially available immediate-release tablet containing 7.5 mg oxycodone/ 325 mg administered orally Q6h for two (2) doses under fed conditions.

The crossover design allowed for within-subject comparisons among the test formulations with differing release profiles. Subjects received each of the study drug treatments (A-D) separated by at least a 7-day interval between the start of each period at Hour 0. During each period, subjects remained in the clinical facility from the time of check-in (on the day prior to dosing) until discharge on Day 3 (after the 48 hour blood draw).

Physical examinations, electrocardiograms and clinical laboratory tests were performed at screening and at the conclusion of the study (or early termination). Vital sign measurements (including pulse oximetry) and adverse events were monitored during the study. Subjects were administered a 50 mg naltrexone tablet 12 hours prior to Hour 0 dosing, at Hour 0, and 12 hours post-dose to block the effects and potential risks of oxycodone. After a 10 hour overnight fast, subjects were served a standardized FDA high-fat breakfast to be consumed in 30 minutes or less prior to Hour 0 dosing for the first oral dosage. All subjects in each period were served a standardized meal to be consumed in 30 minutes or less prior to Hour 6. Only subjects randomized to Treatment D were administered the second oral dosage of the commercially available immediate-release tablet containing 7.5 mg oxycodone/325 mg acetaminophen at Hour 6 in each period.

Blood was drawn at designated times for PK analysis. Samples (6 mL in pre-chilled vacuum blood collection tubes, containing K2EDTA as the anticoagulant) were taken pre-dose (up to 60 minutes prior to dose), 10 min, 20 min, 30 min, 40 min and 1, 2, 3, 4, 5, 6, 6.5, 7, 8, 9, 10, 12, 16, 18, 20, 24, 36 and 48 hours post-dose. The collected plasma samples were analyzed for the active pharmaceutical ingredients (APIs), i.e., oxycodone and acetaminophen, using validated liquid chromatography/tandem mass spectrometry (LC-MS/MS) assays.

The following PK parameters were calculated for oxycodone and acetaminophen using standard non-compartmental methods:

area under the plasma concentration curve to last quantifiable concentration $AUC_{(0-t)}$ area under the plasma concentration curve to infinite time $AUC_{(0-inf)}$ maximum observed plasma concentration ($C_{max}$)

time observed maximum plasma concentration ($t_{max}$)

lag time ($t_{lag}$)

apparent first-order terminal elimination rate constant ($k_{el}$)

apparent plasma terminal elimination half-life ($t_{1/2}$)

Parametric general linear model (GLM) methodology was used in the analysis of all pharmacokinetic parameters. The SAS GLM procedure was used to perform analysis of variance (ANOVA) on each pharmacokinetic parameter with sequence, treatment, period, and subjects nested within sequences, as sources of variation. For each formulation, least squares means and the associated standard errors were obtained using the LSMEANS option. All treatment pairwise comparisons were performed, without adjustment for multiplicity. AUC and $C_{max}$ were dose-adjusted for comparative purposes for acetaminophen and the commercially available immediate-release tablet containing 7.5 mg oxycodone/325 mg acetaminophen.

The pharmacokinetic data for oxycodone and APAP are presented in Tables 6-8 and 9-11, respectively.

TABLE 6

Oxycodone Pharmacokinetics (15/500)

| Parameter | Fast Release Formulation | | | | Commercially available immediate-release tablet |
|---|---|---|---|---|---|
| | Mean (% CV) | LSM Ratio | 90% CI Lower | 90% CI Upper | Mean (% CV) |
| $C_{max}$ (ng/mL) | 18.803 (21) | 82.92 | 78.02 | 88.12 | 22.428 (20) |
| $C_{1\,hr}$ (ng/mL) | 6.891 (77) | 72.79 | 49.02 | 108.1 | 10.226 (65) |
| $C_{2\,hr}{}^a$ (ng/mL) | 12.355 (32) | 80.74 | 71.2 | 91.56 | 14.94 (26) |
| $AUC_{0-t}$ (ng · hr/mL) | 209.949 (26) | 89.73 | 86.52 | 93.06 | 229.788 (22) |
| $AUC_{0-inf}$ (ng · hr/mL) | 211.8 (25) | 89.95 | 86.77 | 93..24 | 231.421 (22) |
| $AUC_{0-1\,hr}$ (ng · hr/mL) | 2.565 (104) | 61.32 | 37.64 | 99.92 | 4.334 (80) |
| $AUC_{0-2\,hr}{}^b$ (ng · hr/mL) | 12.189 (53) | 70.16 | 55.97 | 87.95 | 16.917 (46) |
| $AUC_{0-4\,hr}{}^c$ (ng · hr/mL) | 41.3 (29) | 88.76 | 80.61 | 97.73 | 45.699 (24) |
| $T_{max}$ (hr) | 4.954 (34) | na | na | na | 7.954 (22) |
| $T_{lag}$ (hr) | 0.31 (68) | na | na | na | 0.219 (77) |
| $T_{1/2}$ (hr) | 4.584 (17) | na | na | na | 4.495 (14) |
| $K_{el}$ (1/hr) | 0.155 (16) | na | na | na | 0.157 (13) |

$^a$Concentration at the median $T_{max}$ for commercially-available immediate release tablet
$^b$AUC from zero to the median $T_{max}$ for commercially-available immediate release tablet
$^c$AUC from the zero to the median $T_{max}$ + 2SD for commercially-available immediate release tablet

TABLE 7

Oxycodone Pharmacokinetics (15/500)

| Parameter | Medium Release Formulation | | | | Commercially-available immediate release tablet |
|---|---|---|---|---|---|
| | Mean (% CV) | LSM Ratio | 90% CI Lower | 90% CI Upper | Mean (% CV) |
| $C_{max}$ (ng/mL) | 18.266 (25) | 80.87 | 76.09 | 85.95 | 22.428 (20) |
| $C_{1\,hr}$ (ng/mL) | 7.364 (81) | 67.62 | 45.75 | 99.95 | 10.226 (65) |
| $C_{2\,hr}{}^a$ (ng/mL) | 12.388 (45) | 79.04 | 69.69 | 89.64 | 14.94 (26) |
| $AUC_{0-t}$ (ng · hr/mL) | 217.188 (23) | 94.19 | 90.82 | 97.68 | 229.788 (22) |
| $AUC_{0-inf}$ (ng · hr/mL) | 218.545 (23) | 94.09 | 90.77 | 97.54 | 231.421 (22) |
| $AUC_{0-1\,hr}$ (ng · hr/mL) | 3.248 (118) | 64.69 | 39.93 | 104.8 | 4.334 (80) |

TABLE 7-continued

Oxycodone Pharmacokinetics (15/500)

| Parameter | Medium Release Formulation | | | | Commercially-available immediate release tablet |
|---|---|---|---|---|---|
| | Mean (% CV) | LSM Ratio | 90% CI Lower | 90% CI Upper | Mean (% CV) |
| $AUC_{0-2\ hr}{}^{b}$ (ng · hr/mL) | 13.124 (70) | 71.74 | 57.22 | 89.96 | 16.917 (46) |
| $AUC_{0-4\ hr}{}^{c}$ (ng · hr/mL) | 42.101 (43) | 88.61 | 80.47 | 97.58 | 45.699 (24) |
| $T_{max}$ (hr) | 5.31 (38) | na | na | na | 7.954 (22) |
| $T_{lag}$ (hr) | 0.264 (64) | na | na | na | 0.219 (77) |
| $T_{1/2}$ (hr) | 4.557 (16) | na | na | na | 4.495 (14) |
| $K_{el}$ (1/hr) | 0.156 (16) | na | na | na | 0.157 (13) |

[a] Concentration at the median $T_{max}$ for commercially-available immediate release tablet
[b] AUC from zero to the median $T_{max}$ for commercially-available immediate release tablet
[c] AUC from the zero to the median $T_{max}$ + 2SD for commercially-available immediate release tablet

TABLE 8

Oxycodone Pharmacokinetics (15/500)

| Parameter | Slow Release Formulation | | | | Commercially-available immediate release tablet |
|---|---|---|---|---|---|
| | Mean (% CV) | LSM Ratio | 90% CI Lower | 90% CI Upper | Mean (% CV) |
| $C_{max}$ (ng/mL) | 17.403 (25) | 76.75 | 72.21 | 81.58 | 22.428 (20) |
| $C_{1\ hr}$ (ng/mL) | 7.601 (79) | 69.63 | 47.08 | 102.97 | 10.226 (65) |
| $C_{2\ hr}{}^{a}$ (ng/mL) | 11.237 (39) | 73.55 | 64.84 | 83.43 | 14.94 (26) |
| $AUC_{0-t}$ (ng · hr/mL) | 222.096 (25) | 95.62 | 92.2 | 99.18 | 229.788 (22) |
| $AUC_{0-inf}$ (ng · hr/mL) | 223.553 (25) | 95.61 | 92.22 | 99.11 | 231.421 (22) |
| $AUC_{0-1\ hr}$ (ng · hr/mL) | 2.893 (112) | 57.34 | 35.37 | 92.95 | 4.334 (80) |
| $AUC_{0-2\ hr}{}^{b}$ (ng · hr/mL) | 12.312 (66) | 68.63 | 54.72 | 86.08 | 16.917 (46) |
| $AUC_{0-4\ hr}{}^{c}$ (ng · hr/mL) | 38.842 (35) | 83.46 | 75.78 | 91.92 | 45.699 (24) |
| $T_{max}$ (hr) | 5.655 (27) | na | na | na | 7.954 (22) |
| $T_{lag}$ (hr) | 0.299 (74) | na | na | na | 0.219 (77) |
| $T_{1/2}$ (hr) | 4.647 (19) | na | na | na | 4.495 (14) |
| $K_{el}$ (1/hr) | 0.154 (18) | na | na | na | 0.157 (13) |

[a] Concentration at the median $T_{max}$ for commercially-available immediate release tablet
[b] AUC from zero to the median $T_{max}$ for commercially-available immediate release tablet
[c] AUC from the zero to the median $T_{max}$ + 2SD for commercially-available immediate release tablet

TABLE 9

Acetaminophen Pharmacokinetics (15/500)

| Parameter | Fast Release Formulation | | | | Commercially-available immediate release tablet* |
|---|---|---|---|---|---|
| | Mean (% CV) | LSM Ratio | 90% CI Lower | 90% CI Upper | Mean (% CV) |
| $C_{max}$ (ng/mL) | 2612 (26) | 94.46 | 87.25 | 102.26 | 2721 (22) |
| $C_{1\ hr}$ (ng/mL) | 1627 (66) | 113.22 | 84.91 | 150.98 | 1516 (58) |
| $C_{2\ hr}^{a}$ (ng/mL) | 2248 (30) | 118.49 | 107.61 | 130.48 | 1841 (20) |
| $AUC_{0-t}$ (ng · hr/mL) | 21944 (27) | 98.78 | 95.91 | 101.75 | 21962 (22) |
| $AUC_{0-inf}$ (ng · hr/mL) | 23090 (27) | 98.73 | 95.85 | 101.7 | 23104 (21) |
| $AUC_{0-1\ hr}$ (ng · hr/mL) | 823 (96) | 105.42 | 68.75 | 161.64 | 814 (82) |
| $AUC_{0-2\ hr}^{b}$ (ng · hr/mL) | 2761 (52) | 106.73 | 86.55 | 131.62 | 2492 (47) |
| $AUC_{0-4\ hr}^{c}$ (ng · hr/mL) | 7006 (28) | 119.91 | 110.42 | 130.2 | 5726 (22) |
| $T_{max}$ (hr) | 2.328 (58) | na | na | na | 6.971 (34) |
| $T_{lag}$ (hr) | 0.276 (81) | na | na | na | 0.219 (98) |
| $T_{1/2}$ (hr) | 5.235 (35) | na | na | na | 6.461 (66) |
| $K_{el}$ (1/hr) | 0.145 (28) | na | na | na | 0.137 (39) |

*Dose Normalized to 500 mg
[a] Concentration at the median $T_{max}$ for commercially-available immediate release tablet
[b] AUC from zero to the median $T_{max}$ for commercially-available immediate release tablet
[c] AUC from the zero to the median $T_{max}$ + 2SD for commercially-available immediate release tablet

TABLE 10

Acetaminophen Pharmacokinetics (15/500)

| Parameter | Medium Release Formulation | | | | Commercially-available immediate release tablet* |
|---|---|---|---|---|---|
| | Mean (% CV) | LSM Ratio | 90% CI Lower | 90% CI Upper | Mean (% CV) |
| $C_{max}$ (ng/mL) | 2720 (22) | 99.19 | 91.61 | 107.39 | 2721 (22) |
| $C_{1\ hr}$ (ng/mL) | 1831 (54) | 121.62 | 91.51 | 161.65 | 1516 (58) |
| $C_{2\ hr}^{a}$ (ng/mL) | 2170 (23) | 116.69 | 105.96 | 128.51 | 1841 (20) |
| $AUC_{0-t}$ (ng · hr/mL) | 22184 (22) | 100.68 | 97.74 | 103.7 | 21962 (22) |
| $AUC_{0-inf}$ (ng · hr/mL) | 23554 (22) | 101.39 | 98.43 | 104.44 | 23104 (21) |
| $AUC_{0-1\ hr}$ (ng · hr/mL) | 974 (85) | 124.39 | 81.52 | 189.79 | 814 (82) |
| $AUC_{0-2\ hr}^{b}$ (ng · hr/mL) | 2974 (47) | 117.9 | 95.58 | 145.43 | 2492 (47) |
| $AUC_{0-4\ hr}^{c}$ (ng · hr/mL) | 7122 (23) | 123.98 | 114.17 | 134.64 | 5726 (22) |
| $T_{max}$ (hr) | 2.069 (66) | na | na | na | 6.971 (34) |
| $T_{lag}$ (hr) | 0.218 (77) | na | na | na | 0.219 (98) |

TABLE 10-continued

Acetaminophen Pharmacokinetics (15/500)

|  | Medium Release Formulation | | | | Commercially-available immediate release tablet* |
|---|---|---|---|---|---|
|  | Mean | LSM | 90% CI | | Mean |
| Parameter | (% CV) | Ratio | Lower | Upper | (% CV) |
| $T_{1/2}$ (hr) | 5.696 (33) | na | na | na | 6.461 (66) |
| $K_{el}$ (1/hr) | 0.133 (29) | na | na | na | 0.137 (39) |

*Dose Normalized to 500 mg
[a] Concentration at the median $T_{max}$ for commercially-available immediate release tablet
[b] AUC from zero to the median $T_{max}$ for commercially-available immediate release tablet
[c] AUC from the zero to the median $T_{max}$ + 2SD for commercially-available immediate release tablet

TABLE 11

Acetaminophen Pharmacokinetics (15/500)

|  | Slow Release Formulation | | | | Commercially-available immediate release tablet* |
|---|---|---|---|---|---|
|  | Mean | LSM | 90% CI | | Mean |
| Parameter | (% CV) | Ratio | Lower | Upper | (% CV) |
| $C_{max}$ (ng/mL) | 2521 (18) | 93.6 | 86.44 | 101.35 | 2721 (22) |
| $C_{1\,hr}$ (ng/mL) | 1766 (51) | 126.26 | 94.96 | 167.87 | 1516 (58) |
| $C_{2\,hr}{}^{a}$ (ng/mL) | 2113 (18) | 116.18 | 105.48 | 127.96 | 1841 (20) |
| $AUC_{0-t}$ (ng · hr/mL) | 21947 (25) | 99.61 | 96.7 | 102.61 | 21962 (22) |
| $AUC_{0-inf}$ (ng · hr/mL) | 23279 (25) | 100.47 | 97.53 | 103.49 | 23104 (21) |
| $AUC_{0-1\,hr}$ (ng · hr/mL) | 872 (83) | 115.25 | 75.49 | 175.95 | 814 (82) |
| $AUC_{0-2\,hr}{}^{b}$ (ng · hr/mL) | 2811 (43) | 116.49 | 94.42 | 143.73 | 2492 (47) |
| $AUC_{0-4\,hr}{}^{c}$ (ng · hr/mL) | 6828 (19) | 120.68 | 111.11 | 131.07 | 5726 (22) |
| $T_{max}$ (hr) | 2.184 (59) | na | na | na | 6.971 (34) |
| $T_{lag}$ (hr) | 0.253 (86) | na | na | na | 0.219 (98) |
| $T_{1/2}$ (hr) | 5.366 (32) | na | na | na | 6.461 (66) |
| $K_{el}$ (1/hr) | 0.141 (28) | na | na | na | 0.137 (39) |

*Dose Normalized to 500 mg
[a] Concentration at the median $T_{max}$ for commercially-available immediate release tablet
[b] AUC from zero to the median $T_{max}$ for commercially-available immediate release tablet
[c] AUC from the zero to the median $T_{max}$ + 2SD for commercially-available immediate release tablet The pharmacokinetic parameters for the medium release 15/500 formulation and the commercially-available immediate release tablet are shown in Table 12.

TABLE 12

Pharmacokinetic Profile (Mean ± SD) of Oxycodone/APAP versus commercially-available immediate release tablet (N = 29)

| Dosage | $C_{max}$ (ng/mL) | $AUC_{0-t}$ (ng · hr/mL) | $AUC_{0-inf}$ (ng · hr/mL) | $T_{max}$ (hr) | $K_{el}$ (1/hr) | $t_{1/2}$ (hr) |
|---|---|---|---|---|---|---|
| Oxycodone | | | | | | |
| 15 mg OC/ 500 mg APAP | 18.3 ± 4.6 | 217 ± 49.2 | 219 ± 49.5 | 5.3 ± 2.0 | 0.156 ± 0.024 | 4.6 ± 0.7 |

TABLE 12-continued

Pharmacokinetic Profile (Mean ± SD) of Oxycodone/APAP versus commercially-available immediate release tablet (N = 29)

| Dosage | $C_{max}$ (ng/mL) | $AUC_{0-t}$ (ng · hr/mL) | $AUC_{0-inf}$ (ng · hr/mL) | $T_{max}$ (hr) | $K_{el}$ (1/hr) | $t_{1/2}$ (hr) |
|---|---|---|---|---|---|---|
| Commercially-available immediate release tablet (7.5 mg OC/325 mg APAP) | 22.4 ± 4.5* | 230 ± 49.8 | 231 ± 50.0 | 8.0 ± 1.7* | 0.157 ± 0.020 | 4.5 ± 0.6 |
| Acetaminophen | | | | | | |
| 15 mg OC/500 mg APAP | 2720 ± 608 | 221184 ± 4804 | 23554 ± 5234 | 2.1 ± 1.4 | 0.133 ± 0.039 | 5.7 ± 1.9 |
| Commercially-available immediate release tablet[a] (7.5 mg OC/325 mg APAP) | 2721 ± 584* | 21962 ± 4772 | 23104 ± 4882 | 7.0 ± 2.4* | 0.137 ± 0.054 | 6.5 ± 4.3 |

*Most values occurred after the second dose.
[a]AUC and $C_{max}$ dose-normalized to 500 mg for APAP.

The oxycodone mean plasma concentration as a function of time after administration of 15/500 tablets is shown in Table 13 and FIG. 5. The APAP mean plasma concentration over time after administration of 15/500 tablets is shown in Table 14 and FIG. 6.

TABLE 13

Time Course of Oxycodone Plasma Concentration (ng/mL)

| Time (hr) | Mean Fast | SEM | Mean Medium | SEM | Mean Slow | SEM | Mean commercially-available immediate release tablet | SEM |
|---|---|---|---|---|---|---|---|---|
| 0 | 0 | 0 | 0 | 0 | 0 | 0 | 0 | 0 |
| 0.17 | 0 | 0 | 0.13 | 0.11 | 0.06 | 0.02 | 0.03 | 0.03 |
| 0.33 | 0.65 | 0.29 | 1.08 | 0.44 | 0.93 | 0.41 | 1.16 | 0.36 |
| 0.5 | 2.09 | 0.55 | 2.98 | 0.95 | 2.55 | 0.96 | 4.03 | 0.9 |
| 0.67 | 3.74 | 0.91 | 5.29 | 1.25 | 4.15 | 1.1 | 7.04 | 0.93 |
| 1 | 6.89 | 0.98 | 7.36 | 1.11 | 7.6 | 1.24 | 10.23 | 1.11 |
| 2 | 12.36 | 0.74 | 12.39 | 1.04 | 11.24 | 0.73 | 14.94 | 0.81 |
| 3 | 14.77 | 0.82 | 14.73 | 0.91 | 13.35 | 0.53 | 14.84 | 0.62 |
| 4 | 16.33 | 0.8 | 16.1 | 0.82 | 15.12 | 0.44 | 12.95 | 0.58 |
| 5 | 16.28 | 0.67 | 15.89 | 0.81 | 15.83 | 0.41 | 10.58 | 0.8 |
| 6 | 17.4 | 0.72 | 16.43 | 0.81 | 15.76 | 0.41 | 9.1 | 0.67 |
| 6.5 | 16.59 | 0.64 | 15.89 | 0.72 | 15.22 | 0.96 | 10.76 | 0.7 |
| 7 | 15.28 | 0.58 | 14.83 | 0.69 | 14.49 | 1.43 | 16.84 | 0.69 |
| 8 | 14.02 | 0.6 | 14.29 | 0.64 | 13.77 | 0.85 | 19.7 | 0.7 |
| 9 | 13.13 | 0.57 | 13.39 | 0.55 | 13 | 0.78 | 19.08 | 0.65 |
| 10 | 11.9 | 0.64 | 12.52 | 0.53 | 11.92 | 0.68 | 16.63 | 0.57 |
| 12 | 8.86 | 0.6 | 9.59 | 0.49 | 10.04 | 0.59 | 10.88 | 0.53 |

TABLE 14

Time Course of Acetaminophen Plasma Concentration (ng/mL)

| Time (hr) | Mean Fast | SEM | Mean Medium | SEM | Mean Slow | SEM | Mean commercially-available immediate release tablet | SEM |
|---|---|---|---|---|---|---|---|---|
| 0 | 0 | 0 | 0 | 0 | 0 | 0 | 0 | 0 |
| 0.17 | 31 | 18 | 284 | 151 | 220 | 88 | 107 | 47 |
| 0.33 | 673 | 210 | 751 | 221 | 678 | 197 | 607 | 173 |
| 0.5 | 1216 | 266 | 1299 | 275 | 1133 | 248 | 1181 | 229 |
| 0.67 | 1624 | 301 | 1922 | 301 | 1647 | 252 | 1653 | 255 |
| 1 | 2116 | 258 | 2380 | 239 | 2296 | 217 | 1971 | 210 |
| 2 | 2922 | 160 | 2821 | 123 | 2747 | 93 | 2393 | 90 |
| 3 | 2736 | 129 | 2719 | 90 | 2636 | 94 | 2150 | 65 |
| 4 | 2643 | 120 | 2524 | 103 | 2424 | 110 | 1717 | 71 |
| 5 | 2376 | 112 | 2246 | 121 | 2130 | 118 | 1290 | 59 |
| 6 | 2263 | 100 | 2080 | 143 | 1965 | 107 | 1006 | 58 |
| 6.5 | 2068 | 93 | 1903 | 126 | 1774 | 102 | 1742 | 212 |
| 7 | 1830 | 80 | 1744 | 116 | 1644 | 98 | 2749 | 232 |
| 8 | 1577 | 81 | 1573 | 103 | 1495 | 93 | 2790 | 114 |
| 9 | 1416 | 79 | 1407 | 88 | 1330 | 80 | 2482 | 111 |
| 10 | 1286 | 82 | 1314 | 84 | 1198 | 71 | 1968 | 105 |
| 12 | 1069 | 89 | 1131 | 86 | 1089 | 66 | 1188 | 82 |

Example 3

Clinical Pharmacokinetic Analysis of Controlled-Release 30 mg Oxycodone/500 mg Acetaminophen Bilayer Tablets—Single Dose A single dose, four-period crossover study was conducted essentially as described in Example 2, except the controlled-release bilayer tablets contained 30 mg oxycodone and 500 mg APAP. (See selected examples from Chart No. 2.) Tables 15-17 and 18-20 present the PK data for oxycodone and APAP, respectively. The plasma concentrations of oxycodone and APAP are presented in FIG. 7 and FIG. 8, respectively.

TABLE 15

Oxycodone Pharmacokinetics (30/500)

| | Fast Release Formulation | | | | Commercially-available immediate release tablet |
|---|---|---|---|---|---|
| | Mean | LSM | 90% CI | | Mean |
| Parameter | (% CV) | Ratio | Lower | Upper | (% CV) |
| $C_{max}$ (ng/mL) | 39.159 (28) | 82.17 | 75.96 | 88.9 | 47.597 (26) |
| $C_{1\,hr}$ (ng/mL) | 20.462 (74) | 77.25 | 54.37 | 109.76 | 25.911 (67) |
| $C_{2\,hr}{}^a$ (ng/mL) | 28.221 (39) | 95.18 | 83.82 | 108.08 | 29.579 (32) |
| $AUC_{0-t}$ (ng · hr/mL) | 393.952 (30) | 92.84 | 89.3 | 96.53 | 425.978 (29) |
| $AUC_{0-inf}$ (ng · hr/mL) | 396.135 (29) | 92.4 | 88.94 | 95.99 | 430.196 (29) |
| $AUC_{0-1\,hr}$ (ng · hr/mL) | 9.106 (100) | 71.09 | 46.05 | 109.76 | 11.55 (93) |
| $AUC_{0-2\,hr}{}^b$ (ng · hr/mL) | 33.448 (61) | 82.59 | 67.9 | 100.46 | 39.295 (53) |
| $AUC_{0-4\,hr}{}^c$ (ng · hr/mL) | 96.47 (38) | 101.27 | 91.51 | 112.06 | 93.706 (29) |
| $AUC_{4\,hr-t}{}^d$ | 395.522 (29) | 92.4 | 88.95 | 95.99 | 429.507 (29) |
| $T_{max}$ (hr) | 4.057 (51) | na | na | na | 6.948 (33) |
| $T_{lag}$ (hr) | 0.213 (107) | na | na | na | 0.184 (66) |
| $T_{1/2}$ (hr) | 4.398 (15) | na | na | na | 4.32 (15) |
| $K_{el}$ (1/hr) | 0.161 (15) | na | na | na | 0.164 (16) |

[a] Concentration at the median $T_{max}$ for commercially-available immediate release tablet
[b] AUC from zero to the median $T_{max}$ for commercially-available immediate release tablet
[c] AUC from the zero to the median $T_{max}$ + 2SD for commercially-available immediate release tablet

TABLE 16

Oxycodone Pharmacokinetics (30/500)

| | Medium Release Formulation | | | | Commercially-available immediate release tablet |
|---|---|---|---|---|---|
| | Mean | LSM | 90% CI | | Mean |
| Parameter | (% CV) | Ratio | Lower | Upper | (% CV) |
| $C_{max}$ (ng/mL) | 36.731 (30) | 77.14 | 71.27 | 83.48 | 47.597 (26) |
| $C_{1\,hr}$ (ng/mL) | 19.758 (70) | 86.12 | 60.48 | 122.62 | 25.911 (67) |
| $C_{2\,hr}{}^a$ (ng/mL) | 27.655 (39) | 93.53 | 82.31 | 106.28 | 29.579 (32) |
| $AUC_{0-t}$ (ng · hr/mL) | 396.026 (29) | 94.17 | 90.55 | 97.92 | 425.978 (29) |
| $AUC_{0-inf}$ (ng · hr/mL) | 398.084 (29) | 93.68 | 90.16 | 97.34 | 430.196 (29) |
| $AUC_{0-1\,hr}$ (ng · hr/mL) | 8.988 (85) | 93.06 | 60.12 | 144.04 | 11.55 (93) |
| $AUC_{0-2\,hr}{}^b$ (ng · hr/mL) | 32.695 (56) | 86.02 | 70.64 | 104.74 | 39.295 (53) |
| $AUC_{0-4\,hr}{}^c$ (ng · hr/mL) | 91.998 (36) | 98.13 | 88.63 | 108.65 | 93.706 (29) |
| $AUC_{4\,hr-t}{}^d$ | 397.436 (29) | 93.68 | 90.16 | 97.34 | 429.507 (29) |
| $T_{max}$ (hr) | 4.523 (51) | na | na | na | 6.948 (33) |
| $T_{lag}$ (hr) | 0.207 (95) | na | na | na | 0.184 (66) |
| $T_{1/2}$ (hr) | 4.369 (14) | na | na | na | 4.32 (15) |
| $K_{el}$ (1/hr) | 0.162 (14) | na | na | na | 0.164 (16) |

[a] Concentration at the median $T_{max}$ for commercially-available immediate release tablet
[b] AUC from zero to the median $T_{max}$ for commercially-available immediate release tablet
[c] AUC from the zero to the median $T_{max}$ + 2SD for commercially-available immediate release tablet

TABLE 17

Oxycodone Pharmacokinetics (30/500)

| | Slow Release Formulation | | | | Commercially-available immediate release tablet |
|---|---|---|---|---|---|
| | Mean | LSM | 90% CI | | Mean |
| Parameter | (% CV) | Ratio | Lower | Upper | (% CV) |
| $C_{max}$ (ng/mL) | 32.976 (29) | 68.96 | 63.74 | 74.6 | 47.597 (26) |
| $C_{1\,hr}$ (ng/mL) | 17.897 (74) | 73.61 | 52.01 | 104.18 | 25.911 (67) |
| $C_{2\,hr}{}^a$ (ng/mL) | 23.183 (33) | 78.42 | 69.06 | 89.05 | 29.579 (32) |
| $AUC_{0-t}$ (ng · hr/mL) | 399.623 (26) | 94.5 | 90.9 | 98.25 | 425.978 (29) |
| $AUC_{0-inf}$ (ng · hr/mL) | 401.362 (26) | 93.88 | 90.36 | 97.52 | 430.196 (29) |
| $AUC_{0-1\,hr}$ (ng · hr/mL) | 7.643 (96) | 69.93 | 45.52 | 107.44 | 11.55 (93) |
| $AUC_{0-2\,hr}{}^b$ (ng · hr/mL) | 28.183 (59) | 71.58 | 58.85 | 87.06 | 39.295 (53) |
| $AUC_{0-4\,hr}{}^c$ (ng · hr/mL) | 82.171 (36) | 86.17 | 77.87 | 95.35 | 93.706 (29) |
| $AUC_{4\,hr-t}{}^d$ | 400.56 (26) | 93.85 | 90.34 | 97.49 | 429.507 (29) |
| $T_{max}$ (hr) | 3.96 (48) | na | na | na | 6.948 (33) |
| $T_{lag}$ (hr) | 0.201 (78) | na | na | na | 0.184 (66) |
| $T_{1/2}$ (hr) | 4.418 (17) | na | na | na | 4.32 (15) |
| $K_{el}$ (1/hr) | 0.161 (17) | na | na | na | 0.164 (16) |

[a] Concentration at the median $T_{max}$ for commercially-available immediate release tablet
[b] AUC from zero to the median $T_{max}$ for commercially-available immediate release tablet
[c] AUC from the zero to the median $T_{max}$ + 2SD for commercially-available immediate release tablet

TABLE 18

Acetaminophen Pharmacokinetics (30/500)

| | Fast Release Formulation | | | | Commercially-available immediate release tablet |
|---|---|---|---|---|---|
| | Mean | LSM | 90% CI | | Mean |
| Parameter | (% CV) | Ratio | Lower | Upper | (% CV) |
| $C_{max}$ (ng/mL) | 3138 (32) | 101.52 | 91.58 | 122.53 | 3085 (29) |
| $C_{1\,hr}$ (ng/mL) | 2163 (59) | 130.98 | 101.04 | 169.78 | 1777 (59) |
| $C_{2\,hr}{}^a$ (ng/mL) | 2386 (32) | 125.37 | 113.22 | 138.82 | 1892 (28) |
| $AUC_{0-t}$ (ng · hr/mL) | 21742 (26) | 98.53 | 95.07 | 102.13 | 21897 (23) |
| $AUC_{0-inf}$ (ng · hr/mL) | 22798 (26) | 99.02 | 95.5 | 102.66 | 22881 (23) |
| $AUC_{0-1\,hr}$ (ng · hr/mL) | 1260 (85) | 122.71 | 85.05 | 177.03 | 1005 (80) |
| $AUC_{0-2\,hr}{}^b$ (ng · hr/mL) | 3534 (53) | 120.52 | 100.69 | 144.26 | 2839 (48) |
| $AUC_{0-4\,hr}{}^c$ (ng · hr/mL) | 8038 (33) | 130.54 | 119.98 | 142.02 | 6041 (27) |
| $AUC_{4\,hr-t}{}^d$ | 14707 (32) | 86.22 | 82.35 | 90.27 | 16720 (26) |
| $T_{max}$ (hr) | 1.908 (69) | na | na | na | 5.615 (54) |
| $T_{lag}$ (hr) | 0.236 (106) | na | na | na | 0.178 (90) |
| $T_{1/2}$ (hr) | 4.798 (26) | na | na | na | 5.3 (43) |
| $K_{el}$ (1/hr) | 0.153 (25) | na | na | na | 0.152 (36) |

* Dose Normalized to 500 mg
[a] Concentration at the median $T_{max}$ for commercially-available immediate release tablet
[b] AUC from zero to the median $T_{max}$ for commercially-available immediate release tablet
[c] AUC from the zero to the median $T_{max}$ + 2SD for commercially-available immediate release tablet

TABLE 19

Acetaminophen Pharmacokinetics (30/500)

| Parameter | Medium Release Formulation | | | | Commercially-available immediate release tablet |
|---|---|---|---|---|---|
| | Mean (% CV) | LSM Ratio | 90% CI Lower | 90% CI Upper | Mean (% CV) |
| $C_{max}$ (ng/mL) | 2940 (38) | 93.8 | 84.57 | 104.03 | 3085 (29) |
| $C_{1\ hr}$ (ng/mL) | 2161 (56) | 139.29 | 107.29 | 180.84 | 1777 (59) |
| $C_{2\ hr}{}^a$ (ng/mL) | 2349 (27) | 125.86 | 113.61 | 139.44 | 1892 (28) |
| $AUC_{0-t}$ (ng · hr/mL) | 21822 (26) | 99.42 | 95.9 | 103.06 | 21897 (23) |
| $AUC_{0-inf}$ (ng · hr/mL) | 23107 (26) | 100.76 | 97.16 | 104.49 | 22881 (23) |
| $AUC_{0-1\ hr}$ (ng · hr/mL) | 1342 (81) | 155.89 | 107.81 | 225.4 | 1005 (80) |
| $AUC_{0-2\ hr}{}^b$ (ng · hr/mL) | 3596 (52) | 129.14 | 107.79 | 154.73 | 2839 (48) |
| $AUC_{0-4\ hr}{}^c$ (ng · hr/mL) | 7880 (32) | 130.08 | 119.51 | 141.59 | 6041 (27) |
| $AUC_{4\ hr-t}{}^d$ | 15040 (29) | 88.93 | 84.92 | 93.13 | 16720 (26) |
| $T_{max}$ (hr) | 1.724 (62) | na | na | na | 5.615 (54) |
| $T_{lag}$ (hr) | 0.19 (114) | na | na | na | 0.178 (90) |
| $T_{1/2}$ (hr) | 6.116 (63) | na | na | na | 5.3 (43) |
| $K_{el}$ (1/hr) | .0139 (37) | na | na | na | 0.152 (36) |

*Dose Normalized to 500 mg
[a]Concentration at the median $T_{max}$ for commercially-available immediate release tablet
[b]AUC from zero to the median $T_{max}$ for commercially-available immediate release tablet
[c]AUC from the zero to the median $T_{max}$ + 2SD for commercially-available immediate release tablet

TABLE 20

Acetaminophen Pharmacokinetics (30/500)

| Parameter | Slow Release Formulation | | | | Commercially-available immediate release tablet |
|---|---|---|---|---|---|
| | Mean (% CV) | LSM Ratio | 90% CI Lower | 90% CI Upper | Mean (% CV) |
| $C_{max}$ (ng/mL) | 2734 (33) | 88.33 | 79.68 | 97.91 | 3085 (29) |
| $C_{1\ hr}$ (ng/mL) | 1989 (53) | 120.26 | 93.05 | 155.44 | 1777 (59) |
| $C_{2\ hr}{}^a$ (ng/mL) | 2131 (25) | 112.77 | 101.84 | 124.86 | 1892 (28) |
| $AUC_{0-t}$ (ng · hr/mL) | 21272 (23) | 97.1 | 93.68 | 100.64 | 21897 (23) |
| $AUC_{0-inf}$ (ng · hr/mL) | 22504 (22) | 98.45 | 94.95 | 102.07 | 22881 (23) |
| $AUC_{0-1\ hr}$ (ng · hr/mL) | 1092 (76) | 120.91 | 84.15 | 173.72 | 1005 (80) |
| $AUC_{0-2\ hr}{}^b$ (ng · hr/mL) | 3152 (45) | 112.74 | 94.19 | 134.94 | 2839 (48) |
| $AUC_{0-4\ hr}{}^c$ (ng · hr/mL) | 7217 (26) | 119.31 | 109.5 | 129.61 | 6041 (27) |
| $AUC_{4\ hr-t}{}^d$ | 15227 (26) | 90.59 | 86.52 | 94.85 | 16720 (26) |
| $T_{max}$ (hr) | 1.897 (56) | na | na | na | 5.615 (54) |
| $T_{lag}$ (hr) | 0.196 (79) | na | na | na | 0.178 (90) |

TABLE 20-continued

Acetaminophen Pharmacokinetics (30/500)

| | Slow Release Formulation | | | | Commercially-available immediate release tablet |
|---|---|---|---|---|---|
| | Mean | LSM | 90% CI | | Mean |
| Parameter | (% CV) | Ratio | Lower | Upper | (% CV) |
| $T_{1/2}$ (hr) | 4.843 (27) | na | na | na | 5.3 (43) |
| $K_{el}$ (1/hr) | 0.152 (24) | na | na | na | 0.152 (36) |

*Dose Normalized to 500 mg
[a] Concentration at the median $T_{max}$ for commercially-available immediate release tablet
[b] AUC from zero to the median $T_{max}$ for commercially-available immediate release tablet
[c] AUC from the zero to the median $T_{max}$ + 2SD for commercially-available immediate release tablet The pharmacokinetic parameters for the medium release 30/500 formulation and the commercially-available immediate release tablet are shown in Table 21.

TABLE 21

Pharmacokinetic Profile (Mean ± SD) of Oxycodone/APAP versus Commercially-available immediate release tablet (N = 29)

| Dosage | $C_{max}$ (ng/mL) | $AUC_{0-t}$ (ng·hr/mL) | $AUC_{0-inf}$ (ng·hr/mL) | $T_{max}$ (hr) | $K_{el}$ (1/hr) | $t_{1/2}$ (hr) |
|---|---|---|---|---|---|---|
| Oxycodone | | | | | | |
| 30 mg OC/500 mg APAP | 36.7 ± 10.9 | 396 ± 116 | 398 ± 115 | 4.5 ± 2.3 | 0.162 ± 0.023 | 4.4 ± 0.6 |
| Commercially-available immediate release tablet[a] (7.5 mg OC/325 mg APAP) | 47.6 ± 12.3* | 426 ± 125 | 430 ± 124 | 6.9 ± 2.3* | 0.164 ± 0.026 | 4.3 ± 0.6 |
| Acetaminophen | | | | | | |
| 30 mg OC/500 mg APAP | 2940 ± 1105 | 21822 ± 5630 | 23107 ± 5927 | 1.7 ± 1.1 | 0.139 ± 0.052 | 6.1 ± 3.9 |
| Commercially-available immediate release tablet[a] (7.5 mg OC/325 mg APAP) | 3085 ± 899* | 21897 ± 5125 | 22881 ± 5362 | 5.6 ± 3.0* | 0.152 ± 0.055 | 5.3 ± 2.3 |

*Most values occurred after the second dose.
[a] AUC and Cmax dose-normalized to 30 mg for OC and 500 mg for APAP.

Example 4

Clinical Pharmacokinetic Analysis of Controlled-Release 15 mg Oxycodone/650 mg Acetaminophen Bilayer Tablets—Single Dose The following study evaluated the bioavailability, pharmacokinetics, dose-proportionality, and safety of 1 or 2 tablets of a formulation comprising 15 mg OC/650 mg APAP (1 dose) (see selected example from Chart No. 1) compared to 1 tablet of the commercially-available immediate release tablet under fed conditions. The ER layer contained 75% of the total amount of the oxycodone in the tablet, 50% of the total amount of APAP in the tablet, and 45% (w/w) POLYOX® 1105. The IR layer contained 25% of the total amount of oxycodone in the tablet and 50% of the total amount of APAP. This study was conducted in 42 male and female healthy subjects.

PK parameters for oxycodone are presented in Table 22. Plasma concentrations of OC for the 1 tablet dosing configuration of 15/650 showed a median $t_{lag}$ of 0.25 hours, while there was no lag time for plasma concentrations of OC for the 2 tablet dosing configuration of 15/650 and the commercially-available immediate release tablet under fed conditions. As illustrated in FIG. 9 demonstrating the plasma concentrations of oxycodone versus time of treatment (i.e., Treatment A was one tablet of 15 mg oxycodone/650 mg acetaminophen administered orally under fed conditions; Treatment B was two tablets of 15 mg oxycodone/650 mg acetaminophen administered orally one at a time under fed conditions; and Treatment C was one tablet of the commercially-available immediate release tablet (7.5 mg oxycodone/325 mg acetaminophen) administered orally every 6 hours for 2 doses under fed conditions). Plasma concentrations of OC rose rapidly after administration of 15/650 formulation in a similar fashion to commercially-available immediate release tablet. Peak plasma levels of OC for the 15/650 tablets, however, were biphasic. Peak levels were observed at about 2-3 hours and about 6 hours for the 1 or 2 tablet dosing configuration of the 15/650 formulation. In contrast, the peak plasma level of OC for the commercially-available immediate release tablet was about 7-8 hours after the initial dose of the commercially-available immediate release tablet (~1-2 hr after the second dose). Mean plasma concentrations of OC from 15/650 formulations were detectable through 48 hours following all treatments and $t_{1/2}$ was about 4 hours across all treatments.

TABLE 22

Pharmacokinetic Parameter Estimates (Mean ± SD) of Oxycodone Following Administration of 15 mg Oxycodone/650 mg APAP versus Commercially-available immediate release tablet

| Dosage | $C_{max}$ (ng/mL) | $AUC_{0-t}$ (ng · hr/mL) | $AUC_{0-inf}$ (ng · hr/mL) | $T_{max}{}^a$ (hr) | $T_{lag}{}^a$ (hr) | $t_{1/2}$ (hr) |
|---|---|---|---|---|---|---|
| One tablet (N = 25) Treatment A | 17.68 (4.42) | 199.60 (59.52) | 201.6 (59.27) | 3.00 (1.00-12.45) | 0.25 (0.00-0.75) | 4.18 (0.77) |
| Two tablets (N = 25) Treatment B | 29.18 (6.53) | 414.73 (109.87) | 417.41[b] (112.17) | 5.00 (1.00-12.00) | 0.00 (0.00-0.50) | 4.11[b] (0.67) |
| Commercially-available immediate release tablet (7.5 mg OC/325 mg APAP (N = 25) Treatment C | 20.34 (4.81) | 199.63 (60.53) | 201.76 (60.24) | 7.00 (0.50-9.00) | 0.00 (0.00-1.00) | 4.08 (0.64) |

[a] $T_{max}$ and $t_{lag}$ median (minimum-maximum)
[b] N = 24

PK parameters for APAP are presented in Table 23. Plasma concentrations of APAP for the 1 tablet dosing configuration of 15/650 showed a median $t_{lag}$ of 0.25 hour, while there was no lag in the appearance of APAP in plasma for the 2 tablet dosing configuration of 15/650 and the commercially-available immediate release tablet. Plasma concentrations of APAP rose rapidly after administration of the 15/650 formulations, similar to that observed with RDL. (See FIG. 10). Peak plasma levels of APAP following administration of the 1 tablet and 2 tablet dosing configurations of 15/650 were observed at approximately 2 hours (with a shoulder peak at 5-6 hours) after dosing compared with 1 hour after the second dose of the commercially-available immediate release tablet. Mean plasma concentrations of APAP were detectable through 36 hours following all treatments and the mean $t_{1/2}$ was approximately 6 to 8 hours across treatment groups.

TABLE 23

Pharmacokinetic Parameter Estimates (Mean ± SD) of APAP Following Administration of 15 mg Oxycodone/650 mg APAP versus Commercially-available immediate release tablet

| Dosage | $C_{max}$ (ng/mL) | $AUC_{0-t}$ (ng · hr/mL) | $AUC_{0-inf}$ (ng · hr/mL) | $T_{max}{}^a$ (hr) | $T_{lag}{}^a$ (hr) | $t_{1/2}$ (hr) |
|---|---|---|---|---|---|---|
| One tablet (N = 25) | 3822 (874) | 30239 (5673) | 32194[c] (6437) | 2.00 (0.50-4.00) | 0.25 (0.00-1.00) | 6.17[c] (2.22) |
| Two tablets (N = 25) | 6941 (1989) | 64783 (15017) | 67600[d] (14655) | 2.00 (0.50-5.00) | 0.00 (0.00-0.50) | 7.67[d] (4.06) |
| Commercially-available immediate release tablet (7.5 mg OC/325 mg APAP (N = 25) | 3629 (841) | 30137 (6426) | 30802[c] (6697) | 6.50 (0.50-9.00) | 0.00 (0.00-1.00) | 5.89[c] (2.63) |

[a] $T_{max}$ and $t_{lag}$ median (minimum-maximum)
[c] N = 21
[d] N = 23

Example 5

Clinical Pharmacokinetic Analysis of Controlled-Release 15 mg Oxycodone/650 mg Acetaminophen Bilayer Tablets—Multiple Doses The following study evaluated the steady state bioavailability, pharmacokinetics, and safety of a 15 mg OC/650 mg APAP formulation administered (see selected example from Chart No. 2) orally as 1 tablet (Treatment A) or 2 tablets (Treatment B) every 12 hours (9 doses) compared to 2 tablets of the commercially-available immediate release tablet (2×7.5 mg OC/325 mg APAP) (Treatment C) dosed every 6 hours for 4.5 days (18 doses) under fed conditions with 48 male and female subjects in equal distribution.

The pharmacokinetic (PK) parameters of OC are presented in Table 24. The PK behavior of OC on Study Day 1 was similar to that observed in the single dose study (see Table 22). There was a slight lag (median tlag 0.25 hr) in the appearance of OC following the 1 tablet dose of 15 mg OC/650 mg APAP. No lag was observed following dosing with 2 tablets of 15 mg OC/650 mg APAP or the commercially-available immediate release tablet. Peak plasma levels were observed at 4 and 6 hours after administration of 1 and 2 tablets of the 15/650 formulation, respectively, and at 1.5 hours after the second dose of the commercially-available immediate release tablet. (See FIG. 11). Minimum (trough) plasma concentrations ($C_{min}$) of OC achieved steady-state levels by Day 2 for 15/650 formulations and by Day 3 for the commercially-available immediate release tablet.

On Day 5 of the study, the maximum plasma OC concentration at steady-state ($C_{max}^{ss}$) was 27.3 ng/mL following 4.5 days of dosing with 1 tablet of 15 mg OC/650 mg APAP administered every 12 hours. $C_{max}^{ss}$ following 2 tablets of 15 mg OC/650 mg APAP administered every 12 hours or the commercially-available immediate release tablet administered Q6 hours for 4.5 days were 50.7 ng/mL and 52.4 ng/mL, respectively. Median $T_{max}^{ss}$ was observed at 3 hours following 1 tablet or 2 tablets of 15/650 and at 2 hours following the first daily dose of the commercially-available immediate release tablet.

PK parameters for APAP are presented in Table 25. Acetaminophen was rapidly absorbed following a single dose of 1 or 2 tablets of 15/650 and in a similar fashion to the commercially-available immediate release tablet (see FIG. 12). There was no lag in plasma concentrations following any of the three dosing regimens. Peak APAP plasma concentrations were observed at 1 hour after administration of 1 or 2 tablets of 15/650 and at 0.9 hours after the first dose of the commercially-available immediate release tablet on Day 1. After a single administration of 15/650, $C_{max}$ for APAP was proportional with respect to the amount of APAP in 1 or 2 tablets of 15/650 (i.e., 1 tablet—3942 ng/mL; 2 tablets—7536 ng/mL). Minimum (trough) concentrations ($C_{min}$) of APAP achieved steady-state levels by Day 2 for 1 tablet of 15/650, by Day 4 for 2 tablets of 15/650 and by the second dose on Day 1 for the commercially-available immediate release tablet.

TABLE 24

Oxycodone Pharmacokinetic Parameters

| Dosage | $C_{max}$ (ng/mL) | $AUC_{0-t}$ (ng · hr/mL) | $T_{max}^a$ (hr) | $T_{lag}^a$ (hr) | $t_{1/2}$ (hr) |
|---|---|---|---|---|---|
| A: One tablet Day 1 (N = 20) | 18.79 (5.00) | 149.68[c] (37.92) | 4.00 (2.00-8.00) | 0.25 (0.00-0.50) | Day 1 |
| B: Two tablets Day 1 (N = 20) | 33.57 (8.41) | 280.45[c] (62.61) | 5.93 (1.00-11.92) | 0.00 (0.00-0.25) | Day 1 |
| C: Commercially-available immediate release tablet (7.5 mg OC/325 mg APAP Day 1 (N = 20) | 36.02 (10.52) | 278.60[c] (67.17) | 7.50 (0.75-11.92) | 0.00 (0.00-0.33) | Day 1 |
| A: One tablet Day 5 (N = 20) | 27.26 (6.33) | 223.10[c] (59.45) | 3.00 (1.00-5.92) | Day 5 | 6.06[d] (1.91) |
| B: Two tablets Day 5 (N = 20) | 50.70 (10.95) | 433.37[c] (93.21) | 3.00 (2.00-7.00) | Day 5 | 6.35 (1.89) |
| C: Commercially-available immediate release tablet (7.5 mg OC/325 mg APAP Day 5 (N = 20) | 52.41 (12.40) | 435.70[c] (98.68) | 2.00 (0.50-8.02) | Day 5 | 5.93[d] (1.68) |

[a] $T_{max}$ and $t_{lag}$ median (minimum-maximum)
[c] Day 1 - $AUC_{0-12\,h}$; Day 5 - $AUC_{0-12\,h}^{ss}$
[d] N = 19

TABLE 25

Acetaminophen Pharmacokinetic Parameters

| Dosage | $C_{max}$ (ng/mL) | $AUC_{0-t}$ (ng·hr/mL) | $T_{max}{}^a$ (hr) | $T_{lag}{}^a$ (hr) | $t_{1/2}$ (hr) |
|---|---|---|---|---|---|
| A: One tablet Day 1 (N = 20) | 3942 (1168) | 22928[g] (7331) | 1.00 (0.50-5.93) | 0.00 (0.00-0.28) | Day 1 |
| B: Two tablets Day 1 (N = 20) | 7536 (2205) | 44254[g] (13885) | 1.00 (0.28-4.00) | 0.00 (0.00-0.25) | Day 1 |
| C: Commercially-available immediate release tablet (7.5 mg OC/325 mg APAP Day 1 (N = 20) | 6757 (1949) | 43634[g] (12357) | 0.90 (0.32-11.92) | 0.00 (0.00-0.25) | Day 1 |
| A: One tablet Day 5 (N = 20) | 4635 (1330) | 26968[g] (9134) | 1.00 (0.50-3.00) | Day 5 | 7.06 (2.24) |
| B: Two tablets Day 5 (N = 20) | 8206 (2666) | 50221[g] (18415) | 1.00 (0.30-4.00) | Day 5 | 7.46 (1.85) |
| C: Commercially-available immediate release tablet (7.5 mg OC/325 mg APAP Day 5 (N = 20) | 7433 (1979) | 50678[g] (15565) | 1.50 (0.25-8.02) | Day 5 | 6.79[h] (2.47) |

[a] $T_{max}$ and $t_{lag}$ median (minimum-maximum)
[g] Day 1 - $AUC_{0-12 h}$; Day 5 - $AUC_{0-12 h}{}^{ss}$
[h] N = 17

On Day 5 of the study, median $T_{max}{}^{ss}$ for APAP was observed at 1 hour following 1 or 2 tablets of 15/650 and at 1.5 hours following the first daily dose of the commercially-available immediate release tablet on Day 5. Maximum plasma APAP concentration at steady-state ($C_{max}{}^{ss}$) was 4635 ng/mL following 4.5 days of dosing with 1 tablet of 15/650 every 12 hours (Table 25). $C_{max}{}^{ss}$ following 2 tablets of 15/650 administered every 12 hours and for the commercially-available immediate release tablet administered Q6 hours for 4.5 days were 8206 and 7433 ng/mL, respectively.

Example 6

Clinical Pharmacokinetic Analysis of Controlled-Release 15 mg Oxycodone/650 mg Acetaminophen Bilayer Tablets Under Fed and Fasted Conditions Two open-label, randomized, two-period crossover studies were conducted to evaluate the effect of food on the pharmacokinetics, bioavailability and safety of the 15 mg oxycodone/650 mg APAP composition (see selected example from Chart No. 2) using a 1 tablet or 2 tablet dosing configuration in normal, healthy subjects. Studies were conducted in 48 subjects under fed (FDA high fat breakfast) or fasted conditions.

Tables 26 and 27 present the pharmacokinetic data for oxycodone (OC) and APAP, respectively. FIGS. 13 and 14 present the plasma concentration of OC following administration of one tablet and two tablets, respectively, under fed (Treatment A) or fasted (Treatment B) conditions. FIGS. 15 and 16 present the plasma concentration of APAP following administration of one tablet and two tablets, respectively, under fed (Treatment A) or fasted (Treatment B) conditions.

TABLE 26

Oxycodone Pharmacokinetics (15/650)

| Dose | State (N) | $C_{max}$ (ng/mL) | $AUC_{0-t}$ (ng·hr/mL) | $AUC_{0-inf}$ (ng·hr/mL) | $T_{max}{}^a$ (hr) | $t_{lag}{}^a$ (hr) | $t_{1/2}$ (hr) |
|---|---|---|---|---|---|---|---|
| One tablet | fed (28) | 19.03 (4.20) | 219.23 (55.99) | 221.06 (55.88) | 5.00 (1.00-12.00) | 0.25 (0.00-0.50) | 3.94 (0.69) |
| Two tablets | fed (17) | 30.58 (6.57) | 414.01 (104.76) | 415.88 (104.86) | 5.00 (0.75-12.00) | 0.25 (0.00-0.27) | 4.42 (0.97) |
| One tablet | fasted (28) | 18.31 (4.67) | 196.51 (53.04) | 198.33 (52.82) | 3.50 (0.50-10.00) | 0.00 (0.00-0.25) | 4.25 (0.59) |
| Two tablets | fasted (17) | 33.69 (7.45) | 390.33 (145.27) | 392.15 (145.81) | 5.00 (2.00-5.20) | 0.00 (0.00-0.25) | 4.80 (1.07) |

[a] $T_{max}$ and $t_{lag}$ median (minimum-maximum)

Plasma concentrations (Table 26; FIGS. 13 and 14) of OC rose rapidly with the median $T_{max}$ observed at about 4 to 5 hr under both fed and fasted conditions for both the 1- and 2-tablet dose configurations. OC plasma levels were biphasic—with a first peak at about 3 hours and a second peak at about 5 hours. The $C_{max}$ values (at 5 hours) for OC under fed (1 and 2 tablets, 19.0 and 30.6 ng/mL) conditions were equivalent to those observed under fasted (1 and 2 tablets, 18.3 and 33.7 ng/mL) conditions for both the 1 tablet and 2 tablet dosing configurations.

TABLE 27

Acetaminophen Pharmacokinetics (15/650)

| Dose | State (N) | $C_{max}$ (ng/mL) | $AUC_{0-t}$ (ng · hr/mL) | $AUC_{0-inf}$ (ng · hr/mL) | $T_{max}^a$ (hr) | $t_{lag}^a$ (hr) | $t_{1/2}$ (hr) |
|---|---|---|---|---|---|---|---|
| One tablet | fed (28) | 4374 (1286) | 31480 (9316) | 32552 (9489) | 1.00 (0.50-5.00) | 0.00 (0.00-0.50) | 4.65 (1.26) |
| Two tablets | fed (17) | 6341 (1698) | 62904 (19294) | 68839[b] (19826) | 2.00 (0.75-6.00) | 0.00 (0.00-0.25) | 7.02[b] (1.77) |
| One tablet | fasted (28) | 5511 (2095) | 31876 (103339) | 33860 (10731) | 0.75 (0.25-5.00) | 0.00 (0.00-0.25) | 5.19[e] (1.50) |
| Two tablets | fasted (17) | 10428 (3529) | 61164 (16552) | 65281 (15711) | 0.75 (0.25-5.00) | 0.00 (0.00-0.00) | 5.6 (1.49) |

[a] $T_{max}$ and $t_{lag}$ median (minimum-maximum)
[b] N = 12
[e] N = 27
[f] N = 13

Plasma concentrations (Table 27; FIGS. 15 and 16) of APAP rose rapidly following 1 tablet dosed under fed and fasted conditions with similar $T_{max}$ values (1.0 hour and 0.8 hour). $T_{max}$ was observed sooner following 2 tablets given under fasted conditions (0.8 hour) than under fed conditions (2 hours). Plasma concentrations of APAP were lower under fed conditions than under fasted conditions with fed $C_{max}$ values of 4374 ng/mL (1 tablet) and 6341 ng/mL (2 tablets) and fasted $C_{max}$ values of 5511 ng/mL (1 tablet) and 10,428 ng/mL (2 tablets). Nevertheless, the peak concentrations demonstrate that there was only a slight, minimal food effect on the absorption of APAP, which is consistent with that observed for other oxycodone and acetaminophen products. Thus, there is no meaningful food effect seen with this composition, and as such, the composition can to be administered without regard to food.

Example 7

Abuse Potential of Controlled-Release Formulations

It has long been theorized that the desirability of a drug of abuse is related to the speed with which it reaches maximum concentration in the plasma of the user. Basic science and clinical observation suggest that a shortened time to maximum plasma concentration ($t_{max}$) and a heightened maximum plasma concentration ($C_{max}$) would increase the euphoric effects conferred by a drug. The abuse quotient (AQ) is a relatively new concept that attempts to predict the abuse potential of drugs. The AQ refers to the two PK parameters expressed as a ratio: $AQ=C_{max}/t_{max}$. The abuse potential of a drug increases as the value of the AQ increases, either by heightening $C_{max}$ or shortening $t_{max}$.

Table 28 presents the AQs for various extended release formulations disclosed herein (see, e.g., selected examples from Chart Nos. 1 and 2) and several commercially available formulations.

TABLE 28

Abuse Quotient

| Formulation | $C_{max}$ (ng/mL) | $t_{max}$ (hr) | AQ |
|---|---|---|---|
| 15/500 - Fast | 18.8 | 4.95 | 3.80 |
| 15/500 - Medium | 18.27 | 5.31 | 3.44 |
| 15/500 - Slow | 17.4 | 5.66 | 3.07 |
| 15/650 - 1 tablet | 17.68 | 3.90 | 4.53 |

TABLE 28-continued

Abuse Quotient

| Formulation | $C_{max}$ (ng/mL) | $t_{max}$ (hr) | AQ |
|---|---|---|---|
| 15/650 - 2 tablets | 14.59* | 5.03 | 2.90 |
| 7.5/325 - 1 tablet | 16.82 | 3.71 | 4.53 |
| 7.5/325 - 2 tablets | 16.39 | 3.17 | 5.17 |
| Percocet | 22.43 | 2.16 | 10.38 |
| Oxycontin | 17.35 | 3.54 | 4.90 |
| OxyER | 19.61 | 4.11 | 4.77 |

*dose normalized to 15 mg

Example 8

Ethanol Release Testing at a 150 rpm Paddle Speed

To asses the potential for dose dumping, the in vitro dissolution of oxycodone and APAP from 7.5 mg OC/325 mg APAP tablets was tested in 0.1 N HCl containing 0%, 5%, 20%, or 40% v/v ethanol. The ER layer of the 7.5/325 tablets contained 5.625 mg of OC, 162.5 mg of APAP, and 45% (w/w) POLYOX® 1105, and the IR layer contained 1.875 mg of OC and 162.5 mg of APAP. (See selected example from Chart No. 2.) For each profile, twelve tablets were weighed, placed in a sinker, and dropped into an equilibrated USP Type II apparatus (paddles) that contained 900 mL of (helium sparged) 0.1 N HCl (containing either 0%, 5%, 20%, or 40% ethanol) heated to ~37° C. The mixture was stirred at ~150 rpm and the temperature was maintained at ~37° C. for 120 minutes. The bath vessel was covered with a low evaporation vessel cover. Samples were removed at 15, 30, 45, 60, 75, 90, 105, and 120 minutes. Each sample was filtered through a 0.45 μm filter and analyzed by HPLC using standard procedures.

Tables 29, 30, 31, and 32 present the percent release of OC and APAP in the presence of 0%, 5%, 20%, and 40% ethanol, respectively. FIG. 17 presents dissolution profiles for OC and FIG. 18 presents dissolution profiles for APAP in the presence of 0%, 5%, 20%, and 40% ethanol. These data reveal that, for both OC and APAP, the dissolution in 5%, 20%, or 40% ethanol was either comparable or slower than the dissolution in 0% ethanol, indicating no dose dumping for this formulation.

TABLE 29

Percent Release in 0% Ethanol

| | OC | | | | APAP | | |
|---|---|---|---|---|---|---|---|
| Time (Min) | Mean | RSD | Minimum | Maximum | Mean | RSD | Minimum | Maximum |
| 15 | 32.0 | 2.7 | 31.1 | 33.4 | 52.9 | 2.7 | 50.6 | 56.0 |
| 30 | 37.6 | 2.4 | 36.5 | 39.2 | 55.6 | 2.5 | 53.5 | 58.6 |
| 45 | 42.3 | 2.6 | 40.9 | 44.4 | 58.1 | 2.5 | 56.0 | 61.1 |
| 60 | 46.5 | 2.5 | 45.0 | 48.7 | 60.5 | 2.4 | 58.4 | 63.5 |
| 75 | 50.4 | 2.5 | 48.7 | 52.5 | 62.9 | 2.4 | 60.8 | 65.9 |
| 90 | 54.1 | 2.4 | 52.1 | 56.2 | 65.0 | 2.3 | 62.9 | 68.0 |
| 105 | 57.7 | 2.1 | 55.6 | 59.8 | 67.1 | 2.3 | 65.0 | 70.1 |
| 120 | 61.1 | 2.2 | 58.9 | 63.5 | 69.1 | 2.2 | 66.9 | 72.1 |

TABLE 30

Percent Release in 5% Ethanol

| | OC | | | | APAP | | | |
|---|---|---|---|---|---|---|---|---|
| Time (Min) | Mean | RSD | Minimum | Maximum | Mean | RSD | Minimum | Maximum |
| 15 | 31.2 | 2.4 | 30.2 | 32.4 | 52.1 | 1.5 | 50.5 | 53.5 |
| 30 | 36.9 | 3.2 | 35.1 | 39.0 | 54.9 | 1.6 | 53.4 | 56.4 |
| 45 | 41.5 | 3.3 | 39.1 | 44.0 | 57.2 | 1.5 | 55.7 | 58.7 |
| 60 | 45.5 | 3.3 | 43.4 | 48.2 | 59.4 | 1.5 | 57.9 | 60.9 |
| 75 | 49.4 | 2.6 | 47.9 | 52.5 | 61.5 | 1.5 | 60.0 | 63.0 |
| 90 | 52.9 | 3.5 | 50.7 | 56.1 | 63.4 | 1.5 | 61.9 | 65.0 |
| 105 | 56.2 | 1.8 | 54.0 | 57.8 | 65.4 | 1.5 | 63.8 | 66.9 |
| 120 | 59.3 | 2.8 | 56.7 | 61.7 | 67.2 | 1.5 | 65.6 | 68.7 |

TABLE 31

Percent Release in 20% Ethanol

| | OC | | | | APAP | | | |
|---|---|---|---|---|---|---|---|---|
| Time (Min) | Mean | RSD | Minimum | Maximum | Mean | RSD | Minimum | Maximum |
| 15 | 28.5 | 4.1 | 26.5 | 30.3 | 51.3 | 2.9 | 48.2 | 53.1 |
| 30 | 33.6 | 3.3 | 32.3 | 35.7 | 54.1 | 2.3 | 51.3 | 55.7 |
| 45 | 38.3 | 2.8 | 35.7 | 39.9 | 56.3 | 2.2 | 53.7 | 58.0 |
| 60 | 41.8 | 3.6 | 38.1 | 44.1 | 58.3 | 2.1 | 55.6 | 59.9 |
| 75 | 45.6 | 3.0 | 43.4 | 48.8 | 60.2 | 2.0 | 57.7 | 61.8 |
| 90 | 48.7 | 3.3 | 46.1 | 52.0 | 62.0 | 2.0 | 59.4 | 63.6 |
| 105 | 51.4 | 3.0 | 49.1 | 53.7 | 63.7 | 1.9 | 61.1 | 65.2 |
| 120 | 54.3 | 2.7 | 51.3 | 56.7 | 65.4 | 1.9 | 62.9 | 66.8 |

TABLE 32

Percent Release in 40% Ethanol

| | OC | | | | APAP | | | |
|---|---|---|---|---|---|---|---|---|
| Time (Min) | Mean | RSD | Minimum | Maximum | Mean | RSD | Minimum | Maximum |
| 15 | 10.3 | 16.3 | 7.8 | 13.7 | 20.7 | 16.3 | 15.8 | 25.9 |
| 30 | 20.7 | 8.6 | 16.5 | 23.0 | 37.1 | 7.7 | 31.4 | 41.4 |
| 45 | 28.6 | 10.4 | 24.4 | 33.4 | 44.4 | 2.6 | 42.2 | 45.8 |
| 60 | 31.3 | 5.9 | 29.2 | 35.0 | 47.0 | 1.4 | 45.9 | 48.0 |

TABLE 32-continued

Percent Release in 40% Ethanol

| | OC | | | | APAP | | | |
|---|---|---|---|---|---|---|---|---|
| Time (Min) | Mean | RSD | Minimum | Maximum | Mean | RSD | Minimum | Maximum |
| 75 | 34.5 | 6.5 | 30.3 | 38.1 | 49.0 | 1.4 | 47.7 | 49.8 |
| 90 | 36.8 | 7.0 | 33.9 | 41.2 | 50.5 | 1.5 | 49.2 | 51.6 |
| 105 | 38.5 | 6.8 | 35.3 | 44.0 | 51.9 | 1.7 | 50.4 | 53.1 |
| 120 | 40.7 | 4.5 | 38.0 | 43.5 | 53.2 | 1.4 | 51.5 | 54.1 |

Example 9

Clinical Pharmacokinetic Analysis of an Extended Release Formulation of Oxycodone/Acetaminophen Administered Under Fed and Fasted Conditions An open-label, randomized, three-period crossover study was conducted to evaluate the pharmacokinetics (PK), bioavailability, and safety of two tablets of a multi-layer extended-release formulation (each tablet comprising 7.5 mg oxycodone hydrochloride/325 mg acetaminophen), administered as a single dose in normal, healthy subjects under fed (high-fat or low-fat meal) and fasted conditions (i.e., 10 hr fast).

This single center, open-label, randomized, 3-period, 6-sequence crossover study in normal, healthy subjects was designed to evaluate the effect of a high-fat and low-fat meal on the PK, bioavailability, and safety of a multilayer ER tablet formulation of 7.5 mg OC/325 mg APAP (see selected example from Chart No. 1). The formulation was orally administered as 2 tablets (15 mg OC/650 mg APAP total dose) under 2 types of fed (high-fat and low-fat) and fasted conditions. Forty-eight subjects were enrolled and 31 subjects completed the study. Only subjects that completed all 3 study periods have been included in the PK evaluation.

Following a 10 hour overnight fast, subjects randomized to Treatment A consumed an entire standardized FDA high-fat breakfast (approximately 1,000±100 calories and approximately 50% from fat); those receiving Treatment B consumed an entire low-fat breakfast (approximately 800±80 calories and approximately 25% to 30% from fat). Breakfasts were consumed within 30 minutes prior to Hour 0 study drug administration. Subjects who could not consume the entire breakfast in the allotted time were dropped from the study. Subjects randomized to Treatment C were administered study drug under fasted conditions following an overnight fast of at least 10 hours. No food was allowed for the first 4 hours postdose. Blood samples were collected pre-dose (up to 60 minutes prior to dose), and at 15 min, 30 min, 45 min and 1, 2, 3, 4, 5, 6, 7, 8, 9, 10, 12, 16, 18, 20, 24, 36 and 48 hours post-dose, and the resulting plasma samples were analyzed for OC and APAP using a validated liquid chromatography-tandem mass spectrometry assay with a linear range of 0.100 to 100 ng/mL for OC and 100 to 50,000 ng/mL for APAP. Pharmacokinetic parameters, as detailed above in Example 2, were determined.

Tables 33 and 34 presents PK parameters for OC under the three treatment conditions, and FIG. 19 presents plasma OC concentration-time profiles for the treatments. Mean plasma concentration profiles of OC revealed that OC was rapidly absorbed under both fed (high and low fat meal) and fasted conditions. There was a slight lag (median 0.25 hours) when the formulation was administered after a meal (high and low fat). The median of the time of observed maximum plasma concentrations ($T_{max}$) were 4 hours and 3 hours after administration under low fat and fasted conditions, respectively. Median $T_{max}$ for OC under high fat conditions was significantly delayed, as compared to fasted conditions (5 hr vs. 3 hr; P<0.05). Average maximum plasma OC concentrations ($C_{max}$) were 19.94 ng/mL after a low fat breakfast, 17.90 ng/mL after a high fat breakfast, and 15.91 ng/mL under fasted conditions.

TABLE 33

Oxycodone Pharmacokinetic Estimates (2 tablets of 7.5/325)

| Parameter | Treatment A<br>High Fat<br>Mean (SD)<br>(N = 31) | Treatment B<br>Low Fat<br>Mean (SD)<br>(N = 31) | Treatment C<br>Fasted<br>Mean (SD)<br>(N = 31) |
|---|---|---|---|
| $AUC_{0-t}$ (ng · h/mL) | 219.41 (54.07) | 219.49 (57.29) | 190.70 (50.03) |
| $AUC_{0-inf}$ (ng · h/mL) | 221.00 (54.14) | 221.38 (56.95) | 192.63 (49.69) |
| $C_{max}$ (ng/mL) | 17.90 (4.25) | 19.94 (4.66) | 15.91 (3.43) |
| $T_{max}$ (h)[a] | 5.00 (1.00-12.00) | 4.00 (1.00-5.00) | 3.00 (0.75-8.00) |
| $K_{el}$ (1/h) | 0.1682 (0.0298) | 0.1693 (0.0321) | 0.1502 (0.0269) |
| $t_{lag}$ (h)[a] | 0.25 (0.00-1.00) | 0.25 (0.00-0.75) | 0.00 (0.00-0.25) |
| $t_{1/2}$ (h) | 4.26 (0.83) | 4.26 (0.91) | 4.76 (0.87) |

[a]Median (minimum-maximum).

A comparison of $C_{max}$ showed that OC concentrations were 12% and 25% higher when the formulation was given under high fat (Treatment A) and low fat (Treatment B) conditions, compared to fasted conditions (Treatment C; see Table 33). The $C_{max}$ for Treatment A was bioequivalent to both Treatments B (84%-96%) and C (105%-120%) as the 90% CIs for the geometric ratios were contained within 80% to 125% (see Table 34). The $C_{max}$ observed for Treatment B was not bioequivalent to Treatment C (117%-134%). AUCs were approximately 15% higher when the formulation was administered under fed conditions (high and low fat), as compared to fasted conditions (Table 33). AUC for both Treatments A and B (high fat and low fat) were bioequivalent to Treatment C (fasted; 111%-121% and 111%-120% for AUC0-t and 111%-120% and 110%-120% for AUC0-inf) (Table 34). The apparent plasma terminal elimination half-life (t½) for OC was similar when the formulation was administered under fed (4 hours) and fasted conditions (5 hours).

TABLE 34

Oxycodone Geometric LSMEANS Ratio (%) (90% CI)

| Parameter | Treatment A/C<br>Fed (High<br>Fat)/Fasted | Treatment B/C<br>Fed (Low<br>Fat)/Fasted | Treatment A/B<br>Fed (High Fat)/<br>Fed (Low Fat) |
|---|---|---|---|
| $AUC_{0-inf}$ (ng · h/mL)[a] | 115.41<br>(110.63, 120.41) | 115.09<br>(110.38, 120.01) | 100.28<br>(96.18, 104.55) |
| $AUC_{0-t}$ (ng · h/mL)[a] | 115.85<br>(111.00, 120.90) | 115.30<br>(110.54, 120.27) | 100.47<br>(96.34, 104.79) |
| $C_{max}$ (ng/mL)[a] | 112.11<br>(104.61, 120.16) | 125.16<br>(116.88, 134.03) | 89.57<br>(83.67, 95.90) |

[a]N = 31.

PK parameters for APAP are presented in Tables 35 and 36 and the plasma APAP concentration-time profiles are presented in FIG. 20. APAP was rapidly absorbed following administration under fed (high and low fat meals) and fasted conditions. There was a slight lag when the formulation was administered after a low fat breakfast (median lag time [$t_{lag}$] 0.25 hours). There was no lag in the absorption of APAP when administered following a high fast breakfast or after fasting. The time to $C_{max}$ was significantly (P<0.05) longer when administered after a meal (high and low fat; median $T_{max}$=2 hours) than when administered under fasted conditions (median $T_{max}$=0.5 hour). Average $C_{max}$ values for APAP were lower after a high (3,775 ng/mL) and low fat (3,863 ng/mL) meal than when administered under fasted conditions (5,175 ng/mL). Geometric mean ratios for $C_{max}$ following Treatments A and B were 24% to 23% lower than for Treatment C (Table 36). The 90% CIs for $C_{max}$ following Treatment A (70%-82%) and Treatment B (72%-83%) with reference to fasted state were outside the bioequivalent range of 80%-125%. The AUCs for APAP were almost identical when the formulation was administered under high fat, low fat, or fasting conditions. (Comparison of geometric mean ratios of $AUC_{0-t}$ and $AUC_{0\,inf}$ for Treatments A (90% CI 97%-103% and 96%-102%) and B (90% CI 96%-101% and 94% to 100%) with those for Treatment C showed that treatments were bioequivalent. The $t_{1/2}$ for APAP after the formulation was administered after a high or low fat meal (5 hours) was slightly shorter than when administered under fasted conditions (7 hours).

TABLE 35

APAP Pharmacokinetic Estimates (2 tablets of 7.5/325)

| Parameter | Treatment A<br>Fed (High Fat)<br>Mean (SD)<br>(N = 31) | Treatment B<br>Fed (Low Fat)<br>Mean (SD)<br>(N = 31) | Treatment C<br>Fasted<br>Mean (SD)<br>(N = 31) |
|---|---|---|---|
| $AUC_{0-t}$ (ng · h/mL) | 29617.96 (7765.99) | 29346.82 (7869.75) | 29763.19 (7592.89) |
| $AUC_{0-inf}$ (ng · h/mL) | 31457.06 (7973.16)[a] | 30550.48 (8051.47) | 31807.70 (7923.30)[a] |
| $C_{max}$ (ng/mL) | 3774.52 (949.84) | 3862.90 (978.08) | 5175.48 (1731.31) |
| $T_{max}$ (h)[b] | 2.00 (0.50-5.00) | 2.00 (0.50-5.00) | 0.53 (0.23-5.00) |
| $K_{el}$ (1/h) | 0.1564 (0.0363)[a] | 0.1593 (0.0408) | 0.1146 (0.0360)[a] |
| $t_{lag}$ (h)[b] | 0.00 (0.00-1.00) | 0.25 (0.00-0.50) | 0.00 (0.00-0.25) |
| $t_{1/2}$ (h) | 4.66 (1.08)[a] | 4.71 (1.60) | 6.63 (1.99)[a] |

[a]N = 29
[b]Median (minimum-maximum).

TABLE 36

APAP Geometric LSMEANS Ratio (%) (90% CI)

| Parameter | Treatment A/C Fed (High Fat)/Fasted | Treatment B/C Fed (Low Fat)/Fasted | Treatment A/B Fed (High Fat)/Fed (Low Fat) |
|---|---|---|---|
| $AUC_{0-inf}$ (ng · h/mL)[a] | 98.60 (95.75, 101.54) | 96.56 (93.80, 99.39) | 102.12 (99.20, 105.11) |
| $AUC_{0-t}$ (ng · h/mL)[b] | 99.88 (97.31, 102.52) | 98.79 (96.27, 101.37) | 101.10 (98.54, 103.74) |
| $C_{max}$ (ng/mL)[b] | 76.00 (70.49, 81.94) | 77.18 (71.65, 83.13) | 98.48 (91.45, 106.05) |

[a]N = 27
[b]N = 31

In summary, total exposure (AUC) for OC was slightly increased (by about 15%) when the formulation was administered with food (after high- or low-fat meal); however, AUCs for OC were equivalent between all treatments (high fat vs. fasted, low fat vs. fasted and high fat vs. low fat). Peak exposure ($C_{max}$) for OC was 12% and 25% higher under high fat and low-fat conditions, respectively, compared to fasted conditions. The $C_{max}$ for OC after a high-fat meal was bioequivalent to fasted conditions, as well as to low fat conditions, whereas the $C_{max}$ under low fat conditions was not equivalent to those under fasted conditions. The AUCs for APAP were equivalent between all treatments (high fat vs. fasted, low fat vs. fasted, and high fat vs. low fat). The peak exposure ($C_{max}$) for APAP was decreased by about 24% in fed (high- and low-fat) states as compared to the fasted state.

Example 10

Clinical Pharmacokinetic Analysis of an Extended Release Formulation of 7.5 mg Oxycodone/325 mg Acetaminophen—Single Dose An open-label, randomized, 3-period crossover study was performed to evaluate the single dose pharmacokinetic (PK) parameters, bioavailability, and safety of an extended-release formulation containing 7.5 mg OC/325 mg APAP (see selected example from Chart No. 1) in healthy subjects under fasted conditions. The PK and bioavailability of the extended-release formulation administered as 1 or 2 tablets were compared to the commercially-available immediate release tablet (immediate release 7.5 mg OC/325 mg APAP) administered as 1 or 2 tablets every 6 hours for 2 doses. This study was conducted in 48 male and female subjects, with equal gender distribution.

Pharmacokinetic parameter estimates for OC are presented in Table 37, and OC plasma concentration-time profiles are presented in FIG. 21. There was no lag in absorption of OC for the 1 and 2 tablet dosing configurations of the extended release formulation and the commercially-available immediate release tablet under fasted conditions. Plasma concentrations of OC rose rapidly after administration of the extended release formulation in a similar fashion to the commercially-available immediate release tablet, and peak plasma levels of OC were observed ($T_{max}$) at 4 and 3 hours for the 1 or 2 tablet dosing configuration of the extended release formulation compared with 7 hours after the initial dose of 1 tablet of the commercially-available immediate release tablet (1 hour after the second dose) and 0.75 hours after the initial dose of 2 tablets of the commercially-available immediate release tablet. Mean plasma concentrations of OC from the extended release formulation were detectable through 36 hours in most subjects following all treatments and $t_{1/2}$ was about 4 to 5 hours across all treatments. The extent of exposure ($AUC_{0-t}$ and $AUC_{0-inf}$) for the 2 tablet dosing configuration of the extended release formulation increased proportionally with dose compared with the 1-tablet dosing configuration of the extended release formulation.

TABLE 37

Oxycodone Pharmacokinetic Estimates (7.5/325)

| Parameter | Treatment A ER Formulation (1 tablet) Mean (SD) (N = 33) | Treatment B ER Formulation (2 tablets) Mean (SD) (N = 33) | Treatment C Commercially-available immediate release tablet (1 tablet twice) Mean (SD) (N = 33) | Treatment D Commercially-available immediate release tablet (2 tablets twice) Mean (SD) (N = 27) |
|---|---|---|---|---|
| $AUC_{0-t}$ (ng · h/mL) | 87.43 (24.59) | 185.98 (47.64) | 191.15 (53.43) | 401.23 (110.56) |
| $AUC_{0-inf}$ (ng · h/mL) | 89.85 (24.73)[b] | 187.71 (47.58) | 193.10 (53.22) | 403.04 (110.45) |
| $C_{max}$ (ng/mL) | 8.41 (2.06) | 16.39 (4.31) | 20.82 (5.98) | 41.24 (12.12) |
| $T_{max}$ (h)[a] | 4.00 (0.75-5.92) | 3.00 (0.75-6.50) | 7.38 (0.50-10.00) | 0.75 (0.50-12.00) |
| $t_{lag}$ (h)[a] | 0.00 (0.00-0.50) | 0.00 (0.00-0.52) | 0.00 (0.00-0.25) | 0.00 (0.00-0.25) |
| $t_{1/2}$ (h) | 4.50 (0.78)[b] | 4.87 (0.93) | 4.08 (0.89) | 4.34 (1.02) |
| $K_{el}$ (h$^{-1}$) | 0.1590 (0.0307)[b] | 0.1473 (0.0274) | 0.1770 (0.0352) | 0.1688 (0.0415) |

[a]Median (minimum-maximum).
[b]N = 32

No dose-dumping was observed in any subject receiving the ER formulation. The interindividual variability (CV %) for $C_{max}$ of OC after administration of 1 or 2 tablets of the ER formulation was comparable to 1 tablet of the commercially-available immediate release tablet and less than 29% for all 3 treatments. Similarly the interindividual variability (CV %) for AUC of OC was 28% or less for 1 and 2 tablets of the ER formulation and 1 tablet of the commercially-available immediate release tablet.

Table 38 presents APAP PK parameter estimates and FIG. 22 presents APAP plasma concentration-time profiles. The appearance of plasma concentrations of APAP for all dose configurations of the extended release formulation and the commercially-available immediate release tablet showed no lag. Plasma concentrations of APAP rose rapidly after administration of the extended release formulation, similar to that observed with the commercially-available immediate release tablet. Peak plasma levels of APAP following administration of the 1 tablet and 2 tablet dosing configurations of the extended release formulation were observed (median $T_{max}$) at 0.75 hours after dosing compared with 0.5 hours after the first dose of the commercially-available immediate release tablet (1 and 2 tablets). Mean plasma concentrations of APAP were detectable through 36 hours following all treatments and the mean $t_{1/2}$ was approximately 4 to 7 hours across treatment groups. The extent of exposure (AUC) to APAP following dosing with 1 and 2 tablets of the extended release formulation increased proportionally with dose.

release) or a composite form, typically consisting of an in vivo release followed by a drug delivery to the general systemic circulation. It can estimate the cumulative amount and fraction absorbed over time for the subjects, given PK profile data and dose. For a pure immediate release (IR) or an extended release (ER) formulation the cumulative absorption plot shows a monoexponential curve whereas for a bilayer formulation (IR+ER) a biexponential (rapid phase followed by slower phase) absorption curve will be observed. FIG. 23 and FIG. 24 present the deconvolution plots for OC and APAP, respectively. For each, there is an early rapid phase of absorption that is followed by a later slower phase of absorption from the ER formulation.

TABLE 38

APAP Pharmacokinetic Estimates (7.5/325)

| Parameter | Treatment A ER Formulation (1 tablet) Mean (SD) (N = 33) | Treatment B ER Formulation (2 tablets) Mean (SD) (N = 33) | Treatment C Commercially-available immediate release tablet (1 tablet twice) Mean (SD) (N = 33) | Treatment D Commercially-available immediate release tablet (2 tablets twice) Mean (SD) (N = 27) |
|---|---|---|---|---|
| $AUC_{0-t}$ (ng · h/mL) | 15871 (4841) | 32665 (10894) | 33040 (9589) | 69837 (22945) |
| $AUC_{0-inf}$ (ng · h/mL) | 16995 (5073) | 34836 (11067)[b] | 34236 (10126)[b] | 71949 (24234)[c] |
| $C_{max}$ (ng/mL) | 2632 (918) | 5230 (2086) | 4878 (1545) | 10741 (4123) |
| $T_{max}$ (h)[a] | 0.75 (0.25-2.02) | 0.75 (0.25-4.00) | 0.50 (0.25-9.00) | 0.50 (0.25-12.00) |
| $t_{lag}$ (h)[a] | 0.00 (0.00-0.50) | 0.00 (0.00-0.25) | 0.00 (0.00-0.00) | 0.00 (0.00-0.00) |
| $t_{1/2}$ (h) | 5.33 (1.53) | 6.88 (2.15)[b] | 4.41 (1.16)[b] | 5.76 (1.47)[c] |
| $K_{el}$ (h$^{-1}$) | 0.1421 (0.0479) | 0.1103 (0.0337)[b] | 0.1669 (0.0411)[b] | 0.1291 (0.0368)[c] |

[a]Median (minimum-maximum).
[b]N = 32
[c]N = 25

No dose-dumping was observed in any subject receiving the ER formulation. The interindividual variability (CV %) for $C_{max}$ of APAP was slightly more after administration of 1 and 2 tablets of the ER formulation (35% and 40%, respectively) than for 1 tablet of the commercially-available immediate release tablet (32%). The interindividual variability (CV %) for AUC of APAP was less than 33% for all 3 treatments.

Both OC and APAP were rapidly absorbed under all conditions with no lag in plasma concentrations. Both OC and APAP levels were sufficiently high within 1 hour after administration of the extended release formulation. Peak exposure to OC was 18% to 21% lower for the ER formulation than for the commercially-available immediate release tablet (1 tablet Q6h). OC levels were sustained over the proposed 12h dosing interval. By 12 hours after dosing with the extended release formulation, APAP plasma levels were less than 20% of $C_{max}$. Total exposure to both OC and APAP from the extended release formulation was equivalent to that of 1 tablet of the commercially-available immediate release tablet.

To further analyze the absorption of OC and APAP from the ER formulation, the plasma concentrations of OC and APAP following administration of 1 tablet of the ER formulation, 2 tablets of the ER formulation, and the commercially-available immediate release tablet were deconvolved using WinNonlin 5.2 (Pharsight). Deconvolution evaluates in vivo drug release and bioavailability based on data for a known drug input. Depending upon the type of reference input information available, the drug transport evaluated will be either a simple in vivo drug release (e.g., gastro-intestinal Example 11

Clinical Pharmacokinetic Analysis of an Extended Release Formulation of 7.5 mg Oxycodone/325 mg Acetaminophen—Multiple Doses An open-label, randomized, 3-period crossover study was performed to evaluate the steady-state PK, bioavailability, and safety of the extended release formulation containing 7.5 mg OC/325 mg APAP in healthy subjects (see selected example from Chart No. 1). The PK and bioavailability of the ER formulation administered as 1 or 2 tablets every 12 hours for 4.5 days (9 doses) was compared to the commercially-available immediate release tablet (immediate release 7.5 mg OC/325 mg APAP) administered as 1 tablet every 6 hours for 4.5 days (18 doses) under fasted conditions (10 hours for the first dose on Days 1 and 5; at least 1 hour for all other doses). This study was conducted in 48 male and female subjects, with equal gender distribution.

The PK behavior of OC on Study Day 1 (see Table 39) was similar to that observed in the single dose study (see Example 10). There was no lag (median $t_{lag}$ 0 hours) in the absorption of OC following administration of the ER formulation (1 or 2 tablets) and the commercially-available immediate release tablet, and no dose-dumping was observed for any subject. Peak plasma levels were observed at 3 hours after administration of 1 and 2 tablets of the ER formulation and at 1 hour after the second dose of the commercially-available immediate release tablet (FIG. 25). On Day 1, interindividual variability (% CV) in the $C_{max}$ for OC was slightly higher for 1 tablet (29%) than for 2 tablets (23%) of the ER formulation or the commercially-available immediate release tablet (up to 22%). The variability in the $AUC_{0-12hr}$ for OC was comparable between all 3 treatments (21% to 23%). Minimum (trough) plasma concentrations (Cmin) of OC achieved steady-state levels by Day 4 for 1 tablet of the ER formulation and the commercially-available immediate release tablet and by Day 3 for 2 tablets of the ER formulation. Trough levels of OC on Days 2 through 5 for 2 tablets of the ER formulation were comparable to those observed for the commercially-available immediate release tablet.

The PK behavior of APAP on Study Day 1 (see Table 41) was similar to that observed in the single dose study (see Example 10). Acetaminophen was rapidly absorbed following a single dose of 1 or 2 tablets of the ER formulation and in a similar fashion to the commercially-available immediate release tablet. (See FIG. 26). There was no lag in plasma concentrations following any of the 3 dosing regimens (median $t_{lag}$ 0 hours), and no dose-dumping was observed for any subject. Peak APAP plasma concentrations were observed 30 to 45 minutes after administration of 1 or 2 tablets of the ER formulation and at 30 minutes after the first

TABLE 39

Oxycodone Pharmacokinetic Estimates - Day 1

| Parameter | Treatment A ER Formulation (1 Tablet Q12h) Mean (SD) (N = 33) | Treatment B ER Formulation (2 Tablets Q12h) Mean (SD) (N = 33) | Treatment C Commercially-available immediate release tablet (1 Tablet Q6h) Mean (SD) (N = 33) |
|---|---|---|---|
| $AUC_{0-12\ h}$ (ng · h/mL) | 66.93 (15.14) | 135.89 (30.81) | 141.73 (29.78) |
| $C_{max}$ (ng/mL) | 8.34 (2.37) | 17.05 (3.97) | 21.93 (4.80) |
| $T_{max}$ (h)[a] | 3.00 (0.75-7.00) | 3.00 (0.50-5.92) | 7.00 (0.50-8.00) |
| $t_{lag}$ (h)[a] | 0.00 (0.00-0.50) | 0.00 (0.00-0.32) | 0.00 (0.00-0.25) |

[a]Median (minimum-maximum).

On Day 5 (see Table 40), steady state was achieved and the median $T_{max}^{ss}$ was observed at 2 hours following 1 tablet or 2 tablets of the ER formulation and at 30 min following the second daily dose of the commercially-available immediate release tablet. Maximum observed plasma concentrations at steady-state ($C_{max}^{ss}$) for OC for the 1 and 2 tablet dosing configurations of the ER formulation were not equivalent to the commercially-available immediate release tablet. On Day 5, interindividual variability (% CV) in $C_{max}^{ss}$ and $AUC_{0-12\ h}^{ss}$ for OC was comparable between all 3 treatments (up to 29%). The degree of fluctuation (DFL) in and the swing of plasma concentrations for the ER formulation over the last 12 hour dosing interval on Day 5 were 15% to 22% less than that observed for the commercially-available immediate release tablet.

dose of the commercially-available immediate release tablet on Day 1. The $C_{max}$ for APAP occurred following the first 325 mg dose of the commercially-available immediate release tablet, rather than after the second dose. Dose proportionality for $C_{max}$ and $AUC_{0-12h}$ was observed over the range of 325 mg to 650 mg APAP after a single administration of 1 or 2 tablets of the ER formulation. The $C_{min}$ of APAP achieved steady-state levels by Day 4 for 1 tablet and by Day 2 for 2 tablets of the ER formulation and for the commercially-available immediate release tablet. Trough levels of APAP on Days 2 through 5 for 2 tablets of the ER formulation were comparable to those observed for the commercially-available immediate release tablet. On Day 1, interindividual variability (% CV) in $C_{max}$ and $AUC_{0-12h}$ for APAP was comparable between all 3 treatments (31% or less).

TABLE 40

Oxycodone Pharmacokinetic Estimates - Day 5

| Parameter | Treatment A ER Formulation (1 Tablet Q12h) Mean (SD) (N = 33) | Treatment B ER Formulation (2 Tablets Q12h) Mean (SD) (N = 33) | Treatment C Commercially-available immediate release tablet (1 Tablet Q6h) Mean (SD) (N = 33) |
|---|---|---|---|
| $AUC_{0-12\ h}^{ss}$ (ng · h/mL) | 102.36 (29.30) | 208.59 (59.28) | 208.93 (57.30) |
| $C_{av}^{ss}$ (ng/mL) | 8.53 (2.44) | 17.38 (4.94) | 17.41 (4.78) |
| $C_{max}^{ss}$ (ng/mL) | 12.67 (3.48) | 25.67 (7.49) | 30.50 (8.91) |
| $C_{min}^{ss}$ (ng/mL) | 4.06 (1.40) | 8.98 (3.52) | 8.78 (3.17) |
| DFL (%) | 101.72 (14.14) | 97.17 (18.80) | 126.83 (27.93) |
| Swing | 2.23 (0.64) | 2.03 (0.70) | 2.67 (0.92) |
| $T_{max}^{ss}$ (h)[a] | 2.00 (0.50-10.00) | 2.00 (0.50-7.00) | 6.50 (0.50-8.02) |
| $t_{1/2}$ (h)[c] | 5.46 (1.24) | 6.11 (1.46) | 5.47 (1.70)[b] |
| $K_{el}$ (1/h)[c] | 0.1326 (0.0269) | 0.1199 (0.0291) | 0.1387 (0.0418)[b] |

[a]Median (minimum-maximum).
[b]N = 32
[c]Days 5 to 7.

TABLE 41

APAP Pharmacokinetic Estimates - Day 1

| Parameter | Treatment A<br>ER Formulation<br>(1 Tablet Q12h)<br>Mean (SD)<br>(N = 33) | Treatment B<br>ER Formulation<br>(2 Tablets Q12h)<br>Mean (SD)<br>(N = 33) | Treatment C<br>Commercially-<br>available immediate<br>release tablet<br>(1 Tablet Q6h)<br>Mean (SD)<br>(N = 33) |
|---|---|---|---|
| $AUC_{0-12\,h}$ (ng · h/mL) | 12192 (3331) | 24141 (6436) | 24884 (6656) |
| $C_{max}$ (ng/mL) | 2631 (815) | 5245 (1473) | 5146 (1553) |
| $T_{max}$ (h)$^a$ | 0.55 (0.25-3.00) | 0.75 (0.25-2.00) | 0.50 (0.25-8.00) |
| $t_{lag}$ (h)$^a$ | 0.00 (0.00-0.25) | 0.00 (0.00-0.25) | 0.00 (0.00-0.00) |

$^a$Median (minimum-maximum).

On Day 5 of the study, median $T_{max}^{ss}$ for APAP was observed at 30 minutes following 1 or 2 tablets of the ER formulation and at 30 minutes following the first daily dose of the commercially-available immediate release tablet (see Table 42). Acetaminophen concentrations following administration of 325 mg or 650 mg APAP (1 or 2 tablets) Q12h were proportional to dose. The DFL in and swing of plasma APAP levels for the ER formulation were equivalent to the commercially-available immediate release tablet. On Day 5, interindividual variability (% CV) in $C_{max}^{ss}$ for APAP was slightly higher following administration of 2 tablets of the ER formulation (33%) than the % CV seen for 1 tablet of the ER formulation and the commercially-available immediate release tablet (~27%). Interindividual variability in $AUC_{0-12h}^{ss}$ for APAP was comparable between all 3 treatments (up to 27%).

TABLE 42

APAP Pharmacokinetic Estimates - Day 5

| Parameter | Treatment A<br>ER Formulation<br>(1 Tablet Q12h)<br>Mean (SD)<br>(N = 33) | Treatment B<br>ER Formulation<br>(2 Tablets Q12h)<br>Mean (SD)<br>(N = 33) | Treatment C<br>Commercially-<br>available<br>immediate release<br>tablet<br>(1 Tablet Q6h)<br>Mean (SD)<br>(N = 33) |
|---|---|---|---|
| $AUC_{0-12\,h}^{ss}$ (ng · h/mL) | 15307 (4092) | 28512 (7714) | 28719 (7023) |
| $C_{av}^{ss}$ (ng/mL) | 1276 (341) | 2376 (643) | 2393 (585) |
| $C_{max}^{ss}$ (ng/mL) | 3117 (840) | 5872 (1932) | 5968 (1639) |
| $C_{min}^{ss}$ (ng/mL) | 474.67 (163) | 870.42 (336) | 922.58 (321) |
| DFL (%) | 212.08 (52.29) | 218.06 (81.14) | 213.79 (50.53) |
| Swing | 5.95 (2.04) | 6.63 (3.61) | 5.94 (2.24) |
| $T_{max}^{ss}$ (h)$^a$ | 0.50 (0.25-3.00) | 0.50 (0.25-3.02) | 0.50 (0.25-8.02) |
| $t_{1/2}$ (h)$^c$ | 5.60 (1.35)$^b$ | 7.47 (2.89) | 5.74 (2.98)$^b$ |
| $K_{el}$ (1/h)$^c$ | 0.1308 (0.0317)$^b$ | 0.1026 (0.0292) | 0.1416 (0.0515)$^b$ |

$^a$Median (minimum-maximum).
$^b$N = 31
$^c$Days 5 to 7.

Both OC and APAP were rapidly absorbed under all conditions with no lag in plasma concentrations. Both OC and APAP levels were sufficiently high within 1 hour after administration of the ER formulation as a single dose and at steady-state. OC levels were sustained over the proposed 12h dosing interval. Plasma APAP concentrations decreased to below 1,000 ng/mL between doses of the ER formulation, thus minimizing the chances of its accumulation and the possibility of hepatotoxicity. Total exposure to both OC and APAP from the ER formulation was equivalent to that of the commercially-available immediate release tablet.

Example 12

Clinical Evaluation of the Safety and Analgesic Efficacy of an Extended Release Formulation of Oxycodone and Acetaminophen for Acute Pain Pain relief for acute post-surgical pain requires immediate-release (IR) compounds acting within 1 hour of administration. These IR compounds, however, have a short half-life and require frequent administration; this is inconvenient to patients and leads to poor compliance. Such patients may benefit from an extended-release (ER) oral formulation of oxycodone hydrochloride (OC) and acetaminophen (APAP) that is designed to (1) provide the immediate-release of each drug to attain rapid therapeutic levels (within 1 hour of dosing) and (2) provide continuous release of each drug to maintain the plasma levels of each drug within therapeutic windows for sustained analgesia (up to 12 hours). Furthermore, combining analgesics with distinct mechanisms of action provides maximum efficacy while reducing the toxicity of each agent, as the amount of OC and APAP can remain within the lower, safer end of their therapeutic windows. This ER formulation may provide the advantages of both immediate and prolonged pain relief from two analgesic compounds, potentially offering greater convenience to patients and greater dosing compliance. Accordingly, a study may be conducted to demonstrate the efficacy of repeated doses of 15 mg OC/650 mg APAP versus placebo, and to determine the safety and tolerability of multiple oral doses of the OC/APAP formulation administered to subjects with acute postoperative, moderate to severe pain.

The study will be conducted in the following phases: 1) pre-treatment phase consisting of a) screening, b) surgery, and c) recovery/qualification periods; 2) double-blind phase consisting of a single dose period followed by a multiple-dose period which begins with the request of the 2nd dose of study medication, and; 3) a voluntary open-label extension phase.

The single dose period of the double-blind phase will evaluate the onset and duration of analgesia of a single dose of 15 mg OC/650 mg APAP (as two 7.5/325 tablets) versus placebo. The time from the initial dose of study medication to the onset of perceptible pain relief and to the onset of meaningful pain relief will be measured. The subject will provide additional pain assessments (e.g., pain intensity will be measured using the 11 point NPRS scale at regular intervals).

The multiple dose period of the double-blind phase will evaluate the analgesic effects of multiple doses of 15 mg OC/650 mg APAP versus placebo with subjects dosed regularly every 12 hours for 48 hours. The multiple dose period will begin upon administration of the second dose after the subject's request for additional pain relief. Pain relief and intensity will be among the data measured in this arm of the study.

After completion of study evaluations 48 hours after the 2nd dose of study medication, subjects will be encouraged to enter the open-label extension phase of the study. During this time they will be provided with doses of 15 mg OC/650 mg APAP to be taken Q12h until no longer needed, for up to 14 days. The open-label extension phase (starting 48 hours after the second dose) will evaluate the safety profile as determined by adverse events (AE) and evaluate subject satisfaction with analgesic effects.

Example 13

Clinical Evaluation of the Safety and Efficacy of an Extended Release Formulation of Oxycodone and Acetaminophen for Chronic Pain An open label safety study of doses of 15 mg OC/650 mg APAP administered at 12 hour intervals for up to 35 days in a patient population having pain associated with osteoarthritis (OA) of the knee or hip or chronic low back pain (CLBP) may be conducted. The primary objective of the study is to determine the safety and tolerability of doses of 15 mg OC/650 mg APAP for up to 35 days of use. Secondary objectives such as pain relief and changes in pain intensity will also be assessed.

Subjects enrolled in the study will be treated with 2 tablets of 7.5 mg OC/325 mg APAP every 12 hours (Q12h) for between 10 days and 35 days. Subjects will initially take 1 tablet of 7.5 mg OC/325 mg APAP under clinic supervision. Subjects will be observed for opioid tolerability symptoms. Subjects who experience opioid tolerability symptoms, or moderate to severe AEs, will be discontinued from the study. Subjects who do not experience opioid tolerability symptoms, or moderate to severe AEs, will be given a second tablet of 7.5 mg OC/325 mg APAP under clinic supervision. If subjects still do not experience opioid tolerability symptoms, or moderate to severe AEs, they will be sent home with supplies for dosing with 2 tablets of 7.5 mg OC/325 mg APAP Q12h for one week. If subjects do experience opioid tolerability symptoms, or moderate to severe AEs, they will be sent home with supplies for dosing with 1 tablet of 7.5 mg OC/325 mg APAP Q12h for one week.

Subjects that continue in the study beyond one week will continue to take 2 tablets Q12h for up to a total of 35 days, during which they will return to the clinic for subsequent assessments of safety and efficacy. After the Day 36 visit, subjects will be instructed to return to pre-study medication. Subjects whose pain subsides prior to the Day 36 visit, or who discontinue for other reasons will be instructed to return remaining study medication.

Example 14

Partial Areas Under the Curve for Oxycodone and Acetaminophen

Partial AUCs were calculated for a bilayer extended release tablet disclosed herein containing acetaminophen and oxycodone, and an immediate release acetaminophen and oxycodone tablet. Specifically, Partial AUCs were calculated for the acetaminophen and oxycodone tablets of (1) Treatment B of Example 10, (2) Treatment C of Example 9, and (3) Treatment D of Example 10. These results are summarized in Tables 43-46.

TABLE 43

Mean (SD) Parameter Estimates for Partial AUCs for Acetaminophen

| Study | $AUC_{0-1.7\,h}$ (ng · h/mL) | $AUC_{1.7-48\,h}$ (ng · h/mL) | $AUC_{0-t}$ (ng · h/mL) |
|---|---|---|---|
| Treatment B (Ex. 10) | 6029 | 28435 | 32644 |
| Treatment C (Ex. 9) | 5854 | 25539 | 29741 |

TABLE 44

Additional Mean (SD) Parameter Estimates for Partial AUCs for Acetaminophen

| Study | $AUC_{0-12\,h}$ (ng · h/mL) | $AUC_{1-12\,h}$ (ng · h/mL) | $AUC_{12-36\,h}$ (ng · h/mL) | $AUC_{8-12\,h}$ (ng · h/mL) | $AUC_{0-t}$ (ng · h/mL) |
|---|---|---|---|---|---|
| Treatment B (Ex. 10) | 25912 | 22615 | 7978 | 4401 | 32644 |
| Treatment C (Ex. 9) | 24102 | 20875 | 6854 | 3910 | 29741 |

TABLE 45

Percent of $AUC_{0-t}$ for Acetaminophen

| Study | $AUC_{0-12\,h}$ (dosing interval) | $AUC_{1-12\,h}$ ($T_{max}$ to end of dosing interval) | $AUC_{12-36\,h}$ (end of dosing interval to last concentration) | $AUC_{8-12\,h}$ |
|---|---|---|---|---|
| Treatment B (Ex. 10) | 79% | 69% | 24% | 13% |
| Treatment C (Ex. 9) | 81% | 70% | 23% | 13% |

TABLE 46

Mean (SD) Parameter Estimates for Partial AUCs for Oxycodone

| Study | $AUC_{0-2.8\,h}$ (ng · h/mL) | $AUC_{2.8-48\,h}$ (ng · h/mL) | $AUC_{0-t}$ (ng · h/mL) |
|---|---|---|---|
| Treatment B (Ex. 10) | 28.75 | 158.49 | 185.93 |
| Treatment C (Ex. 9) | 27.89 | 164.27 | 190.66 |

The bioequivalence determinations between two tablets of a pharmaceutical composition described herein, each containing 7.5 mg oxycodone and 325 mg acetaminophen and an immediate release tablet comprising 7.5 mg oxycodone and 325 mg acetaminophen can be found in Tables 47 and 48.

TABLE 47

Bioequivalence Determination for Acetaminophen

| Parameter | LSM Ratio | 90% CI Lower | 90% CI Upper |
|---|---|---|---|
| $Ln(AUC_{0-1.7\,h})$ | 101.97 | 82.90 | 125.43 |
| $Ln(AUC_{1.7-48\,h})$ | 91.15 | 80.58 | 103.11 |
| $Ln(AUC_{0-t})$ | 93.14 | 82.40 | 105.28 |

TABLE 48

Bioequivalence Determination for Oxycodone

| Parameter | LSM Ratio | 90% CI Lower | 90% CI Upper |
|---|---|---|---|
| $Ln(AUC_{0-2.8\,h})$ | 99.04 | 87.83 | 111.68 |
| $Ln(AUC_{2.8-48\,h})$ | 103.21 | 92.57 | 115.06 |
| $Ln(AUC_{0-t})$ | 102.19 | 92.34 | 113.09 |

The results demonstrate that the plasma concentrations of both oxycodone and acetaminophen rose rapidly with no lag time for a pharmaceutical composition of the present invention and an immediate release tablet comprising 7.5 mg oxycodone and 325 mg acetaminophen. See FIGS. 29(a) and (b). Further, 30 minutes after administration of a dose of a pharmaceutical composition of the present invention (i.e., 2 tablets of 7.5 oxycodone/325 acetaminophen), oxycodone levels were within the therapeutic range (>5 ng/mL). Thus, an analgesic effect will be seen in opioid naïve patients. In addition, a pharmaceutical composition of the present invention was able to maintain oxycodone levels above 5 ng/mL for up to 12 hours after dosing, suggesting that the analgesic effect may extend to the next dosing cycle.

Concentrations of acetaminophen resulting from a dose of a pharmaceutical composition of the present invention (i.e., 2 tablets of 7.5 oxycodone/325 acetaminophen), decreased to less than 900 ng/mL (>17% of Cmax) by 12 hours after administration. This decreased concentration of acetaminophen at the end of the dosing cycle allows for sufficient acetaminophen or "APAP time off" between doses.

Oxycodone and acetaminophen levels from a pharmaceutical composition of the present invention (i.e., 2 tablets of 7.5 oxycodone/325 acetaminophen) declined at a similar rate to an immediate release tablet comprising 7.5 mg oxycodone and 325 mg acetaminophen, with a terminal elimination half-life of approximately 4 to 5 hours.

Example 15

Partial Areas Under the Curve for Oxycodone and Acetaminophen Administered with Food Partial AUCs were calculated for a bilayer extended release tablet disclosed herein containing acetaminophen and oxycodone, and an immediate release acetaminophen and oxycodone tablet. Specifically, Partial AUCs were calculated for the acetaminophen and oxycodone tablets of 1) Treatment A of Example 4, (2) Treatment A of Example 6 (one tablet), and (3) Treatment C of Example 4. These results are summarized in Tables 49-50.

TABLE 49

Mean (SD) Parameter Estimates for Partial AUCs for Acetaminophen.

| Study | $AUC_{0-3.2\,h}$ (ng · h/mL) | $AUC_{3.2-48\,h}$ (ng · h/mL) | $AUC_{0-t}$ (ng · h/mL) |
|---|---|---|---|
| Treatment A (Ex. 4) | 8042 | 23810 | 30245 |
| Treatment A (Ex. 6) (one tablet) | 9145 | 23319 | 31478 |

TABLE 50

Mean (SD) Parameter Estimates for Partial AUCs for Oxycodone.

| Study | $AUC_{0-4.3\,h}$ (ng · h/mL) | $AUC_{4.3-48\,h}$ (ng · h/mL) | $AUC_{0-t}$ (ng · h/mL) |
|---|---|---|---|
| Treatment A (Ex. 4) | 48.62 (15.99) | 152.57 (49.86) | 199.43 (59.47) |
| Treatment A (Ex. 6) (one tablet) | 53.29 (17.12) | 167.50 (51.83) | 219.20 (55.99) |

The bioequivalence determinations between the pharmaceutical composition described herein, containing 15 mg oxycodone and 650 mg acetaminophen and an immediate release product comprising 15 mg oxycodone and 650 mg acetaminophen can be found in Tables 51 and 52.

TABLE 51

Bioequivalence Determination for Acetaminophen

| Parameter | LSM Ratio | 90% CI Lower | 90% CI Upper |
|---|---|---|---|
| $Ln(AUC_{0-3.2\,h})$ | 114.46 | 96.21 | 136.16 |
| $Ln(AUC_{3.2-48\,h})$ | 94.62 | 83.31 | 107.47 |
| $Ln(AUC_{0-t})$ | 101.32 | 90.00 | 114.07 |

TABLE 52

Bioequivalence Determination for Oxycodone

| Parameter | LSM Ratio | 90% CI Lower | 90% CI Upper |
|---|---|---|---|
| $Ln(AUC_{0-4.3\,h})$ | 109.87 | 94.98 | 127.08 |
| $Ln(AUC_{4.3-48\,h})$ | 109.75 | 94.48 | 127.48 |
| $Ln(AUC_{0-t})$ | 110.53 | 97.39 | 125.44 |

Exposure to oxycodone and acetaminophen was comparable between Treatment A of Example 4 and Treatment A of Example 6 (one tablet). Thus, these results indicate that the release of oxycodone and acetaminophen is consistent across studies. Plasma concentration-time profiles are presented in FIGS. 30A and 30B.

The initial exposure to oxycodone ($AUC_{0-4.3h}$) was slightly outside the bioequivalence parameters established by the FDA (upper 90% CI 127%). The initial exposure to acetaminophen ($AUC_{0-3.2h}$) was outside of the FDA's bioequivalence parameters (upper 90% CI 136%).

The extended (sustained) exposure to oxycodone ($AUC_{4.3-48h}$) was slightly outside the FDA's limit for bioequivalence (upper 90% CI 127%). However, the extended exposure to acetaminophen ($AUC_{3.2-48h}$) and total exposure ($AUC_{0-t}$) for both oxycodone and acetaminophen was equivalent between studies.

Example 16

Pharmacokinetic Study Involving Hydrocodone and Acetaminophen

A four-way crossover pharmacokinetic study was conducted. In a first trial (Treatment A), thirty-five subjects in a fasted state were administered a single, two-tablet dose of hydrocodone/acetaminophen, each tablet containing 7.5 mg hydrocodone, 325 mg acetaminophen, and having slow release properties as compared to an immediate release formulation. (See selected examples from Chart Nos. 1 and 3). In a second trial (Treatment B), thirty-five subjects in a fasted state were administered a single, two-tablet dose of hydrocodone/acetaminophen, each tablet containing 7.5 mg hydrocodone, 325 mg acetaminophen, and having medium release properties as compared to an immediate release formulation. (See selected examples from Chart Nos. 1 and 3). In a third trial (Treatment C), thirty-five subjects in a fed state were administered a single, two-tablet medium-release dose of hydrocodone/acetaminophen, each tablet containing 7.5 mg hydrocodone, 325 mg acetaminophen, and having medium release properties as compared to an immediate release formulation. (See selected examples from Chart Nos. 1 and 3). In a fourth trial (Treatment D), thirty-five subjects were administered a single, two-tablet dose of an immediate release tablet containing 7.5 mg hydrocodone and 325 mg acetaminophen.

The pharmacokinetic profiles from time 0 to 36 hours for hydrocodone and acetaminophen in each of these trials are shown in FIGS. 31 and 32, respectively. The pharmacokinetic profiles from time 0 to 12 hours for hydrocodone and acetaminophen in each of these trials are shown in FIGS. 33 and 34, respectively. The pharmacokinetic parameters of hydrocodone and acetaminophen are summarized in Tables 53 and 54, respectively. The simulated pharmacokinetic profiles from time 0 to 144 hours for hydrocodone and acetaminophen in each of these trials are shown in FIGS. 35 and 36, respectively.

TABLE 53

Pharmacokinetic parameters for hydrocodone

| Parameter | Treatment A, Mean (SD) (N = 35) | Treatment B, Mean (SD) (N = 35) | Treatment C, Mean (SD) (N = 35) | Treatment D, Mean (SD) (N = 35) |
|---|---|---|---|---|
| $AUC_{0-t}$ (ng · h/mL) | 254.12 (71.48) | 243.88 (67.86) | 265.08 (73.62) | 261.60 (72.55) |
| $AUC_{0-inf}$ (ng · h/mL) | 264.47 (72.66) | 251.04 (69.72) | 268.73 (75.25) | 264.79 (73.55) |
| $C_{max}$ (ng/mL) | 18.62 (5.38) | 18.93 (5.58) | 19.73 (4.06) | 22.84 (6.51) |
| $T_{max}$ (h)[a] | 4.05 (2.00-7.00) | 4.00 (1.00-7.00) | 5.92 (2.00-12.08) | 8.00 (0.67-10.02) |
| $t_{lag}$ (h)[a] | 0.17 (0.00-0.37) | 0.17 (0.00-0.48) | 0.17 (0.00-0.67) | 0.17 (0.00-0.33) |
| $t_{1/2}$ (h) | 7.14 (2.55) | 6.70 (1.56) | 4.91 (0.59) | 4.87 (0.57) |
| $K_{el}$ (h$^{-1}$) | 0.1087 (0.0351) | 0.1087 (0.0238) | 0.1431 (0.0174) | 0.1442 (0.0171) |

[a]Median (minimum-maximum).

TABLE 54

Pharmacokinetic parameters for acetaminophen

| Parameter | Treatment A, Mean (SD) (N = 35) | Treatment B, Mean (SD) (N = 35) | Treatment C, Mean (SD) (N = 35) | Treatment D Mean (SD) (N = 35) |
|---|---|---|---|---|
| $AUC_{0-t}$ (ng · h/mL) | 30578 (9205) | 28939 (8364) | 29900 (8544) | 30771 (9518) |
| $AUC_{0-inf}$ (ng · h/mL) | 33417 (9306) | 31073 (8688) | 31512 (8943) | 31833 (9831) |
| $C_{max}$ (ng/mL) | 5030 (1678) | 4950 (1586) | 3343 (847) | 4755 (1673) |
| $T_{max}$ (h)[a] | 0.67 (0.33-2.00) | 0.67 (0.22-1.03) | 2.00 (0.33-5.92) | 0.67 (0.33-7.00) |

TABLE 54-continued

Pharmacokinetic parameters for acetaminophen

| Parameter | Treatment A, Mean (SD) (N = 35) | Treatment B, Mean (SD) (N = 35) | Treatment C, Mean (SD) (N = 35) | Treatment D Mean (SD) (N = 35) |
|---|---|---|---|---|
| $t_{lag}$ (h)[a] | 0.00 (0.00-0.33) | 0.00 (0.00-0.17) | 0.17 (0.00-0.50) | 0.00 (0.00-0.33) |
| $t_{1/2}$ (h) | 8.05 (3.33) | 6.57 (2.11) | 5.10 (2.24) | 4.36 (1.32) |
| $K_{el}$ (h$^{-1}$) | 0.1030 (0.0478) | 0.1196 (0.0504) | 0.1529 (0.0498) | 0.1718 (0.0509) |

[a]Median (minimum-maximum).

These results indicate that the subjects exhibited an initial rapid rise in hydrocodone concentrations to provide early onset of action with the concentrations falling slowly over a period of twelve hours. The median $T_{lag}$ was unaffected by the formulations in comparison to an immediate release tablet containing 7.5 mg hydrocodone and 325 mg acetaminophen. Subjects also exhibited an initial rapid rise in acetaminophen concentrations to provide the desired early onset of action with the concentrations reaching levels that were lower than an immediate release tablet containing 7.5 mg hydrocodone and 325 mg acetaminophen at around twelve hours. Accordingly, the pharmaceutical compositions administered in Treatments A-C exhibited the desired APAP "time-off" feature in their pharmacokinetic profiles.

Administration of the pharmaceutical formulations with food had no effect on Cmax and AUC of hydrocodone, although the $T_{max}$ was delayed by two hours. $T_{lag}$ was unaffected. The Cmax of APAP decreased by about 31% when administered with food, but there was no change in AUC. $T_{max}$ of APAP was delayed by a little more than one hour. No dose dumping was observed from any of the formulations.

The pharmacokinetic profiles of both the pharmaceutical formulations having slow and medium release properties as compared to an immediate release formulation satisfy the desired pharmacokinetic parameters for both hydrocodone and acetaminophen. The observed Cmax and AUC values were suitable for hydrocodone/acetaminophen formulations containing an immediate release and extended release portion.

Example 17

Clinical Pharmacokinetic Analysis of an Extended Release Formulation of Hydrocodone/Acetaminophen Administered Under Fed and Fasted Conditions An open-label, randomized, three-period crossover study was conducted to evaluate the pharmacokinetics (PK), bioavailability, and safety of two tablets of a multi-layer extended-release formulation (7.5 mg hydrocodone bitartrate (HB)/325 mg acetaminophen (APAP)), administered as a single dose in normal, healthy subjects under fed (high-fat or and low-fat meal) and fasted conditions (i.e., 10 hr fast).

This single center, open-label, randomized, 3-period, 6-sequence crossover study in normal, healthy subjects was designed to evaluate the effect of a high-fat and low-fat meal on the PK, bioavailability, and safety of a multilayer ER tablet formulation of 7.5 mg HB/325 mg APAP (see selected example from Chart Nos. 1 and 3). The formulation was orally administered as 2 tablets (15 mg HB/650 mg APAP total dose) under 2 types of fed (high-fat and low-fat) and fasted conditions. Forty-eight subjects were enrolled and 40 subjects completed the study. Only subjects that completed all 3 study periods have been included in the PK evaluation.

Following a 10 hour overnight fast, subjects randomized to Treatment A consumed an entire standardized FDA high-fat breakfast (approximately 1,000±100 calories and approximately 50% from fat); those receiving Treatment B consumed an entire low-fat breakfast (approximately 800±80 calories and approximately 25% to 30% from fat). Breakfasts were consumed within 30 minutes prior to Hour 0 study drug administration. Subjects who could not consume the entire breakfast in the allotted time were dropped from the study. Subjects randomized to Treatment C were administered study drug under fasted conditions following an overnight fast of at least 10 hours. No food was allowed for the first 4 hours postdose. Blood samples were collected pre-dose (up to 60 minutes prior to dose), and at 15 min, 30 min, 45 min and 1, 2, 3, 4, 5, 6, 7, 8, 9, 10, 11, 12, 16, 18, 20, 24, 36 and 48 hours post-dose, and the resulting plasma samples were analyzed for Hydrocodone (HC) and APAP using a validated liquid chromatography-tandem mass spectrometry assay with a linear range of 0.100 to 50 ng/mL for HC and 100 to 15,000 ng/mL for APAP. Pharmacokinetic parameters, as detailed above in Example 2, were determined.

Tables 55 and 56 presents PK parameters for HC under the three treatment conditions, and FIG. 37 presents plasma HC concentration-time profiles for the treatments. Mean plasma concentration profiles of HC revealed that HC was rapidly absorbed under both fed (high and low fat meal) and fasted conditions. There was a slight lag (median 0.25 hours) when the formulation was administered after a low fat meal. The median of the time of observed maximum plasma concentrations ($T_{max}$) was 4 hours after administration under both the low fat and fasted conditions. Median $T_{max}$ for HC under high fat conditions was significantly delayed, as compared to fasted conditions (6 hr vs. 4 hr; P<0.05). Average maximum plasma HC concentrations ($C_{max}$) were 23.09 ng/mL after a low fat breakfast, 21.66 ng/mL after a high fat breakfast, and 20.33 ng/mL under fasted conditions.

TABLE 55

Hydrocodone Pharmacokinetic Estimates (2 tablets of 7.5/325)

| Parameter | Treatment A Fed (High Fat) Mean (SD) (N = 31) | Treatment B Fed (Low Fat) Mean (SD) (N = 31) | Treatment C Fasted Mean (SD) (N = 31) |
|---|---|---|---|
| $AUC_{0-t}$ (ng · hr/mL) | 301.50 (52.81) | 299.72 (57.01) | 280.10 (58.80) |
| $AUC_{0-inf}$ (ng · hr/mL) | 303.66 (53.13) | 301.95 (57.83) | 282.94 (59.86) |
| $C_{max}$ (ng/mL) | 21.66 (4.88) | 23.09 (3.79) | 20.33 (4.33) |
| $T_{max}$ (hr)[a] | 6 (2-11) | 4 (2-7) | 4 (2-7) |

TABLE 55-continued

Hydrocodone Pharmacokinetic Estimates (2 tablets of 7.5/325)

| Parameter | Treatment A Fed (High Fat) Mean (SD) (N = 31) | Treatment B Fed (Low Fat) Mean (SD) (N = 31) | Treatment C Fasted Mean (SD) (N = 31) |
|---|---|---|---|
| $K_{el}$ (1/hr) | 0.1273 (0.0207) | 0.1218 (0.0202) | 0.1110 (0.0194) |
| $t_{lag}$ (hr)[a] | 0 (0-1.07) | 0.25 (0-0.75) | 0 (0-0.50) |
| $t_{1/2}$ (hr) | 5.58 (0.85) | 5.85 (1.00) | 6.43 (1.11) |

[a]Median (minimum-maximum).

A comparison of $C_{max}$ showed that HC concentrations were 6% and 14% higher when the formulation was given under high fat (Treatment A) and low fat (Treatment B) conditions, compared to fasted conditions (Treatment C; see Table 55). The $C_{max}$ for Treatment A was bioequivalent to both Treatments B (88%-99%) and C (101%-113%) as the 90% CIs for the geometric ratios were contained within 80% to 125% (see Table 56). The $C_{max}$ observed for Treatment B was also bioequivalent to Treatment C (108%-122%). AUCs were approximately 7% higher when the formulation was administered under fed conditions (high and low fat), as compared to fasted conditions (Table 55). AUC for both Treatments A and B (high fat and low fat) were bioequivalent to Treatment C (fasted; 104%-112% and 103%-111% for AUC0-t and 104%-112% and 103%-111% for $AUC_{0-inf}$) (Table 56). The apparent plasma terminal elimination half-life ($t_{1/2}$) for HC was similar when the formulation was administered under fed (5.58 hours) and fasted conditions (6.43 hours).

TABLE 56

Hydrocodone Geometric LSMEANS Ratio (%) (90% CI)

| Parameter | Treatment A/C Fed (High Fat)/Fasted | Treatment B/C Fed (Low Fat)/Fasted | Treatment A/B Fed (High Fat)/ Fed (Low Fat) |
|---|---|---|---|
| $AUC_{0-t}$ (ng · hr/mL)[a] | 108.40 (104.44-112.51) | 107.45 (103.53-111.52) | 100.89 (97.22-104.69) |
| $AUC_{0-inf}$ (ng · hr/mL)[a] | 108.11 (104.14-112.24) | 107.17 (103.23-111.26) | 100.88 (97.19-104.72) |
| $C_{max}$ (ng/mL)[a] | 106.66 (100.54-113.15) | 114.75 (108.16-121.73) | 92.95 (87.64-98.59) |

[a]N = 40.

PK parameters for APAP are presented in Tables 57 and 58 and the plasma APAP concentration-time profiles are presented in FIG. 38. APAP was rapidly absorbed following administration under fed (high and low fat meals) and fasted conditions. There was a slight lag when the formulation was administered after a low fat breakfast (median lag time [$t_{lag}$] 0.25 hours). There was no lag in the absorption of APAP when administered following a high fast breakfast or after fasting. The time to $C_{max}$ was significantly (P<0.05) longer when administered after a meal (high and low fat; median $T_{max}$=2 hours) than when administered under fasted conditions (median $T_{max}$=0.75 hour). Average $C_{max}$ values for APAP were lower after a high (4.317 ng/mL) and low fat (4,122 ng/mL) meal than when administered under fasted conditions (5307 ng/mL). Geometric mean ratios for $C_{max}$ following Treatments A and B were 20% to 22% lower than for Treatment C (Table 58). The 90% CIs for $C_{max}$ following Treatment A (75%-88%) and Treatment B (73%-83%) with reference to fasted state were outside the bioequivalent range of 80%-125%. The AUCs for APAP were almost identical when the formulation was administered under high fat, low fat, or fasting conditions. Comparison of geometric mean ratios of $AUC_{0-t}$ and $AUC_{0-inf}$ for Treatments A (90% CI 100%-105% and 98%-103%) and B (90% CI 96%-101% and 97% to 103%) with those for Treatment C showed that treatments were bioequivalent. The $t_{1/2}$ for APAP after the formulation was administered after a high or low fat meal (5 hours) was slightly shorter than when administered under fasted conditions (7 hours).

TABLE 57

APAP Pharmacokinetic Estimates (2 tablets of 7.5/325)

| Parameter | Treatment A Fed (High Fat) Mean (SD) (N = 31) | Treatment B Fed (Low Fat) Mean (SD) (N = 31) | Treatment C Fasted Mean (SD) (N = 31) |
|---|---|---|---|
| $AUC_{0-t}$ (ng · hr/mL) | 33210.39 (10402.75) | 32415.11 (9586.52) | 32149.34 (9431.97) |
| $AUC_{0-inf}$ (ng · hr/mL) | 34689.91 (10672.37) | 34092.21 (9949.21) | 34803.59 (9635.34) |
| $C_{max}$ (ng/mL) | 4317.00 (1185.08) | 4122.25 (877.19) | 5307.00 (1419.43) |
| $T_{max}$ (hr)[a] | 2 (0.25-6.05) | 2 (0.75-7.00) | 0.75 (0.25-5.00) |
| $K_{el}$ (1/hr) | 0.1444 (0.0470) | 0.1317 (0.0356) | 0.1072 (0.0402) |
| $t_{lag}$ (hr)[a] | 0 (0-0.63) | 0.25 (0-0.50) | 0.00 (0-0.25) |
| $t_{1/2}$ (hr) | 5.37 (2.02) | 5.68 (1.68) | 7.37 (2.77) |

[a]Median (minimum-maximum).

TABLE 58

APAP Geometric LSMEANS Ratio (%) (90% CI)

| Parameter | Treatment A/C Fed (High Fat)/Fasted | Treatment B/C Fed (Low Fat)/Fasted | Treatment A/B Fed (High Fat)/ Fed (Low Fat) |
|---|---|---|---|
| $AUC_{0-t}$ (ng · hr/mL)[a] | 102.70 (100.05-105.42) | 100.74 (98.15-103.41) | 101.94 (99.32-104.63) |
| $AUC_{0-inf}$ (ng · hr/mL)[a] | 100.32 (97.71-103.01) | 98.66 (96.09-101.30) | 101.69 (99.04-104.40) |
| $C_{max}$ (ng/mL)[a] | 80.49 (75.44-85.88) | 78.10 (73.20-83.33) | 103.06 (96.62-109.93) |

[a]N = 40.

In summary, total exposure (AUC) for HC was slightly increased (by about 7%) when the formulation was administered with food (after high- or low-fat meal); however, AUCs for HC were equivalent between all treatments (high fat vs. fasted, low fat vs. fasted and high fat vs. low fat). Peak exposure ($C_{max}$) for HC was 6% and 14% higher under high fat and low-fat conditions, respectively, compared to fasted conditions. The $C_{max}$ for HC after a high-fat meal and low fat meal were bioequivalent to fasted conditions. The AUCs for APAP were equivalent between all treatments (high fat vs. fasted, low fat vs. fasted, and high fat vs. low fat). The peak exposure ($C_{max}$) for APAP was decreased by about 20% in fed (high- and low-fat) states as compared to the fasted state.

Example 18

Clinical Pharmacokinetic Analysis of an Extended Release Formulation of 7.5 mg Hydrocodone/325 Mg Acetaminophen—Single and Multiple Doses An open-label, randomized, 3-period crossover study was performed to evaluate single and multiple dose pharmacokinetics, bioavailability, and safety of an extended release formulation containing 7.5 mg hydrocodone/325 mg acetaminophen under fasted conditions in normal, healthy subjects. (See example in Chart 2). The pharmacokinetics (PK) and bioavailability following administration of a 7.5 mg hydrocodone/325 mg acetaminophen tablet disclosed herein administered as either 1 or 2 tablets every 12 hours was compared to 1 immediate release tablet containing 7.5 mg hydrocodone/325 mg acetaminophen and administered every 6 hours (Q6h). The study also assessed the PK proportionality between the 1 tablet and 2 tablet dosing configurations of the 7.5 mg hydrocodone/325 mg acetaminophen tablet disclosed herein. In addition, the study evaluated the safety of the 1 tablet and 2 tablet dosing configurations of the 7.5 mg hydrocodone/325 mg acetaminophen tablet disclosed herein compared with immediate release tablet containing 7.5 mg hydrocodone/325 mg acetaminophen.

The subjects were randomly divided into three treatment options:

Treatment A: One tablet of the 7.5 mg hydrocodone/325 mg acetaminophen tablet disclosed herein administered orally under fasted conditions on Day 1 followed by 1 tablet given Q12h (beginning on Day 3 for a total of 9 doses).

Treatment B: Two tablets of the 7.5 mg hydrocodone/325 mg acetaminophen tablet disclosed herein administered orally under fasted conditions on Day 1 followed by 2 tablets given Q12h (beginning on Day 3 for a total of 9 doses).

Treatment C: One tablet of an immediate release tablet containing 7.5 mg hydrocodone/325 mg acetaminophen administered orally Q6h for 2 doses under fasted conditions on Day 1 followed by 1 tablet given Q6h (beginning on Day 3 for a total of 18 doses).

The pharmacokinetic (PK) parameters of a single dose of hydrocodone and acetaminophen are presented below in Tables 59 and 60 respectively. The plasma concentrations of hydrocodone and acetaminophen are presented in FIGS. 39 and 40, respectively. The pharmacokinetic parameters demonstrate that the formulations disclosed herein containing 7.5 mg hydrocodone/325 mg acetaminophen are dose proportional for both hydrocodone and acetaminophen. The pharmacokinetic profiles for hydrocodone showed an initial rapid rise in the concentrations of hydrocodone to provide a subject with the desired early onset of action (the median $t_{lag}$ for the formulation disclosed herein is 0.08 hour and for the immediate release tablet it is 0.04 hour). The hydrocodone concentrations in the subjects that took the formulations disclosed herein containing 7.5 mg hydrocodone/325 mg acetaminophen also fell slowly over a period of 12 hours.

Similarly, the pharmacokinetic profiles for acetaminophen showed an initial rapid rise in the concentrations of acetaminophen to provide the desired early onset of action (the median $t_{lag}$=0 hr for the formulation disclosed herein containing 7.5 mg hydrocodone/325 mg acetaminophen, which is the same as the immediate release tablet containing 7.5 mg hydrocodone/325 mg acetaminophen). The acetaminophen concentrations achieved by the formulation disclosed herein containing 7.5 mg hydrocodone/325 mg acetaminophen fell slowly, reaching levels that were lower than the immediate release tablet at around 12 hours, showing the desired "time off" from acetaminophen.

TABLE 59

Single Dose PK Parameters for Hydrocodone (Mean ± SD)

| PK Parameters | One Tablet (7.5 HC/325 APAP) Treatment A | Two Tablets (7.5 HC/325 APAP) Treatment B | Commercially-available immediate release product (7.5 HC/325 APAP) Treatment C |
|---|---|---|---|
| $C_{max}$ (ng/mL) | 8.98 (2.02) | 17.53 (3.69) | 24.48 (5.69) |
| $AUC_t$ (ng · hr/mL) | 122.43 (30.53) | 248.48 (63.22) | 254.39 (63.21) |
| $AUC_{inf}$ (ng · hr/mL) | 124.24 (30.63) | 251.20 (63.57) | 256.24 (63.71) |
| $t_{lag}$ (hr) | 0.12 (0.14) | 0.08 (0.13) | 0.04 (0.09) |
| $T_{max}$ (hr) | 8.00 (0.25-6.00) | 3.00 (0.25-2.00) | 3.00 (0.25-8.00) |
| $T_{1/2}$ (hr) | 6.26 (1.41) | 6.41 (1.09) | 5.37 (0.83) |

*Tmax values: median (range)

TABLE 60

Single Dose PK Parameters for Acetaminophen (Mean ± SD)

| PK Parameters | One Tablet (7.5 HC/325 APAP) Treatment A | Two Tablets (7.5 HC/325 APAP) Treatment B | Commercially-available immediate release product (7.5 HC/325 APAP) Treatment C |
|---|---|---|---|
| $C_{max}$ (ng/mL) | 2604.55 (925.57) | 5432.05 (1793.44) | 4912.05 (1647.69) |
| $AUC_t$ (ng · hr/mL) | 13248.82 (3889.65) | 28593.91 (8400.40) | 27928.74 (9086.86) |
| $AUC_{inf}$ (ng · hr/mL) | 15124.65 (4179.45) | 31049.83 (8899.91) | 28993.63 (9243.85) |
| $t_{lag}$ (hr) | 0.06 (0.11) | 0.02 (0.07) | 0.01 (0.04) |
| $T_{max}$ (hr) | 0.50 (0.25-6.00) | 0.50 (0.25-2.00) | 0.50 (0.25-8.00) |
| $T_{1/2}$ (hr) | 7.73 (2.88) | 8.32 (4.34) | 4.29 (1.40) |

*Tmax values: median (range)

As shown below in Table 61, the 90% Confidence Intervals for all the pharmacokinetic parameters for hydrocodone dosed as a single dose of either one tablet or two tablets of the formulations disclosed herein containing 7.5 mg hydrocodone/325 mg acetaminophen were contained within the 80-125% bioequivalence range for the immediate release tablet containing 7.5 mg hydrocodone/325 mg acetaminophen. Similarly, as shown below in Table 62, the 90% Confidence Intervals for all the pharmacokinetic parameters for acetaminophen dosed as a single dose of either one tablet or two tablets of the formulations disclosed herein containing 7.5 mg hydrocodone/325 mg acetaminophen were contained within the 80-125% bioequivalence range for the immediate release tablet containing 7.5 mg hydrocodone/325 mg acetaminophen. However, the cmax values for both dosing configurations for the formulations disclosed herein were lower as compared to the immediate release product.

TABLE 61

Single Dose Bioequivalence Parameters for Hydrocodone

|  |  |  | Immediate Release Tablet | |
|---|---|---|---|---|
|  |  |  | 90% CI | |
| Test | PK Parameter | LSM | Lower | Upper |
| One Tablet | $C_{max}$ | 73.53 | 70.46 | 76.74 |
|  | $AUC_t$ | 96.2 | 92.33 | 100.23 |
|  | $AUC_{inf}$ | 96.97 | 93.10 | 100.99 |
| Two Tablets | $C_{max}$ | 71.86 | 68.85 | 74.99 |
|  | $AUC_t$ | 97.59 | 93.66 | 101.68 |
|  | $AUC_{inf}$ | 97.96 | 94.06 | 102.03 |
|  | Reference: Two tablets of the 7.5 mg HC/325 mg APAP | | | |
| One Tablet | $C_{max}$ | 102.33 | 98.05 | 106.80 |
|  | $AUC_t$ | 98.58 | 94.61 | 102.71 |
|  | $AUC_{inf}$ | 98.98 | 95.04 | 103.09 |

TABLE 62

Single Dose Bioequivalence Parameters for Acetaminophen

|  |  |  | Immediate Release Tablet | |
|---|---|---|---|---|
|  |  |  | 90% CI | |
| Test | PK Parameter | LSM | Lower | Upper |
| One Tablet | $C_{max}$ | 105.34 | 97.98 | 113.25 |
|  | $AUC_t$ | 95.16 | 91.89 | 98.55 |
|  | $AUC_{inf}$ | 104.99 | 101.17 | 108.95 |
| Two Tablets | $C_{max}$ | 110.78 | 103.04 | 119.10 |
|  | $AUC_t$ | 102.62 | 99.10 | 106.28 |
|  | $AUC_{inf}$ | 107.42 | 103.52 | 111.48 |
|  | Reference: Two tablets of the 7.5 mg HC/325 mg APAP | | | |
| One Tablet | $C_{max}$ | 95.09 | 88.45 | 102.24 |
|  | $AUC_t$ | 92.73 | 89.54 | 96.03 |
|  | $AUC_{inf}$ | 97.73 | 94.18 | 101.42 |

The pharmacokinetic (PK) parameters of multiple doses of hydrocodone and acetaminophen are presented below in Tables 63 and 64, respectively. The plasma concentrations of hydrocodone and acetaminophen are presented in FIGS. 41 and 42, respectively. The pharmacokinetic parameters demonstrate that the formulations disclosed herein containing 7.5 mg hydrocodone/325 mg acetaminophen are dose proportional for both hydrocodone and acetaminophen. No differences were observed in dose-normalized $C_{max}^{ss}$, $C_{min}^{ss}$, $AUC_{0-12}^{ss}$hr, $C_{av}^{ss}$, and fluctuation of hydrocodone and acetaminophen following administration of the formulation disclosed herein containing 7.5 mg hydrocodone/325 mg acetaminophen as either 1-tablet or 2-tablet dosing configurations, or the immediate release tablet containing 7.5 mg hydrocodone/325 mg acetaminophen. For acetaminophen, the 1-tablet, 2-tablet and immediate release tablet had the same (0.5 hr) median $T_{max}^{ss}$. For hydrocodone, the median $T_{max}$ss of the formulation disclosed herein containing 7.5 mg hydrocodone/325 mg acetaminophen (dosed as either 1 and 2 tablets) was 2 hours while the median $T_{max}$ss for the immediate release tablet containing 7.5 mg hydrocodone/325 mg acetaminophen was 1 hour. No difference was observed in the swing of hydrocodone for the formulation disclosed herein containing 7.5 mg hydrocodone/325 mg acetaminophen dosed as either 1 and 2-tablet and the immediate release tablet containing 7.5 mg hydrocodone/325 mg acetaminophen. In the case of acetaminophen, the swing was partially out of the range to demonstrate no difference (107.33-132.50).

TABLE 63

Multiple Dose PK Parameters for Hydrocodone (Mean ± SD)

| PK Parameters | One Tablet (7.5 HC/325 APAP) Treatment A | Two Tablets (7.5 HC/325 APAP) Treatment B | Commercially-available immediate release product (7.5 HC/325 APAP) Treatment C |
|---|---|---|---|
| $C_{max}$ (ss) (ng/mL) | 15.57 (3.85) | 30.54 (6.87) | 33.80 (8.74) |
| $C_{min}$ (ss) (ng/mL) | 6.49 (2.41) | 13.38 (4.12) | 14.13 (4.67) |
| $C_{avg}$ (ss) (ng/mL) | 11.20 (3.16) | 22.54 (5.36) | 22.38 (5.82) |
| $AUC_{0-12}$ (ss) (ng · hr/mL) | 134.36 (37.91) | 270.52 (64.29) | 268.57 (69.87) |
| $T_{max}$ (SS) (hr) | 146.00 (144.50-150.00) | 146.00 (144.50-150.00) | 145.00 (144.50-142.00) |
| Swing | 1.53 (1.00) | 1.37 (1.42) | 1.53 (3.16) |
| Fluctuation (%) | 83.76 (19.00) | 77.54 (16.70) | 90.60 (3054) |
| Accumulation Index | 1.43 (0.20) | 1.43 (0.20) | 1.23 (0.29) |

*Tmax values: median (range)

TABLE 64

Multiple Dose PK Parameters for Acetaminophen (Mean ± SD)

| PK Parameters | One Tablet (7.5 HC/325 APAP) Treatment A | Two Tablets (7.5 HC/325 APAP) Treatment B | Commercially-available immediate release product (7.5 HC/325 APAP) Treatment C |
|---|---|---|---|
| $C_{min}$ (ss) (ng/mL) | 464.89 (166.72) | 844.68 (293.41) | 893.86 (310.09) |
| $C_{avg}$ (ss) (ng/mL) | 1169.43 (316.86) | 2238.75 (577.32) | 2267.63 (592.95) |
| $AUC_{0-12}$ (ss) (ng · hr/mL) | 14033.21 (3802.32) | 26864.94 (6927.89) | 27211.55 (7115.37) |
| $T_{max}$ (SS) (hr) | 144.5 (144.25-148.00) | 144.5 (144.25-146.00) | 144.5 (144.25-152.00) |
| Swing | 6.43 (0.96) | 6.78 (0.44) | 5.76 (2.80) |
| Fluctuation (%) | 237.58 (85.70) | 237.66 (74.05) | 211.43 (76.05) |
| Accumulation Index | 1.28 (0.21) | 1.21 (0.17) | 1.05 (0.06) |

*Tmax values: median (range)

As shown below in Table 65, the 90% Confidence Intervals for all the pharmacokinetic parameters for hydrocodone dosed as multiple doses of either one tablet or two tablets of the formulations disclosed herein containing 7.5 mg hydrocodone/325 mg acetaminophen were contained within the 80-125% bioequivalence range for the immediate release tablet containing 7.5 mg hydrocodone/325 mg acetaminophen. Similarly, as shown below in Table 66, the 90% Confidence Intervals for all the pharmacokinetic parameters (except the swing) for acetaminophen dosed as multiple doses of either one tablet or two tablets of the formulations disclosed herein containing 7.5 mg hydrocodone/325 mg acetaminophen were contained within the 80-125% bioequivalence range for the immediate release tablet containing 7.5 mg hydrocodone/325 mg acetaminophen.

TABLE 65

Multiple Dose Bioequivalence Parameters for Hydrocodone

| | | | Immediate Release Tablet | |
|---|---|---|---|---|
| | | | | 90% CI |
| Test | PK Parameter | LSM | Lower | Upper |
| One Tablet | $C_{max}$ (ss) | 92.46 | 89.07 | 95.98 |
| | $C_{min}$ (ss) | 91.22 | 87.61 | 94.98 |
| | $C_{avg}$ (ss) | 99.7 | 96.85 | 102.64 |
| | $AUC_{0-12}$ (ss) | 99.71 | 96.85 | 102.65 |
| | Swing | 103.98 | 97.05 | 111.4 |
| | Fluctuation | 95.13 | 90.54 | 99.94 |
| Two Tablets | $C_{max}$ (ss) | 90.91 | 87.58 | 94.38 |
| | $C_{min}$ (ss) | 95.33 | 91.56 | 99.26 |
| | $C_{avg}$ (ss) | 101.15 | 98.25 | 104.14 |
| | $AUC_{0-12}$ (ss) | 101.15 | 98.26 | 104.14 |
| | Swing | 93.88 | 87.62 | 100.58 |
| | Fluctuation | 88.47 | 84.21 | 92.95 |
| | Reference: Two tablets of the 7.5 mg HC/325 mg APAP | | | |
| One Tablet | $C_{max}$ (ss) | 101.7 | 97.97 | 105.57 |
| | $C_{min}$ (ss) | 95.69 | 91.9 | 99.64 |
| | $C_{avg}$ (ss) | 98.57 | 95.74 | 101.48 |
| | $AUC_{0-12}$ (ss) | 98.57 | 95.75 | 101.48 |
| | Swing | 110.76 | 103.38 | 118.66 |
| | Fluctuation | 107.52 | 102.34 | 112.96 |

TABLE 66

Multiple Dose Bioequivalence Parameters for Acetaminophen

| | | | Immediate Release Tablet | |
|---|---|---|---|---|
| | | | | 90% CI |
| Test | PK Parameter | LSM | Lower | Upper |
| One Tablet | $C_{max}$ (ss) | 113.39 | 105.69 | 121.66 |
| | $C_{min}$ (ss) | 102.92 | 98.12 | 107.95 |
| | $C_{avg}$ (ss) | 102.81 | 100.19 | 105.49 |
| | $AUC_{0-12}$ (ss) | 102.81 | 100.19 | 105.49 |
| | Swing | 112.44 | 101.2 | 124.93 |
| | Fluctuation | 112.56 | 103.72 | 122.17 |

TABLE 66-continued

Multiple Dose Bioequivalence Parameters for Acetaminophen

| | | | Immediate Release Tablet | |
|---|---|---|---|---|
| | | | | 90% CI |
| Test | PK Parameter | LSM | Lower | Upper |
| Two Tablets | $C_{max}$ (ss) | 109.25 | 101.83 | 117.21 |
| | $C_{min}$ (ss) | 94.27 | 89.87 | 98.88 |
| | $C_{avg}$ (ss) | 98.76 | 96.25 | 101.33 |
| | $AUC_{0-12}$ (ss) | 98.76 | 96.25 | 101.33 |
| | Swing | 119.25 | 107.33 | 132.5 |
| | Fluctuation | 113.83 | 104.88 | 123.54 |
| | Reference: Two tablets of the 7.5 mg HC/325 mg APAP | | | |
| One Tablet | $C_{max}$ (ss) | 103.79 | 96.74 | 111.36 |
| | $C_{min}$ (ss) | 109.17 | 104.08 | 114.51 |
| | $C_{avg}$ (ss) | 104.1 | 101.45 | 106.82 |
| | $AUC_{0-12}$ (ss) | 104.1 | 101.45 | 106.82 |
| | Swing | 94.29 | 84.86 | 104.76 |
| | Fluctuation | 98.89 | 91.11 | 107.32 |

Example 19

Partial Areas Under the Curve for Hydrocodone and Acetaminophen

A cross-study comparison of the partial AUCs for acetaminophen following oral administration of the pharmaceutical compositions described in Treatment A of Example 16, and Treatment C of Example 17 was performed. These results are summarized in Tables 67 and 68. Additionally, the partial AUCs for hydrocodone were determined and are summarized in Tables 69.

TABLE 67

Mean (SD) Parameter Estimates for Partial AUCs for Acetaminophen.

| Study | $AUC_{0-1h}$ | $AUC_{1-12h}$ | $AUC_{12-36h}$ | $AUC_{0-1.27h}$ | $AUC_{1.27-36h}$ | $AUC_{0-t}$ |
|---|---|---|---|---|---|---|
| Treatment A (Ex. 16) | 3276.62 | 20624.53 | 7774.64 | 3816.89 | 27858.88 | 30618.62 |
| Treatment C (Ex. 17) | 3264.68 | 22299.56 | 8284.15 | 4428.19 | 20420.21 | 32441.45 |

TABLE 68

Percent of the partial AUC compared to $AUC_{0-t}$.

| Study | $AUC_{1-12h}$ | $AUC_{12-36h}$ |
|---|---|---|
| Treatment A (Ex. 16) | 67% | 25% |
| Treatment C (Ex. 17) | 69% | 26% |

TABLE 69

Mean (SD) Parameter Estimates for Partial AUCs for Hydrocodone.

| Study | AUC$_{0-t}$ (ng · h/mL) | AUC$_{0-2.44\,h}$ (ng · h/mL) | AUC$_{2.44-36\,h}$ (ng · h/mL) |
|---|---|---|---|
| Treatment A (Ex. 16) | 254.16 (71.57) | 26.33 (8.70) | 227.93 (65.32) |
| Treatment C (Ex. 17) | 280.08 (59.58) | 27.41 (9.34) | 246.25 (52.99) |

Further, it was determined that Tmax for an immediate release tablet containing 7.5 mg hydrocodone and 325 mg acetaminophen plus two standard deviations was about 3 hr. Some of the partial AUCs of the pharmaceutical formulation described herein were determined in accordance with this time interval.

The bioequivalence determinations between two tablets of a pharmaceutical composition described herein, each containing 7.5 mg hydrocodone and 325 mg acetaminophen (in fed and fasted states) and an immediate release tablet containing 7.5 mg hydrocodone and 325 mg acetaminophen can be found in Tables 70 and 71.

TABLE 70

Bioequivalence Determination for Acetaminophen

| Parameter | LSM Ratio | 90% CI Lower | 90% CI Upper |
|---|---|---|---|
| Ln (AUC$_{0-1.27\,h}$) | 103.62 | 87.18 | 123.16 |
| Ln (AUC$_{1.27-36\,h}$) | 93.32 | 83.11 | 104.78 |
| Ln (AUC$_{0-t}$) | 94.52 | 84.34 | 105.93 |

TABLE 71

Bioequivalence Determination for Hydrocodone

| Parameter | LSM Ratio | 90% CI Lower | 90% CI Upper |
|---|---|---|---|
| Ln (AUC$_{0-2.44\,h}$) | 91.49 | 82.77 | 101.13 |
| Ln (AUC$_{2.44-36\,h}$) | 96.78 | 83.19 | 112.61 |
| Ln (AUC$_{0-t}$) | 89.71 | 81.51 | 98.74 |

Example 20

In Vitro Dissolution of Controlled-Release Bilayer Tablets Containing 7.5 mg Oxycodone and 325 mg Acetaminophen Performed at a 100 rpm Paddle Speed Three batches of bilayer formulations described herein were prepared, each containing a total of 7.5 mg of oxycodone HCl and a total of 325 mg of acetaminophen. 50% of the acetaminophen was contained in the immediate release portion, and the other 50% was contained in the ER layer. 25% of the oxycodone HCl was contained in the immediate release portion of the formulation, and the other 75% was contained in the ER layer. POLYOX® 1105 was employed as the extended release component in an amount of 45% by weight of the ER portion.

Dissolution profiles for the formulations of each batch were determined in a USP Type II apparatus. Six tablets from each batch were weighed, placed in a sinker, and dropped into an equilibrated dissolution bath vessel containing 900 mL of (helium sparged) 0.1 N HCl heated to 37° C.±0.5° C. The mixture was stirred at 100±4 rpm, and the temperature was maintained at 37° C.±0.5° C. for 12 hr. The bath vessel was covered with a low evaporation vessel cover. Samples (5 mL) were removed at 0.25 hr, 0.5 hr, 1 hr, 2 hr, 4 hr, 6, hr, 8 hr, and 12 hr. Each sample was filtered through a 0.45 µm filter and analyzed by HPLC using standard procedures.

The cumulative percent release of acetaminophen and oxycodone from each batch are described in Table 72.

TABLE 72

Release rate data of bilayer tablets (7.5 mg oxycodone HCl; 325 mg acetaminophen) using a 100 rpm dissolution method.

| Time (Hours) | Oxycodone HCl Mean (%) | RSD | Min (%) | Max (%) | Acetaminophen Mean (%) | RSD | Min (%) | Max (%) |
|---|---|---|---|---|---|---|---|---|
| Batch 1 | | | | | | | | |
| 0.25 | 31.7 | 2.1 | 30.6 | 32.5 | 51.8 | 1.4 | 50.9 | 53.1 |
| 0.5 | 37.1 | 1.3 | 36.3 | 37.8 | 54.3 | 1.3 | 53.5 | 55.6 |
| 1.0 | 45.4 | 1.0 | 44.9 | 46.0 | 58.6 | 1.2 | 57.7 | 60.1 |
| 2.0 | 58.5 | 1.3 | 57.4 | 59.7 | 66.0 | 1.2 | 64.8 | 67.7 |
| 4.0 | 78.6 | 1.7 | 76.8 | 80.5 | 78.5 | 1.5 | 77.0 | 80.6 |
| 6.0 | 92.2 | 1.8 | 90.0 | 94.7 | 88.0 | 1.6 | 86.0 | 90.3 |
| 8.0 | 99.5 | 1.8 | 97.4 | 102.7 | 93.8 | 1.5 | 91.8 | 96.3 |
| 12.0 | 101.7 | 1.4 | 99.7 | 104.3 | 96.1 | 1.0 | 94.9 | 98.2 |
| Batch 2 | | | | | | | | |
| 0.25 | 31.6 | 3.5 | 29.6 | 34.0 | 52.1 | 4.0 | 48.8 | 55.8 |
| 0.5 | 37.2 | 3.2 | 34.9 | 39.9 | 54.5 | 3.8 | 51.4 | 58.3 |
| 1.0 | 45.4 | 3.3 | 42.4 | 48.3 | 59.1 | 3.5 | 56.0 | 63.1 |
| 2.0 | 58.9 | 1.7 | 57.3 | 61.1 | 66.4 | 3.0 | 63.6 | 70.0 |
| 4.0 | 79.1 | 1.5 | 77.7 | 81.5 | 78.7 | 2.5 | 75.4 | 81.8 |
| 6.0 | 93.1 | 1.3 | 91.5 | 95.8 | 87.7 | 2.2 | 84.4 | 90.7 |
| 8.0 | 100.2 | 1.2 | 98.7 | 102.3 | 93.5 | 1.9 | 90.4 | 96.2 |
| 12.0 | 102.7 | 1.3 | 100.4 | 104.4 | 95.6 | 2.0 | 92.6 | 98.4 |
| Batch 3 | | | | | | | | |
| 0.25 | 30.4 | 1.6 | 29.3 | 31.0 | 52.2 | 2.3 | 49.6 | 54.2 |
| 0.5 | 35.7 | 1.6 | 34.2 | 36.7 | 54.6 | 2.3 | 52.0 | 56.6 |
| 1.0 | 43.5 | 1.8 | 42.0 | 45.1 | 58.6 | 2.2 | 56.0 | 60.8 |
| 2.0 | 56.1 | 1.9 | 54.4 | 58.0 | 65.5 | 2.1 | 63.1 | 68.0 |
| 4.0 | 75.4 | 1.8 | 73.3 | 77.6 | 77.3 | 2.0 | 74.8 | 80.0 |
| 6.0 | 88.9 | 1.7 | 86.1 | 91.4 | 86.5 | 2.2 | 83.7 | 90.1 |
| 8.0 | 97.0 | 1.5 | 94.7 | 99.8 | 93.0 | 2.1 | 90.1 | 96.8 |
| 12.0 | 100.4 | 1.1 | 98.7 | 102.4 | 96.5 | 1.6 | 93.2 | 98.3 |

Example 21

In Vitro Dissolution of Controlled-Release Bilayer Tablets Comprising 7.5 mg Hydrocodone and 325 mg Acetaminophen Performed at a 100 rpm Paddle Speed Three batches of bilayer formulations described herein were prepared, each containing a total of 7.5 mg of hydrocodone bitartrate and a total of 325 mg of acetaminophen. 50% of the acetaminophen was contained in the immediate release portion, and the other 50% was contained in the ER layer. 25% of the hydrocodone bitartrate was contained in the immediate release portion of the formulation, and the other 75% was contained in the ER layer. POLYOX® N-60K was employed as the extended release component in an amount of 45% by weight of the ER portion.

Dissolution profiles for the formulations of each batch were determined in a USP Type II apparatus. Six tablets from each batch were weighed, placed in a sinker, and dropped into an equilibrated dissolution bath vessel containing 900 mL of (helium sparged) 0.1 N HCl heated to 37° C.±0.5° C. The mixture was stirred at 100±4 rpm, and the temperature was maintained at 37° C.±0.5° C. for 12 hr. The bath vessel was covered with a low evaporation vessel cover. Samples (5 mL) were removed at 0.25 hr, 0.5 hr, 1 hr, 2 hr, 4 hr, 6, hr, 8 hr, and 12 hr. Each sample was filtered through a 0.45 μm filter and analyzed by HPLC using standard procedures.

The cumulative percent release of acetaminophen and hydrocodone from each batch are described in Table 73.

TABLE 73

Release rate data of bilayer tablets (7.5 mg hydrocodone bitartrate; 325 mg acetaminophen) using a 100 rpm dissolution method.

| Time (Hours) | Hydrocodone Bitartrate | | | | Acetaminophen | | | |
|---|---|---|---|---|---|---|---|---|
| | Mean (%) | RSD | Min (%) | Max (%) | Mean (%) | RSD | Min (%) | Max (%) |
| Batch 1 | | | | | | | | |
| 0.25 | 31.4 | 6.3 | 27.1 | 33.6 | 52.7 | 5.1 | 46.7 | 54.6 |
| 0.5 | 36.5 | 3.6 | 34.1 | 38.6 | 55.5 | 2.5 | 52.2 | 56.8 |
| 1.0 | 43.7 | 2.1 | 42.2 | 45.2 | 59.1 | 1.4 | 57.3 | 60.1 |
| 2.0 | 54.5 | 1.7 | 53.0 | 56.6 | 64.7 | 0.9 | 63.8 | 65.8 |
| 4.0 | 70.9 | 1.3 | 69.4 | 72.9 | 74.0 | 0.8 | 73.1 | 75.2 |
| 6.0 | 83.0 | 1.5 | 81.1 | 85.3 | 81.8 | 0.9 | 80.6 | 83.3 |
| 8.0 | 91.9 | 1.5 | 89.7 | 93.8 | 88.4 | 0.9 | 87.4 | 89.9 |
| 12.0 | 100.5 | 1.4 | 98.1 | 102.5 | 96.1 | 0.8 | 94.9 | 97.2 |
| Batch 2 | | | | | | | | |
| 0.25 | 30.8 | 3.0 | 29.6 | 32.5 | 53.6 | 1.7 | 52.4 | 55.1 |
| 0.5 | 35.6 | 2.1 | 34.5 | 37.0 | 55.8 | 1.4 | 54.9 | 57.1 |
| 1.0 | 42.4 | 2.3 | 40.7 | 44.5 | 59.1 | 1.3 | 58.4 | 60.6 |
| 2.0 | 52.7 | 2.1 | 51.6 | 54.8 | 64.6 | 1.3 | 63.9 | 66.5 |
| 4.0 | 69.0 | 2.0 | 67.4 | 71.5 | 73.9 | 1.3 | 72.8 | 76.2 |
| 6.0 | 81.8 | 1.7 | 79.5 | 83.5 | 82.4 | 1.4 | 80.9 | 85.1 |
| 8.0 | 90.3 | 1.5 | 87.9 | 92.5 | 88.6 | 1.6 | 86.6 | 91.9 |
| 12.0 | 98.9 | 1.6 | 96.0 | 101.0 | 96.5 | 1.5 | 94.4 | 99.8 |
| Batch 3 | | | | | | | | |
| 0.25 | 31.7 | 3.2 | 29.7 | 33.6 | 52.7 | 2.5 | 49.9 | 54.9 |
| 0.5 | 36.4 | 2.8 | 34.7 | 38.2 | 55.1 | 2.0 | 53.1 | 56.9 |
| 1.0 | 43.5 | 2.3 | 42.1 | 45.1 | 58.7 | 1.8 | 57.5 | 60.7 |
| 2.0 | 54.5 | 2.4 | 52.9 | 56.5 | 64.5 | 1.7 | 63.3 | 66.8 |
| 4.0 | 70.2 | 2.5 | 68.2 | 72.7 | 73.7 | 1.7 | 72.1 | 76.4 |
| 6.0 | 81.8 | 2.2 | 79.8 | 85.6 | 81.3 | 1.6 | 79.2 | 84.3 |
| 8.0 | 90.5 | 2.3 | 88.0 | 95.1 | 87.8 | 1.6 | 85.5 | 91.0 |
| 12.0 | 98.9 | 1.9 | 97.1 | 103.0 | 95.2 | 1.4 | 92.9 | 98.2 |

Example 22

In Vitro Dissolution of Controlled-Release Bilayer Tablets Comprising 7.5 mg Hydrocodone and 325 mg Acetaminophen Performed at a 150 rpm Paddle Speed Dissolution studies were performed on fast-release, medium-release, and slow-release pharmaceutical formulations described herein containing 7.5 mg hydrocodone and 325 mg acetaminophen.

Dissolution profiles for the three above-described compositions were determined in USP Type II apparatus. Six tablets of each composition were weighed, placed in a sinker, and dropped into an equilibrated dissolution bath vessel that contained 900 mL of (helium sparged) 0.1 N HCl that was heated to 37° C.±0.5° C. The mixture was stirred at 150±6 rpm and the temperature was maintained at 37° C.±0.5° C. for 12 hr. The bath vessel was covered with a low evaporation vessel cover. Samples (5 mL) were removed at 0.25, 0.5, 1, 2, 4, 6, 8, and 12 hours. Each sample was filtered through a 0.45 μm filter and analyzed by HPLC using standard procedures.

The results of these dissolution studies are summarized in Table 74 and FIGS. 43 and 44.

TABLE 74

Mean acetaminophen and hydrocodone dissolution data.

| Time (hr) | Fast (%) (RSD) | | Medium (%) (RSD) | | Slow (%) (RSD) | |
|---|---|---|---|---|---|---|
| | APAP | Hydrocodone | APAP | Hydrocodone | APAP | Hydrocodone |
| 0.08 | 52.6 (2.2) | 26.3 (4.1) | 52.4 (2.7) | 28.4 (4.3) | 52.2 (2.1) | 28.8 (4.0) |
| 0.25 | 55.8 (2.0) | 34.3 (2.1) | 54.4 (2.7) | 33.4 (2.9) | 54.2 (1.7) | 33.8 (2.8) |
| 0.5 | 58.9 (1.9) | 41.2 (1.4) | 56.9 (2.5) | 38.6 (2.4) | 56.2 (1.5) | 38.2 (3.3) |
| 1.0 | 64.0 (1.8) | 51.1 (1.4) | 60.9 (2.3) | 46.8 (1.9) | 59.5 (1.5) | 45.2 (3.5) |
| 2.0 | 72.8 (1.6) | 65.9 (2.0) | 67.9 (2.0) | 59.7 (2.1) | 65.0 (1.4) | 56.3 (3.5) |
| 4.0 | 87.0 (1.8) | 86.7 (2.6) | 79.8 (1.6) | 79.6 (2.1) | 74.6 (1.4) | 74.0 (2.6) |
| 8.0 | 98.5 (1.1) | 100.7 (1.2) | 93.9 (1.0) | 99.7 (1.9) | 88.2 (1.4) | 94.9 (2.4) |
| 12.0 | 97.9 (1.2) | 100.5 (1.5) | 96.9 (0.8) | 102.9 (1.6) | 95.6 (1.7) | 103.0 (2.4) |
| 18.0 | 96.8 (1.2) | 100.3 (1.6) | 96.1 (0.8) | 102.8 (1.7) | 97.0 (1.5) | 104.6 (2.1) |

Example 23

Varying Polyox Grades Comprising 25% by Weight of the Extended Release Portion of Bilayer Formulations Containing Oxycodone Single layer tablet formulations containing only the extended release portion were prepared, each tablet containing a total of 9 mg of oxycodone HCl and a total of 250 mg of acetaminophen. Since these tablets contained only the extended release portion, they contained 50% of the total acetaminophen for the bilayer tablet and 60% of the total oxycodone HCl for the bilayer tablet. In a first formulation, POLYOX® 205 was employed as the extended release component in an amount of 25% by weight of the ER portion, and therefore, the tablet weight. In a second formulation, POLYOX® 1105 was employed as the extended release component in an amount of 25% by weight of the tablet of ER portion. In a third formulation, POLYOX® N-60K was employed as the extended release component in an amount of 25% by weight of the tablet or ER portion.

Dissolution profiles for the three above-described compositions were determined in USP Type II apparatus. Six tablets of each composition were weighed, placed in a sinker, and dropped into an equilibrated dissolution bath vessel containing 900 mL of (helium sparged) 0.1 N HCl heated to 37° C.±0.5° C. The mixture was stirred at 150±6 rpm, and the temperature was maintained at 37° C.±0.5° C. through 12 hr. The bath vessel was covered with a low evaporation vessel cover. Samples (5 mL) were removed at 0.25 hr, 0.5 hr, 1 hr, 2 hr, 4 hr, 6, hr, 8 hr, and 12 hr. The final time point for the Polyox 205 was 17 hrs; the final time point for the Polyox 1105 was 15 hrs; and the final time point for the Polyox N60k was 18 hrs and 40 minutes. Each sample was filtered through a 0.45 μm filter and analyzed by HPLC using standard procedures.

The cumulative release profiles of acetaminophen and oxycodone from these compositions are shown in FIGS. 45 and 46, respectively. This data represents dissolution for the ER portion with the IR data theoretically added. These figures demonstrate that as the average molecular weight of the POLYOX® extended release component increases, the rate of dissolution at each time point decreases. For example, the formulations containing POLYOX® 205, 1105, and N-60K had released about 59%, about 56%, and about 55% acetaminophen after 15 minutes, respectively; about 63%, about 59%, and about 57% acetaminophen after 30 minutes, respectively; about 69%, about 64%, and about 61% acetaminophen after 1 hr, respectively; about 78%, about 73%, and about 67% acetaminophen after 2 hr, respectively; about 91%, about 87%, and about 76% acetaminophen after 4 hr, respectively; about 97%, about 95%, and about 84% acetaminophen after 6 hr, respectively; and about 98%, about 97%, and about 90% acetaminophen after 8 hr, respectively.

The same general trend of a decreased release rate with a higher molecular weight POLYOX® grade was also observed for the oxycodone. For example, the formulations containing POLYOX® 205, 1105, and N-60K had released about 53%, about 50%, and about 48% oxycodone after 15 minutes, respectively; about 60%, about 56%, and about 53% oxycodone after 30 minutes, respectively; about 68%, about 63%, and about 59% oxycodone after 1 hr, respectively; about 80%, about 75%, and about 67% oxycodone after 2 hr, respectively; about 94%, about 91%, and about 80% oxycodone after 4 hr, respectively; about 100%, about 98%, and about 89% oxycodone after 6 hr, respectively; and about 100%, about 99%, and about 95% oxycodone after 8 hr, respectively.

Example 24

Varying Polyox Grades Comprising 45% by Weight of the Extended Release Portion of Bilayer Formulations Containing Oxycodone Single layer formulations containing only the extended release portion described herein were prepared, each tablet containing a total of 9 mg of oxycodone HCl and a total of 250 mg of acetaminophen. Since these tablets contained only the extended release portion, they contained 50% of the total acetaminophen for a bilayer tablet and 60% of the total oxycodone HCl for a bilayer tablet. In a first formulation, POLYOX® 205 was employed as the extended release component in an amount of 45% by weight of the tablet or ER portion. In a second formulation, POLYOX® 1105 was employed as the extended release component in an amount of 45% by weight of the tablet or ER portion. In a third formulation, POLYOX® N-60K was employed as the extended release component in an amount of 45% by weight of the tablet or ER portion. The other excipients in the extended release portion were microcrystalline cellulose, spress B825, citric acid anhydrous, EDTA, hydroxypropyl cellulose, silicon dioxide, and magnesium stearate.

Dissolution profiles for the three above-described formulations were determined in USP Type II apparatus. Six tablets of each formulation were weighed, placed in a sinker, and dropped into an equilibrated dissolution bath vessel containing 900 mL of (helium sparged) 0.1 N HCl heated to 37° C.±0.5° C. The mixture was stirred at 150±6 rpm, and the temperature was maintained at 37° C.±0.5° C. through 12 hr. The bath vessel was covered with a low evaporation vessel cover. Samples (5 mL) were removed at 0.25 hr, 0.5 hr, 1 hr, 2 hr, 4 hr, 6, hr, 8 hr, and 12 hr. The final time point for the Polyox 205 was 17 hours; the final time point for Polyox 1105 was 17.5 hours; and the final time point for Polyox N60k was 23.5 hours. Each sample was filtered through a 0.45 μm filter and analyzed by HPLC using standard procedures.

The cumulative release profiles of acetaminophen and oxycodone from these compositions are shown in FIGS. 47 and 48, respectively. This data represents dissolution for the extended release portion with the immediate release data theoretically added. Consistent with the results of Example 23, the rate of dissolution at each time point decreases as the molecular weight of POLYOX® increases. For example, the formulations containing POLYOX® 205, 1105, and N-60K had released about 53%, about 53%, and about 53% acetaminophen after 15 minutes, respectively; about 56%, about 55%, and about 54% acetaminophen after 30 minutes, respectively; about 61%, about 60%, and about 57% acetaminophen after 1 hr, respectively; about 70%, about 67%, and about 63% acetaminophen after 2 hr, respectively; about 85%, about 81%, and about 71% acetaminophen after 4 hr, respectively; about 95%, about 90%, and about 79% acetaminophen after 6 hr, respectively; about 99%, about 95%, and about 85% acetaminophen after 8 hr, respectively; and about 99%, about 96% and about 93% acetaminophen after 12 hr.

The formulations containing POLYOX® 205, 1105, and N-60K also released about 47%, about 47%, and about 46% oxycodone after 15 minutes, respectively; about 51%, about 50%, and about 49% after 30 minutes, respectively; about 59%, about 56%, and about 53% oxycodone after 1 hr, respectively; about 70%, about 67%, and about 62% oxycodone after 2 hr, respectively; about 88%, about 83%, and about 74% oxycodone after 4 hr, respectively; about 99%, about 93%, and about 83% oxycodone after 6 hr, respectively; and about 100%, about 97%, and about 90% oxycodone after 8 hr, respectively.

Example 25

Varying the Concentrations of a Specific Polyox Grade in the Extended Release Portion of Bilayer Formulations Containing Oxycodone The data from Examples 23 and 24 indicate that an increase in the amount of POLYOX® in the pharmaceutical composition retards the release of oxycodone and acetaminophen from the pharmaceutical composition. To confirm this observation, single layer ER formulations described herein were prepared, each containing a total of 9 mg of oxycodone HCl and a total of 250 mg of acetaminophen. Since these tablets contained only the extended release portion, they contained 50% of the total acetaminophen for the bilayer tablet and 60% of the total oxycodone for the bilayer tablet. In a first formulation, POLYOX® 1105 was employed as the extended release component in an amount of 25% by weight of the tablet or ER portion. In a second formulation, POLYOX™ 1105 was employed as the extended release component in an amount of 35% by weight of the tablet or ER portion. In a third formulation, POLYOX™ 1105 was employed as the extended release component in an amount of 45% by weight of the tablet or ER portion. In a fourth formulation, POLYOX® 1105 was employed as the extended release component in an amount of 55% by weight of the tablet or ER portion. The amount of the microcrystalline cellulose in the four formulations was adjusted to account for the differing amounts of POLYOX® 1105 in each formulation. The other excipients in the extended release portion were B825, citric acid anhydrous, EDTA, hydroxypropyl cellulose, silicon dioxide, and magnesium stearate. However, the percentages for all the other excipients remained the same for each formulation, and were consistent with the percentages used in Example 24.

Dissolution profiles for the above-described formulations were determined in USP Type II apparatus. Six tablets of each formulation were weighed, placed in a sinker, and dropped into an equilibrated dissolution bath vessel containing 900 mL of (helium sparged) 0.1 N HCl heated to 37° C.±0.5° C. The mixture was stirred at 150±6 rpm, and the temperature was maintained at 37° C.±0.5° C. through 12 hr. The bath vessel was covered with a low evaporation vessel cover. Samples (5 mL) were removed at 0.25 hr, 0.5 hr, 1 hr, 2 hr, 4 hr, 6, hr, 8 hr, and 12 hr. The final time point for the 25%, 35%, 45%, and 55% formulations was 15 hr, 15 hr, 17.5 hr, and 17.5 hr, respectively. Each sample was filtered through a 0.45 µm filter and analyzed by HPLC using standard procedures.

The cumulative release profiles of acetaminophen and oxycodone from these compositions are shown in FIGS. 49 and 50, respectively. These profiles confirm that as the amount of POLYOX® 1105 used in the pharmaceutical formulations increase, the release rate of the acetaminophen and oxycodone generally decreases. For example, the formulations containing 25%, 45%, and 55% POLYOX® 1105 had released about 56%, about 53%, and about 53% acetaminophen after 15 minutes, respectively; about 59%, about 56%, and about 55% acetaminophen after 30 minutes, respectively; about 64%, about 61%, about 60%, and about 59% acetaminophen after 1 hr, respectively; about 73%, about 70%, about 67%, and about 66% acetaminophen after 2 hr, respectively; about 87%, about 84%, about 81%, and about 79% acetaminophen after 4 hr, respectively; about 95%, about 93%, about 90%, and about 89% acetaminophen after 6 hr, respectively; about 97%, about 97%, about 95%, and about 95% acetaminophen after 8 hr, respectively; and about 97%, about 97%, about 96%, and about 98% acetaminophen after 12 hr, respectively.

Similar trends were observed for the cumulative release of oxycodone. However, there was no observable difference in the release of oxycodone from the formulations containing 45% and 55% POLYOX® 1105. For example, the formulations containing 25%, 45%, and 55% POLYOX® 1105 had released about 50%, about 47%, and about 45% oxycodone after 15 minutes, respectively; about 56%, about 51%, about 50%, and about 50% oxycodone after 30 minutes, respectively; about 63%, about 58%, about 56%, and about 56% oxycodone after 1 hr, respectively; about 75%, about 70%, about 67%, and about 66% oxycodone after 2 hr, respectively; about 91%, about 87%, about 83%, and about 82% oxycodone after 4 hr, respectively; about 98%, about 96%, about 93%, and about 93% oxycodone after 6 hr, respectively; about 99%, about 99%, about 97%, and about 98% oxycodone after 8 hr, respectively; and about 99%, about 100%, about 97%, and about 100% oxycodone after 12 hr, respectively.

Example 26

Varying Polyox Grades Comprising 25% by Weight of the Extended Release Portion of Bilayer Formulations Containing Hydrocodone Bilayer formulations described herein were prepared, each containing a total of 15 mg of hydrocodone bitartrate and a total of 500 mg of acetaminophen. 50% of the acetaminophen was contained in the immediate release portion, and the other 50% was contained in the ER layer. 25% of the hydrocodone bitartrate was contained in the immediate release portion of the formulation, and the other 75% was contained in the ER layer. In a first formulation, POLYOX® 205 was employed as the extended release component in an amount of 25% by weight of the ER portion. In a second formulation, POLYOX® 1105 was employed as the extended release component in an amount of 25% by weight of the ER portion. In a third formulation, POLYOX® N-12K was employed as the extended release component in an amount of 25% by weight of the ER portion. In a fourth formulation, POLYOX® N-60K was employed as the extended release component in an amount of 25% by weight of the ER portion. In a fifth formulation, POLYOX® 301 was employed as the extended release component in an amount of 25% by weight of the ER portion. The other excipients in the extended release portion were microcrystalline cellulose, spress B825, citric acid anhydrous, EDTA, hydroxypropyl cellulose, silicon dioxide, and magnesium stearate.

Dissolution profiles for the five above-described compositions were determined in a USP Type II apparatus. Five tablets of each composition were weighed, placed in a sinker, and dropped into an equilibrated dissolution bath vessel containing 900 mL of (helium sparged) 0.1 N HCl heated to 37° C.±0.5° C. The mixture was stirred at 150±6 rpm, and the temperature was maintained at 37° C.±0.5° C.

for 12 hr. The bath vessel was covered with a low evaporation vessel cover. Samples (5 mL) were removed at 0.25 hr, 0.5 hr, 1 hr, 2 hr, 4 hr, 6, hr, 8 hr, 12 hr, and 18 hr. Each sample was filtered through a 0.45 μm filter and analyzed by HPLC using standard procedures.

The cumulative release profiles of acetaminophen and hydrocodone from these compositions are shown in FIGS. 51 and 52, respectively. These figures demonstrate that as the average molecular weight of the POLYOX® extended release component increases, the rate of dissolution at each time point decreases. For example, the formulations containing POLYOX® 205, 1105, N-12K, N-60K, and 301 had released about 59%, about 58%, about 56%, about 55%, and about 52% acetaminophen after 15 minutes, respectively; about 62%, about 61%, about 58%, about 57%, and about 56% acetaminophen after 30 minutes, respectively; about 68%, about 66%, about 63%, about 61%, and about 60% acetaminophen after 1 hr, respectively; about 78%, about 76%, about 71%, about 67%, and about 65% acetaminophen after 2 hr, respectively; about 92%, about 90%, about 83%, about 76%, and about 73% acetaminophen after 4 hr, respectively; about 98%, about 97%, about 92%, about 84%, and about 79% acetaminophen after 6 hr, respectively; about 99%, about 98%, about 96%, about 90%, and about 85% acetaminophen after 8 hr, respectively; about 98%, about 97%, about 96%, about 97%, and about 92% acetaminophen after 12 hr, respectively; and about 98%, about 97%, about 96%, about 97%, and about 97% acetaminophen after 18 hr, respectively.

The same general trend of a decreased release rate with a higher molecular weight POLYOX® grade was also observed for the hydrocodone bitratrate. For example, the formulations containing POLYOX® 205, 1105, N-12K, N-60K, and 301 had released about 38%, about 39%, about 39%, about 34%, and about 32% hydrocodone bitratrate after 15 minutes, respectively; about 48%, about 47%, about 46%, about 41%, and about 39% hydrocodone bitratrate after 30 minutes, respectively; about 60%, about 57%, about 55%, about 49%, and about 47% hydrocodone bitratrate after 1 hr, respectively; about 76%, about 72%, about 68%, about 60%, and about 58% hydrocodone bitratrate after 2 hr, respectively; about 96%, about 93%, about 87%, about 77%, and about 73% hydrocodone bitratrate after 4 hr, respectively; about 105%, about 102%, about 99%, about 89%, and about 83% hydrocodone bitratrate after 6 hr, respectively; about 105%, about 102%, about 103%, about 97%, and about 91% hydrocodone bitratrate after 8 hr, respectively; about 105%, about 102%, 103%, about 104%, and about 100% hydrocodone bitratrate after 12 hr, respectively; and about 106%, about 103%, about 104%, about 104%, and about 104% hydrocodone bitratrate after 18 hr, respectively.

Example 27

Varying Polyox Grades Comprising 45% by Weight of the Extended Release Portion of Bilayer Formulations Containing Hydrocodone The release rate studies described in Example 26 were repeated, except that the five bilayer formulations were prepared such that they included POLYOX® 205, 1105, N-12K, N-60K, and 301 in an amount of 45% by weight of the ER portion.

The cumulative release profiles of acetaminophen and hydrocodone from these compositions are shown in FIGS. 53 and 54, respectively. Consistent with the results of Example 26, the rate of dissolution at each time point generally decreases as the average molecular weight of POLYOX® increases. For example, the formulations containing POLYOX® 205, 1105, N-12K, N-60K, and 301 had released about 55%, about 53%, about 55%, about 54%, and about 54% acetaminophen after 15 minutes, respectively; about 57%, about 56%, about 57%, about 55%, and about 56% acetaminophen after 30 minutes, respectively; about 62%, about 60%, about 60%, about 58%, and about 59% acetaminophen after 1 hr, respectively; about 70%, about 68%, about 67%, about 64%, and about 63% acetaminophen after 2 hr, respectively; about 84%, about 81%, about 78%, about 72%, and about 70% acetaminophen after 4 hr, respectively; about 95%, about 91%, about 87%, about 80%, and about 77% acetaminophen after 6 hr, respectively; about 99%, about 96%, about 93%, about 86%, and about 82% acetaminophen after 8 hr, respectively; about 99%, about 98%, about 99%, about 95%, and about 90% acetaminophen after 12 hr, respectively; and about 98%, about 97%, about 98%, about 99%, and about 96% acetaminophen after 18 hr, respectively.

The same general trend of a decreased release rate with a higher molecular weight POLYOX® grade was also observed for the hydrocodone bitratrate. For example, the formulations containing POLYOX® 205, 1105, N-12K, N-60K, and 301 had released about 33%, about 33%, about 32%, about 31%, and about 32% hydrocodone bitratrate after 15 minutes, respectively; about 39%, about 39%, about 38%, about 36%, and about 37% hydrocodone bitratrate after 30 minutes, respectively; about 48%, about 48%, about 46%, about 43%, and about 43% hydrocodone bitratrate after 1 hr, respectively; about 63%, about 63%, about 59%, about 54%, and about 53% hydrocodone bitratrate after 2 hr, respectively; about 85%, about 84%, about 79%, about 71%, and about 68% hydrocodone bitratrate after 4 hr, respectively; about 99%, about 97%, about 92%, about 84%, and about 79% hydrocodone bitratrate after 6 hr, respectively; about 102%, about 103%, about 100%, about 93%, and about 88% hydrocodone bitratrate after 8 hr, respectively; about 103%, about 104%, about 104%, about 102%, and about 98% hydrocodone bitratrate after 12 hr, respectively; and about 104%, about 103%, about 104%, about 105%, and about 103% hydrocodone bitratrate after 18 hr, respectively.

Example 28

Varying the Concentrations of a Specific Polyox Grade in the Extended Release Portion of Bilayer Formulations Containing Hydrocodone The data from Examples 26 and 27 indicate that an increase in the amount of POLYOX® in the pharmaceutical composition also retards release of the actives from the pharmaceutical composition. To confirm this observation, bilayer formulations described herein were prepared, each containing a total of 15 mg of hydrocodone bitartrate and a total of 500 mg of acetaminophen. 50% of the acetaminophen was contained in the immediate release portion, and the other 50% was contained in the ER layer. 25% of the hydrocodone bitartrate was contained in the immediate release portion of the formulation, and the other 75% was contained in the ER layer. In a first formulation, POLYOX® 1105 was employed as the extended release component in an amount of 25% by weight of the ER portion. In a second formulation, POLYOX™ 1105 was employed as the extended release component in an amount of 35% by weight of the ER portion. In a third formulation, POLYOX™ 1105 was employed as the extended release component in an amount of 45% by weight of the ER portion.

The cumulative release profiles of acetaminophen and hydrocodone bitartrate from these compositions are shown in FIGS. 55 and 56, respectively. These profiles confirm that as the amount of POLYOX® 1105 used in the pharmaceutical formulations increase, the release rate of the actives generally decreases. For example, the formulations containing 25%, 35%, and 45% POLYOX® 1105 had released about 58%, about 54%, and about 53% acetaminophen after 15 minutes, respectively; about 61%, about 56%, and about 56% acetaminophen after 30 minutes, respectively; about 66%, about 61%, and about 60% acetaminophen after 1 hr, respectively; about 76%, about 70%, and about 68% acetaminophen after 2 hr, respectively; about 90%, about 85%, and about 81% acetaminophen after 4 hr, respectively; about 97%, about 94%, and about 91% acetaminophen after 6 hr, respectively; about 98%, about 97%, and about 96% acetaminophen after 8 hr, respectively; about 97%, about 97%, and about 98% acetaminophen after 12 hr, respectively; and about 97%, about 96%, and about 97% acetaminophen after 18 hr, respectively.

Similar trends were observed for the cumulative release of hydrocodone bitartrate. For example, the formulations containing 25%, 35%, and 45% POLYOX® 1105 had released about 39%, about 34%, and about 33% hydrocodone bitartrate after 15 minutes, respectively; about 47%, about 39%, and about 39% hydrocodone bitartrate after 30 minutes, respectively; about 57%, about 49%, and about 48% hydrocodone bitartrate after 1 hr, respectively; about 72%, about 65%, and about 63% hydrocodone bitartrate after 2 hr, respectively; about 93%, about 88%, and about 84% hydrocodone bitartrate after 4 hr, respectively; about 102%, about 100%, about 97% hydrocodone bitartrate after 6 hr, respectively; about 102%, about 103%, and about 103% hydrocodone bitartrate after 8 hr, respectively; about 102%, about 104%, and about 104% hydrocodone bitartrate after 12 hr, respectively; and about 103%, about 103%, and about 103% hydrocodone bitartrate after 18 hr, respectively.

Example 29

Varying the Concentrations of a Specific Polyox Grade in the Extended Release Portion of Bilayer Formulations Containing Hydrocodone The release rate studies described in Example 28 were repeated, except that the three bilayer formulations were prepared such that they included POLYOX® N-60K instead of 1105.

The cumulative release profiles of acetaminophen and hydrocodone bitartrate from these compositions are shown in FIGS. 57 and 58, respectively. These profiles confirm that as the amount of POLYOX® N-60K used in the pharmaceutical formulations increase, the release rate of the actives generally decreases. For example, the formulations containing 25%, 35%, and 45% POLYOX® N-60K had released about 55%, about 54%, and about 54% acetaminophen after 15 minutes, respectively; about 57%, about 56%, and about 55% acetaminophen after 30 minutes, respectively; about 61%, about 60%, and about 58% acetaminophen after 1 hr, respectively; about 67%, about 65%, and about 64% acetaminophen after 2 hr, respectively; about 76%, about 74%, and about 72% acetaminophen after 4 hr, respectively; about 84%, about 82%, and about 80% acetaminophen after 6 hr, respectively; about 90%, about 88%, and about 86% acetaminophen after 8 hr, respectively; about 97%, about 96%, and about 95% acetaminophen after 12 hr, respectively; and about 97%, about 98%, and about 99% acetaminophen after 18 hr, respectively.

Similar trends were observed for the cumulative release of hydrocodone bitartrate. For example, the formulations containing 25%, 35%, and 45% POLYOX® N-60K had released about 34%, about 32%, and about 31% hydrocodone bitartrate after 15 minutes, respectively; about 41%, about 37%, and about 36% hydrocodone bitartrate after 30 minutes, respectively; about 49%, about 44%, and about 43% hydrocodone bitartrate after 1 hr, respectively; about 60%, about 55%, and about 54% hydrocodone bitartrate after 2 hr, respectively; about 77%, about 72%, and about 71% hydrocodone bitartrate after 4 hr, respectively; about 89%, about 85%, and about 84% hydrocodone bitartrate after 6 hr, respectively; about 97%, about 93%, and about 93% hydrocodone bitartrate after 8 hr, respectively; about 104%, about 100%, and about 102% hydrocodone bitartrate after 12 hr, respectively; and about 104%, about 102%, and about 105% hydrocodone bitartrate after 18 hr, respectively.

While the cumulative release profiles of the formulations generally decrease as the amount of the extended release component is increased, this trend is more pronounced for POLYOX® 1105 than for POLYOX® N-60K.

Example 30

In Vitro Dissolution of Controlled-Release Bilayer Tablets Containing 15 mg Oxycodone and 650 mg Acetaminophen Performed at a 150 rpm Paddle Speed Bilayer formulations described herein were prepared, each containing a total of 15 mg of oxycodone HCl and a total of 650 mg of acetaminophen. 50% of the acetaminophen was contained in the immediate release portion, and the other 50% was contained in the ER layer. 25% of the oxycodone HCl was contained in the immediate release portion of the formulation, and the other 75% was contained in the ER layer. POLYOX® 1105 was employed as the extended release component in an amount of 45% by weight of the ER portion.

Dissolution profiles for the formulations were determined in a USP Type II apparatus. Six tablets were weighed, placed in a sinker, and dropped into an equilibrated dissolution bath vessel containing 900 mL of (helium sparged) 0.1 N HCl heated to 37° C.±0.5° C. The mixture was stirred at 150±6 rpm, and the temperature was maintained at 37° C.±0.5° C. for 12 hr. The bath vessel was covered with a low evaporation vessel cover. Samples (5 mL) were removed at 0.25 hr, 0.5 hr, 1 hr, 2 hr, 4 hr, 6, hr, 8 hr, and 12 hr. Each sample was filtered through a 0.45 µm filter and analyzed by HPLC using standard procedures.

The cumulative percent release of acetaminophen and oxycodone from each batch are described in Table 75.

TABLE 75

Release rate data of bilayer tablets (15 mg oxycodone HCl; 325 mg acetaminophen) using a 150 rpm dissolution method.

| Time (hr) | Oxycodone HCl (%) | Acetaminophen (%) |
|---|---|---|
| 0.25 | 33.7 | 54.4 |
| 0.50 | 39.0 | 56.5 |
| 1 | 47.4 | 60.6 |
| 2 | 61.4 | 68.1 |
| 4 | 81.7 | 81.1 |

TABLE 75-continued

Release rate data of bilayer tablets (15 mg oxycodone HCl; 325 mg acetaminophen) using a 150 rpm dissolution method.

| Time (hr) | Oxycodone HCl (%) | Acetaminophen (%) |
|---|---|---|
| 6 | 95.2 | 90.8 |
| 8 | 101.2 | 96.0 |
| 12 | 102.3 | 97.6 |

Example 31

In Vitro Dissolution of Controlled-Release Bilayer Tablets Containing 15 mg Hydrocodone and 650 mg Acetaminophen Performed at a 150 rpm Paddle Speed Bilayer formulations described herein were prepared, each containing a total of 15 mg of hydrocodone bitartrate and a total of 650 mg of acetaminophen. 50% of the acetaminophen was contained in the immediate release portion, and the other 50% was contained in the ER layer. 25% of the hydrocodone bitartrate was contained in the immediate release portion of the formulation, and the other 75% was contained in the ER layer. POLYOX® N60k was employed as the extended release component in an amount of 45% by weight of the ER portion.

Dissolution profiles for the formulations were determined in a USP Type II apparatus. Six tablets were weighed, placed in a sinker, and dropped into an equilibrated dissolution bath vessel containing 900 mL of (helium sparged) 0.1 N HCl heated to 37° C.±0.5° C. The mixture was stirred at 150±6 rpm, and the temperature was maintained at 37° C.±0.5° C. for 12 hr. The bath vessel was covered with a low evaporation vessel cover. Samples (5 mL) were removed at 0.25 hr, 0.5 hr, 1 hr, 2 hr, 4 hr, 6, hr, 8 hr, 12 hr, and 18 hr. Each sample was filtered through a 0.45 μm filter and analyzed by HPLC using standard procedures.

The cumulative percent release of acetaminophen and hydrocodone bitartrate from each batch are described in Table 76.

TABLE 76

Release rate data of bilayer tablets (15 mg hydrocodone bitartrate; 325 mg acetaminophen) using a 150 rpm dissolution method.

| Time | Hydrocodone Bitartrate | | Acetaminophen | |
|---|---|---|---|---|
| (hr) | Mean (%) | RSD (%) | Mean (%) | RSD (%) |
| 0.25 | 32.6 | 1.5 | 53.4 | 0.9 |
| 0.50 | 37.1 | 2.1 | 55.3 | 1.0 |
| 1 | 44.2 | 2.2 | 58.4 | 0.9 |
| 2 | 55.0 | 1.3 | 63.4 | 1.0 |
| 4 | 71.8 | 0.8 | 72.3 | 1.2 |
| 6 | 83.9 | 1.3 | 79.6 | 1.1 |
| 8 | 92.2 | 0.6 | 85.7 | 1.1 |
| 12 | 99.5 | 0.7 | 93.7 | 1.1 |
| 18 | 101.0 | 0.7 | 97.2 | 1.0 |

Example 32

Ethanol Release Testing at a 100 rpm Paddle Speed

The ethanol release studies discussed above in Example 8 were repeated, except that the solutions were stirred at a paddle speed of 100 rpm and additional aliquots were sampled at 240 min and 480 min. Tables 77, 78, 79, 80, and 81 present the percent release of OC and APAP in the presence of 0%, 5%, 10%, 20%, and 40% ethanol, respectively. FIG. 59 presents dissolution profiles for OC and FIG. 60 presents dissolution profiles for APAP in the presence of 0%, 5%, 20%, and 40% ethanol. Like the results at a paddle speed of 150 rpm, these data reveal that, for both OO and APAP, the dissolution in 5%, 20%, or 40% ethanol was either comparable or slower than the dissolution in 0% ethanol, indicating no dose dumping for this formulation.

TABLE 77

Percent Release in 0% Ethanol

| | OC | | | | APAP | | | |
|---|---|---|---|---|---|---|---|---|
| Time (Min) | Mean | RSD | Minimum | Maximum | Mean | RSD | Minimum | Maximum |
| 15 | 32.5 | 3.7 | 31.5 | 36.0 | 52.2 | 1.6 | 50.7 | 53.4 |
| 30 | 37.6 | 2.5 | 36.6 | 39.9 | 54.6 | 1.4 | 53.2 | 55.7 |
| 45 | 42.1 | 2.7 | 40.9 | 44.8 | 56.8 | 1.4 | 55.3 | 57.9 |
| 60 | 45.8 | 2.1 | 44.6 | 48.1 | 58.8 | 1.4 | 57.4 | 59.8 |
| 75 | 49.6 | 2.3 | 48.2 | 52.2 | 60.8 | 1.4 | 59.2 | 61.8 |
| 90 | 53.1 | 2.4 | 51.7 | 55.8 | 62.6 | 1.4 | 60.9 | 63.8 |
| 105 | 56.3 | 2.4 | 54.8 | 59.3 | 64.3 | 1.4 | 62.6 | 65.6 |
| 120 | 59.5 | 2.5 | 57.6 | 63.0 | 66.0 | 1.4 | 64.2 | 67.3 |
| 240 | 80.3 | 2.5 | 77.3 | 84.9 | 78.6 | 1.8 | 76.3 | 80.6 |
| 480 | 102.4 | 1.8 | 100.5 | 107.2 | 95.5 | 1.6 | 92.6 | 97.7 |

TABLE 78

Percent Release in 5% Ethanol

| | OC | | | | APAP | | | |
|---|---|---|---|---|---|---|---|---|
| Time (Min) | Mean | RSD | Minimum | Maximum | Mean | RSD | Minimum | Maximum |
| 15 | 31.5 | 2.5 | 30.0 | 32.9 | 52.6 | 2.1 | 51.4 | 55.1 |
| 30 | 36.8 | 2.4 | 35.6 | 38.5 | 55.1 | 2.0 | 53.8 | 57.6 |
| 45 | 40.9 | 2.8 | 38.9 | 43.5 | 57.1 | 2.0 | 55.8 | 59.6 |
| 60 | 44.6 | 3.7 | 42.1 | 48.4 | 58.9 | 2.0 | 57.6 | 61.4 |
| 75 | 48.0 | 3.6 | 46.0 | 52.6 | 60.7 | 1.9 | 59.4 | 63.2 |
| 90 | 51.0 | 3.1 | 49.3 | 55.3 | 62.3 | 1.9 | 61.0 | 64.7 |
| 105 | 54.3 | 3.2 | 51.8 | 58.6 | 63.9 | 2.0 | 62.6 | 66.4 |
| 120 | 57.1 | 3.2 | 54.6 | 61.7 | 65.5 | 1.9 | 64.1 | 67.8 |
| 240 | 76.6 | 3.2 | 73.8 | 83.0 | 77.2 | 2.1 | 75.5 | 80.6 |
| 480 | 99.9 | 2.7 | 95.8 | 106.8 | 94.4 | 1.7 | 92.6 | 98.1 |

TABLE 79

Percent Release in 10% Ethanol

| | OC | | | | APAP | | | |
|---|---|---|---|---|---|---|---|---|
| Time (Min) | Mean | RSD | Minimum | Maximum | Mean | RSD | Minimum | Maximum |
| 15 | 30.3 | 3.1 | 28.9 | 32.1 | 51.7 | 1.8 | 50.1 | 53.4 |
| 30 | 35.6 | 3.3 | 33.7 | 37.3 | 54.1 | 1.9 | 52.4 | 55.8 |
| 45 | 39.6 | 2.6 | 37.6 | 40.9 | 56.0 | 1.9 | 54.3 | 57.8 |
| 60 | 43.1 | 2.6 | 41.2 | 44.7 | 57.8 | 1.9 | 56.1 | 59.5 |
| 75 | 46.2 | 2.3 | 44.1 | 47.5 | 59.5 | 1.8 | 57.7 | 61.1 |
| 90 | 49.3 | 2.1 | 47.3 | 50.6 | 61.1 | 1.8 | 59.3 | 62.8 |
| 105 | 52.2 | 2.2 | 50.1 | 53.6 | 62.6 | 1.8 | 60.9 | 64.2 |
| 120 | 54.8 | 2.3 | 52.8 | 56.4 | 64.1 | 1.8 | 62.3 | 65.6 |
| 240 | 73.8 | 2.2 | 70.8 | 76.1 | 75.5 | 1.7 | 73.4 | 77.4 |
| 480 | 98.4 | 2.1 | 94.7 | 101.1 | 93.5 | 1.6 | 91.0 | 95.9 |

TABLE 80

Percent Release in 20% Ethanol

| | OC | | | | APAP | | | |
|---|---|---|---|---|---|---|---|---|
| Time (Min) | Mean | RSD | Minimum | Maximum | Mean | RSD | Minimum | Maximum |
| 15 | 28.0 | 6.0 | 23.9 | 30.3 | 50.2 | 5.1 | 43.0 | 53.0 |
| 30 | 33.6 | 4.5 | 30.7 | 35.6 | 53.4 | 3.1 | 49.5 | 55.9 |
| 45 | 37.9 | 2.9 | 35.7 | 39.6 | 55.5 | 2.6 | 52.6 | 57.9 |
| 60 | 41.2 | 3.1 | 39.2 | 43.2 | 57.3 | 2.3 | 55.1 | 59.8 |
| 75 | 44.1 | 2.9 | 42.3 | 46.6 | 59.0 | 2.2 | 57.0 | 61.4 |
| 90 | 46.5 | 3.5 | 42.7 | 49.1 | 60.5 | 2.1 | 58.6 | 62.9 |
| 105 | 49.8 | 2.9 | 48.0 | 52.8 | 61.9 | 2.1 | 60.2 | 64.4 |
| 120 | 52.2 | 2.8 | 49.9 | 54.8 | 63.3 | 2.0 | 61.7 | 65.9 |
| 240 | 72.2 | 2.1 | 69.4 | 74.7 | 76.0 | 1.7 | 74.1 | 78.4 |
| 480 | 95.7 | 2.3 | 91.7 | 98.7 | 91.9 | 1.7 | 89.3 | 94.6 |

TABLE 81

Percent Release in 40% Ethanol

| | OC | | | | APAP | | | |
|---|---|---|---|---|---|---|---|---|
| Time (Min) | Mean | RSD | Minimum | Maximum | Mean | RSD | Minimum | Maximum |
| 15 | 11.9 | 13.9 | 10.0 | 15.1 | 16.7 | 23.2 | 12.3 | 22.9 |
| 30 | 21.1 | 15.4 | 17.3 | 26.2 | 30.4 | 22.3 | 21.7 | 40.7 |
| 45 | 26.8 | 11.6 | 22.4 | 30.3 | 38.5 | 15.3 | 29.6 | 44.8 |
| 60 | 30.8 | 7.0 | 26.8 | 34.0 | 43.1 | 9.2 | 35.9 | 47.1 |
| 75 | 34.2 | 5.0 | 31.5 | 36.8 | 46.1 | 5.3 | 41.1 | 49.2 |
| 90 | 36.9 | 3.2 | 35.1 | 38.8 | 48.3 | 3.3 | 44.6 | 50.2 |
| 105 | 39.6 | 3.3 | 37.3 | 41.2 | 49.8 | 2.4 | 47.3 | 51.3 |
| 120 | 41.9 | 3.3 | 39.4 | 44.2 | 51.1 | 2.3 | 48.3 | 52.7 |
| 240 | 57.0 | 1.8 | 55.7 | 58.9 | 60.8 | 2.0 | 58.9 | 63.6 |
| 480 | 80.6 | 1.6 | 78.4 | 83.7 | 77.2 | 1.3 | 75.7 | 78.7 |

All references cited herein are hereby incorporated by reference. The foregoing is offered primarily for purposes of illustration. It will be readily apparent to those skilled in the art that further drugs can be included, and that the shapes, components, additives, proportions, methods of formulation, and other parameters described herein can be modified further or substituted in various ways without departing from the spirit and scope of the invention.

What is claimed is:

1. A pharmaceutical composition comprising:
   (a) at least one immediate release portion comprising about 125 mg to about 325 mg of acetaminophen and about 1.5 mg to about 4.0 mg hydrocodone or a pharmaceutically acceptable salt thereof; and
   (b) at least one extended release portion comprising about 125 mg to about 325 mg of acetaminophen and about 4.5 mg to about 6.5 mg hydrocodone or a pharmaceutically acceptable salt thereof, and an extended release-component;
   wherein the total amount of acetaminophen in the composition is about 325 mg to about 650 mg, and the total amount of hydrocodone or a pharmaceutically acceptable salt thereof in the composition is about 7.5 mg to about 10 mg, wherein upon placement of the composition in an in vitro dissolution test comprising USP Paddle Method at a paddle speed of about 100 rpm in 900 mL of 0.1N HCl using a USP type II apparatus at a constant temperature of about 37° C., about 20% to about 40% of the total amount of hydrocodone or a pharmaceutically acceptable salt thereof in the composition is released at about 15 minutes in the test and about 50% to about 55% of the total amount of acetaminophen in the composition is released at about 15 minutes in the test.

2. The pharmaceutical composition of claim 1, wherein upon oral administration of a single dose of the composition to a subject, the composition provides a $C_{max}$ for hydrocodone from about 0.9 ng/mL/mg to about 2.0 ng/mL/mg, a $C_{max}$ for acetaminophen from about 4.0 ng/mL/mg to about 11.0 ng/mL/mg, a $T_{max}$ for hydrocodone from about 2 hours to about 8 hours, and a $T_{max}$ for acetaminophen from about 0.5 hour to about 6 hours.

3. The pharmaceutical composition of claim 1, wherein from about 45% to about 65%, by weight, of the hydrocodone or a pharmaceutically acceptable salt thereof is released from the composition at about 2 hours in the test, from about 60% to about 85%, by weight, of the hydrocodone or a pharmaceutically acceptable salt thereof is released from the composition at about 4 hours in the test, from about 80% to about 100%, by weight, of the hydrocodone or a pharmaceutically acceptable salt thereof is released from the composition at about 8 hours in the test, from about 60% to about 75%, by weight, of the acetaminophen is released from the composition at about 2 hours in the test, and from about 75% to about 85%, by weight, of the acetaminophen is released from the composition at about 4 hours in the test.

4. The pharmaceutical composition of claim 1, wherein upon oral administration of multiple doses to a subject in need of analgesia, the composition produces a blood plasma profile characterized by a mean AUC for hydrocodone from about 10.0 ng·hr/mL/mg to about 22.0 ng·hr/mL/mg, a steady state AUC for hydrocodone from about 13.0 ng·hr/mL/mg to about 18.0 ng·hr/mL/mg, a mean AUC for acetaminophen from about 35.0 ng·hr/mL/mg to about 80.0 ng·hr/mL/mg, and a steady state AUC for acetaminophen from about 37.0 ng·hr/mL/mg to about 42.0 ng·hr/mL/mg.

5. The pharmaceutical composition of claim 1, wherein upon oral administration of multiple doses to a subject in need of analgesia, the composition produces a blood plasma profile characterized by a median $T_{max}$ for hydrocodone from about 3.0 hours to about 6.0 hours, a steady state $T_{max}$ for hydrocodone from about 2.0 hours to about 4.0 hours, a median $T_{max}$ for acetaminophen from about 1.0 hour to about 5.0 hours, and a steady state $T_{max}$ for acetaminophen from about 0.5 hour to about 1.0 hours.

6. The pharmaceutical composition of claim 1, wherein upon placement of the composition in an in vitro dissolution test comprising USP Paddle Method at a paddle speed of about 100 rpm in 900 mL of 0.1N HCl using a USP type II apparatus at a constant temperature of about 37° C, about 35% to about 40% of the hydrocodone or a pharmaceutically acceptable salt thereof is released at about 30 minutes in the test and about 51% to about 58% of the acetaminophen is released at about 30 minutes in the test.

7. The pharmaceutical composition of claim 1, Wherein the extended release component comprises polyethylene oxide.

8. The pharmaceutical composition of claim 7, wherein the polyethylene oxide has a molecular weight from about 500,000 Daltons to about 10,000,000 Daltons.

9. The pharmaceutical composition of claim 1, wherein the at least one immediate release portion comprises from about 20% to about 30% of the total amount of hydrocodone or a pharmaceutically acceptable salt thereof in the composition and from about 40% to about 60% of the total amount of acetaminophen in the composition, and the at least one extended release portion comprises the balance of each of the hydrocodone or a pharmaceutically acceptable salt thereof and the acetaminophen.

10. The pharmaceutical composition of claim 1, wherein the immediate release portion comprises, by weight of the immediate release portion, from about 70% to about 80% acetaminophen and from about 0.5% to about 1% of hydrocodone or a pharmaceutically acceptable salt thereof;and the extended release portion comprises, by weight of the extended release portion, from about 30% to about 50% of the extended release component, from about 20% to about 40% of acetaminophen, and from about 0.5% to about 2% of hydrocodone or a pharmaceutically acceptable salt thereof.

11. The pharmaceutical composition of claim 1, wherein the extended release component comprises a polymer selected from the group consisting of linear, branched, dendrimeric, or star polymers, hydrophilic polymers, and mixtures thereof.

12. The pharmaceutical composition of claim 1, wherein the extended release component comprises a polymer selected from the group consisting of a polyalkylene oxide, poly(ethylene oxide), polyethylene glycol and poly(ethylene oxide) poly(propylene oxide), methylcetlulose, hydroxymethylcellulose, laydroxyethylcellulose, hydroxypropylcellulose, hydroxypropylmethylceliulose, carboxymethylcellulose, microcrystalline cellulose, acrylic acid, methacrylic acid, methyl acrylate, ethyl acrylate, methyl methacrylate, ethyl methacrylate, aminoethyl acrylate, maleic anhydride copolymer, polymaleic acid, poly(acrylamide), poly(methacrylanaide), poly(dimethylacrylamide), poly(N-isopropylacrylamide), poly(oiefinic alcohol), poly(vinyi alcohol), poly(N-vinyl lactam), poly(vinyl pyrrolidone), poly(N-vinyl caprolactam), polyol, glycerol, polyglycerol, propylene glycol, trimethylene glycol, mono-, di- and tri-polyoxyethylated glycerol, mono- and di-polyoxyethylated propylene glycol, mono- and di-polyoxyethylated trirnethylene glycol, polyoxyethylated sorbitol, polyoxyethylated glucose, polyoxazolines, poly(methyloxazoline), poly(ethyloxazoline), polyvinylamine, polyvinylacetate, ethylene-vinyl acetate copolymer, polyvinyl acetate phthalate, polyimines, polyethyleneimine, starch, starch-based polymer, polyurethane hydrogel, chitosan, polysaccharide gums, xanthan gum, zein, shellac, ammoniated shellac, shellac-acetyl alcohol, shellac n-butyl, stearate, and mixtures thereof.

13. A pharmaceutical composition comprising:
(a) at least one immediate release portion comprising about 125 mg to about 325 mg of acetaminophen and about 1.5 mg to about 4.0 mg hydrocodone or a pharmaceutically acceptable salt thereof; and
(b) at least one extended release portion comprising about 125 mg to about 32.5 mg of acetaminophen and about 4.5 mg to about 6.5 mg hydrocodone or a pharmaceutically acceptable salt thereof, and an extended release component;
wherein the total amount of acetaminophen in the composition is about 325 mg to about 650 mg, and the total amount of hydrocodone or a pharmaceutically acceptable salt thereof in the composition is about 7.5 mg to about 10 mg; and
wherein upon placement of the composition in an in vitro dissolution test comprising USP Paddle Method at a paddle speed of about 150 rpm in 900 mL of 0.1N HCl using a USP type II apparatus at a constant temperature of about 37° C, the drug release profile substantially corresponds to the following:
after 15 minutes, no more than about 35%, by weight, of the total amount of the hydrocodone or a pharmaceutically acceptable salt thereof is released and no more than about 55%, by weight, of the total amount of the acetaminophen is released;
after 1 hour, no more than about 50%, by weight, of the total amount of the hydrocodone or a pharmaceutically acceptable salt thereof is released and no more than about 63%, by weight, of the total amount of the acetaminophen is released;
after 2 hours, no more than about 65%, by weight, of the total amount of the hydrocodone or a pharmaceutically acceptable salt thereof is released and no more than about 75%, by weight, of the total amount of the acetaminophen is released;
after 4 hours, from about 65% to about 85%, by weight, of the total amount of the hydrocodone or a pharmaceutically acceptable salt thereof is released and from about 70% to about 90%, by weight, of the total amount of the acetaminophen is released;
after 8 hours, from about 85% to about 100%, by weight, of the total amount of the hydrocodone or a pharmaceutically acceptable salt thereof is released and from about 85% to about 100%, by weight, of the total amount of the acetaminophen is released; and
after 12 hours, from about 95% to about 100%, by weight, of the total amount of the hydrocodone or a pharmaceutically acceptable salt thereof is released and from about 90% to about 100%, by weight, of the total amount of the acetaminophen is released.

14. The pharmaceutical composition of claim 13, wherein the composition comprises about 325 mg of acetaminophen and about 7.5 mg of hydrocodone or a pharmaceutically acceptable salt thereof.

15. The pharmaceutical composition of claim 13, wherein when orally administered to a subject, the composition produces a blood plasma concentration profile characterized by a biphasic increase in blood plasma concentrations of hydrocodone and acetaminophen.

16. The pharmaceutical composition of claim 15, wherein the biphasic increase in blood plasma concentrations of hydrocodone is characterized by a plasma concentration-time profile for hydrocodone in which the slope of a line drawn between 0 hour and about 2 hours is greater than the slope of a line drawn between about 2 hours and about 5 hours.

17. A pharmaceutical composition as a solid oral dosage form comprising:
(a) at least one immediate release portion comprising about 125 mg to about 325 mg of acetaminophen and about 1.5 mg to about 4.0 mg hydrocodone or a pharmaceutically acceptable salt thereof; and
(b) at least one extended release portion comprising about 125 mg to about 325 mg of acetaminophen and about 4.5 mg to about 6.5 mg hydrocodone or a pharmaceutically acceptable salt thereof, and an extended release component;
wherein the total amount of acetaminophen in the composition is about 325 mg and the total amount of hydrocodone or a pharmaceutically acceptable salt thereof in the composition is about 7.5 mg; and
wherein upon oral administration of two solid oral dosage forms of the composition wherein upon oral administration of two solid oral dosage forms of the composition, the composition provides the composition provides an $AUC_{0-1.7h}$ for acetaminophen of about 5.0 ng·h/mL/mg to about 13.0 ng·h/mL/mg; an $AUC_{1.7-48h}$ for acetaminophen of about 25.0 ng·h/mL/mg to about 75.0 ng·h/mL/mg, an $AUC_{0-2.44h}$ for hydrocodone or a pharmaceutically acceptable salt thereof of about 1.0 ng·h/mL/mg to about 4.25 ng·h/mL/mg; and $AUC_{2.44-36h}$ of about 10 ng·h/mL/mg to about 20.0 ng·h/mL/mg.

18. The pharmaceutical composition of claim 17 wherein the $AUC_{0-1hr}$ for acetaminophen is from about 1.25 ng·hr/mL/mg to about 3.25 ng·hr/mL/mg.

19. The pharmaceutical composition of claim 17 wherein the $AUC_{0-2hr}$ for acetaminophen is from about 4.25 ng·hr/mL/mg to about 8.75 ng·hr/mL/mg.

20. The pharmaceutical composition of claim 17 wherein the $AUC_{0-4hr}$ for acetaminophen is from about 10.0 ng·hr/mL/mg to about 20.0 ng·hr/mL/mg.

21. The pharmaceutical composition of claim 17 wherein the $AUC_{0-3hr}$ for hydrocodone is from about 1.0 ng·hr/mL/mg to about 5.0 ng·h/mL/mg.

22. The pharmaceutical composition of claim 21 wherein the $AUC_{3-36hr}$ for hydrocodone is from about 5.0 ng·h/mL/mg to about 25.0 ng·hr/mL/mg.

23. A pharmaceutical composition as a solid oral dosage form comprising:
   (a) at least one immediate release portion comprising about 125 mg to about 325 mg of acetaminophen and about 1.5 mg to about 4.0 mg hydrocodone or a pharmaceutically acceptable salt thereof; and
   (b) at least one extended release portion comprising about 125 mg to about 325 mg of acetaminophen and about 4.5 mg to about 6.5 mg hydrocodone or a pharmaceutically acceptable salt thereof thereof, and an extended release component;
   wherein the total amount of acetaminophen in the composition is about 325 mg to about 650 mg, and the total amount of hydrocodone or a pharmaceutically acceptable salt thereof in the composition is about 7.5 mg to about 10 mg; and
   wherein upon oral administration of two solid oral dosage forms of the composition wherein upon oral administration of two solid oral dosage forms of the composition, the composition maintains the composition maintains a therapeutic blood plasma concentration of hydrocodone of at least about 5 ng/mL from about 0.75 hours to about 10 hours after administration of the composition, and wherein at least about 90% of the acetaminophen is released from the composition by about 8 hours after administration of the composition such that, by about 10 hours after administration of the composition, acetaminophen has a blood plasma concentration that is less than about 30% of acetaminophen's maximum plasma concentration.

24. The pharmaceutical composition of claim 23, wherein the $AUC_{Tmax-t}$ for acetaminophen is from about 20.0 ng·hr/mL/mg to about 40.0 ng·hr/mL/mg.

25. The pharmaceutical composition of claim 23, wherein the $AUC_{(1.7-48hr)}$ for acetaminophen is from about 25.0 ng·hr/mL/mg to about 75.0 ng·hr/mL/mg.

26. The pharmaceutical composition of claim 23, wherein the composition is administered to a subject as a bilayer tablet.

27. The pharmaceutical composition of claim 26, wherein the bilayer tablet comprises about 325 mg of acetaminophen and about 7.5 mg of hydrocodone or a pharmaceutically acceptable salt thereof.

28. The pharmaceutical composition of claim 27, wherein a single dose comprises two bilayer tablets.

29. The solid oral dosage form of claim 23, wherein the solid oral dosage form is a tablet or capsule.

30. The solid oral dosage form of claim 23, wherein the solid oral dosage form is used in the treatment of acute pain.

* * * * *